(12) United States Patent
Kley et al.

(10) Patent No.: US 7,148,249 B2
(45) Date of Patent: Dec. 12, 2006

(54) INDOLINONES SUBSTITUTED BY HETEROCYCLES, THE PREPARATION THEREOF AND THEIR USE AS MEDICAMENTS

(75) Inventors: Joerg Kley, Mittelbiberach (DE); Frank Hilberg, Vienna (AT); Armin Heckel, Biberach (DE); Gerald Juergen Roth, Biberach (DE); Thorsten Lehmann-Lintz, Ochsenhausen (DE); Ralf R. H. Lotz, Schemmerhofen (DE); Ulrike Tontsch-Grunt, Baden (AT); Jacobus C. A. Van Meel, Moedling (AT)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 590 days.

(21) Appl. No.: 10/656,863

(22) Filed: Sep. 5, 2003

(65) Prior Publication Data

US 2005/0054710 A1    Mar. 10, 2005

Related U.S. Application Data

(60) Provisional application No. 60/414,938, filed on Sep. 30, 2002, provisional application No. 60/430,790, filed on Dec. 4, 2002.

(30) Foreign Application Priority Data

Sep. 12, 2002  (DE) .............................. 102 42 350
Nov. 14, 2002  (DE) .............................. 102 52 969

(51) Int. Cl.
*A61K 31/403* (2006.01)
*C07D 209/34* (2006.01)

(52) U.S. Cl. .................. 514/414; 514/235.2; 514/249; 514/252.06; 514/323; 514/339; 514/338; 514/377; 514/383; 514/394; 514/217.08; 546/201; 546/277.7; 548/266.4; 548/454; 548/455; 548/468; 540/575; 544/144; 544/235; 544/238

(58) Field of Classification Search ............... 546/201, 546/277.7; 548/266.4, 454, 455, 468; 540/575; 544/144, 235, 238; 514/414
See application file for complete search history.

(56) References Cited

U.S. PATENT DOCUMENTS 6,762,180 B1 * 7/2004  Roth et al. ............... 514/228.2
6,858,641 B1 * 2/2005  Roth et al. ................ 514/415

FOREIGN PATENT DOCUMENTS

| WO | WO 01/16130 A1 | 3/2001 |
| WO | WO 01/27080 A2 | 4/2001 |
| WO | WO 01/27081 A1 | 4/2001 |

OTHER PUBLICATIONS

Kandile, N. G. et al. Revue Roumaine de Chimie 1991, 36(1-3), 245.*
Copy of International Search Report Reference #PCT/EP 03/09978.

* cited by examiner

*Primary Examiner*—Kamal A. Saeed
*Assistant Examiner*—Jason M. Nolan
(74) *Attorney, Agent, or Firm*—Michael P. Morris; Mary-Ellen M. Devlin; Alan R. Stempel

(57) ABSTRACT

The present invention relates to heterocyclically substituted indolinones of general formula

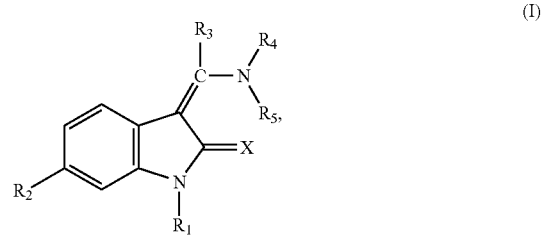

(I)

wherein
$R_1$ to $R_5$ and X are defined as in claim 1, the tautomers, the diastereomers, the enantiomers, the mixtures thereof, the prodrugs thereof and the salts thereof, particularly the physiologically acceptable salts thereof which have valuable pharmacological properties, in particular an inhibiting effect on various receptor tyrosine kinases and cyclin/CDK complexes and on the proliferation of endothelial cells and various tumour cells, pharmaceutical compositions containing these compounds, their use and processes for preparing them.

7 Claims, No Drawings

INDOLINONES SUBSTITUTED BY HETEROCYCLES, THE PREPARATION THEREOF AND THEIR USE AS MEDICAMENTS

RELATED APPLICATIONS

Benefit of U.S. Provisional Application Ser. No. 60/414,938, filed on Sep. 30, 2002 and U.S. Provisional Application Ser. No. 60/430,790, filed on Dec. 4, 2002 are hereby claimed.

FIELD OF THE INVENTION

The present invention relates to new heterocyclically substituted indolinones of general formula

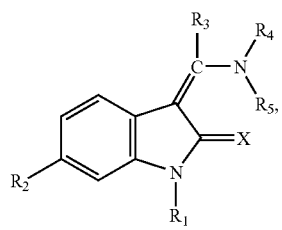

(I)

the tautomers, diastereomers, enantiomers and mixtures thereof, the prodrugs thereof and the salts thereof, particularly the physiologically acceptable salts thereof which have valuable properties.

The above compounds of general formula I have valuable pharmacological properties, in particular an inhibiting effect on various kinases, especially receptor tyrosine kinases such as VEGFR1, VEGFR2, VEGFR3, PDGFRα, PDGFRβ, FGFR1, FGFR3, EGFR, HER2, IGF1R and HGFR, as well as complexes of CDKs (Cyclin Dependent Kinases) such as CDK1, CDK2, CDK3, CDK4, CDK5, CDK6, CDK7, CDK8 and CDK9 with their specific cyclins (A, B1, B2, C, D1, D2, D3, E, F, G1, G2, H, I and K) and on viral cyclin (cf. L. Mengtao in J. Virology 71(3), 1984–1991 (1997)), and on the proliferation of cultivated human cells, in particular endothelial cells, e.g. in angiogenesis, but also on the proliferation of other cells, in particular tumour cells.

The present invention thus relates to the above compounds of general formula I which have valuable pharmacological properties, the pharmaceutical compositions containing the pharmacologically effective compounds, the use thereof and processes for the preparation thereof.

In the above general formula I

X denotes an oxygen or sulphur atom, $R_1$ denotes a hydrogen atom or a prodrug group such as a $C_{1-4}$-alkoxy-carbonyl or $C_{2-4}$-alkanoyl group, $R_2$ denotes a hydrogen, fluorine, chlorine or bromine atom, a cyano or nitro group, a carboxy group, a straight-chain or branched $C_{1-6}$-alkoxy-carbonyl group, a $C_{3-6}$-cycloalkoxy-carbonyl or an aryloxycarbonyl group, an allyloxy-carbonyl group optionally substituted by one or two methyl groups, a straight-chain or branched $C_{1-4}$-alkoxy-carbonyl group which is terminally substituted in the alkyl moiety by a phenyl, heteroaryl, carboxy, $C_{1-3}$-alkoxy-carbonyl, aminocarbonyl, $C_{1-3}$-alkylamino-carbonyl or di-($C_{1-3}$-alkyl)-aminocarbonyl group, a straight-chain or branched $C_{2-6}$-alkoxy-carbonyl group which is terminally substituted in the alkyl moiety by a chlorine atom or a hydroxy, $C_{1-3}$-alkoxy, amino, $C_{1-3}$-alkylamino or di-($C_{1-3}$-alkyl)-amino group, or an aminocarbonyl, $C_{1-4}$-alkyl-aminocarbonyl or a di-($C_{1-4}$-alkyl)-aminocarbonyl group, while the alkyl groups, if they have more than one carbon atom, may be terminally substituted by a hydroxy, $C_{1-3}$-alkoxy or di-($C_{1-3}$-alkyl)-amino group, $R_3$ denotes a five or six-membered heteroaryl group, where
the 6-membered heteroaryl group contains one, two or three nitrogen atoms and
the 5-membered heteroaryl group contains an imino group optionally substituted by a $C_{1-3}$-alkyl, carboxy-$C_{1-3}$-alkyl or phenyl-$C_{1-3}$-alkyl group, an oxygen or sulphur atom or
an imino group optionally substituted by a $C_{1-3}$-alkyl, carboxy-$C_{1-3}$-alkyl or phenyl-$C_{1-3}$-alkyl group or an oxygen or sulphur atom and additionally a nitrogen atom or
an imino group optionally substituted by a $C_{1-3}$-alkyl or phenyl-$C_{1-3}$-alkyl group, an oxygen atom or a sulphur atom and two nitrogen atoms,
and furthermore a phenyl ring may be fused to the abovementioned monocyclic heterocyclic groups via two adjacent carbon atoms, the hydrogen atom of a methyne group may be replaced by a $C_{1-3}$-alkyl, carboxy-$C_{1-3}$-alkyl, amino, $C_{1-3}$-alkyl-amino, di-($C_{1-3}$-alkyl)-amino, phenyl-$C_{1-3}$-alkyl-amino or di-(phenyl-$C_{1-3}$-alkyl)-amino group and the bond is made via a carbon atom of the heterocyclic moiety, a 5- to 6-membered cyclic oxime ether which is linked to the methylidene group via the carbon atom adjacent to the nitrogen atom, an imidazo[1,2-a]pyridin-6-yl or imidazo[1,2-a]pyridin-7-yl group or a bicyclic group consisting of
a phenyl ring which is linked to the methylidene group, and an —O—$CH_2$—$CH_2$—, —O—$CH_2$—O—, —O—$CF_2$—O—, —O—$CH_2$—$CH_2$—O—, —O—CH=CH—O—, —S—CH=N—, —NH—CH=N—, —N=C($C_{1-3}$-alkyl)-NH—, —N=C(carboxy-$C_{1-3}$-alkyl)-NH—, —N($C_{1-3}$-alkyl)-CH=N—, —N(carboxy-$C_{1-3}$-alkyl)-CH=N—, —N($C_{1-3}$-alkyl)-C($C_{1-3}$-alkyl)-N—, —N=CH—CH=N—, —N=CH—N=CH—, —N=CH—N=C($C_{1-3}$-alkyl)—, —N=CH—N=C(carboxy-$C_{1-3}$-alkyl)—, —N=CH—CH=CH—, —N=CH—CH=C($C_{1-3}$-alkyl)—, —N=CH—CH=C(carboxy-$C_{1-3}$-alkyl)—, —N=N—NH—, —N=N—N($C_{1-3}$-alkyl)—, —N=N—N(carboxy-$C_{1-3}$-alkyl)—, —CH=CH—NH—, —CH=CH—N($C_{1-3}$-alkyl)—, —CH=CH—N(carboxy-$C_{1-3}$-alkyl)—, —N=CH—C(O)—N($C_{1-3}$-alkyl)—, —O—$CH_2$—C(O)—N($C_{1-3}$-alkyl)—, —CH=N—N=CH, —O—C(O)—$CH_2$—N($C_{1-3}$-alkyl)—, —O—$CH_2$—C(O)—NH, —O—$CH_2$—$CH_2$—N($C_{1-3}$-alkyl)—, —O—C(O)—N($C_{1-3}$-alkyl)—, —O—C(O)—NH, —CO—NH—CO or —CO—N($C_{1-3}$-alkyl)-CO bridge, which is linked in each case to two adjacent carbon atoms of the phenyl ring, while the hydrogen atom of any carboxy group contained in $R_3$ may be replaced by a prodrug group, $R_4$ denotes a $C_{3-7}$-cycloalkyl group,
while the methylene group in the 4 position of a 6- or 7-membered cycloalkyl group may be substituted by an amino, $C_{1-3}$-alkylamino or di-($C_{1-3}$-alkyl)-amino group or may be replaced by an —NH or —N($C_{1-3}$-alkyl) group, or a phenyl group substituted by the group $R_6$ in the 3- or 4-position which may additionally be mono- or disubstituted by fluorine, chlorine, bromine or iodine atoms, by $C_{1-5}$-alkyl, trifluoromethyl, hydroxy, $C_{1-3}$-alkoxy, carboxy, $C_{1-3}$-alkoxycarbonyl, amino, acetylamino, $C_{1-3}$-alkyl-sulphonylamino, aminocarbonyl, $C_{1-3}$-alkyl-aminocarbonyl, di-($C_{1-3}$-alkyl)-aminocarbonyl, aminosulphonyl, $C_{1-3}$-alkyl-aminosulphonyl, di-($C_{1-3}$-alkyl)-aminosulphonyl, nitro or cyano groups, while the substituents may be identical or different and $R_6$ denotes a hydrogen, fluorine, chlorine, bromine or iodine atom,
a cyano, nitro, amino, $C_{1-5}$-alkyl, $C_{3-7}$-cycloalkyl, trifluoromethyl, phenyl or heteroaryl group,
a tetrazolyl group optionally substituted by a $C_{1-3}$-alkyl group,
a 2-pyrrolidon-1-yl group wherein the methylene group adjacent to the carbonyl group may be replaced by an oxygen atom or an —NH or —N($C_{1-3}$-alkyl) group,
the group of formula

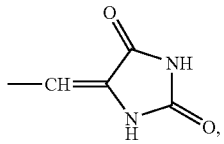

wherein the hydrogen atoms bound to a nitrogen atom may each be replaced independently of one another by a $C_{1-3}$-alkyl group,
a group of formula

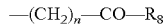

wherein
$R_8$ denotes a hydroxy or $C_{1-4}$-alkoxy group,
a 5- to 7-membered cycloalkyleneimino group,
while the methylene group in position 3 or 4 of a 5-, 6- or 7-membered cycloalkyleneimino group may be substituted by an amino, $C_{1-3}$-alkyl-amino or di-($C_{1-3}$-alkyl)-amino group
or the methylene group in the 4 position of a 6- or 7-membered cycloalkyleneimino group may be replaced by an oxygen atom, a sulphur atom, a sulphinyl or sulphonyl group, an —NH, —N(allyl) or —N($C_{1-3}$-alkyl) group
and in the abovementioned cyclic groups one or two hydrogen atoms may be replaced by a $C_{1-3}$-alkyl group,
a 2,5-dihydropyrrol-1-yl group or
a $C_{3-7}$-cycloalkyl group,
while the methylene group in position 3 or 4 of the 5-, 6- or 7-membered cycloalkyl moiety may be substituted by an amino, $C_{1-3}$-alkylamino or di-($C_{1-3}$-alkyl)-amino group or
the methylene group in the 4 position of the 6- or 7-membered cycloalkyl moiety may be replaced by an —NH, —N(allyl) or —N($C_{1-3}$-alkyl) group,
and n denotes one of the numbers 0, 1 or 2,
a group of formula

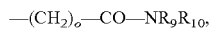

wherein
$R_9$ denotes a hydrogen atom,
an allyl group,
a $C_{1-4}$-alkyl group optionally substituted by a cyano, carboxy, phenyl or pyridyl group or a $C_{2-4}$-alkyl group terminally substituted by a hydroxy or $C_{1-3}$-alkoxy group,
$R_{10}$ denotes a hydrogen atom,
a $C_{1-3}$-alkyl group,
a $C_{2-3}$-alkyl group terminally substituted by a hydroxy, $C_{1-3}$-alkoxy, $C_{1-3}$-alkylamino or di-($C_{1-3}$-alkyl)-amino group or
a 3- to 7-membered cycloalkyl group,
wherein a methylene group may be replaced by an oxygen atom or an —NH or —N($C_{1-3}$-alkyl) group and independently thereof a methylene group may be replaced by a carbonyl group,
and o denotes one of the numbers 0, 1 or 2,
a $C_{1-3}$-alkyl group substituted by the group $R_7$, where
$R_7$ denotes a $C_{3-7}$-cycloalkyl group,
while one of the methylene groups may be substituted by an amino, $C_{1-3}$-alkylamino or di-($C_{1-3}$-alkyl)-amino group or
the methylene group in position 3 or 4 of a 5-, 6- or 7-membered cycloalkyl group may be replaced by an —NH, —N(allyl) or —N($C_{1-3}$-alkyl) group or
in a 5- to 7-membered cycloalkyl group a —$(CH_2)_2$— group may be replaced by a —CO—NH group, a —$(CH_2)_3$— group may be replaced by an —NH—CO—NH or —CO—NH—CO group or a —$(CH_2)_4$— group may be replaced by an —NH—CO—NH—CO group, while in each case a hydrogen atom bound to a nitrogen atom may be replaced by a $C_{1-3}$-alkyl group,
an aryl or heteroaryl group,
a triazolyl group,
a hydroxy or $C_{1-3}$-alkoxy group,
an amino, $C_{1-7}$-alkylamino, di-($C_{1-7}$-alkyl)-amino, N—($C_{1-7}$-alkyl)-allylamino, phenylamino, N-phenyl-$C_{1-3}$-alkyl-amino, phenyl-$C_{1-3}$-alkylamino, N—($C_{1-3}$-alkyl)-phenyl-$C_{1-3}$-alkylamino or di-(phenyl-$C_{1-3}$-alkyl)-amino group,
an allylamino group wherein one or two vinylic hydrogen atoms may each be replaced by a methyl group,
a ω-hydroxy-$C_{2-3}$-alkyl-amino, N—($C_{1-3}$-alkyl)-ω-hydroxy-$C_{2-3}$-alkyl-amino, di-(ω-hydroxy-$C_{2-3}$-alkyl)-amino, ω-($C_{1-3}$-alkoxy)-$C_{2-3}$-alkyl-amino-N-($C_{1-3}$-alkyl)-[ω-($C_{1-3}$-alkoxy)-$C_{2-3}$-alkyl]-amino, di-[ω-($C_{1-3}$-alkoxy)-$C_{2-3}$-alkyl]-amino or N-(dioxolan-2-yl)-$C_{1-3}$-alkyl-amino group,
a $C_{1-3}$-alkylcarbonylamino-$C_{2-3}$-alkyl-amino or $C_{1-3}$-alkylcarbonylamino-$C_{2-3}$-alkyl-N-($C_{1-3}$-alkyl)-amino group,
a pyridylamino group,
a $C_{1-3}$-alkylsulphonylamino, N—($C_{1-3}$-alkyl)-$C_{1-3}$-alkyl-sulphonylamino, $C_{1-3}$-alkyl-sulphonylamino-$C_{2-3}$-alkyl-amino or $C_{1-3}$-alkylsulphonylamino-$C_{2-3}$-alkyl-N—($C_{1-3}$-alkyl)-amino group,
a hydroxycarbonyl-$C_{1-3}$-alkylamino or N—($C_{1-3}$-alkyl)-hydroxycarbonyl-$C_{1-3}$-alkyl-amino group,
a guanidino group wherein one or two hydrogen atoms may each be replaced by a $C_{1-3}$-alkyl group,
a 2-pyrrolidon-1-yl group wherein the methylene group adjacent to the carbonyl group may be replaced by an oxygen atom or by an —NH or —N($C_{1-3}$-alkyl) group,
a group of formula

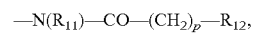

wherein
$R_{11}$ denotes a hydrogen atom or an allyl, $C_{1-3}$-alkyl, $C_{1-3}$alkyl-amino-$C_{2-3}$-alkyl or di-($C_{1-3}$-alkyl)-amino-$C_{2-3}$-alkyl group, p denotes one of the numbers 0, 1, 2 or 3 and $R_{12}$ denotes an amino, $C_{1-4}$-alkylamino, allylamino, di-allyl-amino, di-($C_{1-4}$-alkyl)-amino, phenylamino, N—($C_{1-4}$-alkyl)-phenylamino, benzylamino, N—($C_{1-4}$-alkyl)-benzylamino, $C_{1-4}$-alkoxy or 2,5-dihydropyrrol-1-yl group or a 4- to 7-membered cycloalkyleneimino group, while in each case the methylene group in the 4 position of a 6- or 7-membered cycloalkyleneimino group may be replaced by an oxygen or sulphur atom, by a sulphinyl, sulphonyl, —NH, —N($C_{1-3}$-alkyl), —N(allyl), —N(phenyl), —N($C_{1-3}$-alkyl-carbonyl) or —N(benzoyl) group, or, if n denotes one of the numbers 1, 2 or 3, it may also represent a hydrogen atom, a group of formula

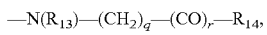
—N($R_{13}$)—(CH$_2$)$_q$—(CO)$_r$—$R_{14}$, wherein $R_{13}$ denotes a hydrogen atom or a $C_{1-3}$-alkyl, allyl, $C_{1-3}$-alkyl-carbonyl, arylcarbonyl, pyridylcarbonyl, phenyl-$C_{1-3}$-alkyl-carbonyl, $C_{1-3}$-alkylsulphonyl, arylsulphonyl or phenyl-$C_{1-3}$-alkylsulphonyl group, q denotes one of the numbers 1, 2, 3 or 4, r denotes the number 1 or, if q denotes one of the numbers 2, 3 or 4, r may also denote the number 0 and $R_{14}$ denotes a hydroxy, amino, $C_{1-4}$-alkylamino, di-($C_{1-4}$-alkyl)-amino, phenylamino, N—($C_{1-4}$-alkyl)-phenylamino, benzylamino, N—($C_{1-4}$-alkyl)-benzylamino, $C_{1-4}$-alkoxy or $C_{1-3}$-alkoxy-$C_{1-3}$-alkoxy group, a di-($C_{1-4}$-alkyl)-amino-$C_{1-3}$-alkylamino group optionally substituted in the 1 position by a $C_{1-3}$-alkyl group or a 4- to 7-membered cycloalkyleneimino group, while the cycloalkylene moiety may be fused to a phenyl ring or in each case the methylene group in the 4 position of a 6- or 7-membered cycloalkyleneimino group may be replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl) group, a $C_{4-7}$-cycloalkylamino, $C_{4-7}$-cycloalkyl-$C_{1-3}$-alkylamino or $C_{4-7}$-cycloalkenylamino group wherein position 1 of the ring is not involved in the double bond and the abovementioned groups may each additionally be substituted at the amino-nitrogen atom by a $C_{5-7}$-cycloalkyl, $C_{2-4}$-alkenyl or $C_{1-4}$-alkyl group, a 2,5-dihydro-pyrrol-1-yl group or a 4- to 7-membered cycloalkyleneimino group wherein the cycloalkylene moiety may be fused to a phenyl group or to an oxazolo, imidazolo, thiazolo, pyridino, pyrazino or pyrimidino group optionally substituted by a fluorine, chlorine, bromine or iodine atom, by a nitro, $C_{1-3}$-alkyl, $C_{1-3}$-alkoxy or amino group and/or one or two hydrogen atoms may each be replaced by a $C_{1-3}$-alkyl, $C_{3-7}$-cyclo-alkyl, hydroxy, $C_{1-3}$-alkoxy, hydroxy-$C_{1-3}$-alkyl, $C_{1-3}$-alkoxy-$C_{1-3}$-alkyl or phenyl group and/or the methylene group in position 3 of a 5-membered cycloalkyleneimino group may be substituted by a hydroxy, hydroxy-$C_{1-3}$-alkyl, $C_{1-3}$-alkoxy or $C_{1-3}$-alkoxy-$C_{1-3}$-alkyl group, in each case the methylene group in position 3 or 4 of a 6- or 7-membered cycloalkyleneimino group may be substituted by a hydroxy, hydroxy-$C_{1-3}$-alkyl, $C_{1-3}$-alkoxy, $C_{1-3}$-alkoxy-$C_{1-3}$-alkyl, carboxy, $C_{1-4}$-alkoxycarbonyl, aminocarbonyl, $C_{1-3}$-alkylaminocarbonyl, di-($C_{1-3}$-alkyl)-aminocarbonyl, di-($C_{1-3}$-alkyl)-amino, phenyl-$C_{1-3}$-alkylamino or N—($C_{1-3}$-alkyl)-phenyl-$C_{1-3}$-alkylamino group or the methylene group in the 4 position of a 6- or 7-membered cycloalkyleneimino group may be replaced by an oxygen or sulphur atom, by a sulphinyl, sulphonyl, —NH, —N($C_{1-3}$-alkyl), —N(allyl), —N(phenyl), —N(phenyl-$C_{1-3}$-alkyl), —N($C_{1-3}$-alkyl-carbonyl), —N($C_{1-4}$-hydroxy-carbonyl), —N($C_{1-4}$-alkoxy-carbonyl), —N(benzoyl) or —N(phenyl-$C_{1-3}$-alkyl-carbonyl) group, while a methylene group linked to an imino-nitrogen atom of the cycloalkyleneimino group may be replaced by a carbonyl or sulphonyl group or in a 5- to 7-membered monocyclic cycloalkyleneimino group or a cycloalkyleneimino group fused to a phenyl group the two methylene groups linked to the imino-nitrogen atom may each be replaced by a carbonyl group, or $R_6$ denotes a group of formula

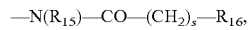
—N($R_{15}$)—CO—(CH$_2$)$_s$—$R_{16}$, wherein $R_{15}$ denotes a hydrogen atom, an allyl, $C_{1-6}$-alkyl, $C_{3-7}$-cycloalkyl or pyridinyl group, a $C_{1-3}$-alkyl group terminally substituted by a phenyl, heteroaryl, trifluoromethyl, aminocarbonyl, $C_{1-4}$-alkylamino-carbonyl, di-($C_{1-4}$-alkyl)-amino-carbonyl, $C_{1-3}$-alkyl-carbonyl, $C_{1-3}$-alkyl-aminosulphonyl or di-($C_{1-3}$-alkyl)-aminosulphonyl group or a $C_{2-3}$-alkyl group terminally substituted by a hydroxy, $C_{1-3}$-alkoxy, amino, $C_{1-3}$-alkylamino, allylamino, di-($C_{1-3}$-alkyl)-amino, $C_{1-3}$-alkyl-sulphonylamino or N—($C_{1-3}$-alkyl)-$C_{1-3}$-alkyl-sulphonylamino group and s denotes one of the numbers 0, 1, 2 or 3 and $R_{16}$ takes on the meanings of the abovementioned group $R_7$ or denotes a carboxy group or, if s denotes one of the numbers 1, 2 or 3, $R_{16}$ also denotes a hydrogen atom, a group of formula

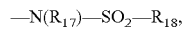
—N($R_{17}$)—SO$_2$—$R_{18}$, wherein $R_{17}$ denotes a hydrogen atom, an allyl, $C_{1-4}$-alkyl or cyanomethyl group or a $C_{2-4}$-alkyl group terminally substituted by a cyano, amino, $C_{1-3}$-alkylamino, di-($C_{1-3}$-alkyl)-amino, trifluoromethyl-carbonyl-amino or N—($C_{1-3}$-alkyl)-trifluoromethyl-carbonyl-amino group and $R_{18}$ denotes a $C_{1-4}$-alkyl, phenyl or pyridyl group, an amino group substituted by a di-($C_{1-3}$-alkyl)-amino-$C_{1-3}$-alkyl-carbonyl or di-($C_{1-3}$-alkyl)-amino-$C_{1-3}$-alkyl-sulphonyl group and a di-($C_{1-3}$-alkyl)-aminocarbonyl-$C_{1-3}$-alkyl group, or a group of formula

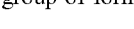
-A-(CH$_2$)$_t$—$R_{19}$, wherein

A denotes an oxygen or sulphur atom or a sulphinyl or sulphonyl group, $R_{19}$ denotes a hydrogen atom, a hydroxy, $C_{1-3}$-alkoxy, aryl, heteroaryl, amino, $C_{1-4}$-alkylamino or di-($C_{1-3}$-alkyl)-amino group or a 4- to 7-membered cycloalkyleneimino group,
while the methylene group in position 3 of a 5-membered cycloalkyleneimino group may be substituted by a hydroxy, hydroxy-$C_{1-3}$-alkyl, $C_{1-3}$-alkoxy-$C_{1-3}$-alkyl group,
in each case the methylene group in position 3 or 4 of a 6- or 7-membered cycloalkyleneimino group may be substituted by a hydroxy, hydroxy-$C_{1-3}$-alkyl, $C_{1-3}$-alkoxy, $C_{1-3}$-alkoxy-$C_{1-3}$-alkyl, carboxy, $C_{1-4}$-alkoxycarbonyl, aminocarbonyl, $C_{1-3}$-alkylaminocarbonyl or di-($C_{1-3}$-alkyl)-aminocarbonyl group or
may be replaced by an oxygen or sulphur atom, by a sulphinyl, sulphonyl, —NH or —N($C_{1-3}$-alkyl-) group, and t denotes one of the numbers 2 or 3 or,
if $R_{19}$ denotes a hydrogen atom, an aryl or heteroaryl group, it may also denote the number 1 or,
if A denotes a sulphonyl group, it may also denote the number 0,
or a group of formula

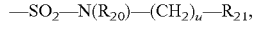
—SO$_2$—N($R_{20}$)—(CH$_2$)$_u$—$R_{21}$, wherein
$R_{20}$ denotes a hydrogen atom, an allyl or $C_{1-3}$-alkyl group,
$R_{21}$ denotes a hydrogen atom, a hydroxy, $C_{1-3}$-alkoxy, amino, $C_{1-3}$-alkylamino or a di-($C_{1-3}$-alkyl)-amino group and
u denotes one of the numbers 2, 3 or 4 or,
if $R_{21}$ denotes a hydrogen atom, it may also denote the number 1,
while all the single-bonded or fused-on phenyl groups contained in the groups mentioned under $R_6$ may be mono- or disubstituted by fluorine, chlorine, bromine or iodine atoms, by $C_{1-5}$-alkyl, trifluoromethyl, hydroxy, $C_{1-3}$-alkoxy, carboxy, $C_{1-3}$-alkoxy-carbonyl, aminocarbonyl, $C_{1-4}$-alkylamino-carbonyl, di-($C_{1-4}$-alkyl)-amino-carbonyl, aminosulphonyl, $C_{1-3}$-alkyl-aminosulphonyl, di-($C_{1-3}$-alkyl)-aminosulphonyl, $C_{1-3}$-alkyl-sulphonylamino, nitro or cyano groups, while the substituents may be identical or different, or two adjacent hydrogen atoms of the phenyl groups may be replaced by a methylenedioxy group,
or $R_4$ denotes a group of formula

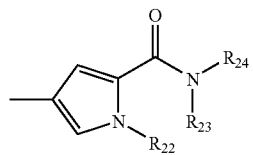

wherein
$R_{22}$ denotes a $C_{1-3}$-alkyl group,
$R_{23}$ denotes a hydrogen atom,
an allyl group,
a $C_{1-4}$-alkyl group optionally substituted by a cyano, carboxy, phenyl or pyridyl group or
a $C_{2-4}$-alkyl group terminally substituted by a hydroxy or $C_{1-3}$-alkoxy group and
$R_{24}$ denotes a hydrogen atom, a $C_{1-3}$-alkyl group,
a $C_{2-3}$-alkyl group terminally substituted by a hydroxy, $C_{1-3}$-alkoxy, $C_{1-3}$-alkylamino or di-($C_{1-3}$-alkyl)-amino group,
or a 3–7-membered cycloalkyl group,
while a methylene group may be replaced by an oxygen atom or by a —NH or —N($C_{1-3}$-alkyl) group and independently thereof a methylene group may be replaced by a carbonyl group,
or $R_{23}$ and $R_{24}$ together with the nitrogen atom to which they are linked form
a 2,5-dihydro-pyrrol-1-yl group or
a 5- to 7-membered cycloalkyleneimino group,
while the methylene group in the 4 position of a 6- or 7-membered cycloalkyleneimino group may be substituted by an amino, $C_{1-3}$-alkylamino or di-($C_{1-3}$-alkyl)-amino group or may be replaced by an oxygen atom, a sulphur atom, a sulphinyl or sulphonyl group or an —NH or —N($C_{1-3}$-alkyl) group
and one or two hydrogen atoms in the 5- to 7-membered cycloalkyleneimino group may be replaced by a $C_{1-3}$-alkyl group, and
$R_5$ denotes a hydrogen atom or a $C_{1-3}$-alkyl group,
while by the term aryl group is meant a phenyl or naphthyl group optionally mono- or disubstituted by a fluorine, chlorine, bromine or iodine atom, by a cyano, trifluoromethyl, nitro, carboxy, aminocarbonyl, $C_{1-3}$-alkyl or $C_{1-3}$-alkoxy group and
by the term heteroaryl group is meant, unless otherwise stated, a monocyclic 5- or 6-membered heteroaryl group optionally substituted in the carbon skeleton by one or two $C_{1-3}$-alkyl groups, wherein
the 6-membered heteroaryl group contains one, two or three nitrogen atoms and
the 5-membered heteroaryl group contains an imino group optionally substituted by a $C_{1-3}$-alkyl or phenyl-$C_{1-3}$-alkyl group, an oxygen or sulphur atom or
an imino group optionally substituted by a $C_{1-3}$-alkyl or phenyl-$C_{1-3}$-alkyl group or an oxygen or sulphur atom and additionally a nitrogen atom or
an imino group optionally substituted by a $C_{1-3}$-alkyl or phenyl-$C_{1-3}$-alkyl group and two nitrogen atoms,
and moreover a phenyl ring may be fused to the abovementioned monocyclic heterocyclic groups via two adjacent carbon atoms, the hydrogen atom of one or two methyne groups may be replaced by a $C_{1-3}$-alkyl, amino, $C_{1-3}$-alkyl-amino or di-($C_{1-3}$-alkyl)-amino group and the bond is via a nitrogen atom or via a carbon atom of the heterocyclic moiety or of a fused phenyl ring,
the hydrogen atoms in the abovementioned alkyl and alkoxy groups or in the alkyl moieties contained in the above-defined groups of formula I may be wholly or partly replaced by fluorine atoms,
the saturated alkyl and alkoxy moieties containing more than 2 carbon atoms present in the groups defined above, also include the branched isomers thereof such as for example the isopropyl, tert butyl, isobutyl group, unless otherwise stated, and
wherein additionally the hydrogen atom of any carboxy group present or a hydrogen atom bound to a nitrogen atom, for example an amino, alkylamino or imino group or a saturated N-heterocycle such as the piperidinyl group, may each be replaced by a group which can be cleaved in vivo.

By a group which can be cleaved in vivo from an imino or amino group is meant, for example, a hydroxy group, an acyl group such as the benzoyl or pyridinoyl group or a $C_{1-6}$-alkanoyl group such as the formyl, acetyl, propionyl, butanoyl, pentanoyl or hexanoyl group, an allyloxycarbonyl group, a $C_{1-16}$-alkoxycarbonyl group such as the methoxycarbonyl, ethoxycarbonyl, propoxycarbonyl, isopropoxycarbonyl, butoxycarbonyl, tert.butoxycarbonyl, pentoxycarbonyl, hexyloxycarbonyl, octyloxycarbonyl, nonyloxycarbonyl, decyloxycarbonyl, undecyloxycarbonyl, dodecyloxycarbonyl or hexadecyloxycarbonyl group, a phenyl-$C_{1-6}$-alkoxycarbonyl group such as the benzyloxycarbonyl, phenylethoxycarbonyl or phenylpropoxycarbonyl groups, a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl or $R_e$CO—O—($R_f$C$R_g$)—O—CO group wherein $R_e$ denotes a $C_{1-8}$-alkyl, $C_{5-7}$-cycloalkyl, phenyl or phenyl-$C_{1-3}$-alkyl group, $R_f$ denotes a hydrogen atom, a $C_{1-3}$-alkyl, $C_{5-7}$-cycloalkyl or phenyl group and $R_g$ denotes a hydrogen atom or a $C_{1-3}$-alkyl group, wherein additionally the amino group may be a phthalimido group, while the ester groups mentioned above may also be used as a group which can be converted in vivo into a carboxy group.

Preferred prodrug groups which may replace the hydrogen atom of a carboxy group include a $C_{1-6}$-alkyl group such as the methyl, ethyl, n-propyl, isopropyl, n-butyl, n-pentyl, n-hexyl or cyclohexyl group or phenyl-$C_{1-3}$-alkyl group such as the benzyl group.

Preferred compounds of general formula I are those wherein

X denotes an oxygen atom, $R_1$ denotes a hydrogen atom or a prodrug group such as a $C_{1-4}$-alkoxy-carbonyl or $C_{2-4}$-alkanoyl group, $R_2$ denotes a hydrogen, fluorine, chlorine or bromine atom, a cyano or nitro group, a carboxy group, a straight-chain or branched $C_{1-4}$-alkoxycarbonyl group or a $C_{3-4}$-cycloalkoxy-carbonyl group, an allyloxycarbonyl group optionally substituted by one or two methyl groups, a straight-chain or branched $C_{2-3}$-alkoxy-carbonyl group which is terminally substituted in the alkyl moiety by a hydroxy or $C_{1-3}$-alkoxy group, or an aminocarbonyl, $C_{1-4}$-alkyl-aminocarbonyl or a di-($C_{1-3}$-alkyl)-aminocarbonyl group, while the alkyl groups, if they have more than one carbon atom, may be terminally substituted by a $C_{1-3}$-alkoxy group, $R_3$ denotes a 2-pyrrolyl, 3-pyrrolyl, 1-($C_{1-3}$-alkyl)-3-pyrrolyl-, 1-(carboxy-$C_{1-3}$-alkyl)-3-pyrrolyl, 2-furyl, 3-furyl, 2-thienyl, 3-thienyl, 2-(carboxy-$C_{1-3}$-alkyl)-thien-5-yl, 2-(carboxy-$C_{1-3}$-alkyl)-thien-4-yl, 3-(carboxy-$C_{1-3}$-alkyl)-thien-5-yl, 4-imidazolyl, 1-($C_{1-3}$-alkyl)-5-imidazolyl, 1-($C_{1-3}$-alkyl)-4-imidazolyl, 1-benzyl-5-imidazolyl, 5-($C_{1-3}$-alkyl)-isoxazol-3-yl, 3-pyridyl, 4-pyridyl, 2-(carboxy-$C_{1-3}$-alkyl)-pyridin-5-yl, 3-(carboxy-$C_{1-3}$-alkyl)-pyridin-5-yl, 2-(carboxy-$C_{1-3}$-alkyl)-pyridin-4-yl, 2-pyrazinyl, 4-pyridazinyl group or a pyrazol-3-yl group, in which independently of one another the 1- and/or 5-position may be substituted in each case by a $C_{1-3}$-alkyl or carboxy-$C_{1-3}$-alkyl group, a 5- to 6-membered cyclic oxime ether which is linked to the methylidene group via the carbon atom adjacent to the nitrogen atom, an imidazo[1,2-a]pyridin-6-yl or imidazo[1,2-a]pyridin-7-yl group or a bicyclic group consisting of a phenyl ring which is linked to the methylidene group, and an —O—CH$_2$—CH$_2$, —O—CH$_2$—O, —O—CF$_2$—O, —O—CH$_2$—CH$_2$—O, —O—CH=CH—O, —S—CH=N, —NH—CH=N, —N=C($C_{1-3}$-alkyl)-NH, —N=C(carboxy-$C_{1-3}$-alkyl)-NH, —N($C_{1-3}$-alkyl)-CH=N, —N(carboxy-$C_{1-3}$-alkyl)-CH=N, —N($C_{1-3}$-alkyl)-C($C_{1-3}$-alkyl)-N—, N=CH—CH=N, —N=CH—N=CH, —N=CH—N=C($C_{1-3}$-alkyl), —N=CH—CH=CH—, —N=CH—CH=C($C_{1-3}$-alkyl), —CH=N—N=CH, —CH=CH—NH, —CH=CH—N($C_{1-3}$-alkyl), —N=N—NH, —N=N—N($C_{1-3}$-alkyl), —O—CH$_2$—C(O)—N($C_{1-3}$-alkyl), —O—C(O)—CH$_2$—N($C_{1-3}$-alkyl), —O—C(O)—N($C_{1-3}$-alkyl), —O—C(O)—NH, —O—CH$_2$—CH$_2$—N($C_{1-3}$-alkyl), or —CO—N($C_{1-3}$-alkyl)-CO bridge, which is linked in each case to two adjacent carbon atoms of the phenyl ring, while the hydrogen atom of a carboxy group optionally contained in $R_3$ may be replaced by a prodrug group, $R_4$ denotes a phenyl group substituted in the 3- or 4-position by the group $R_6$ which may additionally be substituted in a remaining 3, 4 or 5 position by a fluorine, chlorine, bromine or iodine atom or by a $C_{1-3}$-alkyl, trifluoromethyl, hydroxy, $C_{1-3}$-alkoxy, amino, nitro or cyano group, while $R_6$ denotes a hydrogen, fluorine, chlorine, bromine or iodine atom, a tetrazolyl group optionally substituted by a $C_{1-3}$-alkyl group, an imidazolyl group substituted at the imino-nitrogen and/or at a carbon atom by a $C_{1-3}$-alkyl group, a pyrazolyl group substituted at the imino-nitrogen and/or at one or two carbon atoms in each case independently of one another by a $C_{1-3}$-alkyl group, a 2-pyrrolidon-1-yl group wherein the methylene group adjacent to the carbonyl group may be replaced by an oxygen atom or an —NH or —N($C_{1-3}$-alkyl) group, a group of formula

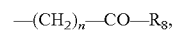
—(CH$_2$)$_n$—CO—R$_8$, wherein $R_8$ denotes a hydroxy group, a 2,5-dihydropyrrol-1-yl group or a 5- to 7-membered cycloalkyleneimino group, while the methylene group in the 3 or 4 position of a 5-, 6- or 7-membered cycloalkyleneimino group may be substituted by an amino, $C_{1-3}$-alkyl-amino or di-($C_{1-3}$-alkyl)-amino group or the methylene group in the 4 position of a 6- or 7-membered cycloalkyleneimino group may be replaced by an oxygen atom, a sulphur atom, a sulphinyl or sulphonyl group, an —NH or —N($C_{1-3}$-alkyl) group and in the abovementioned cyclic groups one or two hydrogen atoms may be replaced by a $C_{1-3}$-alkyl group, and n denotes one of the numbers 0 or 1, a group of formula

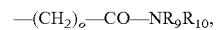
—(CH$_2$)$_o$—CO—NR$_9$R$_{10}$, wherein $R_9$ denotes a hydrogen atom, an allyl group, a C$_{1-4}$-alkyl group optionally substituted by a cyano or carboxy group or a C$_{2-4}$-alkyl group terminally substituted by a hydroxy or C$_{1-3}$-alkoxy group, R$_{10}$ denotes a hydrogen atom, a C$_{1-3}$-alkyl group, a C$_{2-3}$-alkyl group terminally substituted by a hydroxy, C$_{1-3}$-alkoxy, C$_{1-3}$-alkylamino or di-(C$_{1-3}$-alkyl)-amino group or a 3- to 7-membered cycloalkyl group,
wherein a methylene group may be replaced by an oxygen atom or an —NH or —N(C$_{1-3}$-alkyl) group, and o denotes one of the numbers 0 or 1, a C$_{1-2}$-alkyl group substituted by the group R$_7$, where R$_7$ denotes a C$_{3-7}$-cycloalkyl group,
while the methylene group in the 4 position of a 6- or 7-membered cycloalkyl group may be replaced by an —NH or —N(C$_{1-3}$-alkyl) group or a pyridyl or imidazolyl group optionally substituted by a C$_{1-3}$-alkyl group, a triazolyl group, a hydroxy or C$_{1-3}$-alkoxy group, an amino, C$_{1-4}$-alkylamino, di-(C$_{1-3}$-alkyl)-amino, N—(C$_{1-3}$-alkyl)-allylamino, phenyl-C$_{1-2}$-alkylamino or N—(C$_{1-3}$-alkyl)-phenyl-C$_{1-2}$-alkylamino group, an allylamino group wherein one or two vinylic hydrogen atoms may each be replaced by a methyl group, a ω-hydroxy-C$_{2-3}$-alkyl-amino, N—(C$_{1-3}$-alkyl)-ω-hydroxy-C$_{2-3}$-alkyl-amino, di-(ω-hydroxy-C$_{2-3}$-alkyl)-amino, ω-(C$_{1-3}$-alkoxy)-C$_{2-3}$-alkyl-amino-N—(C$_{1-3}$-alkyl)-[ω-(C$_{1-3}$-alkoxy)-C$_{2-3}$-alkyl]-amino or di-[ω-(C$_{1-3}$-alkoxy)-C$_{2-3}$-alkyl]-amino group, a pyridylamino group, an N—(C$_{1-3}$-alkyl)-C$_{1-3}$-alkylsulphonylamino group, a hydroxycarbonyl-C$_{1-3}$-alkylamino or N—(C$_{1-3}$-alkyl)-hydroxycarbonyl-C$_{1-3}$-alkyl-amino group, a 2-pyrrolidon-1-yl group wherein the methylene group adjacent to the carbonyl group may be replaced by an oxygen atom or an —NH or —N(C$_{1-3}$-alkyl) group, a group of formula

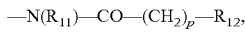
—N(R$_{11}$)—CO—(CH$_2$)$_p$—R$_{12}$, wherein

R$_{11}$ denotes a hydrogen atom or an allyl, C$_{1-3}$-alkyl group, C$_{1-3}$-alkyl-amino-C$_{2-3}$-alkyl or di-(C$_{1-3}$-alkyl)-amino-C$_{2-3}$-alkyl group, p denotes one of the numbers 0, 1 or 2 and R$_{12}$ denotes an amino, C$_{1-3}$-alkylamino, allylamino, di-(C$_{1-2}$-alkyl)-amino, C$_{1-3}$-alkoxy or 2,5-dihydro-pyrrol-1-yl group or a 4- to 7-membered cycloalkyleneimino group,
while in each case the methylene group in the 4 position of a 6- or 7-membered cycloalkyleneimino group may be replaced by an oxygen or sulphur atom or by an —NH, —N(allyl) or —N(C$_{1-3}$-alkyl) group, or, if n denotes one of the numbers 1 or 2, it may also represent a hydrogen atom, a group of formula

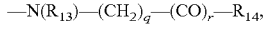
—N(R$_{13}$)—(CH$_2$)$_q$—(CO)$_r$—R$_{14}$, wherein

R$_{13}$ denotes a hydrogen atom or a C$_{1-3}$-alkyl or pyridyl-carbonyl group, q denotes one of the numbers 1 or 2, r denotes the number 1 or, if q is the number 2, it may also denote the number 0 and R$_{14}$ denotes a hydroxy, amino, C$_{1-3}$-alkylamino, di-(C$_{1-3}$-alkyl)-amino, C$_{1-3}$-alkoxy group or a 4- to 7-membered cycloalkyleneimino group,
while in each case the methylene group in the 4 position of a 6- or 7-membered cycloalkyleneimino group may be replaced by an oxygen or sulphur atom, by an —NH or —N(C$_{1-3}$-alkyl) group, a C$_{4-7}$-cycloalkylamino, C$_{3-5}$-cycloalkyl-C$_{1-2}$-alkylamino or C$_{4-7}$-cycloalkenylamino group wherein position 1 of the ring is not involved in the double bond and the abovementioned groups may each additionally be substituted at the amino-nitrogen atom by a C$_{2-4}$-alkenyl or C$_{1-3}$-alkyl group, a 2,5-dihydro-pyrrol-1-yl group or a 4- to 7-membered cycloalkyleneimino group wherein
one or two hydrogen atoms may each be replaced by a C$_{1-3}$-alkyl, hydroxy, C$_{1-3}$-alkoxy, hydroxy-C$_{1-3}$-alkyl or C$_{1-3}$-alkoxy-C$_{1-3}$-alkyl group and/or in each case the methylene group in the 3 or 4 position of a 6- or 7-membered cycloalkyleneimino group may be substituted by a carboxy, aminocarbonyl, C$_{1-3}$-alkylaminocarbonyl or di-(C$_{1-3}$-alkyl)-aminocarbonyl group or the methylene group in the 4 position of a 6- or 7-membered cycloalkyleneimino group may be replaced by an oxygen or sulphur atom, by a sulphinyl, sulphonyl, —NH, —N(C$_{1-3}$-alkyl-), —N(allyl) or —N(C$_{1-3}$-alkyl-carbonyl) group, while a methylene group linked to an imino-nitrogen atom of the cycloalkyleneimino group may be replaced by a carbonyl or sulphonyl group, or R$_6$ denotes a group of formula

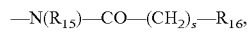
—N(R$_{15}$)—CO—(CH$_2$)$_s$—R$_{16}$, wherein

R$_{15}$ denotes a hydrogen atom, an allyl, C$_{1-4}$-alkyl, C$_{3-5}$-cycloalkyl or pyridinyl group, a C$_{1-3}$-alkyl group terminally substituted by a pyridyl, trifluoromethyl or di-(C$_{1-2}$-alkyl)-amino-carbonyl group or a C$_{2-3}$-alkyl group terminally substituted by a hydroxy, C$_{1-3}$-alkoxy, amino, C$_{1-3}$-alkylamino or di-(C$_{1-3}$-alkyl)-amino group and s denotes one of the numbers 0, 1, 2 or 3 and R$_{16}$ denotes a hydroxy, C$_{1-3}$-alkoxy, carboxy, amino, C$_{1-3}$-alkylamino, di-(C$_{1-3}$-alkyl)-amino, 2,5-dihydro-pyrrol-1-yl or pyridinyl group or a 5- to 7-membered cycloalkyleneimino group, while the methylene group in position 3 of a 5-membered cycloalkyleneimino group may be substituted by a hydroxy, hydroxy-C$_{1-3}$-alkyl or C$_{1-3}$-alkoxy-C$_{1-3}$-alkyl group, in each case the methylene group in the 3 or 4 position of a 6- or 7-membered cycloalkyleneimino group may be substituted by a di-(C$_{1-3}$-alkyl)-amino, hydroxy, hydroxy-C$_{1-3}$-alkyl, C$_{1-3}$-alkoxy or C$_{1-3}$-alkoxy-C$_{1-3}$-alkyl group or the methylene group in the 4 position of a 6- or 7-membered cycloalkyleneimino group may be replaced by an oxygen or sulphur atom or by an —NH or —N(C$_{1-3}$-alkyl-) group, or, if s denotes one of the numbers 1, 2 or 3, it may also denote a hydrogen atom, a group of formula

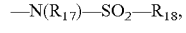
—N(R$_{17}$)—SO$_2$—R$_{18}$, wherein
R$_{17}$ denotes a hydrogen atom,
a C$_{1-3}$-alkyl or cyanomethyl group or
a C$_{2-3}$-alkyl group terminally substituted by a cyano, amino, C$_{1-3}$-alkylamino or di-(C$_{1-3}$-alkyl)-amino group and
R$_{18}$ denotes a C$_{1-4}$-alkyl or pyridyl group,
or a group of formula -A-(CH$_2$)$_t$—R$_{19}$, wherein
A denotes an oxygen or sulphur atom or a sulphinyl or sulphonyl group,
R$_{19}$ denotes a hydrogen atom or a hydroxy, C$_{1-3}$-alkoxy, amino, C$_{1-4}$-alkylamino or di-(C$_{1-3}$-alkyl)-amino group or a 4- to 7-membered cycloalkyleneimino group,
while in each case the methylene group in the 3 or 4 position of a 6- or 7-membered may be replaced by an oxygen or sulphur atom, by an —NH or —N (C$_{1-3}$-alkyl-) group,
and t denotes one of the numbers 2 or 3
or, if R$_{19}$ is a hydrogen atom, it may also denote the number 1,
or a group of formula —SO$_2$—N(R$_{20}$)—(CH$_2$)$_u$—R$_{21}$, wherein
R$_{20}$ denotes a hydrogen atom or an allyl or C$_{1-3}$-alkyl group,
R$_{21}$ denotes a hydrogen atom, a hydroxy, C$_{1-3}$-alkoxy, amino, C$_{1-3}$-alkylamino or a di-(C$_{1-3}$-alkyl)-amino group and
u denotes one of the numbers 2, 3 or 4
or, if R$_{21}$ is a hydrogen atom, it may also denote the number 1,
or R$_4$ denotes a group of formula

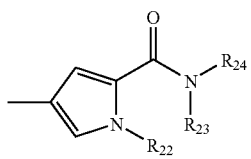

wherein
R$_{22}$ denotes a methyl group,
R$_{23}$ denotes a hydrogen atom or an allyl or C$_{1-3}$-alkyl group and
R$_{24}$ denotes a hydrogen atom, a C$_{1-3}$-alkyl group or
a C$_{2-3}$-alkyl group terminally substituted by a hydroxy, C$_{1-3}$-alkoxy, C$_{1-3}$-alkylamino group or by a di-(C$_{1-3}$-alkyl)-amino group,
or R$_{23}$ and R$_{24}$ together with the nitrogen atom to which they are linked form
a 2,5-dihydro-pyrrol-1-yl group or
a 5- to 7-membered cycloalkyleneimino group,
while the methylene group in the 4 position of a 6- or 7-membered cycloalkyleneimino group may be substituted by an amino, C$_{1-3}$-alkylamino or di-(C$_{1-3}$-alkyl)-amino group or may be replaced by an oxygen atom, an —NH or —N(C$_{1-3}$-alkyl) group,
and
R$_5$ denotes a hydrogen atom,
while the hydrogen atoms in the abovementioned alkyl and alkoxy groups or in the alkyl moieties contained in the above-defined groups of formula I may be wholly or partially replaced by fluorine atoms,
the saturated alkyl and alkoxy moieties containing more than 2 carbon atoms present in the groups defined above, also include the branched isomers thereof, such as for example the isopropyl, tert.butyl, isobutyl group, unless otherwise stated.

Particularly preferred compounds of general formula I are those wherein
X denotes an oxygen atom,
R$_1$ and R$_5$ in each case denote a hydrogen atom,
R$_2$ denotes a hydrogen, fluorine, chlorine or bromine atom, a cyano group or
a carboxy-C$_{1-2}$-alkoxycarbonyl, allyloxycarbonyl, C$_{1-3}$-alkylaminocarbonyl or di-(C$_{1-2}$-alkyl)-aminocarbonyl group
R$_3$ denotes a 2-pyrrolyl, 2-furyl, 3-furyl, 2-thienyl, 3-thienyl, 2-(carboxy-C$_{1-3}$-alkyl)-thien-5-yl, 2-(carboxy-C$_{1-3}$-alkyl)-thien-4-yl, 3-(carboxy-C$_{1-3}$-alkyl)-thien-5-yl, 4-imidazolyl, 5-(C$_{1-3}$-alkyl)-pyrazol-3-yl, 5-(C$_{1-3}$-alkyl)-isoxazol-3-yl, 3-pyridyl, 4-pyridyl, 2-pyrazinyl, 4-pyridazinyl, benzimidazol-5-yl, 1-(C$_{1-3}$-alkyl)-benzimidazol-5-yl, 2-(C$_{1-3}$-alkyl)-benzimidazol-5-yl, 2,3-dihydro-benzofuran-5-yl, 2,3-dihydro-benzofuran-6-yl, 3,4-methylenedioxy-1-phenyl, 3,4-ethylenedioxy-1-phenyl, 3,4-(difluoromethylenedioxy)-1-phenyl, 2-(C$_{1-3}$-alkyl)-isoindol-1,3-dion-5-yl, quinoxalin-6-yl or 1-(C$_{1-3}$-alkyl)-benzotriazol-5-yl group,
R$_4$ denotes a phenyl group substituted in the 3 or 4 position by the group R$_6$ which may additionally be substituted in the remaining 3 or 4 position by a fluorine or chlorine atom or by a (C$_{1-3}$)-alkoxy or cyano group, while
R$_6$ denotes a 1-(C$_{1-3}$-alkyl)-imidazol-2-yl group,
a 5-(C$_{1-3}$-alkyl)-pyrazol-1-yl group which may additionally be substituted in the 3 position by a C$_{1-3}$-alkyl group,
a pyrrolid-2-on-1-yl group,
a C$_{1-2}$-alkyl group terminally substituted by the group R$_7$, where
R$_7$ denotes an amino, allylamino, C$_{1-4}$-alkylamino or di-(C$_{1-3}$-alkyl)-amino group,
a ω-hydroxy-C$_{2-3}$-alkyl-amino, N—(C$_{1-3}$-alkyl)-ω-hydroxy-C$_{2-3}$-alkyl-amino, ω-(C$_{1-3}$-alkoxy)-C$_{2-3}$-alkyl-amino or N—(C$_{1-3}$-alkyl)-[ω-(C$_{1-3}$-alkoxy)-C$_{2-3}$-alkyl]-amino group,
a pyridylamino group,
a 5- to 7-membered cycloalkyleneimino group wherein a carbon atom may be substituted with a hydroxy or hydroxymethyl group, with the exception of substitution by a hydroxyl group at a carbon atom adjacent to the nitrogen atom,
a 6- to 7-membered cycloalkyleneimino group wherein the methylene group in the 4 position may be replaced by an oxygen atom or an —NH, —N-(allyl) or —N (C$_{1-3}$-alkyl) group, or
a triazolyl group bonded via the nitrogen atom in position 1 or 2,
or R$_6$ denotes a group of formula —(CH$_2$)$_n$—CO—R$_8$ wherein
R$_8$ denotes a pyrrolidino, 2,5-dihydro-pyrrol-1-yl, piperidino, morpholino, thiomorpholino or a piperazino or perhydro-1,4-diazepino group optionally substituted in the 4 position by a C$_{1-3}$-alkyl group
and n denotes one of the numbers 0 or 1, a group of formula

—CO—NR$_9$R$_{10}$ wherein
R$_9$ denotes a hydrogen atom, an allyl group or a C$_{1-3}$-alkyl group optionally terminally substituted by a cyano group and
R$_{10}$ denotes a hydrogen atom,
a C$_{1-3}$-alkyl group,
a C$_{2-3}$-alkyl group terminally substituted by a C$_{1-3}$-alkylamino or di-(C$_{1-3}$-alkyl)-amino group or
a 3- to 7-membered cycloalkyl group wherein a methylene group may be replaced by an —NH or —N(C$_{1-3}$-alkyl) group,
a group of formula —N(R$_{15}$)—CO—(CH$_2$)$_s$—R$_{16}$, wherein
R$_{15}$ denotes a hydrogen atom, an allyl, C$_{1-3}$-alkyl, pyridinyl, ω-[(C$_{1-3}$-alkyl)-amino]—C$_{2-3}$-alkyl or ω-[di-(C$_{1-3}$-alkyl)-amino]—C$_{2-3}$-alkyl group,
s denotes one of the numbers 0, 1 or 2 and
R$_{16}$ denotes a C$_{1-3}$-alkoxy, amino, C$_{1-3}$-alkylamino, di-(C$_{1-3}$-alkyl)-amino or pyridinyl group,
a pyrrolidino, 2,5-dihydropyrrol-1-yl, piperidino, morpholino or thiomorpholino group or
a piperazino or perhydro-1,4-diazepino group optionally substituted in the 4 position by a C$_{1-3}$-alkyl group
or, if s denotes the number 1 or 2, it may also represent a hydrogen atom,
a group of formula

—N(R$_{17}$)—SO$_2$—R$_{18}$, wherein
R$_{17}$ denotes a hydrogen atom,
a C$_{1-3}$-alkyl group or
a C$_{2-3}$-alkyl group terminally substituted by an amino, C$_{1-3}$-alkyl-amino or di-(C$_{1-3}$-alkyl)-amino group and
R$_{18}$ denotes a C$_{1-3}$-alkyl group,
a group of formula —SO$_2$—(CH$_2$)$_t$—R$_{19}$, wherein
t denotes one of the numbers 1, 2 or 3 and
R$_{19}$ denotes a hydrogen atom or, if n denotes one of the numbers 2 or 3, it may also represent a di-(C$_{1-3}$-alkyl)-amino group,
or a group of formula —O—(CH$_2$)$_t$—R$_{19}$, wherein
t denotes one of the numbers 1, 2 or 3 and
R$_{19}$ denotes a hydrogen atom or, if n denotes one of the numbers 2 or 3, it may also represent a di-(C$_{1-3}$-alkyl)-amino group,
or a group of formula

—SO$_2$—NR$_{20}$R$_{25}$, wherein
R$_{20}$ denotes a hydrogen atom or an allyl or C$_{1-3}$-alkyl group and
R$_{25}$ denotes a C$_{1-3}$-alkyl group or
a C$_{2-3}$-alkyl group substituted by an amino, C$_{1-3}$-alkylamino or di-(C$_{1-3}$-alkyl)-amino group, while the dialkylamino groups contained in the abovementioned groups may contain two identical or different alkyl groups and
the saturated alkyl and alkoxy moieties which contain more than 2 carbon atoms present in the abovementioned groups may be straight-chain or branched, unless otherwise stated,
the tautomers, diastereomers, enantiomers, the mixtures thereof and the salts thereof.
Most particularly preferred compounds of general formula I are those wherein
X denotes an oxygen atom,
R$_1$ and R$_5$ in each case denote a hydrogen atom,
R$_2$ denotes a hydrogen, fluorine or chlorine atom or a methoxycarbonyl, ethoxycarbonyl, dimethylaminocarbonyl, N-ethyl-N-methyl-aminocarbonyl or diethylaminocarbonyl group,
R$_3$ denotes a 3,4-methylenedioxy-1-phenyl, 3,4-ethylenedioxy-1-phenyl, quinoxalin-6-yl, benzimidazol-5-yl, 2-methylbenzimidazol-5-yl or 1-methyl-benzimidazol-5-yl group and
R$_4$ denotes a phenyl group substituted in the 4 position by the group R$_6$ which may additionally be substituted in the 3 position by a fluorine or chlorine atom or a methoxy group, while
R$_6$ denotes a 1-(C$_{1-2}$-alkyl)-imidazol-2-yl group,
a 3,5-dimethyl-pyrazol-1-yl group,
a pyrrolid-2-on-1-yl group,
a methyl group substituted by the group R$_7$, where
R$_7$ denotes a methylamino, ethylamino, isobutylamino, di-(C$_{1-2}$-alkyl)-amino, N-(2-hydroxyethyl)-methylamino or N-(2-methoxyethyl)-methylamino group,
a pyrrolidino, 3-hydroxypyrrolidino, 2-hydroxymethylpyrrolidino, 4-hydroxypiperidino, morpholino, piperazin-1-yl or 1-methyl-piperazin-4-yl group or
a 1,2,4-triazol-1-yl, 1,2,3-triazol-1-yl or 1,2,3-triazol-2-yl group,
or R$_6$ denotes an N-acetyl-methylamino or N-methoxyacetyl-methylamino group,
a group of formula

—CO—R$_8$, wherein
R$_8$ denotes a piperazino or perhydro-1,4-diazepino group optionally substituted by a methyl group in the 4 position,
a 4-methyl-piperazin-1-yl-carbonyl-methyl group,
a group of formula

—CO—NR$_9$R$_{10}$ wherein
R$_9$ denotes a methyl, cyanomethyl or ethyl group and
R$_{10}$ denotes a methyl, 1-methylpiperidin-4-yl, 2-methylamino-ethyl, 2-dimethyl-amino-ethyl or 3-dimethylamino-propyl group,
a group of formula —N(R$_{15}$)—CO—(CH$_2$)$_s$—NMe$_2$, wherein
s denotes one of the numbers 1 or 2 and
R$_{15}$ denotes a methyl or ethyl group or, if n denotes the number 2, it may also represent a 3-pyridyl group,
a group of formula —N(R$_{15}$')—CO—(CH$_2$)$_s$—H, wherein
s denotes one of the numbers 1 or 2 and
$R_{15}'$ denotes a 2-(dimethylamino)-ethyl or 3-(dimethylamino)-propyl group,
or a group of formula —N(Me)—CO—(CH$_2$)$_s$—R$_{16}'$, wherein
s denotes one of the numbers 1 or 2 and
$R_{16}'$ denotes a dimethylamino group, or, if s denotes the number 1, it may also represent a 4-(C$_{1-2}$-alkyl)-piperazin-1-yl group,
a group of formula

—N(R$_{17}$)—SO$_2$—R$_{18}$, wherein a) $R_{17}$ denotes a dimethylaminoethyl group and $R_{18}$ denotes a methyl, ethyl or propyl group or
wherein b) $R_{17}$ and $R_{18}$ in each case represent a methyl group,
a group of formula —SO$_2$—N(R$_{20}$)—(CH$_2$)$_u$—NMe$_2$, wherein
$R_{20}$ denotes a hydrogen atom or a methyl group and
u denotes one of the numbers 2 or 3,
a group of formula

—SO$_2$—R$_{26}$, wherein
$R_{26}$ denotes a methyl group or a 2-di-(C$_{1-2}$-alkyl)-amino-ethyl group,
or a 2-di-(C$_{1-2}$-alkyl)-amino-ethoxy group,
while the dialkylamino groups contained in the abovementioned groups may contain two identical or two different alkyl groups,
the tautomers, diastereomers, enantiomers, the mixtures thereof and the salts thereof.

The following are mentioned as examples of particularly preferred compounds:
(a) 3-(Z)-{1-[4-(dimethylaminomethyl)-phenylamino]-1-(3,4-methylenedioxyphenyl)-methylene}-6-chloro-2-indolinone
(b) 3-(Z)-{1-(4-[N-methyl-N-(4-methylpiperazin-1-yl-methylcarbonyl)-amino]-phenylamino)-1-(quinoxalin-6-yl)-methylene}-6-chloro-2-indolinone
(c) 3-(Z)-{1-[4-(N-ethyl-N-methyl-aminomethyl)-phenylamino]-1-(3,4-methylenedioxyphenyl)-methylene}-6-chloro-2-indolinone
(d) 3-(Z)-{1-[4-(N-methyl-N-{2-(dimethylamino)-ethylcarbonyl}-amino)-phenylamino]-1-(3,4-ethylenedioxyphenyl)-methylene}-6-fluoro-2-indolinone
(e) 3-(Z)-{1-[4-(1,2,4-triazol-1-yl-methyl)-phenylamino]-1-(1-methyl-benzimidazol-5-yl)-methylene}-6-fluoro-2-indolinone
(f) 3-(Z)-{1-[4-(dimethylaminomethyl)-phenylamino]-1-(1-methyl-benzimidazol-5-yl)-methylene}-6-chloro-2-indolinone
(g) 3-(Z)-{1-[4-(dimethylaminomethyl)-phenylamino]-1-(3,4-ethylenedioxyphenyl)-methylene}-6-chloro-2-indolinone
(h) 3-(Z)-{1-(4-[N-methanesulphonyl-N-(2-dimethylaminoethyl)-amino]-phenylamino)-1-(3,4-ethylenedioxyphenyl)-methylene}-6-chloro-2-indolinone
(i) 3-(Z)-{1-[4-(dimethylaminomethyl)-phenylamino]-1-(3,4-ethylenedioxyphenyl)-methylene}-6-methoxycarbonyl-2-indolinone
(j) 3-(Z)-{1-(4-[N-methyl-N-(4-methylpiperazin-1-yl-methylcarbonyl)-amino]-phenyl-amino)-1-(3,4-ethylenedioxyphenyl)-methylene}-6-methoxycarbonyl-2-indolinone
(k) 3-(Z)-{1-(4-[N-acetyl-N-(2-dimethylaminoethyl)-amino]-phenylamino)-1-(3,4-ethylenedioxyphenyl)-methylene}-6-fluoro-2-indolinone
(l) 3-(Z)-{1-[4-(ethylaminomethyl)-phenylamino]-1-(3,4-ethylenedioxyphenyl)-methylene}-6-fluoro-2-indolinone
(m) 3-(Z)-{1-(4-[N-acetyl-N-(3-dimethylaminopropyl)-amino]-phenylamino)-1-(3,4-ethylenedioxyphenyl)-methylene}-6-chloro-2-indolinone
(n) 3-(Z)-{1-(4-[N-propionyl-N-(3-dimethylaminopropyl)-amino]-phenylamino)-1-(3,4-ethylenedioxyphenyl)-methylene}-6-chloro-2-indolinone
(o) 3-(Z)-{1-(4-[N-propionyl-N-(2-dimethylaminoethyl)-amino]-phenylamino)-1-(3,4-ethylenedioxyphenyl)-methylene}-6-chloro-2-indolinone
(p) 3-(Z)-{1-(4-[N-acetyl-N-(2-dimethylaminoethyl)-amino]-phenylamino)-1-(3,4-ethylenedioxyphenyl)-methylene}-6-chloro-2-indolinone
(q) 3-(Z)-{1-(4-[4-methylpiperazin-1-yl-methyl]-phenylamino)-1-(3,4-methylenedioxyphenyl)-methylene}-6-chloro-2-indolinone
(r) 3-(Z)-{1-(4-[N-methanesulphonyl-N-(2-dimethylaminoethyl)-amino]-phenylamino)-1-(3,4-ethylenedioxyphenyl)-methylene}-6-methoxycarbonyl-2-indolinone
(s) 3-(Z)-{1-(4-[pyrrolidin-1-yl-methyl]-phenylamino)-1-(3,4-ethylenedioxyphenyl)-methylene}-6-methoxycarbonyl-2-indolinone
(t) 3-(Z)-{1-(4-[N-methyl-N-(dimethylaminomethylcarbonyl)-amino]-phenylamino)-1-(3,4-ethylenedioxyphenyl)-methylene}-6-methoxycarbonyl-2-indolinone
(u) 3-(Z)-{1-(4-[ethylamino-methyl]-phenylamino)-1-(3,4-ethylenedioxyphenyl)-methylene}-6-methoxycarbonyl-2-indolinone
(v) 3-(Z)-{1-(4-[4-methylpiperazin-1-yl-methyl]-phenylamino)-1-(3,4-ethylenedioxy-phenyl)-methylene}-6-methoxycarbonyl-2-indolinone
(w) 3-(Z)-{1-(4-[dimethylamino-methyl]-phenylamino)-1-(3,4-methylenedioxyphenyl)-methylene}-6-methoxycarbonyl-2-indolinone
(x) 3-(Z)-{1-(4-[diethylamino-methyl]-phenylamino)-1-(3,4-methylenedioxyphenyl)-methylene}-6-methoxycarbonyl-2-indolinone
(y) 3-(Z)-{1-[4-(dimethylaminocarbonyl)-phenylamino]-1-(1-methyl-benzimidazol-5-yl)-methylene}-6-fluoro-2-indolinone
(z) 3-(Z)-{1-(4-[N-propionyl-N-(3-dimethylaminopropyl)-amino]-phenylamino)-1-(3,4-ethylenedioxyphenyl)-methylene}-6-fluoro-2-indolinone
(aa) 3-(Z)-{1-(4-[N-propionyl-N-(2-dimethylaminoethyl)-amino]-phenylamino)-1-(3,4-ethylenedioxyphenyl)-methylene}-6-fluoro-2-indolinone
(ab) 3-(Z)-{1-(4-[N-methanesulphonyl-N-(2-dimethylaminoethyl)-amino]-phenylamino)-1-(3,4-ethylenedioxyphenyl)-methylene}-6-fluoro-2-indolinone
(ac) 3-(Z)-{1-(4-[N-acetyl-N-(2-dimethylaminoethyl)-amino]-phenylamino)-1-(3,4-ethylenedioxyphenyl)-methylene}-6-methoxycarbonyl-2-indolinone
(ad) 3-(Z)-{1-(4-[N-methyl-N-(2-dimethylaminoethyl)aminocarbonyl]-phenylamino)-1-(3,4-ethylenedioxyphenyl)-methylene}-6-methoxycarbonyl-2-indolinone
(ae) 3-(Z)-{1-(4-[N-methyl-N-(3-dimethylaminopropyl)aminocarbonyl]-phenylamino)-1-(3,4-ethylenedioxyphenyl)-methylene}-6-methoxycarbonyl-2-indolinone (af) 3-(Z)-{1-(4-[N-methyl-N-(2-dimethylaminoethyl)ami-nocarbonyl]-phenylamino)-1-(3,4-methylenedioxyphe-nyl)-methylene}-6-methoxycarbonyl-2-indolinone
(az) 3-(Z)-{1-(4-[N-methyl-N-(4-methylpiperazin-1-yl-me-thylcarbonyl)-amino]-phenyl-amino)-1-(3,4-methylene-dioxyphenyl)-methylene}-6-chloro-2-indolinone
(be) 3-(Z)-{1-(4-[N-methyl-N-(4-methylpiperazin-1-yl-me-thylcarbonyl)-amino]-phenyl-amino)-1-(3,4-methylene-dioxyphenyl)-methylene}-6-fluoro-2-indolinone and
(bf) 3-(Z)-{1-(4-[N-methyl-N-(4-methylpiperazin-1-yl-me-thylcarbonyl)-amino]-phenyl-amino)-1-(3,4-methylene-dioxyphenyl)-methylene}-6-bromo-2-indolinone,
the tautomers and the salts thereof.

According to the invention the new compounds are obtained, for example, by the following methods known in principle from the literature:

a. reacting a compound of general formula

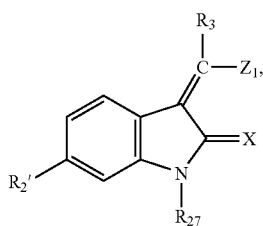

(II)

wherein
X and $R_3$ are as hereinbefore defined,
$R_2'$ has the meanings given for $R_2$ hereinbefore,
$R_{27}$ denotes a hydrogen atom or a protective group for the nitrogen atom of the lactam group, while one of the groups $R_2'$ and $R_{27}$ may also denote a bond to a solid phase optionally formed via a spacer and the other of the groups $R_2'$ and $R_{27}$ is as hereinbefore defined, and $Z_1$ denotes a halogen atom, a hydroxy, alkoxy or aryl-alkoxy group, e.g. a chlorine or bromine atom, a methoxy, ethoxy or benzyloxy group,
with an amine of general formula

(III)

wherein
$R_4$ and $R_5$ are as hereinbefore defined,
and if necessary subsequently cleaving any protective group used for the nitrogen atom of the lactam group or from a solid phase.

A protecting group for the nitrogen atom of the lactam group might be for example an acetyl, benzoyl, ethoxycar-bonyl, tert.butyloxycarbonyl or benzyloxycarbonyl group and
the solid phase might be a resin such as a 4-(2',4'-dimethox-yphenylaminomethyl)-phenoxy resin, whilst the bond may conveniently be formed via the amino group, or a p-benzyloxybenzylalcohol resin, whilst the bond may conveniently be formed via an intermediate member such as a 2,5-dimethoxy-4-hydroxy-benzyl derivative.

The reaction is conveniently carried out in a solvent such as dimethylformamide, toluene, acetonitrile, tetrahydrofu-ran, dioxan, methanol, ethanol, 2-propanol, dimethylsul-phoxide, methylene chloride or mixtures thereof, optionally in the presence of an inert base such as triethylamine, N-ethyl-diisopropylamine or sodium hydrogen carbonate at temperatures between 20 and 175° C., whilst any protecting group used can be cleaved simultaneously by transamida-tion.

If $Z_1$ in a compound of general formula II denotes a halogen atom, the reaction is preferably carried out in the presence of an inert base at temperatures between 20 and 120° C.

If $Z_1$ in a compound of general formula II denotes a hydroxy, alkoxy or arylalkoxy group, the reaction is pref-erably carried out at temperatures between 20 and 200° C.

If any protecting group used subsequently has to be cleaved, this is conveniently carried out either hydrolytically in an aqueous or alcoholic solvent, e.g. in methanol/water, ethanol/water, isopropanol/water, tetrahydrofuran/water, dioxane/water, dimethylformamide/water, methanol or etha-nol in the presence of an alkali metal base such as lithium hydroxide, sodium hydroxide or potassium hydroxide at temperatures between 0 and 100° C., preferably at tempera-tures between 10 and 50° C., or advantageously by transamidation with an organic base such as ammonia, butylamine, dimethylamine or piperi-dine in a solvent such as methanol, ethanol, dimethylfor-mamide and mixtures thereof or in an excess of the amine used at temperatures between 0 and 100° C., preferably at temperatures between 10 and 50° C.

Any solid phase used is preferably cleaved using trifluo-roacetic acid and water at temperatures between 0 and 35° C., preferably at ambient temperature.

b. In order to prepare a compound of general formula I wherein
$R_2$ denotes a straight-chain or branched $C_{1-6}$-alkoxy-carbo-nyl group, a $C_{3-6}$-cycloalkoxy-carbonyl or an aryloxycar-bonyl group,
an allyloxy-carbonyl group optionally substituted by one or two methyl groups,
a straight-chain or branched $C_{1-4}$-alkoxy-carbonyl group which is terminally substituted in the alkyl moiety by a phenyl, heteroaryl, carboxy, $C_{1-3}$-alkoxy-carbonyl, ami-nocarbonyl, $C_{1-3}$-alkylamino-carbonyl or di-($C_{1-3}$-alkyl)-aminocarbonyl group,
a straight-chain or branched $C_{2-6}$-alkoxy-carbonyl group which is terminally substituted in the alkyl moiety by a chlorine atom or a hydroxy, $C_{1-3}$-alkoxy, amino, $C_{1-3}$-alkylamino or di-($C_{1-3}$-alkyl)-amino group, or
an aminocarbonyl, $C_{1-4}$-alkyl-aminocarbonyl or a di-($C_{1-4}$-alkyl)-aminocarbonyl group, while the alkyl groups, if they have more than one carbon atom, may be terminally substituted by a hydroxy, $C_{1-3}$-alkoxy or di-($C_{1-3}$-alkyl)-amino group:
reacting a compound of general formula

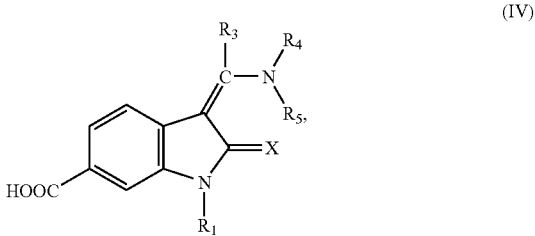

(IV)

wherein
X, $R_1$ and $R_3$ to $R_5$ are as hereinbefore defined, or the reactive derivatives thereof, with a compound of general formula

H—$R_{28}$ (V), wherein

R$_{28}$ denotes a straight-chain or branched C$_{1-6}$-alkanol, a C$_{3-6}$-cycloalkanol or an aromatic alcohol, an allyl-alcohol optionally substituted by one or two methyl groups, a straight-chain or branched C$_{1-4}$-alkanol which is terminally substituted in the alkyl moiety by a phenyl, heteroaryl, carboxy, C$_{1-3}$-alkoxy-carbonyl, aminocarbonyl, C$_{1-3}$-alkylamino-carbonyl or di-(C$_{1-3}$-alkyl)-aminocarbonyl group, a straight-chain or branched C$_{2-6}$-alkanol which is terminally substituted in the alkyl moiety by a chlorine atom or a hydroxy, C$_{1-3}$-alkoxy, amino, C$_{1-3}$-alkylamino or di-(C$_{1-3}$-alkyl)-amino group, or an amino, C$_{1-4}$-alkyl-amino or a di-(C$_{1-4}$-alkyl)-amino group, while the alkyl groups, if they have more than one carbon atom, may be terminally substituted by a hydroxy, C$_{1-3}$-alkoxy or di-(C$_{1-3}$-alkyl)-amino group.

The esterification or amidation is preferably carried out in a solvent such as methylene chloride, diethyl ether, tetrahydrofuran, toluene, dioxane, acetonitrile, dimethylsulphoxide or dimethylformamide, optionally in the presence of an inorganic or a tertiary organic base, preferably at temperatures between 20° C. and the boiling temperature of the solvent used. The reaction is carried out with a corresponding acid, preferably in the presence of a dehydrating agent, e.g. in the presence of isobutyl chloroformate, tetraethyl orthocarbonate, trimethyl orthoacetate, 2,2-dimethoxypropane, tetramethoxysilane, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxy-benzotriazole, 2-(1H-benzotriazol-1-yl)-1,1,3,3-tetramethyluronium-tetrafluoroborate, 2-(1H-benzotriazol-1-yl)-1,1,3,3-tetramethyluronium-tetrafluoroborate/1-hydroxy-benzotriazole, N,N'-carbonyldiimidazole or triphenylphosphine/carbon tetrachloride, and optionally with the addition of a base such as pyridine, 4-dimethylaminopyridine, N-methyl-morpholine or triethylamine, conveniently at temperatures between 0 and 150° C., preferably at temperatures between 0 and 100° C., and the acylation is carried out with a corresponding reactive compound such as the anhydrides, esters, imidazolides or halides thereof, optionally in the presence of a tertiary organic base such as triethylamine, N-ethyl-diisopropylamine or N-methyl-morpholine at temperatures between 0 and 150° C., preferably at temperatures between 50 and 100° C.

c. In order to prepare a compound of general formula

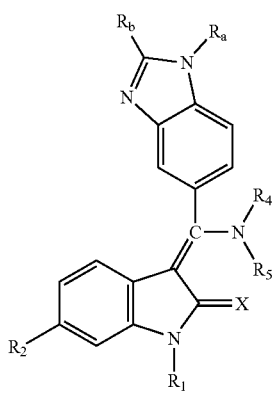

(VIa)

or

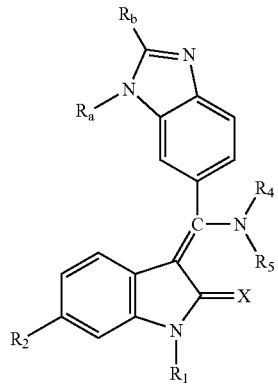

(VIb)

wherein

X, R$_1$, R$_2$, R$_4$ and R$_5$ are as hereinbefore defined and

R$_a$ and R$_b$ in each case independently of one another may be a hydrogen atom, a C$_{1-3}$-alkyl group or a carboxy-C$_{1-3}$-alkyl group:

reduction of a compound of general formula

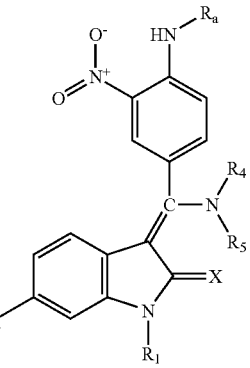

(VIIa)

or

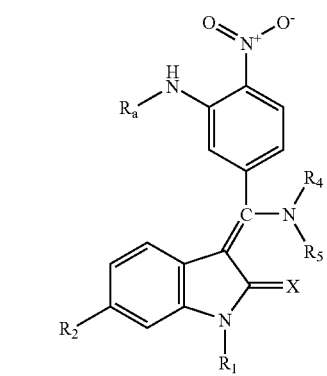

(VIIb)

wherein

X, R$_1$, R$_2$, R$_4$ and R$_5$ are as hereinbefore defined and

R$_a$ may be a hydrogen atom, a C$_{1-3}$-alkyl group or an optionally protected carboxy-C$_{1-3}$-alkyl group, with hydrogen (1–10 bar) or a reagent for transfer hydrogenation, such as for example cyclohexene, 1,3-cyclohexadiene or ammonium formate in the presence of a hydrogenation catalyst such as for example Raney nickel or palladium on activated charcoal at temperatures from 0° C. to 150° C., preferably from 10° C. to the boiling temperature of the solvent or mixture of solvents, either c1. in formic acid, optionally using a cosolvent, to obtain compounds of general formula VIa or VIb wherein
$R_b$ is a hydrogen atom and
$R_a$ is a hydrogen atom, a $C_{1-3}$-alkyl group or an optionally protected carboxy-$C_{1-3}$-alkyl group, or c2. in a solvent such as for example acetic acid, propionic acid, methanol, ethanol or mixtures thereof with one another or with other solvents such as for example ethyl acetate, THF or dioxane, to obtain compounds of general formula I wherein $R_3$ is a 3,4-diaminophenyl group substituted with $R_a$ at one of the amino groups, which are further reacted in $R_b$—COOH or also, if $R_b$ is a carboxyalkyl group, in a protected derivative such as a corresponding hemiester, as the solvent and reactant or optionally—particularly if $R_b$—COOH is a solid at the reaction temperature chosen—with the addition of a solvent such as for example methanol, ethanol, 2-propanol, acetic acid, propionic acid, THF, dioxane, dichloromethane or ethyl acetate at temperatures from 10° C.-150° C., preferably from 20° C. to the boiling point of the solvent or mixture of solvents, to obtain compounds of general formula VIa or VIb wherein $R_a$ and $R_b$ independently of one another may be a hydrogen atom, a $C_{1-3}$-alkyl group or an optionally protected carboxy-$C_{1-3}$-alkyl group.

d. In order to prepare a compound of general formula I wherein $R_4$ denotes a phenyl group substituted by the group $R_6$ in the 3- or 4-position which may additionally be substituted as described above, and $R_6$ denotes a $C_{1-3}$-alkyl group substituted by $R_7$, where $R_7$ denotes a heteroaryl group which is bound via an imino-nitrogen, a hydroxy or $C_{1-3}$-alkoxy group, an amino, $C_{1-7}$-alkylamino, di-($C_{1-7}$-alkyl)-amino, N—($C_{1-7}$-alkyl)-allylamino, phenylamino, N-phenyl-$C_{1-3}$-alkyl-amino, phenyl-$C_{1-3}$-alkylamino, N—($C_{1-3}$-alkyl)-phenyl-$C_{1-3}$-alkylamino or di-(phenyl-$C_{1-3}$-alkyl)-amino group, an allylamino group wherein one or two vinylic hydrogen atoms may each be replaced by a methyl group, a ω-hydroxy-$C_{2-3}$-alkyl-amino, N—($C_{1-3}$-alkyl)-ω-hydroxy-$C_{2-3}$-alkyl-amino, di-(ω-hydroxy-$C_{2-3}$-alkyl)-amino, N—($C_{1-3}$-alkyl)-[ω-($C_{1-3}$-alkoxy)-$C_{2-3}$-alkyl]-amino, di-(ω-($C_{1-3}$-alkoxy)-$C_{2-3}$-alkyl)-amino or N-(dioxolan-2-yl)-$C_{1-3}$-alkyl-amino group, a $C_{1-3}$-alkyl-carbonylamino-$C_{2-3}$-alkyl-amino or $C_{1-3}$-alkyl-carbonylamino-$C_{2-3}$-alkyl-N—($C_{1-3}$-alkyl)-amino group, a pyridylamino group, a $C_{1-3}$-alkylsulphonylamino, N—($C_{1-3}$-alkyl)-$C_{1-3}$-alkyl-sulphonylamino, $C_{1-3}$-alkyl-sulphonylamino-$C_{2-3}$-alkyl-amino or $C_{1-3}$-alkylsulphonylamino-$C_{2-3}$-alkyl-N—($C_{1-3}$-alkyl)-amino group, a hydroxycarbonyl-$C_{1-3}$-alkylamino or N—($C_{1-3}$-alkyl)-hydroxycarbonyl-$C_{1-3}$-alkyl-amino group, a guanidino group wherein one or two hydrogen atoms in each case may be replaced by a $C_{1-3}$-alkyl group, a 2-pyrrolidon-1-yl group wherein the methylene group adjacent to the carbonyl group may be replaced by an oxygen atom or by an —NH or —N($C_{1-3}$-alkyl) group, a group of formula

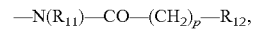
—N($R_{11}$)—CO—$(CH_2)_p$—$R_{12}$, wherein $R_1$ denotes a hydrogen atom or an allyl, $C_{1-3}$-alkyl, $C_{1-3}$-alkyl-amino-$C_{2-3}$-alkyl or di-($C_{1-3}$-alkyl)-amino-$C_{2-3}$-alkyl group, p denotes one of the numbers 0, 1, 2 or 3 and $R_{12}$ denotes an amino, $C_{1-4}$-alkylamino, allylamino, di-allyl-amino, di-($C_{1-4}$-alkyl)-amino, phenylamino, N—($C_{1-4}$-alkyl)-phenylamino, benzylamino, N—($C_{1-4}$-alkyl)-benzylamino, $C_{1-4}$-alkoxy or 2,5-dihydropyrrol-1-yl group or a 4- to 7-membered cycloalkyleneimino group, while in each case the methylene group in the 4 position of a 6- or 7-membered cycloalkylene-imino group may be replaced by an oxygen or sulphur atom, by a sulphinyl, sulphonyl, —NH, —N($C_{1-3}$-alkyl), —N(allyl), —N(phenyl), —N($C_{1-3}$-alkyl-carbonyl) or —N(benzoyl) group, or, if n denotes one of the numbers 1, 2 or 3, may also represent a hydrogen atom, a group of formula

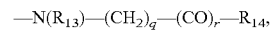
—N($R_{13}$)—$(CH_2)_q$—(CO)$_r$—$R_{14}$, wherein $R_{13}$ denotes a hydrogen atom or a $C_{1-3}$-alkyl, allyl, $C_{1-3}$-alkyl-carbonyl, arylcarbonyl, pyridylcarbonyl, phenyl-$C_{1-3}$-alkyl-carbonyl, $C_{1-3}$-alkylsulphonyl, arylsulphonyl or phenyl-$C_{1-3}$-alkylsulphonyl group, q denotes one of the numbers 1, 2, 3 or 4, r denotes the number 1 or, if q is one of the numbers 2, 3 or 4, may also represent the number 0 and $R_{14}$ denotes a hydroxy, amino, $C_{1-4}$-alkylamino, di-($C_{1-4}$-alkyl)-amino, phenyl-amino, N—($C_{1-4}$-alkyl)-phenylamino, benzylamino, N—($C_{1-4}$-alkyl)-benzylamino, $C_{1-4}$-alkoxy or $C_{1-3}$-alkoxy-$C_{1-3}$-alkoxy group, a di-($C_{1-4}$-alkyl)-amino-$C_{1-3}$-alkylamino group optionally substituted in the 1 position by a $C_{1-3}$-alkyl group or a 4- to 7-membered cycloalkyleneimino group, while the cycloalkylene moiety may be fused to a phenyl ring or in each case the methylene group in the 4 position of a 6- or 7-membered cycloalkyleneimino group may be replaced by an oxygen or sulphur atom or by a sulphinyl, sulphonyl, —NH, —N($C_{1-3}$-alkyl), —N(phenyl), —N($C_{1-3}$-alkyl-carbonyl) or —N(benzoyl) group, a $C_{4-7}$-cycloalkylamino, $C_{4-7}$-cycloalkyl-$C_{1-3}$-alkylamino or $C_{4-7}$-cycloalkenylamino group wherein position 1 of the ring is not involved in the double bond and the abovementioned groups in each case may additionally be substituted at the amino-nitrogen atom by a $C_{5-7}$-cycloalkyl, $C_{2-4}$-alkenyl or $C_{1-4}$-alkyl group, a 2,5-dihydro-pyrrol-1-yl group or a 4- to 7-membered cycloalkyleneimino group wherein the cycloalkylene moiety may be fused with a phenyl group or with an oxazolo, imidazolo, thiazolo, pyridino, pyrazino or pyrimidino group optionally substituted by a fluorine, chlorine, bromine or iodine atom or by a nitro, $C_{1-3}$-alkyl, $C_{1-3}$-alkoxy or amino group and/or one or two hydrogen atoms may each be replaced by a $C_{1-3}$-alkyl, $C_{3-7}$-cyclo-alkyl, hydroxy, $C_{1-3}$-alkoxy, hydroxy-$C_{1-3}$-alkyl or $C_{1-3}$-alkoxy-$C_{1-3}$-alkyl or phenyl group and/or the methylene group in position 3 of a 5-membered cycloalkyleneimino group may be substituted by a hydroxy, hydroxy-$C_{1-3}$-alkyl, $C_{1-3}$-alkoxy or $C_{1-3}$-alkoxy-$C_{1-3}$-alkyl group, in each case the methylene group in the 3 or 4 position of a 6- or 7-membered cycloalkyleneimino group may be substituted by a hydroxy, hydroxy-$C_{1-3}$-alkyl, $C_{1-3}$-alkoxy, $C_{1-3}$-alkoxy-$C_{1-3}$-alkyl, carboxy, $C_{1-4}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkylamino group or the methylene group in the 4 position of a 6- or 7-membered cycloalkyleneimino group may be replaced by an oxygen or sulphur atom, by a sulphinyl, sulphonyl, —NH, —N($C_{1-3}$-alkyl), —N(allyl), —N(phenyl), —N(phenyl-$C_{1-3}$-alkyl), —N($C_{1-3}$-alkyl-carbonyl), —N($C_{1-4}$-hydroxy-carbonyl), —N($C_{1-4}$-alkoxy-carbonyl), —N(benzoyl) or —N(phenyl-$C_{1-13}$-alkyl-carbonyl) group, while a methylene group linked to an imino-nitrogen atom of the cycloalkyleneimino group may be replaced by a carbonyl or sulphonyl group or in a 5- to 7-membered monocyclic cycloalkyleneimino group or a cycloalkyleneimino group fused to a phenyl group the two methylene groups linked to the imino-nitrogen atom may each be replaced by a carbonyl group:

reacting a compound of general formula

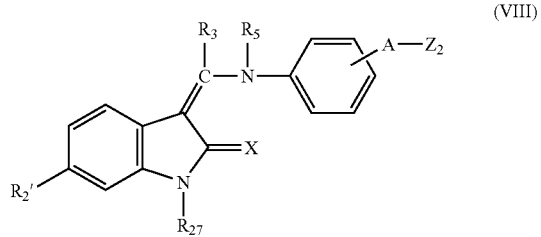

(VIII)

wherein $R_3$, $R_5$ and X are as hereinbefore defined, $R_2'$ has the meanings given for $R_2$ hereinbefore, $R_{27}$ denotes a hydrogen atom or a protective group for the nitrogen atom of the lactam group, while one of the groups $R_2'$ and $R_{27}$ may also denote a bond to a solid phase optionally formed via a spacer and the other of the groups $R_2'$ and $R_{27}$ is as hereinbefore defined, A denotes a $C_{1-3}$-alkyl group and $Z_2$ denotes a leaving group, for example an alkyl or arylsulphonyloxy group such as the methylsulphonyloxy, ethylsulphonyloxy, p-toluenesulphonyloxy, or trifluoromethanesulphonyloxy group, with a compound of general formula

H—$R_7$, (IX), wherein $R_7$, has the meanings given for $R_7$ hereinbefore, and if necessary subsequently cleaving any protective group used for the nitrogen atom of the lactam group or from a solid phase.

The reaction is expediently carried out in a solvent such as methylene chloride, tetrahydrofuran, 1,4-dioxane, toluene, acetonitrile, dimethylsulphoxide, dimethylformamide, dimethylacetamide, N-methylpyrrolidone or mixtures thereof, optionally with the addition of water as cosolvent and/or with the addition of an inert auxiliary base, for example sodium hydrogen carbonate, pyridine, 2,4,6-trimethylpyridine, quinoline, triethylamine, N-ethyldiisopropylamine, N-ethyl-dicyclohexylamine, 1,4-diazabicyclo[2,2,2]octane or 1,8-diazabicyclo[5,4,0]undec-7-ene, at temperatures between −50° C. and +100° C., preferably between −10° C. and +50° C., while any protective group used may simultaneously be cleaved as a result of transamidation.

If any protecting group used for the nitrogen atom of the lactam group has to be cleaved or removed from a solid phase this is done as described above under method (a).

If according to the invention a compound of general formula I is obtained which contains an alkoxycarbonyl group, this can be converted by hydrolysis into a corresponding carboxy compound, or if a compound of general formula I is obtained which contains an amino or alkylamino group, this may be converted by reductive alkylation into a corresponding alkylamino or dialkylamino compound, or if a compound of general formula I is obtained which contains an amino or alkylamino group, this may be converted by acylation or sulphonylation into a corresponding acyl or sulphonyl compound, or if a compound of general formula I is obtained which contains a carboxy group, this may be converted by esterification or amidation into a corresponding ester or aminocarbonyl compound, or if a compound of general formula I is obtained which contains a cycloalkyleneimino group wherein a methylene group is replaced by a sulphur atom, this may be converted by oxidation into a corresponding sulphinyl or sulphonyl compound, or if a compound of general formula I is obtained which contains a nitro group, this may be converted by reduction into a corresponding amino compound, or if a compound of general formula I is obtained wherein $R_4$ denotes a phenyl group substituted by an amino, alkylamino, aminoalkyl or N-alkyl-amino group, this may subsequently be converted by reacting with a corresponding cyanate, isocyanate or carbamoyl halide into a corresponding urea compound of general formula I or if a compound of general formula I is obtained wherein $R_4$ denotes a phenyl group substituted by an amino, alkylamino, aminoalkyl or N-alkyl-amino group, this may subsequently be converted by reacting with a corresponding compound which transfers the amidino group or by reacting with a corresponding nitrile into a corresponding guanidino compound of general formula I.

The subsequent hydrolysis is preferably carried out in an aqueous solvent, e.g. in water, methanol/water, ethanol/water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide at temperatures between 0 and 100° C., preferably at temperatures between 10 and 50° C.

The subsequent reductive alkylation is preferably carried out in a suitable solvent such as methanol, methanol/water, methanol/water/ammonia, ethanol, ether, tetrahydrofuran, dioxane or dimethylformamide optionally with the addition of an acid such as hydrochloric acid in the presence of catalytically activated hydrogen, e.g. hydrogen in the presence of Raney nickel, platinum or palladium/charcoal, or in the presence of a metal hydride such as sodium borohydride, sodium cyanoborohydride, lithium borohydride or lithium aluminium hydride at temperatures between 0 and 100° C., preferably at temperatures between 20 and 80° C.

The subsequent acylation or sulphonylation is conveniently carried out with the corresponding free acid or a corresponding reactive compound such as an anhydride, ester, imidazolide or halide thereof, preferably in a solvent such as methylene chloride, diethyl ether, tetrahydrofuran, toluene, dioxane, acetonitrile, dimethylsulphoxide or dimethylformamide, optionally in the presence of an inorganic or a tertiary organic base, at temperatures between −20° C. and 200° C., preferably at temperatures between 20° C. and the boiling temperature of the solvent used. The reaction with the free acid may optionally be carried out in the presence of an acid activating agent or a dehydrating agent, e.g. in the presence of isobutyl chloroformate, tetraethyl orthocarbonate, trimethyl orthoacetate, 2,2-dimethoxypropane, tetramethoxysilane, thionylchloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxybenzotriazole, 2-(1H-benzotriazol-1-yl)-1,1,3,3-tetramethyluronium tetrafluoroborate, 2-(1H-benzotriazol-1-yl)-1,1,3,3-tetramethyluronium tetrafluoroborate/1-hydroxybenzotriazole, N,N'-carbonyldiimidazole or triphenylphosphine/carbon tetrachloride, and optionally with the addition of a base such as pyridine, 4-dimethylaminopyridine, N-methyl-morpholine or triethylamine, conveniently at temperatures between 0 and 150° C., preferably at temperatures between 0 and 100° C. The reaction with a corresponding reactive compound may optionally be carried out in the presence of a tertiary organic base such as triethylamine, N-ethyl-diisopropylamine, N-methyl-morpholine or pyridine, or, if an anhydride is used, in the presence of the corresponding acid, at temperatures between 0 and 150° C., preferably at temperatures between 50 and 100° C.

The subsequent esterification or amidation is conveniently carried out by reacting a corresponding reactive carboxylic acid derivative with a corresponding alcohol or amine as hereinbefore described.

The subsequent oxidation of the sulphur atom is preferably carried out in a solvent or mixture of solvents, e.g. in water, water/pyridine, acetone, methylene chloride, acetic acid, acetic acid/acetic anhydride, dilute sulphuric acid or trifluoroacetic acid, conveniently at temperatures between −80 and 100° C., depending on the oxidising agent used.

In order to prepare a corresponding sulphinyl compound of general formula I the oxidation is conveniently carried out with one equivalent of the oxidising agent used, e.g. with hydrogen peroxide in glacial acetic acid, trifluoroacetic acid or formic acid at 0 to 20° C. or in acetone at 0 to 60° C., with a peracid such as performic acid in glacial acetic acid or trifluoroacetic acid at 0 to 50° C. or with m-chloroperbenzoic acid in methylene chloride, chloroform or dioxane at −20 to 80° C., with sodium metaperiodate in aqueous methanol or ethanol at −15 to 25° C., with bromine in glacial acetic acid or aqueous acetic acid, optionally in the presence of a weak base such as sodium acetate, with N-bromosuccinimide in ethanol, with tert.butylhypochlorite in methanol at −80 to −30° C., with iodobenzodichloride in aqueous pyridine at 0 to 50° C., with nitric acid in glacial acetic acid at 0 to 20° C., with chromic acid in glacial acetic acid or in acetone at 0 to 20° C. and with sulphurylchloride in methylene chloride at −70° C., and the thioether-chlorine complex thus obtained is conveniently hydrolysed with aqueous ethanol.

In order to prepare a sulphonyl compound of general formula I the oxidation is carried out starting from a corresponding sulphinyl compound, conveniently with one or more equivalents of the oxidising agent used, or starting from a corresponding mercapto compound conveniently with two or more equivalents of the oxidising agent used, e.g. with hydrogen peroxide in glacial acetic acid/acetic anhydride, trifluoroacetic acid or in formic acid at 20 to 100° C. or in acetone at 0 to 60° C., with a peracid such as performic acid or m-chloroperbenzoic acid in glacial acetic acid, trifluoroacetic acid, methylene chloride or chloroform at temperatures between 0 and 60° C., with nitric acid in glacial acetic acid at 0 to 20° C., with chromic acid, sodium periodate or potassium permanganate in acetic acid, water/sulphuric acid or in acetone at 0 to 20° C.

The subsequent reduction of a nitro group is preferably carried out by hydrogenolysis, e.g. with hydrogen in the presence of a catalyst such as palladium/charcoal or Raney nickel in a solvent such as methanol, ethanol, ethyl acetate, dimethylformamide, dimethylformamide/acetone or glacial acetic acid, optionally with the addition of an acid such as hydrochloric acid or glacial acetic acid at temperatures between 0 and 50° C., but preferably at ambient temperature, and at a hydrogen pressure of 1 to 7 bar, but preferably 3 to 5 bar.

The subsequent preparation of a corresponding urea compound of general formula I is conveniently carried out with an inorganic cyanate or a corresponding isocyanate or carbamoylchloride, preferably in a solvent such as dimethylformamide and optionally in the presence of a tertiary organic base such as triethylamine at temperatures between 0 and 50° C., preferably at ambient temperature.

The subsequent preparation of a corresponding guanidino compound of general formula I is conveniently carried out by reacting with a compound that transfers the amidino group, such as 3,5-dimethylpyrazol-1-carboxylic acid amidine, preferably in a solvent such as dimethylformamide and optionally in the presence of a tertiary organic base such as triethylamine at temperatures between 0 and 50° C., preferably at ambient temperature.

In the reactions described hereinbefore, any reactive groups present such as carboxy, hydroxy, amino, alkylamino or imino groups may be protected during the reaction by conventional protecting groups which are cleaved again after the reaction.

For example, a protecting group for a carboxyl group may be a trimethylsilyl, methyl, ethyl, tert.butyl, benzyl or tetrahydropyranyl group and protecting groups for a hydroxy, amino, alkylamino or imino group may be an acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide, at temperatures between 0 and 100° C., preferably at temperatures between 10 and 50° C.

However, a benzyl, methoxybenzyl or benzyloxycarbonyl group is cleaved, for example, hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid or glacial acetic acid at temperatures between 0 and 50° C., but preferably at ambient temperature, and at a hydrogen pressure of 1 to 7 bar, but preferably 3 to 5 bar.

A methoxybenzyl group may also be cleaved in the presence of an oxidising agent such as cerium(IV) ammonium nitrate in a solvent such as methylene chloride, acetonitrile or acetonitrile/water at temperatures of between 0 and 50° C., but preferably at ambient temperature.

A 2,4-dimethoxybenzyl group, however, is preferably cleaved in trifluoroacetic acid in the presence of anisol.

A tert.butyl or tert.butyloxycarbonyl group is preferably cleaved by treating with an acid such as trifluoroacetic acid or hydrochloric acid, optionally using a solvent such as methylene chloride, dioxane, ethyl acetate or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

Moreover, chiral compounds obtained of general formula I may be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, N-acetylglutamic acid, aspartic acid, N-acetylaspartic acid or quinic acid. An optically active alcohol may be, for example, (+)- or (−)-menthol and an optically active acyl group in amides may be, for example, a (+)- or (−)-menthyloxycarbonyl group.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid, maleic acid, methanesulphonic acid or ethanesulphonic acid.

Moreover, if the new compounds of formula I thus obtained contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

The compounds of general formulae II to IX used as starting materials are known from the literature in some cases or may be obtained by methods known from the literature or may be obtained by methods as described hereinbefore and in the Examples. For example, the compounds of general formula VIII may be obtained from the compounds of general formula I wherein $R_4$ denotes a phenyl group substituted by a hydroxy-$C_{1-3}$-alkyl group, for example by reacting with alkyl- or arylsulphonyl chlorides.

As already mentioned, the new compounds of general formula I wherein $R_1$ denotes a hydrogen atom or a prodrug group have valuable pharmacological properties, particularly inhibitory effects on various kinases, especially on receptor-tyrosine kinases such as VEGFR1, VEGFR2, VEGFR3, PDGFRα, PDGFRβ, FGFR1, FGFR3, EGFR, HER2, IGF1R and HGFR, as well as on complexes of CDKs (Cyclin Dependent Kinases) such as CDK1, CDK2, CDK3, CDK4, CDK5, CDK6, CDK7, CDK8 and CDK9 with their specific cyclins (A, B1, B2, C, D1, D2, D3, E, F, G1, G2, H, I and K) and on viral cyclin, on the proliferation of cultivated human cells, particularly endothelial cells, e.g. in angiogenesis, but also on the proliferation of other cells, particularly tumour cells.

The biological properties of the new compounds were tested by the following standard procedure, as follows:

Human umbilical endothelial cells (HUVEC) were cultivated in IMDM (Gibco BRL), supplemented with 10% foetal calf serum (FBS) (Sigma), 50 μM of β-mercaptoethanol (Fluka), standard antibiotics, 15 μg/ml of endothelial cell growth factor (ECGS, Collaborative Biomedical Products) and 100 μg/ml of heparin (Sigma) on gelatine-coated culture dishes (0.2% gelatine, Sigma) at 37° C., under 5% $CO_2$ in a water-saturated atmosphere.

In order to investigate the inhibitory activity of the compounds according to the invention the cells were "starved" for 16 hours, i.e. kept in culture medium without growth factors (ECGS+heparin). The cells were detached from the culture dishes using trypsin/EDTA and washed once in serum-containing medium. Then they were seeded out in amounts of $2.5 \times 10^3$ cells per well.

The proliferation of the cells was stimulated with 5 ng/ml of $VEGF_{165}$ (vascular endothelial growth factor; H. Weich, GBF Braunschweig) and 10 μg/ml of heparin. As a control, 6 wells in each dish were not stimulated.

The compounds according to the invention were dissolved in 100% dimethylsulphoxide and added to the cultures in various dilutions as triple measurements, the maximum dimethylsulphoxide concentration being 0.3%.

The cells were incubated for 76 hours at 37° C., then for a further 16 hours $^3$H-thymidine (0.1 μCi/well, Amersham) was added in order to determine the DNA synthesis. Then the radioactively labelled cells were immobilised on filter mats and the radioactivity incorporated was measured in a β-counter. In order to determine the inhibitory activity of the compounds according to the invention the mean value of the non-stimulated cells was subtracted from the mean value of the factor-stimulated cells (in the presence or absence of the compounds according to the invention).

The relative cell proliferation was calculated as a percentage of the control (HUVEC without inhibitor) and the concentration of active substance which inhibits the proliferation of the cells by 50% (IC$_{50}$) was determined.

The test results of the following compounds (a) to (bd) of general formula I are provided by way of example:

(a) 3-(Z)-{1-[4-(dimethylaminomethyl)-phenylamino]-1-(3,4-methylenedioxyphenyl)-methylene}-6-chloro-2-indolinone (b) 3-(Z)-{1-(4-[N-methyl-N-(4-methylpiperazin-1-yl-methylcarbonyl)-amino]-phenyl-amino)-1-(quinoxalin-6-yl)-methylene}-6-chloro-2-indolinone (c) 3-(Z)-{1-[4-(N-ethyl-N-methyl-aminomethyl)-phenylamino]-1-(3,4-methylenedioxy-phenyl)-methylene}-6-chloro-2-indolinone (d) 3-(Z)-{1-[4-(N-methyl-N-{2-(dimethylamino)-ethylcarbonyl}-amino)-phenylamino]-1-(3,4-ethylenedioxyphenyl)-methylene}-6-fluoro-2-indolinone (e) 3-(Z)-{1-[4-(1,2,4-triazol-1-yl-methyl)-phenylamino]-1-(1-methyl-benzimidazol-5-yl)-methylene}-6-fluoro-2-indolinone (f) 3-(Z)-{1-[4-(dimethylaminomethyl)-phenylamino]-1-(1-methyl-benzimidazol-5-yl)-methylene}-6-chloro-2-indolinone (g) 3-(Z)-{1-[4-(dimethylaminomethyl)-phenylamino]-1-(3,4-ethylenedioxyphenyl)-methylene}-6-chloro-2-indolinone (h) 3-(Z)-{-(4-[N-methanesulphonyl-N-(2-dimethylaminoethyl)-amino]-phenylamino)-1-(3,4-ethylenedioxyphenyl)-methylene}-6-chloro-2-indolinone (i) 3-(Z)-{1-[4-(dimethylaminomethyl)-phenylamino]-1-(3,4-ethylenedioxyphenyl)-methylene}-6-methoxycarbonyl-2-indolinone (j) 3-(Z)-{1-(4-[N-methyl-N-(4-methylpiperazin-1-yl-methylcarbonyl)-amino]-phenyl-amino)-1-(3,4-ethylenedioxyphenyl)-methylene}-6-methoxycarbonyl-2-indolinone (k) 3-(Z)-{1-(4-[N-acetyl-N-(2-dimethylaminoethyl)-amino]-phenylamino)-1-(3,4-ethylenedioxyphenyl)-methylene}-6-fluoro-2-indolinone (l) 3-(Z)-{1-[4-(ethylaminomethyl)-phenylamino]-1-(3,4-ethylenedioxyphenyl)-methylene}-6-fluoro-2-indolinone (m) 3-(Z)-{1-(4-[N-acetyl-N-(3-dimethylaminopropyl)-amino]-phenylamino)-1-(3,4-ethylenedioxyphenyl)-methylene}-6-chloro-2-indolinone (n) 3-(Z)-{1-(4-[N-propionyl-N-(3-dimethylaminopropyl)-amino]-phenylamino)-1-(3,4-ethylenedioxyphenyl)-methylene}-6-chloro-2-indolinone (o) 3-(Z)-{1-(4-[N-propionyl-N-(2-dimethylaminoethyl)-amino]-phenylamino)-1-(3,4-ethylenedioxyphenyl)-methylene}-6-chloro-2-indolinone (p) 3-(Z)-{1-(4-[N-acetyl-N-(2-dimethylaminoethyl)-amino]-phenylamino)-1-(3,4-ethylenedioxyphenyl)-methylene}-6-chloro-2-indolinone (q) 3-(Z)-{1-(4-[4-methylpiperazin-1-yl-methyl]-phenylamino)-1-(3,4-methylenedioxy-phenyl)-methylene}-6-chloro-2-indolinone (r) 3-(Z)-{1-(4-[N-methanesulphonyl-N-(2-dimethylaminoethyl)-amino]-phenylamino)—(3,4-ethylenedioxyphenyl)-methylene}-6-methoxycarbonyl-2-indolinone (s) 3-(Z)-{1-(4-[pyrrolidin-1-yl-methyl]-phenylamino)-1-(3,4-ethylenedioxyphenyl)-methylene}-6-methoxycarbonyl-2-indolinone (t) 3-(Z)-{1-(4-[N-methyl-N-(dimethylaminomethylcarbonyl)-amino]-phenylamino)-1-(3,4-ethylenedioxyphenyl)-methylene}-6-methoxycarbonyl-2-indolinone (u) 3-(Z)-{1-(4-[ethylamino-methyl]-phenylamino)-1-(3,4-ethylenedioxyphenyl)-methylene}-6-methoxycarbonyl-2-indolinone (v) 3-(Z)-{1-(4-[4-methylpiperazin-1-yl-methyl]-phenylamino)-1-(3,4-ethylenedioxy-phenyl)-methylene}-6-methoxycarbonyl-2-indolinone (w) 3-(Z)-{1-(4-[dimethylamino-methyl]-phenylamino)-1-(3,4-methylenedioxyphenyl)-methylene}-6-methoxycarbonyl-2-indolinone (x) 3-(Z)-{1-(4-[diethylamino-methyl]-phenylamino)-1-(3,4-methylenedioxyphenyl)-methylene}-6-methoxycarbonyl-2-indolinone (y) 3-(Z)-{1-[4-(dimethylaminocarbonyl)-phenylamino]-1-(1-methyl-benzimidazol-5-yl)-methylene}-6-fluoro-2-indolinone (z) 3-(Z)-{1-(4-[N-propionyl-N-(3-dimethylaminopropyl)-amino]-phenylamino)-1-(3,4-ethylenedioxyphenyl)-methylene}-6-fluoro-2-indolinone (aa) 3-(Z)-{1-(4-[N-propionyl-N-(2-dimethylaminoethyl)-amino]-phenylamino)-1-(3,4-ethylenedioxyphenyl)-methylene}-6-fluoro-2-indolinone (ab) 3-(Z)-{1-(4-[N-methanesulphonyl-N-(2-dimethylaminoethyl)-amino]-phenylamino)-1-(3,4-ethylenedioxyphenyl)-methylene}-6-fluoro-2-indolinone (ac) 3-(Z)-{1-(4-[N-acetyl-N-(2-dimethylaminoethyl)-amino]-phenylamino)-1-(3,4-ethylenedioxyphenyl)-methylene}-6-methoxycarbonyl-2-indolinone (ad) 3-(Z)-{1-(4-[N-methyl-N-(2-dimethylaminoethyl)aminocarbonyl]-phenylamino)-1-(3,4-ethylenedioxyphenyl)-methylene}-6-methoxycarbonyl-2-indolinone (ae) 3-(Z)-{1-(4-[N-methyl-N-(3-dimethylaminopropyl)aminocarbonyl]-phenylamino)-1-(3,4-ethylenedioxyphenyl)-methylene}-6-methoxycarbonyl-2-indolinone (af) 3-(Z)-{1-(4-[N-methyl-N-(2-dimethylaminoethyl)aminocarbonyl]-phenylamino)-1-(3,4-methylenedioxyphenyl)-methylene}-6-methoxycarbonyl-2-indolinone (ag) 3-(Z)-{1-[4-(dimethylaminomethyl)-phenylamino]-1-(benzimidazol-5-yl)-methylene}-2-indolinone (ah) 3-(Z)-{1-(4-[1-methyl-piperazin-4-yl-methyl]-phenylamino)-1-(3,4-ethylenedioxy-phenyl)-methylene}-6-dimethylaminocarbonyl-2-indolinone (ai) 3-(Z)-{1-[4-(pyrrolidin-1-yl-methyl)-phenylamino]-1-(benzimidazol-5-yl)-methylene}-6-chloro-2-indolinone (aj) 3-(Z)-{1-(4-[N-methyl-N-(dimethylaminomethylcarbonyl)-amino]-phenylamino)-1-(3,4-methylenedioxyphenyl)-methylene}-2-indolinone (ak) 3-(Z)-{1-(4-[N-methyl-N-(dimethylaminomethylcarbonyl)-amino]-phenylamino)-1-(1-methyl-benzimidazol-5-yl)-methylene}-6-chloro-2-indolinone (al) 3-(Z)-{1-(4-[N-acetyl-N-(2-dimethylaminoethyl)-amino]-phenylamino)-1-(3,4-difluoromethylenedioxy)phenyl)-methylene}-6-chloro-2-indolinone (am) 3-(Z)-{1-(4-[N-methyl-N-(1-methyl-4-piperidinyl)-aminocarbonyl]-phenylamino)-1-(3,4-ethylenedioxyphenyl)-methylene}-6-fluoro-2-indolinone (an) 3-(Z)-{1-(4-[N-methyl-N-(dimethylaminomethylcarbonyl)-amino]-phenylamino)-1-(3-furyl)-methylene}-2-indolinone (ao) 3-(Z)-{1-(4-[N-(3-pyridylcarbonyl)-N-(2-dimethylaminoethyl)-amino]-phenyl-amino)-1-(3,4-methylenedioxyphenyl)-methylene}-6-chloro-2-indolinone (ap) 3-(Z)-{1-(4-[2-(diethylamino)ethyl-sulphonyl]-phenylamino)-1-(3,4-methylenedioxyphenyl)-methylene}-6-chloro-2-indolinone (aq) 3-(Z)-{1-[4-(dimethylaminomethyl)-phenylamino]-1-(1-methyl-benzimidazol-5-yl)-methylene}-2-indolinone (ar) 3-(Z)-{1-(4-[1-methylimidazol-2-yl]-phenylamino)-1-(quinoxalin-6-yl)-methylene}-6-chloro-2-indolinone (as) 3-(Z)-{1-[4-(pyrrolid-2-on-1-yl)-phenylamino]-1-(1-methyl-benzimidazol-5-yl)-methylene}-6-fluoro-2-indolinone
(at) 3-(Z)-{1-[4-(3,5-dimethyl-pyrazol-1-yl)-phenylamino]-1-(1-methyl-benzimidazol-5-yl)-methylene}-6-fluoro-2-indolinone
(au) 3-(Z)-{1-[4-(N-methyl-N-{2-dimethylamino-ethyl}-aminosulphonyl)-phenylamino]-1-(1-methyl-benzimidazol-5-yl)-methylene}-6-fluoro-2-indolinone
(av) 3-(Z)-{1-[4-(dimethylaminomethyl)-phenylamino]-1-(1-methyl-benzotriazol-5-yl)-methylene}-2-indolinone
(aw) 3-(Z)-{1-(4-[(1-methyl-piperazin-4-yl)-carbonylmethyl]-phenylamino)-1-(3,4-ethylenedioxyphenyl)-methylene}-6-fluoro-2-indolinone
(ax) 3-(Z)-{1-(4-[N-(propanesulphonyl)-N-(2-dimethylaminoethyl)-amino]-phenylamino)-1-(4-pyridyl)-methylene}-6-chloro-2-indolinone
(ay) 3-(Z)-{1-[4-(pyrrolidin-1-yl-methyl)-phenylamino]-1-(2-methyl-benzimidazol-5-yl)-methylene}-6-chloro-2-indolinone
(az) 3-(Z)-{1-(4-[N-methyl-N-(4-methylpiperazin-1-yl-methylcarbonyl)-amino]-phenyl-amino)-1-(3,4-methylenedioxyphenyl)-methylene}-6-chloro-2-indolinone
(ba) 6-chloro-3-(Z)-[1-(4-{N-(2-dimethylamino-ethyl)-N-methanesulphonyl-amino}-3-chloro-phenylamino)-1-(1,2-ethylenedioxyphen-4-yl)-methylene]-2-indolinone
(bb) 6-chloro-3-(Z)-{1-[4-(N-dimethylaminomethylcarbonyl-N-methyl-amino)-3-methoxy-phenylamino]-1-(1,2-ethylenedioxyphen-4-yl)-methylene}-2-indolinone
(bc) 6-fluoro-3-(Z)-{1-[4-(N-dimethylaminomethylcarbonyl-N-methyl-amino)-3-methoxy-phenylamino]-1-(1,2-ethylenedioxyphen-4-yl)-methylene}-2-indolinone
(bd) 6-fluoro-3-(Z)-[1-(4-{N-(2-dimethylamino-ethyl)-N-methanesulphonyl-amino}-3-chloro-phenylamino)-1-(1,2-ethylenedioxyphen-4-yl)-methylene]-2-indolinone The Table that follows contains the results found:

| compound | IC$_{50}$ [nM] |
|---|---|
| (a) | 11 |
| (b) | 4 |
| (c) | 2 |
| (d) | 3 |
| (e) | 16 |
| (f) | 2 |
| (g) | 9 |
| (h) | 3 |
| (i) | 0.5 |
| (j) | 0.2 |
| (k) | 0.7 |
| (l) | 10 |
| (m) | 0.3 |
| (n) | 1 |
| (o) | 1 |
| (p) | 2 |
| (q) | 2 |
| (r) | 0.2 |
| (s) | 0.6 |
| (t) | 0.6 |
| (u) | 0.8 |
| (v) | 1 |
| (w) | 0.5 |
| (x) | 1 |
| (y) | 14 |
| (z) | 0.5 |
| (aa) | 0.6 |
| (ab) | 1 |
| (ac) | 0.2 |
| (ad) | 0.4 |
| (ae) | 0.5 |
| (af) | 0.5 |
| (ag) | 31 |
| (ah) | 100 |
| (ai) | 3 |
| (aj) | 13 |
| (ak) | 30 |
| (al) | 83 |
| (am) | 5 |
| (an) | 58 |
| (ao) | 6 |
| (ap) | 120 |
| (aq) | 24 |
| (ar) | 71 |
| (as) | 18 |
| (at) | 30 |
| (au) | 13 |
| (av) | 94 |
| (aw) | 4 |
| (ax) | 37 |
| (ay) | 19 |
| (az) | 6 |
| (ba) | 30 |
| (bb) | 33 |
| (bc) | 5 |
| (bd) | 5 |

In view of their inhibitory effect on the proliferation of cells, particularly endothelial cells and tumour cells, the compounds of general formula I are suitable for treating diseases in which the proliferation of cells, particularly endothelial cells, plays a part.

Thus, for example, the proliferation of endothelial cells and the concomitant neovascularisation constitute a crucial stage in tumour progression (Folkman J. et al., Nature 339, 58–61, (1989); Hanahan D. and Folkman J., Cell 86, 353–365, (1996)). Furthermore, the proliferation of endothelial cells is also important in haemangiomas, in metastasisation, rheumatoid arthritis, psoriasis and ocular neovascularisation (Folkman J., Nature Med. 1, 27–31, (1995)). The therapeutic usefulness of inhibitors of endothelial cell proliferation was demonstrated in the animal model for example by O'Reilly et al. and Parangi et al. (O'Reilly M. S. et al., Cell 88, 277–285, (1997); Parangi S. et al., Proc Natl Acad Sci USA 93, 2002–2007, (1996)).

The compounds of general formula I, their tautomers, their stereoisomers or the physiologically acceptable salts thereof are thus suitable, for example, for treating tumours (e.g. plate epithelial carcinoma, astrocytoma, Kaposi's sarcoma, glioblastoma, lung cancer, bladder cancer, head and neck carcinoma, melanoma, ovarian cancer, prostate cancer, breast cancer, small-cell lung cancer, glioma, colorectal cancer, urogenital cancer and gastrointestinal cancer as well as haematological cancers such as multiple myeloma), psoriasis, arthritis (e.g. rheumatoid arthritis), haemangioma, angiofibroma, eye diseases (e.g. diabetic retinopathy), neovascular glaucoma, kidney diseases (e.g. glomerulonephritis), diabetic retinopathy, malignant nephrosclerosis, thrombic microangiopathic syndrome, transplant rejections and glomerulopathy, fibrotic diseases (e.g. cirrhosis of the liver), mesangial cell proliferative diseases, arteriosclerosis, damage to the nerve tissue and for inhibiting the reocclusion of blood vessels after treatment with a balloon catheter, in vascular prosthetics or after the fitting of mechanical devices for holding the blood vessels open (e.g. stents), or other diseases in which cell proliferation or angiogenesis are involved.

By reason of their biological properties the compounds according to the invention may be used on their own or in conjunction with other pharmacologically active compounds, for example in tumour therapy, in monotherapy or in conjunction with other anti-tumour therapeutic agents, for example in combination with topoisomerase inhibitors (e.g. etoposide), mitosis inhibitors (e.g. vinblastine, taxol), compounds which interact with nucleic acids (e.g. cisplatin, cyclophosphamide, adriamycin), hormone antagonists (e.g. tamoxifen), inhibitors of metabolic processes (e.g. 5-FU etc.), cytokines (e.g. interferons), receptor tyrosine kinase and kinase inhibitors, antibodies, or in conjunction with radiotherapy, etc. These combinations may be administered either simultaneously or sequentially.

For pharmaceutical use the compounds according to the invention are generally used for warm-blooded vertebrates, particularly humans, in doses of 0.01–100 mg/kg of body weight, preferably 0.1–20 mg/kg. For administration they are formulated with one or more conventional inert carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof in conventional galenic preparations such as plain or coated tablets, capsules, powders, injectable solutions, ampoules, suspensions, solutions, sprays or suppositories.

The following Examples are intended to illustrate the present invention without restricting it:
Abbreviations used:
DMF=N,N-dimethylformamide
DMSO=dimethylsulphoxide
HOBT=1-hydroxy-1H-benzotriazole
TBTU=O-benzotriazol-1-yl-N,N,N',N'-tetramethyluronium-tetrafluoroborate
THF=tetrahydrofuran Preparation of the Starting Compounds:

EXAMPLE I 5-carboxy-2-methyl-isoindol-1,3-dione 19.2 g of trimellitic anhydride are stirred in 100 ml of N-methylformamide for 4 hours at 140° C. and then overnight at ambient temperature. After the addition of 300 ml of water the mixture is stirred for a further 12 hours; then the precipitate is suction filtered, washed with water and dried at 80° C.
Yield: 15.5 g (75% of theory)
$R_f$ value: 0.59 (RP-8, methanol/5% sodium chloride solution=7:3) $C_{10}H_7NO_4$
Mass spectrum: m/z=204 [M–H]$^-$

EXAMPLE II 3,4-ethylenedioxybenzoic acid

A suspension of 80.1 g of calcium hypochlorite in 360 ml of water and a suspension of 6.72 g of sodium hydroxide and 56.4 g of sodium carbonate in 170 ml of water are combined and heated to 50° C. with stirring. The precipitate is removed by filtration and the solution obtained is combined with 25.0 g of 1,4-benzodioxan-6-yl-methylketone. The mixture is stirred for 15 h at 60° C., and after cooling to ambient temperature extracted with ethyl acetate. The aqueous phase is adjusted to a pH of 3 by the addition of concentrated hydrochloric acid while cooling with ice. The product precipitated is suction filtered, washed with water and dried at 90° C.
Yield: 18.8 g (74% of theory)
$R_f$ value: 0.65 (silica gel, dichloromethane/methanol/acetic acid=90:10:1) $C_9H_8O_4$

EXAMPLE III 1-methylbenzimidazol-5-carboxylic acid 25.0 g of 4-methylamino-3-nitrobenzoic acid, dissolved in 200 ml DMF, are hydrogenated for 5 hours at a hydrogen pressure of 30 psi with the addition of 2.5 g of palladium on activated charcoal (10%). The catalyst is suction filtered and the solvent is distilled off. The residue is stirred with diethyl ether, suction filtered and dried. The crude product thus obtained (19.7 g) is refluxed for 2 hours in 250 ml formic acid. After the solvent has been distilled off the residue is stirred with diethyl ether, suction filtered and dried.
Yield: 21 g (94% of theory)
$R_f$ value: 0.25 (silica gel, dichloromethane/methanol/acetic acid=90:10:1) $C_9H_8N_2O_2$

EXAMPLE IV

2-Dibenzylaminooxazole-4-carboxylic acid 21.6 g N-benzylurea and 28.7 g ethyl bromopyruvate are refluxed in 120 ml of ethanol for 18 hours. The oily residue obtained by distilling off the solvent is combined with soda solution (10 g in 170 ml of water) and 100 ml of diethyl ether and stirred for 2 hours. After the addition of 200 ml of ethyl acetate the phases are separated, the organic phase is extracted twice with water and evaporated to dryness.

The intermediate product (11.8 g) is dissolved in 80 ml DMSO and combined with 5.95 g potassium-tert-butoxide. After 90 minutes' stirring at ambient temperature 6.43 ml benzylbromide are slowly added dropwise and the mixture is stirred for a further 3 hours. The mixture is poured onto 400 ml ice water and extracted twice with ethyl acetate. The organic phases are combined, counter-extracted with water and evaporated to dryness. To saponify the ester the residue is dissolved in 200 ml of ethanol, combined with 100 ml of 1 molar sodium hydroxide solution and stirred for 2 hours. After the ethanol has been distilled off the residue is extracted with diethyl ether, the aqueous phase is neutralised with 100 ml 1 molar hydrochloric acid and extracted with ethyl acetate. The ethyl acetate phase is counter-extracted with water, dried with sodium sulphate and evaporated to dryness. The oily crude product is stirred with petroleum ether/diethyl ether, suction filtered and dried at 40° C.
Yield: 11.6 g (28% of theory)
$R_f$ value: 0.4 (silica gel, dichloromethane/methanol/acetic acid 90:10:1) $C_{18}H_{16}N_2O_3$
Mass spectrum: m/z=309 [M+H]$^+$

EXAMPLE V

Dimethyl 2-(4-fluoro-2-nitrophenyl)-malonate 185 g potassium-tert-butoxide are added to a solution of 188 ml of dimethyl malonate in 970 ml N-methylpyrrolidone while cooling with ice and the mixture is stirred for 2 hours. Over a period of 30 minutes 150 ml of 2,5-difluoronitrobenzene are added dropwise to the slurry formed and then the mixture is stirred for 6 hours at 85° C. The mixture is poured onto 4 litres of ice water and 250 ml of concentrated hydrochloric acid and extracted with 2 litres of ethyl acetate. The organic phase is dried with sodium sulphate and evaporated down. The oily residue is stirred twice with water and then taken up in 600 ml of ethyl acetate. The solution is dried with sodium sulphate and evaporated to dryness. The crude product crystallised is recrystallised from 600 ml of ethyl acetate/hexane=2:8 and dried.

Yield: 222 g (59% of theory)

$R_f$ value: 0.4 (silica gel, cyclohexane/ethyl acetate=5:1) $C_{11}H_{10}FNO_6$ Mass spectrum: m/z=270 [M−H]⁻

The following compound is prepared analogously to Example V:

(V.1) diethyl 2-(4-bromo-2-nitrophenyl)-malonate from 2,5-dibromonitrobenzene and diethyl malonate $R_f$ value: 0.40 (silica gel, petroleum ether/ethyl acetate=5:1) $C_{13}H_{14}BrNO_6$ Mass spectrum: m/z=359/361 [M]⁺

EXAMPLE VI 4-fluoro-2-nitrophenylacetic acid 50.0 g of dimethyl 2-(4-fluoro-2-nitrophenyl)-malonate are stirred in 400 ml of 6 molar hydrochloric acid for 20 hours at 100° C., then combined with 400 ml of water and cooled to 0° C. The precipitate formed is suction filtered, washed with water and 100 ml petroleum ether and dried.

Yield: 34.5 g (94% of theory)

$R_f$ value: 0.3 (silica gel, cyclohexane/ethyl acetate=5:2) $C_8H_6FNO_4$

Mass spectrum: m/z=244 [M+2Na—H]⁺

EXAMPLE VII 6-fluoro-2-indolinone 119 g 4-fluoro-2-nitrophenylacetic acid are hydrogenated in 600 ml acetic acid with the addition of 20 g palladium on activated charcoal (10%) under 50 psi of hydrogen pressure. The catalyst is suction filtered, the solvent distilled off. The crude product is stirred with 500 ml petroleum ether, suction filtered, washed with water and dried.

Yield: 82.5 g (91% of theory)

$R_f$ value: 0.31(silica gel, petroleum ether/ethyl acetate=1:1) $C_8H_6FNO$

Mass spectrum: m/z=210 [M+CH₃COO]⁻

The following compound is prepared analogously to Example VII:

(VII.1) 6-bromo-2-indolinone from diethyl 2-(4-bromo-2-nitrophenyl)-malonate (educt V.1) with Raney nickel as hydrogenation catalyst $R_f$ value: 0.45 (silica gel, petroleum ether/ethyl acetate=1:1) $C_8H_6BrNO$ Mass spectrum: m/z=210/212 [M−H]⁻

EXAMPLE VIII 1-acetyl-6-fluoro-2-indolinone 82.5 g of 6-fluoro-2-indolinone are stirred in 180 ml acetic anhydride for 3 hours at 130° C. After cooling to ambient temperature the precipitate is suction filtered, washed with 100 ml petroleum ether and dried.

Yield: 64.8 g (61% of theory)

$R_f$ value: 0.75(silica gel, petroleum ether/ethyl acetate=1:1) $C_{10}H_8FNO_2$ Mass spectrum: m/z=192 [M−H]⁻

The following compounds are prepared analogously to Example VIII:

(VIII.1) 1-acetyl-2-indolinone from 2-indolinone and acetic anhydride (VIII.2) 1-acetyl-6-chloro-2-indolinone from 6-chloro-2-indolinone and acetic anhydride (VIII.3) 1-acetyl-6-methoxycarbonyl-2-indolinone from 6-methoxycarbonyl-2-indolinone and acetic anhydride (VIII.4) 1-acetyl-6-bromo-2-indolinone from 6-bromo-indolinone and acetic anhydride

EXAMPLE IX 1-acetyl-3-[1-hydroxy-1-(2-furyl)methylene]-2-indolinone

An ice-cooled solution of 7.0 g 1-acetyl-2-indolinone and 10.8 g DMAP in 60 ml DMF is combined with 4.4 ml of furan-2-carboxylic acid chloride. The mixture is stirred for 1 hour at ambient temperature, then poured onto 40 ml of conc. hydrochloric acid and 500 ml ice water. The precipitate is suction filtered, washed successively with ethanol and diethyl ether and dried.

Yield: 8.67 g (81% of theory)

$R_f$ value: 0.6 (silica gel, ethyl acetate) $C_{15}H_{11}NO_4$ melting point: 128–130° C.

The following compound is prepared analogously to Example IX:

(IX.1) 1-acetyl-6-chloro-3-[1-hydroxy-1-(2-pyrrolyl)methylene]-2-indolinone from 1-acetyl-6-chloro-2-indolinone and pyrrole-2-carboxylic acid

EXAMPLE X 1-acetyl-3-[1-hydroxy-1-(2-pyrazinyl)methylene]-2-indolinone 4.38 g 1-acetyl-2-indolinone, 3.41 g pyrazine-2-carboxylic acid, 8.83 g TBTU, 4.21 g HOBT-hydrate and 21.8 ml ethyldiisopropylamine are stirred in 70 ml DMF for 15 hours at ambient temperature. The mixture is poured onto 400 ml ice water and 10 ml of conc. hydrochloric acid and stirred for 1 hour. The precipitate is suction filtered, washed with water, stirred with methanol, suction filtered again, washed with methanol and dried at 100° C.

Yield: 4.43 g (63% of theory)

$R_f$ value: 0.2 (silica gel, petroleum ether/dichloromethane/methanol=5:4:1) $C_{15}H_{11}N_3O_3$ Mass spectrum: m/z=280 [M−H]⁻

The following compounds are prepared analogously to Example X:

(X.1) 1-acetyl-3-[1-hydroxy-1-(3,4-methylenedioxyphenyl)methylene]-2-indolinone from 1-acetyl-2-indolinone and 3,4-methylenedioxybenzoic acid (X.2) 1-acetyl-3-[1-hydroxy-1-(3-thienyl)methylene]-2-indolinone from 1-acetyl-2-indolinone and thiophene-3-carboxylic acid (X.3) 1-acetyl-3-[1-hydroxy-1-(5-methylisoxazol-3-yl)methylene]-2-indolinone from 1-acetyl-2-indolinone and 5-methylisoxazole-3-carboxylic acid (X.4) 1-acetyl-3-[1-hydroxy-1-(3-methylpyrazol-5-yl)methylene]-2-indolinone from 1-acetyl-2-indolinone and 3-methylpyrazole-5-carboxylic acid (X.5) 1-acetyl-3-[1-hydroxy-1-(4-acetylamino-3-nitrophenyl)methylene]-2-indolinone from 1-acetyl-2-indolinone and 4-acetylamino-3-nitrobenzoic acid (X.6) 1-acetyl-3-{1-hydroxy-1-[2-(dibenzylamino)oxazol-4-yl]methylene}-2-indolinone from 1-acetyl-2-indolinone and 2-(dibenzylamino)oxazole-4-carboxylic acid, the precipitate obtained after the addition of water and hydrochloric acid being purified by chromatography on silica gel (eluent: petroleum ether/dichloromethane/ethyl acetate=5:4:1), then stirred with diethyl ether, suction filtered and dried.

(X.7) 1-acetyl-3-[1-hydroxy-1-(2-methyl-isoindol-1,3-dion-5-yl)methylene]-2-indolinone from 1-acetyl-2-indolinone and 2-methyl-isoindol-1,3-dione-5-carboxylic acid (X.8) 1-acetyl-6-chloro-3-[1-hydroxy-1-(4-acetylamino-3-nitrophenyl)-methylene]-2-indolinone from 1-acetyl-6-chloro-2-indolinone and 4-acetylamino-3-nitrobenzoic acid (X.9) 1-acetyl-6-chloro-3-[1-hydroxy-1-(4-pyridazinyl)methylene]-2-indolinone from 1-acetyl-6-chloro-2-indolinone and pyridazine-4-carboxylic acid (X.10) 1-acetyl-6-chloro-3-[1-hydroxy-1-(3,4-methylenedioxyphenyl)-methylene]-2-indolinone from 1-acetyl-6-chloro-2-indolinone and 3,4-methylenedioxybenzoic acid (X.11) 1-acetyl-6-chloro-3-[1-hydroxy-1-(3,4-ethylenedioxyphenyl)methylene]-2-indolinone from 1-acetyl-6-chloro-2-indolinone and 3,4-ethylenedioxybenzoic acid (X.12) 1-acetyl-6-chloro-3-{1-hydroxy-1-[3,4-(difluoromethylene)dioxyphenyl]-methylene}-2-indolinone from 1-acetyl-6-chloro-2-indolinone and 3,4-(difluoromethylene)dioxybenzoic acid (X.13) 1-acetyl-6-fluoro-3-[1-hydroxy-1-(3,4-ethylenedioxyphenyl)methylene]-2-indolinone from 1-acetyl-6-fluoro-2-indolinone and 3,4-ethylenedioxybenzoic acid (X.14) 1-acetyl-3-[1-hydroxy-1-(3-furyl)methylene]-2-indolinone from 1-acetyl-2-indolinone and furan-3-carboxylic acid, the solvent being distilled off before the addition of the ice water.

(X.15) 1-acetyl-3-[1-hydroxy-1-(4-methylamino-3-nitrophenyl)methylene]-2-indolinone from 1-acetyl-2-indolinone and 4-methylamino-3-nitrobenzoic acid (X.16) 1-acetyl-6-fluoro-3-[1-hydroxy-1-(4-methylamino-3-nitrophenyl)methylene]-2-indolinone from 1-acetyl-6-fluoro-2-indolinone and 4-methylamino-3-nitrobenzoic acid (X.17) 1-acetyl-6-chloro-3-[1-hydroxy-1-(quinazolin-6-yl)methylene]-2-indolinone from 1-acetyl-6-chloro-2-indolinone and quinazolin-6-carboxylic acid (which is prepared by alkaline saponification of the methyl ester).

(X.18) 1-acetyl-3-[1-hydroxy-1-(1-methyl-benzotriazol-5-yl)methylene]-2-indolinone from 1-acetyl-2-indolinone and 1-methylbenzotriazol-5-carboxylic acid (which is prepared analogously to the preparation of 1-methylbenzotriazole, described in: A. Reissert, Chem. Ber. 47 (1914) 676).

(X.19) 1-acetyl-6-bromo-3-[1-hydroxy-1-(3,4-methylenedioxyphenyl)-methylene]-2-indolinone from 1-acetyl-6-bromo-2-indolinone and 3,4-methylenedioxybenzoic acid (X.20) 1-acetyl-6-fluoro-3-[1-hydroxy-1-(3,4-methylenedioxyphenyl)methylene]-2-indolinone from 1-acetyl-6-fluoro-2-indolinone and 3,4-methylenedioxybenzoic acid

EXAMPLE XI 1-acetyl-6-chloro-3-[1-hydroxy-1-(4-pyridyl)methylene]-2-indolinone 6.3 g of 1-acetyl-6-chloro-2-indolinone, 4.06 g pyridine-4-carboxylic acid, 10.6 g TBTU and 21 ml triethylamine are stirred in 60 ml of DMF for 15 hours at ambient temperature. The mixture is combined with water, then adjusted to pH 5 by the addition of 10% acetic acid. The precipitate is suction filtered, washed with water and taken up in ethyl acetate. The solution obtained is dried with sodium sulphate and evaporated almost to dryness. The precipitate obtained is suction filtered and dried at 100° C.

Yield: 6.5 g (69% of theory)

$R_f$ value: 0.6 (RP8, methanol/5% NaCl=4:1) $C_{16}H_{11}ClN_2O_3$

Mass spectrum: m/z=313 [M–H]$^-$ melting point: 215–217° C.

The following compounds are prepared analogously to Example XI:

(XI.1) 1-acetyl-6-chloro-3-[1-hydroxy-1-(3-pyridyl)methylene]-2-indolinone from 1-acetyl-6-chloro-2-indolinone and pyridine-3-carboxylic acid (XI.2) 1-acetyl-6-methoxycarbonyl-3-[1-hydroxy-1-(3,4-ethylenedioxyphenyl)-methylene]-2-indolinone from 1-acetyl-6-methoxycarbonyl-2-indolinone and 3,4-ethylenedioxybenzoic acid (XI.3) 1-acetyl-3-[1-hydroxy-1-(4-imidazolyl)methylene]-2-indolinone from 1-acetyl-2-indolinone and imidazole-4-carboxylic acid, the solvent being distilled off before the addition of water.

(XI.4) 1-acetyl-6-methoxycarbonyl-3-[1-hydroxy-1-(3,4-methylenedioxyphenyl)-methylene]-2-indolinone from 1-acetyl-6-methoxycarbonyl-2-indolinone and 3,4-methylenedioxybenzoic acid

EXAMPLE XII 1-acetyl-6-chloro-3-[1-hydroxy-1-(1-methyl-5-benzimidazolyl)methylene]-2-indolinone 3.5 g of 1-acetyl-6-chloro-2-indolinone, 3.4 g of 1-methylbenzimidazole-5-carboxylic acid, 6.1 g of TBTU, 2.9 g of HOBT-hydrate and 8.7 ml ethyldiisopropylamine are stirred in 100 ml DMF for 15 hours at ambient temperature. The mixture is combined with water and extracted with ethyl acetate, while the crude product is partially precipitated. The residue obtained by distilling off the solvent is taken up in dichloromethane and a little methanol and extracted with water. The organic phase is evaporated down, the residue stirred successively with ethyl acetate and diethyl ether, suction filtered and dried.

Yield: 2.2 g (35% of theory)

$R_f$ value: 0.17 (silica gel, ethyl acetate/methanol/ammonia solution=80:20:1) $C_{19}H_{14}ClN_3O_3$ Mass spectrum: m/z=368/390 [M+H]$^+$ The following compound is prepared analogously to Example XII:

(XII.1) 1-acetyl-6-chloro-3-[1-hydroxy-1-(1-benzyl-5-imidazolyl)methylene]-2-indolinone from 1-acetyl-6-chloro-2-indolinone and 1-benzylimidazole-5-carboxylic acid, the resulting liquid product being obtained by evaporation of the ethyl acetate phase.

EXAMPLE XIII 1-acetyl-3-[1-chloro-1-(4-acetylamino-3-nitrophenyl)methylene]-2-indolinone A suspension of 11.4 g of 1-acetyl-3-(1-hydroxy-1-(4-acetylamino-3-nitrophenyl)-methylene)-2-indolinone and 9.37 g phosphorus pentachloride in 200 ml dioxane is stirred for 4 hours at 100° C. After the addition of another 2.0 g of phosphorus pentachloride the mixture is stirred for a further 3 hours at 10° C. Then the solvent is distilled off, the residue is stirred with 100 ml of ethyl acetate, suction filtered, washed with ethyl acetate and dried at 60° C.

Yield: 6.40 g (53% of theory)

$R_f$ value: 0.7 (silica gel, dichloromethane/ethyl acetate=9:1) $C_{19}H_{14}ClN_3O_5$ Mass spectrum: m/z=398/400 [M−H]⁻

The following compounds are prepared analogously to Example XIII:

(XIII.1) 1-acetyl-6-chloro-3-[1-chloro-1-(4-acetylamino-3-nitrophenyl)methylene]-2-indolinone from 1-acetyl-6-chloro-3-[1-hydroxy-1-(4-acetylamino-3-nitrophenyl)methylene]-2-indolinone (XIII.2) 1-acetyl-6-chloro-3-[1-chloro-1-(3-pyridyl)methylene]-2-indolinone from 1-acetyl-6-chloro-3-[1-hydroxy-1-(3-pyridyl)methylene]-2-indolinone (XIII.3) 1-acetyl-6-chloro-3-[1-chloro-1-(4-pyridyl)methylene]-2-indolinone from 1-acetyl-6-chloro-3-[1-hydroxy-1-(4-pyridyl)methylene]-2-indolinone (XIII.4) 6-chloro-3-[1-chloro-1-(1-methyl-5-benzimidazolyl)methylene]-2-indolinone from 1-acetyl-6-chloro-3-[1-hydroxy-1-(1-methyl-5-benzimidazolyl)methylene]-2-indolinone (XIII.5) 1-acetyl-6-chloro-3-[1-chloro-1-(1-benzyl-5-imidazolyl)methylene]-2$$-indolinone from 1-acetyl-6-chloro-3-[1-hydroxy-1-(1-benzyl-5-imidazolyl)methylene]-2-indolinone

EXAMPLE XIV 1-acetyl-6-chloro-3-[1-chloro-1-(2-pyrrolyl)methylene]-2-indolinone A suspension of 4.5 g of 1-acetyl-6-chloro-3-[1-hydroxy-1-(2-pyrrolyl)methylene]-2-indolinone and 3.4 g of phosphorus pentachloride in 50 ml of dioxane and 50 ml of toluene is stirred for 3 hours at 90° C. Then the solvent is distilled off and the residue is purified by chromatography on silica gel (eluant: toluene).

Yield: 2.2 g (46% of theory)

$R_f$ value: 0.8 (silica gel, toluene) $C_{15}H_{10}Cl_2N_2O_2$

The following compound is prepared analogously to Example XIV:

(XIV.1) 1-acetyl-6-chloro-3-[1-chloro-1-(4-pyridazinyl)methylene]-2-indolinone from 1-acetyl-6-chloro-3-(1-hydroxy-1-(4-pyridazinyl)methylene)-2-indolinone, using dichloromethane/methanol=9:1 as the eluant system.

EXAMPLE XV 1-acetyl-3-[1-chloro-1-(5-methyl-3-isoxazolyl)methylene]-2-indolinone 3.00 g of 1-acetyl-3-[1-hydroxy-1-(5-methyl-3-isoxazolyl)methylene]-2-indolinone, 5.09 ml carbon tetrachloride and 5.54 g triphenylphosphine are refluxed in 100 ml of THF for 8 hours. The residue obtained after the solvent has been distilled off is purified by chromatography on silica gel (eluant: petroleum ether/ethyl acetate=9:1).

Yield: 2.53 g (79% of theory)

$R_f$ value: 0.7 (silica gel, petroleum ether/dichloromethane/methanol=5:4:1) $C_{15}H_{11}ClN_2O_3$ Mass spectrum: m/z=302/304 [M⁻]⁺

The following compound is prepared analogously to Example XV:

(XV.1) 1-acetyl-3-[1-chloro-1-(3-methyl-5-pyrazolyl)methylene]-2-indolinone from 1-acetyl-3-[1-hydroxy-1-(3-methyl-5-pyrazolyl)methylene]-2-indolinone

EXAMPLE XVI 1-acetyl-6-chloro-3-[1-methoxy-1-(3,4-methylenedioxyphenyl)methylene]-2-indolinone A solution of 20.9 g of 1-acetyl-6-chloro-3-[1-hydroxy-1-(3,4-methylenedioxyphenyl)-methylene]-2-indolinone and 40 ml of ethyldiisopropylamine in 200 ml dichloromethane is combined batchwise with 17.3 g of trimethyloxonium tetrafluoroborate, the mixture is stirred overnight and then extracted twice with water. The organic phase is dried with magnesium sulphate and evaporated to dryness. The residue is stirred with methanol, suction filtered, washed with methanol and dried at 80° C.

Yield: 9.40 g (43% of theory)

$R_f$ value: 0.7 (silica gel, petroleum ether/dichloromethane/methanol=5:4:1) $C_{19}H_{14}ClNO_5$ Mass spectrum: m/z=371/373 [M⁻]⁺

The following compounds are prepared analogously to Example XVI:

(XVI.1) 1-acetyl-6-chloro-3-[1-methoxy-1-(3,4-ethylenedioxyphenyl)-methylene]-2-indolinone from 1-acetyl-6-chloro-3-[1-hydroxy-1-(3,4-ethylenedioxyphenyl)methylene]-2-indolinone (XVI.2) 1-acetyl-6-chloro-3-{1-methoxy-1-[3,4-(difluoromethylenedioxy)phenyl]-methylene}-2-indolinone from 1-acetyl-6-chloro-3-{1-hydroxy-1-[3,4-(difluoromethylenedioxy)phenyl]methylene}-2-indolinone (XVI.3) 1-acetyl-3-[1-methoxy-1-(2-methyl-isoindol-1,3-dion-5-yl)methylene]-2-indolinone from 1-acetyl-3-[1-hydroxy-1-(2-methyl-isoindol-1,3-dion-5-yl)methylene]-2-indolinone (XVI.4) 1-acetyl-3-[1-methoxy-1-(3-furyl)methylene]-2-indolinone from 1-acetyl-3-[1-hydroxy-1-(3-furyl)methylene]-2-indolinone (XVI.5) 1-acetyl-3-[1-methoxy-1-(2-dibenzylamino-4-oxazolyl)methylene]-2-indolinone from 1-acetyl-3-[1-hydroxy-1-(2-dibenzylamino-4-oxazolyl)methylene]-2-indolinone (XVI.6) 1-acetyl-6-methoxycarbonyl-3-[1-methoxy-1-(3,4-ethylenedioxyphenyl)-methylene]-2-indolinone from 1-acetyl-6-methoxycarbonyl-3-[1-hydroxy-1-(3,4-ethylenedioxyphenyl)methylene]-2-indolinone (XVI.7) 1-acetyl-6-fluoro-3-[1-methoxy-1-(3,4-ethylenedioxyphenyl)-methylene]-2-indolinone from 1-acetyl-6-fluoro-3-[1-hydroxy-1-(3,4-ethylenedioxyphenyl)methylene]-2-indolinone (XVI.8) 1-acetyl-3-[1-methoxy-1-(4-methylamino-3-nitrophenyl)methylene]-2-indolinone from 1-acetyl-3-[1-hydroxy-1-(4-methylamino-3-nitrophenyl)methylene]-2-indolinone (XVI.9) 1-acetyl-6-fluoro-3-[1-methoxy-1-(4-methylamino-3-nitrophenyl)methylene]-2-indolinone from 1-acetyl-6-fluoro-3-[1-hydroxy-1-(4-methylamino-3-nitrophenyl)methylene]-2-indolinone (XVI.10) 1-acetyl-6-chloro-3-[1-methoxy-1-(quinazolin-6-yl)-methylene]-2-indolinone from 1-acetyl-6-chloro-3-[1-hydroxy-1-(quinazolin-6-yl)methylene]-2-indolinone (XVI.11) 1-acetyl-6-methoxycarbonyl-3-[1-methoxy-1-(3,4-methylenedioxyphenyl)-methylene]-2-indolinone from 1-acetyl-6-methoxycarbonyl-3-[1-hydroxy-1-(3,4-methylenedioxyphenyl)-methylene]-2-indolinone
(XVI.12) 1-acetyl-3-[1-methoxy-1-(1-methylbenzotriazol-5-yl)methylene]-2-indolinone from 1-acetyl-3-[1-hydroxy-1-(1-methylbenzotriazol-5-yl)methylene]-2-indolinone
(XVI.13) 1-acetyl-6-bromo-3-[1-methoxy-1-(3,4-methylenedioxyphenyl)-methylene]-2-indolinone from 1-acetyl-6-bromo-3-[1-hydroxy-1-(3,4-methylenedioxyphenyl)methylene]-2-indolinone
(XVI.14) 1-acetyl-6-fluoro-3-[1-methoxy-1-(3,4-methylenedioxyphenyl)-methylene]-2-indolinone from 1-acetyl-6-fluoro-3-[1-hydroxy-1-(3,4-methylenedioxyphenyl)methylene]-2-indolinone

EXAMPLE XVII

6-Chloro-3-{1-[4-(4-methyl-1-piperazinyl-carbonyl)phenylamino]-1-(4-amino-3-nitrophenyl)methylene}-2-indolinone 2.61 g of 1-acetyl-6-chloro-3-[1-chloro-1-(4-acetylamino-3-nitrophenyl)methylene]-2-indolinone, 1.75 g of 4-(4-methyl-1-piperazinyl-carbonyl)aniline and 4.7 ml ethyldiisopropylamine are refluxed in 100 ml dioxane for 24 hours. The mixture is filtered while hot, the filtrate is evaporated to dryness. The residue is dissolved in dichloromethane, extracted three times with water, dried with sodium sulphate and evaporated to dryness. The semisolid intermediate product is dissolved in 10 ml DMF and 10 ml of methanol and after the addition of 4 ml of 6 molar sodium hydroxide solution stirred for 2 hours. After the addition of 300 ml of water the precipitate is suction filtered, dried, stirred with 15 ml of ethyl acetate/methanol/ammonia solution=85:15:1.5, suction filtered again and dried at 100° C.

Yield: 1.47 g (46% of theory)
$R_f$ value: 0.3 (silica gel, ethyl acetate/methanol/ammonia solution=80:20:2)
melting point: 190–195° C. $C_{27}H_{25}ClN_6O_4$
Mass spectrum: m/z=533/535 $[M+H]^+$ The following compounds are prepared analogously to Example XVII:
(XVII.1) 6-chloro-3-{1-[4-(pyrrolidin-1-ylmethyl)phenylamino]-1-(4-amino-3-nitrophenyl)methylene}-2-indolinone from 1-acetyl-6-chloro-3-[1-chloro-1-(4-acetylamino-3-nitrophenyl)methylene]-2-indolinone and 4-(pyrrolidin-1-ylmethyl)-aniline
(XVII.2) 6-chloro-3-{1-(4-[N-(dimethylaminomethylcarbonyl)-N-methyl-amino]phenylamino)-1-(4-amino-3-nitrophenyl)methylene}-2-indolinone from 1-acetyl-6-chloro-3-[1-chloro-1-(4-acetylamino-3-nitrophenyl)methylene]-2-indolinone and N-(dimethylaminomethylcarbonyl)-N-methyl-p-phenylenediamine
(XVII.3) 6-chloro-3-{1-(4-[N-acetyl-N-(2-dimethylaminoethyl)amino]phenylamino)-1-(4-amino-3-nitrophenyl)methylene}-2-indolinone from 1-acetyl-6-chloro-3-[1-chloro-1-(4-acetylamino-3-nitrophenyl)methylene]-2-indolinone and N-acetyl-N-(2-dimethylamino-ethyl)-p-phenylenediamine
(XVII.4) 6-chloro-3-{1-(4-[N-acetyl-N-(3-dimethylaminopropyl)amino]phenylamino)-1-(4-amino-3-nitrophenyl)methylene}-2-indolinone from 1-acetyl-6-chloro-3-[1-chloro-1-(4-acetylamino-3-nitrophenyl)methylene]-2-indolinone and N-acetyl-N-(3-dimethylamino-propyl)-p-phenylenediamine
(XVII.5) 6-chloro-3-{1-(4-[N-methanesulphonyl-N-(2-dimethylamino-ethyl)amino]-phenylamino)-1-(4-amino-3-nitrophenyl)methylene}-2-indolinone from 1-acetyl-6-chloro-3-[1-chloro-1-(4-acetylamino-3-nitrophenyl)methylene]-2-indolinone and N-methanesulphonyl-N-(2-dimethylamino-ethyl)-p-phenylenediamine
(XVII.6) 3-{1-[4-(dimethylaminomethyl)phenylamino]-1-(4-amino-3-nitrophenyl)-methylene}-2-indolinone from 1-acetyl-3-[1-chloro-1-(4-acetylamino-3-nitrophenyl)methylene]-2-indolinone and 4-(dimethylaminomethyl)-aniline

EXAMPLE XVIII

6-Chloro-3-{1-[4-(4-methyl-1-piperazinyl-carbonyl)phenylamino]-1-(3,4-diaminophenyl)methylene}-2-indolinone 0.746 g of 6-chloro-3-{1-[4-(4-methyl-1-piperazinyl-carbonyl)phenylamino]-1-(4-amino-3-nitrophenyl)methylene}-2-indolinone are hydrogenated in 30 ml acetic acid with the addition of 0.60 g Raney nickel under 50 psi of hydrogen pressure for 4 hours. After the addition of another 0.30 g of Raney nickel hydrogenation is continued under the same conditions for a further 4 hours, then the catalyst is removed by suction filtering. The residue obtained from the filtrate by distilling off the solvent is dissolved in water, the solution is made alkaline with soda solution. The crude product precipitated is suction filtered, washed with water, dried, dissolved in 70 ml of dichloromethane/methanol/ammonia solution=70:30:3 and filtered through a layer of silica gel. The filtrate is concentrated by evaporation, the residue is stirred with 5 ml of ethyl acetate, suction filtered and dried at 80° C.

Yield: 0.60 g (85% of theory)
$R_f$ value: 0.4 (silica gel, dichloromethane/methanol/ammonia solution=85:15:1.5) $C_{27}H_{27}ClN_6O_2$
Mass spectrum: m/z=503/505 $[M+H]^+$ The following compounds are prepared analogously to Example XVIII:
(XVIII.1) 6-chloro-3-{1-[4-(pyrrolidin-1-ylmethyl)phenylamino]-1-(3,4-diaminophenyl)-methylene}-2-indolinone from 6-chloro-3-{1-[4-(pyrrolidin-1-ylmethyl)phenylamino]-1-(4-amino-3-nitrophenyl)-methylene}-2-indolinone
(XVIII.2) 6-chloro-3-{1-(4-[N-(dimethylaminomethylcarbonyl)-N-methyl-amino]phenyl-amino)-1-(3,4-diaminophenyl)methylene}-2-indolinone from 6-chloro-3-{1-(4-[N-(dimethylaminomethylcarbonyl)-N-methyl-amino]phenyl-amino)-1-(4-amino-3-nitrophenyl)methylene}-2-indolinone
(XVIII.3) 6-chloro-3-{1-(4-[N-acetyl-N-(2-dimethylaminoethyl)amino]phenylamino)-1-(3,4-diaminophenyl)methylene}-2-indolinone from 6-chloro-3-{1-(4-[N-acetyl-N-(2-dimethylamino-ethyl)amino]phenylamino)-1-(4-amino-3-nitrophenyl)methylene}-2-indolinone
(XVIII.4) 6-chloro-3-{1-(4-[N-acetyl-N-(3-dimethylaminopropyl)amino]phenylamino)-1-(3,4-diaminophenyl)methylene}-2-indolinone from 6-chloro-3-{1-(4-[N-acetyl-N-(3-dimethylamino-propyl)amino]phenylamino)-1-(4-amino-3-nitrophenyl)methylene}-2-indolinone

EXAMPLE XIX 1-acetyl-6-fluoro-3-[1-methoxy-1-(1-methylbenzimidazol-5-yl)methylene]-2-indolinone 0.40 g of 1-acetyl-6-fluoro-3-[1-methoxy-1-(4-methylamino-3-nitrophenyl)methylene]-2-indolinone are hydrogenated in 5.0 ml formic acid with the addition of 0.20 g of Raney nickel for 3 hours under 50 psi of hydrogen atmosphere. The catalyst is eliminated by suction filtering and the filtrate is evaporated down. The residue is stirred with diethyl ether, then after crystallisation suction filtered and dried.

Yield: 0.30 g (79% of theory)

$R_f$ value: 0.8 (silica gel, dichloromethane/methanol/conc. ammonia=90:10:1) $C_{20}H_{16}FN_3O_3$ Mass spectrum: m/z=366 [M$^+$H]$^+$ The following compound is prepared analogously to Example XIX:

(XIX.1) 1-acetyl-3-[1-methoxy-1-(1-methylbenzimidazol-5-yl)methylene]-2-indolinone from 1-acetyl-3-[1-methoxy-1-(4-methylamino-3-nitrophenyl)methylene]-2-indolinone

EXAMPLE XX 4-(1-methyl-4-piperazinyl-carbonyl)-1-nitrobenzene

A solution of 20.0 g 4-nitrobenzoylchloride in 100 ml dichloromethane is added dropwise to a solution of 12.0 ml of N-methylpiperazine and 30 ml of triethylamine in 600 ml of dichloromethane at ambient temperature. The reaction solution is stirred for one hour, then washed three times with water, dried with sodium sulphate and evaporated to dryness. The residue is stirred with tert-butylmethylether and dried at 40° C.

Yield: 16.7 g (62% of theory)

$R_f$ value: 0.35 (silica gel, dichloromethane/methanol=9:1) $C_{12}H_{15}N_3O_3$ Mass spectrum: m/z=250 [M+H]$^+$ The following compounds are prepared analogously to Example XX:

(XX.1) 4-[N-methyl-N-(1-methyl-4-piperidinyl)-aminocarbonyl]-1-nitrobenzene from 4-nitrobenzoyl chloride and 1-methyl-4-methylamino-piperidine (XX.2) 4-[N-methyl-N-(2-dimethylamino-ethyl)-aminocarbonyl]-1-nitrobenzene from 4-nitrobenzoyl chloride and N,N,N'-trimethyl-1,2-diaminoethane, omitting the stirring with tert-butylmethylether.

(XX.3) 4-[N-methyl-N-(3-dimethylamino-propyl)-aminocarbonyl]-1-nitrobenzene from 4-nitrobenzoyl chloride and N,N,N'-trimethyl-1,3-diaminopropane, omitting the stirring with tert-butylmethylether.

(XX.4) 4-(1-methyl-4-piperazinyl-carbonyl-methyl)-1-nitrobenzene from 4-nitrophenylacetylchloride and 1-methylpiperazine (XX.5) 4-(dimethylamino-carbonyl)-1-nitrobenzene from 4-nitrobenzoyl chloride and dimethylamine hydrochloride (XX.6) 4-[N-methyl-N-(2-dimethylamino-ethyl)-aminosulphonyl]-1-nitrobenzene from 4-nitrobenzenesulphonylchloride and N,N,N'-trimethyl-1,2-diaminoethane, omitting the stirring with tert-butylmethylether.

(XX.7) 4-[N-methyl-N-(3-dimethylamino-propyl)-aminosulphonyl]-1-nitrobenzene from 4-nitrobenzenesulphonylchloride and N,N,N'-trimethyl-1,3-diaminopropane, omitting the stirring with tert-butylmethylether.

(XX.8) 4-[N-ethyl-N-(2-dimethylamino-ethyl)-aminocarbonyl]-1-nitrobenzene from 4-nitrobenzoyl chloride and N-ethyl,N',N'-dimethyl-1,2-diaminoethane, omitting the stirring with tert-butylmethylether.

(XX.9) 3-[N-methyl-N-(2-dimethylamino-ethyl)-aminocarbonyl]-1-nitrobenzene from 3-nitrobenzoyl chloride and N,N,N'-trimethyl-1,2-diaminoethane (XX.10) 4-(1-t-butoxycarbonyl-4-piperazinyl-carbonyl)-nitrobenzene from 3-nitrobenzoyl chloride and 1-t-butoxycarbonyl-piperazine (XX.11) 4-(1-t-butoxycarbonyl-perhydro-1,4-diazepin-4-yl-carbonyl)-nitrobenzene from 3-nitrobenzoyl chloride and 1-t-butoxycarbonyl-perhydro-1,4-diazepine (XX.12) 4-[N-methyl-N-(2-{N'-methyl-N'-t-butoxycarbonyl-amino}-ethyl)-aminocarbonyl]-1-nitrobenzene from 4-nitrobenzoyl chloride and N,N'-dimethyl-N-t-butoxycarbonyl-1,2-diaminoethane

EXAMPLE XXI 4-(1-methyl-4-piperazinyl-carbonyl)aniline 10.9 g of 4-(1-methyl-4-piperazinyl-carbonyl)-1-nitrobenzene are hydrogenated in 90 ml of ethanol with the addition of 1.1 g of Raney nickel for 35 minutes at ambient temperature under 50 psi of hydrogen atmosphere. The catalyst is removed by suction filtering, the filtrate is evaporated down, the residue is stirred with diethyl ether and dried.

Yield: 8.43 g (88% of theory)

$R_f$ value: 0.30 (silica gel, dichloromethane/methanol=9:1) $C_{12}H_{17}N_3O$

Mass spectrum: m/z=220 [M+H]$^+$

The following compounds are prepared analogously to Example XXI:

(XXI.1) 4-[N-methyl-N-(1-methyl-4-piperidinyl)-aminocarbonyl]-aniline from 4-[N-methyl-N-(1-methyl-4-piperidinyl)-aminocarbonyl]-1-nitrobenzene (XXI.2) 4-[N-methyl-N-(2-dimethylamino-ethyl)-aminocarbonyl]-1-aniline from 4-[N-methyl-N-(2-dimethylamino-ethyl)-aminocarbonyl]-1-nitrobenzene, omitting the stirring with diethyl ether.

(XXI.3) 4-[N-methyl-N-(3-dimethylamino-propyl)-aminocarbonyl]-1-aniline from 4-[N-methyl-N-(3-dimethylamino-propyl)-aminocarbonyl]-1-nitrobenzene, omitting the stirring with diethyl ether.

(XXI.4) 4-(1-methyl-4-piperazinyl-carbonyl-methyl)aniline from 4-(1-methyl-4-piperazinyl-carbonyl-methyl)-1-nitrobenzene (XXI.5) N-methoxyacetyl-N-methyl-4-amino-aniline from N-methoxyacetyl-N-methyl-4-amino-nitrobenzene (XXI.6) N-acetyl-N-methyl-4-amino-aniline from N-acetyl-N-methyl-4-amino-nitrobenzene (XXI.7) 4-(dimethylamino-carbonyl)-aniline from 4-(dimethylamino-carbonyl)-1-nitrobenzene (XXI.8) 1-(4-aminophenyl)-3,5-dimethylpyrazole from 1-(4-nitrophenyl)-3,5-dimethylpyrazol, which is prepared as described in: K. v. Auwers, A. Kreuder, Chem. Ber. 58 (1925) 1981

(XXI.9) 4-[N-methyl-N-(2-dimethylamino-ethyl)-aminosulphonyl]-1-aniline from 4-[N-methyl-N-(2-dimethylamino-ethyl)-aminosulphonyl]-1-nitrobenzene, omitting the stirring with diethyl ether.

(XXI.10) N-4-aminobenzoyl-N-methyl-aminoacetonitrile from N-4-nitrobenzoyl-N-methyl-aminoacetonitrile (prepared as described in: D. Clerin et al., Tetrahedron 32 (1976) 1055–1059), using Pd/C (5%) as catalyst and ethyl acetate as solvent.

(XXI.11) 4-[N-methyl-N-(3-dimethylamino-propyl)-aminosulphonyl]-1-aniline from 4-[N-methyl-N-(3-dimethylamino-propyl)-aminosulphonyl]-1-nitrobenzene, omitting the stirring with diethyl ether.

(XXI.12) 4-[N-ethyl-N-(2-dimethylamino-ethyl)-aminocarbonyl]-aniline from 4-[N-ethyl-N-(2-dimethylamino-ethyl)-aminocarbonyl]-1-nitrobenzene, omitting the stirring with diethyl ether.

(XXI.13) 3-[N-methyl-N-(2-dimethylamino-ethyl)-aminocarbonyl]-aniline from 3-[N-methyl-N-(2-dimethylamino-ethyl)-aminocarbonyl]-1-nitrobenzene (XXI.14) 4-(1-t-butoxycarbonyl-4-piperazinyl-carbonyl)-aniline from 4-(1-t-butoxycarbonyl-4-piperazinyl-carbonyl)-nitrobenzene (XXI.15) 4-(1-t-butoxycarbonyl-perhydro-1,4-diazepin-4-yl-carbonyl)-aniline from 4-(1-t-butoxycarbonyl-perhydro-1,4-diazepin-4-yl-carbonyl)-nitrobenzene (XXI.16) 4-[N-methyl-N-(2-{N'-methyl-N'-t-butoxycarbonyl-amino}-ethyl)-aminocarbonyl]-aniline from 4-[N-methyl-N-(2-{N'-methyl-N'-t-butoxycarbonyl-amino}-ethyl)-aminocarbonyl]-1-nitrobenzene The syntheses of the following compounds are known from the literature:

(XXII) N-acetyl-N-methyl-p-phenylenediamine is prepared as described in: G. T. Morgan, W. R. Grist, J. Chem. Soc. 113 (1918) 688–694

(XXIII) 4-(2-dimethylamino-ethoxy)-aniline is prepared as described in: D. H. Hunter et al., Can. J. Chem. 62 (1984) 2015–2019

(XXIV) 4-(2-diethylamino-ethylsulphonyl)-aniline is prepared as described in: J. Walker, J. Chem. Soc. (1945) 630–633

The following compound is prepared analogously to Example XXIV:

(XXIV.1) 4-methylsulphonyl-aniline from 4-acetamidophenylsulphinic acid and dimethylsulphate The methods of synthesising the following compounds are described in WO 01/27081:

(XXV) 4-(pyrrolidin-1-ylmethyl)aniline (XXV.1) N-(dimethylaminomethylcarbonyl)-N-methyl-p-phenylenediamine (XXV.2) N-methyl-N-[(1-methylpiperazin-4-yl)methylcarbonyl]-p-phenylenediamine (XXV.3) N-acetyl-N-(2-dimethylamino-ethyl)-p-phenylenediamine (XXV.4) N-acetyl-N-(3-dimethylamino-propyl)-p-phenylenediamine (XXV.5) N-propionyl-N-(3-dimethylamino-propyl)-p-phenylenediamine is prepared analogously to compound XXV.4.

(XXV.6) N-methanesulphonyl-N-(2-dimethylamino-ethyl)-p-phenylenediamine (XXV.7) N-propanesulphonyl-N-(2-dimethylamino-ethyl)-p-phenylenediamine (XXV.8) 4-(dimethylaminomethyl)-aniline (XXV.9) N-(2-dimethylamino-ethyl)-N-(pyridine-3-carbonyl)-p-phenylenediamine (XXV.10) 4-(N-ethyl-N-methyl-aminomethyl)-aniline (XXV.11) 4-[(4-methylpiperazin-1-yl)-methyl]-aniline (XXV.12) 4-(N-ethyl-N-tert-butoxycarbonyl-aminomethyl)-aniline (XXV.13) 4-(N-methyl-N-tert-butoxycarbonyl-aminomethyl)-aniline (XXV.14) 4-{[1-(tert-butoxycarbonyl)-piperazin-4-yl]-methyl}-aniline (XXV.15) 4-(1-methylimidazol-2-yl)-aniline (XXV.16) 4-(diethylaminomethyl)-aniline (XXV.17) 4-(1,2,4-triazol-1-yl-methyl)-aniline (XXV.18) 4-(1,2,3-triazol-1-yl-methyl)-aniline (XXV.19) 4-(1,2,3-triazol-2-yl-methyl)-aniline (XXV.20) N-methanesulphonyl-N-methyl-p-phenylenediamine (XXV.21) N-methanesulphonyl-N-(2-trifluoroacetylamino-ethyl)-p-phenylenediamine (XXV.22) 4-(4-hydroxypiperidin-1-yl-methyl)-aniline (XXV.23) N-[(2-dimethylamino-ethyl)-carbonyl]-N-methyl-p-phenylenediamine (XXV.24) 4-[N-(2-hydroxyethyl)-N-methyl-amino-methyl]-aniline (XXV.25) (R)-4-(3-hydroxypyrrolidin-1-yl-methyl)-aniline is prepared in the same way as the racemic compound described, using (R)-3-hydroxypyrrolidine.

(XXV.26) (S)-4-(3-hydroxypyrrolidin-1-yl-methyl)-aniline is prepared in the same way as the racemic compound described, using (S)-3-hydroxypyrrolidine.

(XXV.27) N-ethanesulphonyl-N-(2-dimethylamino-ethyl)-p-phenylenediamine (XXV.28) N-propionyl-N-(3-dimethylamino-propyl)-p-phenylenediamine is prepared analogously to compound XXV.4, using propionic anhydride instead of acetic anhydride.

(XXV.29) N-propionyl-N-(2-dimethylamino-ethyl)-p-phenylenediamine (XXV.30) 4-(1-ethylimidazol-2-yl)-aniline (XXV.31) 4-[N-(2-methoxyethyl)-N-methyl-amino-methyl]-aniline (XXV.32) (S)-4-([2-hydroxymethyl-pyrrollidin-1-yl]-methyl)-aniline is prepared analogously to the compound 4-(3-hydroxypyrrolidin-1-yl-methyl)-aniline described, starting from (S)-prolinol and 4-nitrobenzylbromide (XXV.33) 4-(morpholin-4-yl-methyl)-aniline (XXV.34) 4-(N-isobutyl-N-tert-butoxycarbonyl-aminomethyl)-aniline is prepared analogously to compound XXV.12, using isobutylamine instead of ethylamine.

(XXV.35) N-methanesulphonyl-N-(2-dimethylamino-ethyl)-3-chloro-p-phenylenediamine

EXAMPLE XXVI

N-methoxyacetyl-N-methyl-4-amino-nitrobenzene

A solution of 10.0 g methoxyacetylchloride in 30 ml THF is added dropwise to a suspension of 15.4 g N-methyl-4-nitroaniline in 100 ml of tetrahydrofuran and 38.5 ml triethylamine. The reaction mixture is stirred for 15 hours, then a further 10 g of methoxyacetylchloride in 30 ml THF are added. After another 5 hours the solvent is distilled off, the residue is taken up in dichloromethane and extracted twice with dilute hydrochloric acid. The organic phase is dried over magnesium sulphate and evaporated down. The residue is purified by chromatography on silica gel (eluant: dichloromethane/ethyl acetate 9:1, then 8:2).

Yield: 19.2 g (93% of theory)

$R_f$ value: 0.66 (silica gel, ethyl acetate/methanol=9:1)
$C_{10}H_{12}N_2O_4$

Mass spectrum: m/z=225 [M+H]$^+$; 247 [M+Na]$^+$

The following compound is prepared analogously to Example XXVI:

(XXVI.1) N-acetyl-N-methyl-4-amino-nitrobenzene

The methods of synthesising the following compounds are known from the literature:

(XXVII) N-(4-aminophenyl)-2-pyrrolidone is prepared as described in: W. Reppe et al., Justus Liebigs Ann. Chem. 596 (1955) 204

(XXVIII) (4-aminobenzyl)-pyridin-2-yl-amine is prepared as described in: V. Martinez-Barrasa, et al., Tetrahedron 56 (2000) 2481–2490

EXAMPLE XXIX

N-[2-(dimethylamino)-ethyl]-sulphanilic acid amide 5.26 g sulphanilic acid fluoride and 16.5 ml of N,N-dimethyl-ethylenediamine are stirred for 4 hours at 100° C., then dissolved in ethyl acetate and extracted three times with saline solution. The residue obtained by evaporation of the organic phase is crystallised from diethyl ether and dried at 60° C.

Yield: 4.1 g (56% of theory)
melting point: 86–88° C. $C_{10}H_{17}N_3O_2S$
Mass spectrum: m/z=244 [M+H]$^+$; 242 [M−H]$^-$ The following compound is prepared analogously to Example XXIX:

(XXIX.1) N-[3-(dimethylamino)-propyl]-sulphanilic acid amide from sulphanilic acid fluoride and N,N-dimethyl-1,3-diaminopropane The synthesis of the following compound is described in International Application WO 01/27081:

(XXX) N-(dimethylaminomethylcarbonyl)-N-methyl-3-methoxy-p-phenylenediamine

Preparation of the end compounds:

EXAMPLE 1.0

3-(Z)-[1-{4-[N-propionyl-N-(3-dimethylamino-propyl)-amino]-phenylamino}-1-(2-dibenzylamino-4-oxazolyl)-methylene]-2-indolinone 0.935 g of 1-acetyl-3-[1-methoxy-1-(2-dibenzylamino-4-oxazolyl)-methylene]-2-indolinone (educt XVI.5) and 0.549 g of N-propionyl-N-(3-dimethylamino-propyl)-p-phenylenediamine (educt XXV.5) are dissolved in 10 ml of dimethylformamide and stirred for 3 hours at 120° C. After cooling 5 ml of methanol and 2 ml of 2 molar sodium hydroxide solution are added and the mixture is stirred for a further hour at ambient temperature. After the addition of 60 ml of water it is extracted twice with ethyl acetate. The residue obtained from the combined organic phases by elimination of the solvent is purified by chromatography through a silica gel column with dichloromethane/methanol/conc. ammonia=90:10:1 as eluant. The crude product thus obtained is stirred with ice-cold diethyl ether, suction filtered and dried at 80° C.

Yield: 0.40 g (31% of theory)
$R_f$ value: 0.5 (silica gel, methylene chloride/methanol/conc. ammonia=85:15:1.5)
mp.: 204–205° C. $C_{40}H_{42}N_6O_3$
Mass spectrum: m/z=655 [M+H]$^+$; m/z=653 [M−H]$^-$ The following compounds of general formula I.1 are prepared analogously to Example 1.0 from the educts specified in each case:

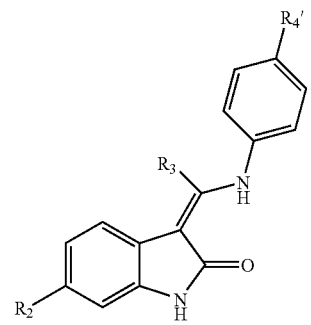

(I.1)

| Example | $R_2$ | $R_3$ | $R_4'$ | Educts | Empirical formula | Mass spectrum | M.p. [° C.] | $R_f$ value * |
|---|---|---|---|---|---|---|---|---|
| 1.1 | H | 3-furyl- | —CH$_2$—NMe$_2$ | XVI.4 XXV.8 | $C_{22}H_{21}N_3O_2$ | 358 [M − H]$^-$ | 220–222 | 0.5 (A) |
| 1.2 | H | 3-furyl- | —N(CH$_3$)—CO—CH$_2$—NMe$_2$ | XVI.4 XXV.1 | $C_{24}H_{24}N_4O_3$ | 417 [M + H]$^+$ 415 [M − H]$^-$ | 243–245 | 0.6 (B) |
| 1.3 | H | 2-methyl-isodinol-1,3-dion-5-yl- | —CH$_2$—NMe$_2$ | XVI.3 XXV.8 | $C_{27}H_{24}N_4O_3$ | 451 [M − H]$^-$ | 248–251 | 0.08 (C) |
| 1.4 | H | 2-methyl-isodinol-1,3-dion-5-yl- | —N(CH$_3$)—CO—CH$_2$—NMe$_2$ | XVI.3 XXV.1 | $C_{29}H_{27}N_5O_4$ | 510 [M + H]$^+$ | 244–246 | 0.33 (D) |
| 1.5 | H | 2-methyl-isodinol-1,3-dion-5-yl- | —N(COMe)—(CH$_2$)$_2$—NMe$_2$ | XVI.3 XXV.3 | $C_{30}H_{29}N_5O_4$ | 524 [M + H]$^+$ | 182–185 | 0.2 (C) |

-continued (I.1)

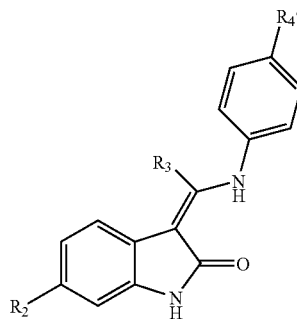

| Example | $R_2$ | $R_3$ | $R_4'$ | Educts | Empirical formula | Mass spectrum | M.p. [°C.] | $R_f$ value * |
|---|---|---|---|---|---|---|---|---|
| 1.6 | Cl | 1,2-(methylene-dioxy)-phen-4-yl- | —N(SO$_2$Me)—(CH$_2$)$_2$—NMe$_2$ | XVI XXV.6 | $C_{27}H_{27}ClN_4O_5S$ | 555/557 [M + H]$^+$ 553/555 [M − H]$^−$ | 235–237 | 0.4 (A) |
| 1.7 | Cl | 1,2-(methylene-dioxy)-phen-4-yl- | —CH$_2$—NMe$_2$ | XVI XXV.8 | $C_{25}H_{22}ClN_3O_3$ | 446/448 [M − H]$^−$ | 256–258 | 0.4 (A) |
| 1.8 | Cl | 1,2-(methylene-dioxy)-phen-4-yl- | —N(CH$_3$)—CO—CH$_2$—NMe$_2$ | XVI XXV.1 | $C_{27}H_{25}ClN_4O_4$ | 505/507 [M + H]$^+$ 503/505 [M − H]$^−$ | 269–270 | 0.3 (A) |
| 1.9 | Cl | 1,2-(methylene-dioxy)-phen-4-yl- | —N(COMe)—(CH$_2$)$_3$NMe$_2$ | XVI XXV.4 | $C_{29}H_{29}ClN_4O_4$ | 533/535 [M + H]$^+$ 531/533 [M − H]$^−$ | 219–220 | 0.3 (A) |
| 1.10 | Cl | 1,2-(methylene-dioxy)-phen-4-yl- | —N(COMe)—(CH$_2$)$_3$NMe$_2$ | XVI XXV.3 | $C_{28}H_{27}ClN_4O_4$ | 519/521 [M + H]$^+$ 517/519 [M − H]$^−$ | 217–218 | 0.3 (A) |
| 1.11 | Cl | 1,2-(methylene-dioxy)-phen-4-yl- | —CH$_2$—pyrrolidin-1-yl | XVI XXV | $C_{27}H_{24}ClN_3O_3$ | 474/476 [M + H]$^+$ 472/474 [M − H]$^−$ | 226–228 | 0.45 (A) |
| 1.12 | Cl | 1,2-(methylene-dioxy)-phen-4-yl- | —CO-(1-methyl-piperazin-4-yl) | XVI XXI | $C_{28}H_{25}ClN_4O_4$ | 517/519 [M + H]$^+$ 515/517 [M − H]$^−$ | n.d. | 0.3 (A) |
| 1.13 | Cl | 1,2-(methylene-dioxy)-phen-4-yl- | —N(CH$_3$)—CO—CH$_2$-(1-methylpipe-razin-4-yl) | XVI XXV.2 | $C_{30}H_{30}ClN_5O_4$ | 560/562 [M + H]$^+$ 558/560 [M − H]$^−$ | 265–266 | 0.3 (A) |
| 1.14 | Cl | 1,2-(methylene-dioxy)-phen-4-yl- | —N(CO-3-pyridyl)-(CH$_2$)$_2$—NMe$_2$ | XVI XXV.9 | $C_{32}H_{28}ClN_5O_4$ | 582/584 [M + H]$^+$ 580/582 [M − H]$^−$ | 241–242 | 0.3 (A) |
| 1.15 | Cl | 1,2-(methylene-dioxy)-phen-4-yl- | —CH$_2$—N(Me)Et | XVI XXV.10 | $C_{26}H_{24}ClN_3O_3$ | 462/464 [M + H]$^+$ | 200–203 | 0.45 (A) |
| 1.16 | Cl | 1,2-(methylene-dioxy)-phen-4-yl- | —CH$_2$-(1-methylpipe-razin-4-yl) | XVI XXV.11 | $C_{28}H_{27}ClN_4O_3$ | 503/505 [M + H]$^+$ | 215–217 | 0.33 (A) |
| 1.17 | Cl | 1,2-(methylene-dioxy)-phen-4-yl- | —CH$_2$—N(Et)—C(O)O-tBu | XVI XXV.12 | $C_{30}H_{30}ClN_3O_5$ | 548/550 [M + H]$^+$ | 234–237 | 0.37 (A) |
| 1.18 | Cl | 1,2-(methylene-dioxy)-phen-4-yl- | —CH$_2$—N(Me)—C(O)O-tBu | XVI XXV.13 | $C_{29}H_{28}ClN_3O_5$ | 534/536 [M + H]$^+$ | 221–224 | 0.57 (A) |
| 1.19 | Cl | 1,2-(methylene-dioxy)-phen-4-yl- | —CH$_2$-(1-(C(O)OtBu)-piperazin-4-yl) | XVI XXV.14 | $C_{32}H_{33}ClN_4O_5$ | 589/591 [M + H]$^+$ | 170–173 | 0.53 (A) |

-continued

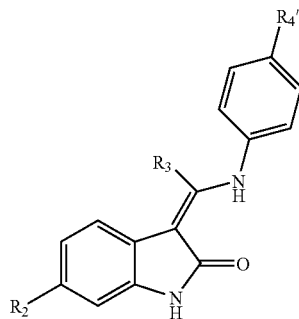

(I.1)

| Example | $R_2$ | $R_3$ | $R_4'$ | Educts | Empirical formula | Mass spectrum | M.p. [° C.] | $R_f$ value * |
|---|---|---|---|---|---|---|---|---|
| 1.20 | Cl | 1,2-(methylenedioxy)-phen-4-yl- | —SO$_2$—(CH$_2$)$_2$—NEt$_2$ | XVI XXIV | $C_{28}H_{28}ClN_3O_5S$ | 554/556 [M + H]$^+$ 552/554 [M − H]$^-$ | 215–217 | 0.4 (E) |
| 1.21 | Cl | 1,2-(methylenedioxy)-phen-4-yl- | —O—(CH$_2$)$_2$—NMe$_2$ | XVI XXIII | $C_{26}H_{24}ClN_3O_4$ | 476/478 [M − H]$^-$ | 196–199 | 0.24 (A) |
| 1.22 | Cl | 1,2-(ethylenedioxy)-phen-4-yl- | —CH$_2$—NMe$_2$ | XVI.1 XXV.8 | $C_{26}H_{24}ClN_3O_3$ | 460/462 [M − H]$^-$ | 195–197 | 0.10 (E) |
| 1.23 | Cl | 1,2-(ethylenedioxy)-phen-4-yl- | —N(SO$_2$Me)—(CH$_2$)$_2$—NMe$_2$ | XXV.6 | $C_{28}H_{29}ClN_4O_5S$ | 569/571 [M + H]$^+$ | 220–223 | 0.17 (E) |
| 1.24 | Cl | 1,2-(ethylenedioxy)-phen-4-yl- | —N(CH$_3$)—CO—CH$_2$—NMe$_2$ | XVI.1 XXV.1 | $C_{28}H_{27}ClN_4O_4$ | 519/521 [M + H]$^+$ | 281–284 | 0.32 (C) |
| 1.25 | Cl | 1,2-(ethylenedioxy)-phen-4-yl- | —CO-(1-methyl-piperazin-4-yl) | XVI.1 XXI | $C_{29}H_{27}ClN_4O_4$ | 531/533 [M + H]$^+$ | 258–262 | 0.08 (C) |
| 1.26 | Cl | 1,2-(ethylenedioxy)-phen-4-yl- | —N(COMe)—(CH$_2$)$_2$—NMe$_2$ | XVI.1 XXV.3 | $C_{29}H_{29}ClN_4O_4$ | 533/535 [M + H]$^+$ | 213–215 | 0.39 (C) |
| 1.27 | Cl | 1,2-(difluoro-methylenedioxy)-phen-4-yl- | —CH$_2$—N(Me)—C(O)O-tBu | XVI.2 XXV.13 | $C_{29}H_{26}ClF_2N_3O_5$ | 592/594 [M + Na]$^+$ | 185–187 | 0.89 (N) |
| 1.28 | Cl | 1,2-(difluoro-methylenedioxy)-phen-4-yl- | —CO-(1-methyl-piperazin-4-yl) | XVI.2 XXI | $C_{28}H_{23}ClF_2N_4O_4$ | 553/555 [M + H]$^+$ | 237–239 | 0.18 (C) |
| 1.29 | Cl | 1,2-(difluoro-methylenedioxy)-phene-4-yl- | —CH$_2$—NMe$_2$ | XVI.2 XXV.8 | $C_{25}H_{20}ClF_2N_3O_3$ | 484/486 [M + H]$^+$ | 225–228 | 0.22 (C) |
| 1.30 | Cl | 1,2-(difluoro-methylenedioxy)-pheny-4-yl- | —N(COMe)—(CH$_2$)$_2$—NMe$_2$ | XVI.2 XXV.3 | $C_{28}H_{25}ClF_2N_4O_4$ | 555/557 [M + H]$^+$ | 202–206 | 0.15 (C) |
| 1.31 | Cl | 1,2-(difluoro-methylenedioxy)-phen-4-yl- | —N(CH$_3$)—CO—CH$_2$—NMe$_2$ | XVI.2 XXV.1 | $C_{27}H_{23}ClF_2N_4O_4$ | 541/543 [M + H]$^+$ | 254–259 | 0.19 (C) |
| 1.32 | COOMe | 1,2-(ethylenedioxy)-phen-4-yl- | —CH$_2$—NMe$_2$ | XVI.6 XXV.8 | $C_{28}H_{27}N_3O_5$ | 486 [M + H]$^+$ 484 [M − H]$^-$ | 220–222 | 0.35 (G) |

-continued

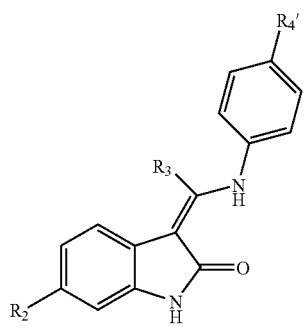

(I.1)

| Example | $R_2$ | $R_3$ | $R_4'$ | Educts | Empirical formula | Mass spectrum | M.p. [° C.] | $R_f$ value * |
|---|---|---|---|---|---|---|---|---|
| 1.33 | COOMe | 1,2-(ethylenedioxy)-phen-4-yl- | —N(CH$_3$)—(CO—CH$_2$-(1-methylpiperazin-4-yl) | XVI.6 XXV.2 | $C_{33}H_{35}N_5O_6$ | 598 $[M + H]^+$ | 176–179 | 0.26 (G) |
| 1.34 | F | 1,2-(ethylenedioxy)-phen-4-yl- | —N(COMe)—(CH$_2$)$_2$—NMe$_2$ | XVI.7 XXV.3 | $C_{29}H_{29}FN_4O_4$ | 517 $[M + H]^+$ | 142–144 | 0.47 (P) |
| 1.35 | F | 1,2-(ethylenedioxy)-phen-4-yl- | —CO—N(Me)-(1-methyl-piperidin-4-yl) | XVI.7 XXI.1 | $C_{31}H_{31}FN_4O_4$ | 543 $[M + H]^+$ | 231–234 | 0.54 (P) |
| 1.36 | F | 1,2-(ethylenedioxy)-phen-4-yl- | —CH$_2$—NMe$_2$ | XVI.7 XXV.8 | $C_{26}H_{24}FN_3O_3$ | 446 $[M + H]^+$ | 201–203 | 0.55 (A) |
| 1.37 | F | 1,2-(ethylenedioxy)-phen-4-yl- | —CH$_2$—N(Et)—C(O)O-tBu | XVI.7 XXV.12 | $C_{31}H_{32}FN_3O_5$ | 568 $[M + Na]^+$ | not determined | 0.67 (P) |
| 1.38 | F | 1,2-(ethylenedioxy)-phen-4-yl- | 1-methyl-imidazol-2-yl | XVI.7 XXV.15 | $C_{27}H_{21}FN_4O_3$ | 469 $[M + H]^+$ | 230–233 | 0.54 (A) |
| 1.39 | F | 1-methyl-benzimidazol-5-yl | —CH$_2$—NMe$_2$ | XIX XXV.8 | $C_{26}H_{24}FN_5O$ | 442 $[M + H]^+$ | 248–252 | 0.62 (P) |
| 1.40 | H | 1-methyl-benzimidazol-5-yl | —CH$_2$—NMe$_2$ | XIX XXV.8 | $C_{26}H_{25}N_5O$ | 424 $[M + H]^+$ | 250–253 | 0.51 (P) |
| 1.41 | Cl | quinoxalin-6-yl | —N(SO$_2$Me)—(CH$_2$)$_2$—NMe$_2$ | XVI.10 XXV.6 | $C_{28}H_{27}ClN_6O_3S$ | 563/565 $[M + H]^+$ | 180–185 | 0.49 (A) |
| 1.42 | Cl | quinoxalin-6-yl | —N(CH$_3$)—CO—CH$_2$-(1-methylpiperazin-4-yl) | XVI.10 XXV.2 | $C_{31}H_{30}ClN_7O_2$ | 568/570 $[M + H]^+$ | 234–227 | 0.35 (A) |
| 1.43 | Cl | quinoxalin-6-yl | —N(COMe)—(CH$_2$)$_2$—NMe$_2$ | XVI.10 XXV.3 | $C_{29}H_{27}ClN_6O_2$ | 527/529 $[M + H]^+$ | 200–205 | 0.34 (A) |
| 1.44 | Cl | quinoxalin-6-yl | —CO-(1-methyl-piperazin-4-yl) | XVI.10 XXI | $C_{29}H_{25}ClN_6O_2$ | 525/527 $[M + H]^+$ | 235–240 | 0.48 (A) |
| 1.45 | Cl | quinoxalin-6-yl | —CH$_2$—NMe$_2$ | XVI.10 XXV.8 | $C_{26}H_{22}ClN_5O$ | 454/456 $[M − H]^-$ | 258–260 | 0.33 (A) |
| 1.46 | Cl | quinoxalin-6-yl | 1-methyl-imidazol-2-yl | XVI.10 XXV.15 | $C_{27}H_{19}ClN_6O$ | 477/479 $[M − H]^-$ | 282–286 | 0.51 (A) |
| 1.47 | COOMe | 1,2-(ethylenedioxy)-phen-4-yl- | —CH$_2$—NEt$_2$ | XXV.6 XXV.16 | $C_{30}H_{31}N_3O_5$ | 512 $[M − H]^-$ | 168–170 | 0.33 (Q) |

-continued

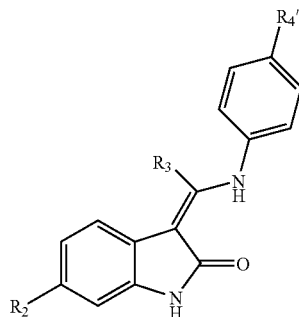

(I.1)

| Example | $R_2$ | $R_3$ | $R_4'$ | Educts | Empirical formula | Mass spectrum | M.p. [°C.] | $R_f$ value * |
|---|---|---|---|---|---|---|---|---|
| 1.48 | COOMe | 1,2-(ethylenedioxy)-phen-4-yl- | —N(COMe)—(CH$_2$)$_2$—NMe$_2$ | XVI.6 XXV.3 | $C_{31}H_{32}N_4O_6$ | 557 [M + H]$^+$ 555 [M − H]$^-$ | 222–224 | 0.31 (G) |
| 1.49 | COOMe | 1,2-(ethylenedioxy)-phen-4-yl- | —CO—N(Me)—(CH$_2$)$_2$—NMe$_2$ | XVI.6 XXI.2 | $C_{31}H_{32}N_4O_6$ | 557 [M + H]$^+$ 555 [M − H]$^-$ | n.d. | 0.23 (G) |
| 1.50 | COOMe | 1,2-(ethylenedioxy)-phen-4-yl- | —CO—N(Me)—(CH$_2$)$_3$—NMe$_2$ | XVI.6 XXI.3 | $C_{32}H_{34}N_4O_6$ | 571 [M + H]$^+$ 569 [M − H]$^-$ | n.d. | 0.10 (G) |
| 1.51 | COOMe | 1,2-(ethylenedioxy)-phen-4-yl- | —CH$_2$—N(Et)—C(O)O-tBu | XVI.6 XXV.12 | $C_{33}H_{35}N_3O_7$ | 586 [M + H]$^+$ 584 [M − H]$^-$ | 238 (decomposition) | 0.31 (G) |
| 1.52 | COOMe | 1,2-(ethylenedioxy)-phen-4-yl- | —CH$_2$—N(Me)Et | XVI.6 XXI.10 | $C_{29}H_{29}N_3O_5$ | 500 [M + H]$^+$ | 192–193 | 0.26 (G) |
| 1.53 | COOMe | 1,2-(ethylenedioxy)-phene-4-yl- | —CH$_2$—pyrrolidin-1-yl | XVI.6 XXV | $C_{30}H_{29}N_3O_5$ | 512 [M + H]$^+$ 510 [M − H]$^-$ | 246–248 | 0.34 (G) |
| 1.54 | COOMe | 1,2-(ethylenedioxy)-phen-4-yl- | —N(CH$_3$)—CO—CH$_2$—NMe$_2$ | XVI.6 XXV.1 | $C_{30}H_{30}N_4O_6$ | 543 [M + H]$^+$ 541 [M − H]$^-$ | 231–233 | 0.35 (G) |
| 1.55 | COOMe | 1,2-(ethylenedioxy)-phen-4-yl- | —N(SO$_2$Me)—(CH$_2$)$_2$—NMe$_2$ | XVI.6 XXV.6 | $C_{30}H_{32}N_4O_7S$ | 591 [M− H]$^-$ | 244–246 | 0.39 (G) |
| 1.56 | COOMe | 1,2-(ethylenedioxy)-phen-4-yl- | —CH$_2$-(1-methylpiperazin-4-yl) | XVI.6 XXV.11 | $C_{31}H_{32}N_4O_5$ | 541 [M + H]$^+$ 539 [M − H]$^-$ | 258–259 | 0.39 (G) |
| 1.57 | COOMe | 1,2-(ethylenedioxy)-phen-4-yl- | —CO-(1-methyl-piperazin-4-yl) | XVI.6 XXI | $C_{31}H_{30}N_4O_6$ | 555 [M + H]$^+$ 553 [M − H]$^-$ | 271–273 | 0.35 (G) |
| 1.58 | COOMe | 1,2-(methylenedioxy)-phen-4-yl- | —CH$_2$—NEt$_2$ | XVI.11 XXV.16 | $C_{29}H_{29}N_3O_5$ | 498 [M − H]$^-$ | 206 | 0.23 (G) |
| 1.59 | COOMe | 1,2-(methylenedioxy)-phen-4-yl- | —CH$_2$—NMe$_2$ | XVI.11 XXV.8 | $C_{27}H_{25}N_3O_5$ | 472 [M + H]$^+$ | 234 | 0.20 (G) |
| 1.60 | COOMe | 1,2-(methylenedioxy)-phen-4-yl- | —N(CH$_3$)—CO—CH$_2$-(1-methylpiperazin-4-yl) | XVI.11 XXV.2 | $C_{32}H_{33}N_5O_6$ | 584 [M + H]$^+$ 582 [M − H]$^-$ | 152 | 0.12 (G) |
| 1.61 | COOMe | 1,2-(methylenedioxy)-phen-4-yl- | —N(COMe)—(CH$_2$)$_2$—NMe$_2$ | XVI.11 XXV.3 | $C_{30}H_{30}N_4O_6$ | 543 [M + H]$^+$ 541 [M − H]$^-$ | 206 | 0.30 (G) |

-continued (I.1)

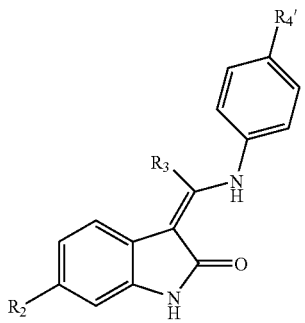

| Example | $R_2$ | $R_3$ | $R_4'$ | Educts | Empirical formula | Mass spectrum | M.p. [°C.] | $R_f$ value * |
|---|---|---|---|---|---|---|---|---|
| 1.62 | COOMe | 1,2-(methylenedioxy)-phen-4-yl- | —CH$_2$—N(Et)—C(O)O-tBu | XVI.11 XXV.12 | $C_{32}H_{33}N_3O_7$ | 572 [M + H]$^+$ 570 [M − H]$^-$ | 233 | 0.29 (R) |
| 1.63 | COOMe | 1,2-(methylenedioxy)-phen-4-yl- | —O(CH$_2$)$_2$—NMe$_2$ | XVI.11 XXIII | $C_{28}H_{27}N_3O_6$ | 500 [M − H]$^-$ | 243 | 0.29 (G) |
| 1.64 | COOMe | 1,2-(methylenedioxy)-phen-4-yl- | —CO—N(Me)—(CH$_2$)$_2$—NMe$_2$ | XVI.11 XXI.2 | $C_{30}H_{30}N_4O_6$ | 543 [M + H]$^+$ 541 [M − H]$^-$ | 173 | 0.30 (G) |
| 1.65 | F | 1-methyl-benzimidazol-5-yl | —CH$_2$—(1,2,4-triazol-1-yl) | XIX XXV.17 | $C_{26}H_{20}FN_7O$ | 466 [M + H]$^+$ | 268–272 | 0.70 (P) |
| 1.66 | F | 1-methyl-benzimidazol-5-yl | —CH$_2$-(1,2,3-triazol-1-yl) | XIX XXV.18 | $C_{26}H_{20}FN_7O$ | 466 [M + H]$^+$ | 200–225 | 0.61 (P) |
| 1.67 | F | 1-methyl-benzimidazol-5-yl | —CH$_2$-(1,2,3-triazol-2-yl) | XIX XXV.19 | $C_{26}H_{20}FN_7O$ | 466 [M + H]$^+$ | 253–256 | 0.71 (P) |
| 1.68 | F | 1-methyl-benzimidazol-5-yl | —CH$_2$—CO-(1-methyl-piperazin-4-yl) | XIX XXI.4 | $C_{30}H_{29}FN_6O_2$ | 525 [M + H]$^+$ | 158–165 | 0.55 (P) |
| 1.69 | F | 1-methyl-benzimidazol-5-yl | —N(COMe)—(CH$_2$)$_2$—NMe$_2$ | XIX XXV.3 | $C_{29}H_{29}FN_6O_2$ | 513 [M + H]$^+$ | 163–167 | 0.49 (P) |
| 1.70 | F | 1-methyl-benzimidazol-5-yl | 1-methyl-imidazol-2-yl | XIX XXV.15 | $C_{27}H_{21}FN_6O$ | 465 [M + H]$^+$ | 279–284 (decomposition) | 0.59 (P) |
| 1.71 | F | 1-methyl-benzimidazol-5-yl | —N(CH$_3$)-CO—CH$_2$—(1-methylpiperazin-4-yl) | XIX XXV.2 | $C_{31}H_{32}FN_7O_2$ | 554 [M + H]$^+$ | 136–143 | 0.3 (P) |
| 1.72 | F | 1-methyl-benzimidazol-5-yl | —N(CH$_3$)—CO—CH$_2$—OCH$_3$ | XIX XXI.5 | $C_{27}H_{24}FN_5O_3$ | 486 [M + H]$^+$ | 168–172 | 0.5 (P) |
| 1.73 | F | 1-methyl-benzimidazol-5-yl | 2-pyrrolidon-1-yl | XIX XXVII | $C_{27}H_{22}FN_5O_2$ | 468 [M + H]$^+$ | 276–279 | 0.5 (P) |
| 1.74 | F | 1-methyl-benzimidazol-5-yl | —N(CH$_3$)—COCH$_3$ | XIX XXI.6 | $C_{26}H_{22}FN_5O_2$ | 456 [M + H]$^+$ | 322–326 | 0.6 (P) |
| 1.75 | F | 1-methyl-benzimidazol-5-yl) | —N(CH$_3$)—SO$_2$CH$_3$ | XIX XXV.20 | $C_{25}H_{22}FN_5O_3S$ | 492 [M + H]$^+$ | 311–317 | 0.6 (P) |
| 1.76 | F | 1-methyl-benzimidazol-5-yl | —SO$_2$CH$_3$ | XIX XXIV.1 | $C_{24}H_{19}FN_4O_3S$ | 463 [M + H]$^+$ | 300–303 | 0.7 (P) |

-continued

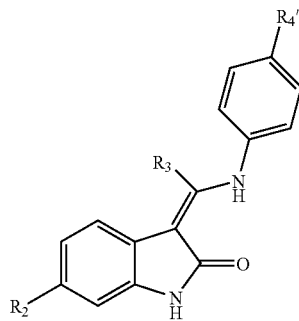

(I.1)

| Example | R₂ | R₃ | R₄' | Educts | Empirical formula | Mass spectrum | M.p. [° C.] | $R_f$ value * |
|---|---|---|---|---|---|---|---|---|
| 1.77 | F | 1-methyl-benzimid-azol-5-yl | —CO—NMe₂ | XIX XXI.7 | $C_{26}H_{22}FN_5O_2$ | 456 [M + H]⁺ | 320 | 0.6 (P) |
| 1.78 | F | 1-methyl-benzimid-azol-5-yl | 3,5-dimethyl-pyrazol-1-yl | XIX XXI.8 | $C_{28}H_{23}FN_6O$ | 479 [M + H]⁺ | 297–301 | 0.8 (P) |
| 1.79 | F | 1-methyl-benzimid-azol-5-yl | —CO-(1-methyl-piperazin-4-yl) | XIX XXI | $C_{29}H_{27}FN_6O_2$ | 511 [M + H]⁺ | 257–262 | 0.6 (P) |
| 1.80 | F | 1-methyl-benzimid-azol-5-yl | —N(CH₃)—CO—CH₂—NMe₂ | XIX XXV.1 | $C_{28}H_{27}FN_6O_2$ | 499 [M + H]⁺ | 248–257 | 0.5 (P) |
| 1.81 | F | 1-methyl-benzimid-azol-5-yl | —SO₂—N(Me)—(CH₂)₂—NMe₂ | XIX XXI.9 | $C_{28}H_{29}FN_6O_3S$ | 549 [M + H]⁺ | 134–138 | 0.4 (P) |
| 1.82 | F | 1-methyl-benzimid-azol-5-yl | —CO—N(Me)—CH₂CN | XIX XXI.10 | $C_{27}H_{21}FN_6O_2$ | 481 [M + H]⁺ | 128–134 | 0.9 (P) |
| 1.83 | F | 1-methyl-benzimid-azol-5-yl | —N(SO₂Me)—(CH₂)₂—NH₂ | XIX XXV.21 | $C_{26}H_{25}FN_6O_3S$ | 521 [M + H]⁺ | 205–211 | 0.6 (P) |
| 1.84 | H | 1-methyl-benzo-triazol-5-yl | —CH₂—NMe₂ | XVI.1 XXV.8 | $C_{25}H_{24}FN_6O$ | 425 [M + H]⁺ | 285–297 | 0.19 (C) |
| 1.85 | Cl | 1,2-(ethylene-dioxy)-phen-4-yl- | —CH₂-(4-hydroxy-piperidin-1-yl) | XVI.1 XXV.22 | $C_{29}H_{28}ClN_3O_4$ | 518/520 [M + H]⁺ | 260–263 | 0.19 (E) |
| 1.86 | Cl | 1,2-(ethylene-dioxy)-phen-4-yl- | —N(CH₃)—CO—(CH₂)₂—NMe₂ | XVI.1 XXV.23 | $C_{29}H_{29}ClN_4O_4$ | 533/535 [M + H]⁺ | 246–248 | 0.05 (E) |
| 1.87 | Cl | 1,2-(ethylene-dioxy)-phen-4-yl- | —CH₂—N(Me)Et | XVI.1 XXV.10 | $C_{27}H_{26}ClN_3O_3$ | 476/478 [M + H]⁺ | 192–195 | 0.19 (E) |
| 1.88 | Cl | 1,2-(ethylene-dioxy)-phen-4-yl- | —CH₂—N(Me)—(CH₂)₂—OH | XVI.1 XXV.24 | $C_{27}H_{26}ClN_3O_4$ | 492/494 [M + H]⁺ | 128–133 | 0.17 (E) |
| 1.89 | Cl | 1,2-(ethylene-dioxy)-phen-4-yl- | (R)—CH₂-(3-hydroxy-pyrrolidin-1-yl) | XVI.1 XXV.25 | $C_{28}H_{26}ClN_3O_4$ | 504/506 [M + H]⁺ | 148–151 | 0.17 (E) |
| 1.90 | Cl | 1,2-(ethylene-dioxy)-phen-4-yl- | —N(SO₂Me)—(CH₂)₂—NMe₂ | XVI.1 XXV.6 | $C_{28}H_{29}ClN_4O_5S$ | 569/571 [M + H]⁺ | 219–223 | 0.18 (E) |
| 1.91 | Cl | 1,2-(ethylene-dioxy)-phen-4-yl- | (S)—CH₂-(3-hydroxy-pyrrolidin-1-yl) | XVI.1 XXV.2 | $C_{28}H_{26}ClN_3O_4$ | 504/506 [M + H]⁺ | 148–151 | 0.17 (E) |

-continued

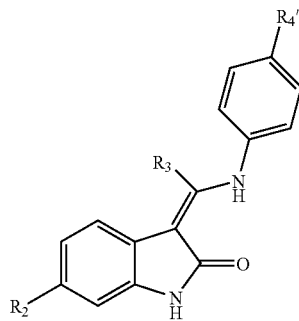

(I.1)

| Example | $R_2$ | $R_3$ | $R_4'$ | Educts | Empirical formula | Mass spectrum | M.p. [° C.] | $R_f$ value * |
|---|---|---|---|---|---|---|---|---|
| 1.92 | Cl | 1,2-(ethylene-dioxy)-phen-4-yl- | —$CH_2$-(1-methylpipe-razin-4-yl) | XVI.1 XXV.11 | $C_{29}H_{29}ClN_4O_3$ | 517/519 $[M + H]^+$ | 150 (decomposition) | 0.05 (E) |
| 1.93 | Cl | 1,2-(ethylene-dioxy)-phen-4-yl- | —$SO_2$—N(Me)—$(CH_2)_3$—$NMe_2$ | XVI.1 XXI.11 | $C_{29}H_{31}ClN_4O_5S$ | 583/585 $[M + H]^+$ | 200–210 | 0.10 (T) |
| 1.94 | Cl | 1,2-(ethylene-dioxy)-phen-4-yl- | —$N(SO_2Et)$—$(CH_2)_2$—$NMe_2$ | XVI.1 XXV.27 | $C_{29}H_{31}ClN_4O_5S$ | 583/585 $[M + H]^+$ | 185–188 | 0.18 (E) |
| 1.95 | Cl | 1,2-(ethylene-dioxy)-phen-4-yl- | —$SO_2$—N(Me)—$(CH_2)_2$—$NMe_2$ | XVI.1 XXI.9 | $C_{28}H_{29}ClN_4O_5S$ | 569/571 $[M + H]^+$ | 178–180 | 0.05 (E) |
| 1.96 | Cl | 1,2-(ethylene-dioxy)-phen-4-yl- | —N(COMe)—$(CH_2)_3$—$NMe_2$ | XVI.1 XXV.2 | $C_{30}H_{31}ClN_4O_4$ | 547/549 $[M + H]^+$ | 133–135 | 0.05 (T) |
| 1.97 | Cl | 1,2-(ethylene-dioxy)-phen-4-yl- | —N(COEt)—$(CH_2)_3$—$NMe_2$ | XVI.1 XXV.28 | $C_{31}H_{33}ClN_4O_4$ | 561/563 $[M + H]^+$ | sinters from 120 | 0.13 (T) |
| 1.98 | Cl | 1,2-(ethylene-dioxy)-phen-4-yl- | —N(COEt)—$(CH_2)_2$—$NMe_2$ | XVI.1 XXV.29 | $C_{30}H_{31}ClN_4O_4$ | 547/549 $[M + H]^+$ | sinters from 130 | 0.05 (E) |
| 1.99 | Cl | 1,2-(ethylene-dioxy)-phen-4-yl- | —$N(CH_3)$—CO—$CH_2$-(1-methylpipe-razin-4-yl) | XVI.1 XXV.2 | $C_{30}H_{31}ClN_5O_4$ | 572/574 $[M - H]^-$ | 235 | 0.2 (G) |
| 1.100 | Cl | 1,2-(ethylene-dioxy)-phen-4-yl- | —CO—N(Et)—$(CH_2)_2$—$NMe_2$ | XVI.1 XXI.12 | $C_{30}H_{31}ClN_4O_4$ | 547/549 $[M + H]^+$ | 212 | 0.2 (G) |
| 1.101 | F | 1,2-(ethylene-dioxy)-phen-4-yl- | 1-ethyl-imidazol-2-yl | XVI.7 XXV.30 | $C_{28}H_{23}FN_4O_3$ | 483 $[M + H]^+$ | 266–268 | 0.6 (P) |
| 1.102 | F | 1,2-(ethylene-dioxy)-phen-4-yl- | —$CH_2$—NH—(2-pyridyl) | XVI.7 XXVIII | $C_{29}H_{23}FN_4O_3$ | 495 $[M + H]^+$ | 137–139 | 0.6 (P) |
| 1.103 | F | 1,2-(ethylene-dioxy)-phen-4-yl- | —$N(CH_3)$—CO—$CH_2$—$NMe_2$ | XVI.7 XXV.1 | $C_{28}H_{27}FN_4O_4$ | 503 $[M + H]^+$ | 150–153 | 0.6 (P) |
| 1.104 | F | 1,2-(ethylene-dioxy)-phen-4-yl- | —CO-(1-methyl-piperazin-4-yl) | XVI.7 XXI | $C_{29}H_{27}FN_4O_4$ | 515 $[M + H]^+$ | 220–223 | 0.6 (P) |
| 1.105 | F | 1,2-(ethylene-dioxy)-phen-4-yl- | —$CH_2$—$NEt_2$ | XVI.7 XXV.16 | $C_{28}H_{28}FN_3O_3$ | 474 $[M + H]^+$ | 108–110 | 0.6 (P) |

-continued (I.1)

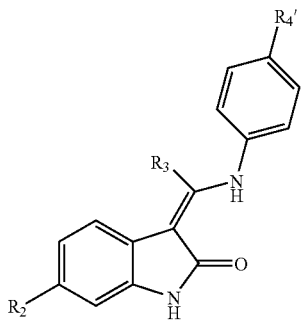

| Example | $R_2$ | $R_3$ | $R_4'$ | Educts | Empirical formula | Mass spectrum | M.p. [° C.] | $R_f$ value * |
|---|---|---|---|---|---|---|---|---|
| 1.106 | F | 1,2-(ethylene-dioxy)-phen-4-yl- | —CH$_2$-(4-hydroxy-piperidin-1-yl) | XVI.7 XXV.22 | $C_{29}H_{28}FN_3O_4$ | 502 [M + H]$^+$ | 237–245 | 0.6 (P) |
| 1.107 | F | 1,2-(ethylene-dioxy)-phen-4-yl- | —N(CH$_3$)—CO—CH$_2$-(1-methylpipe-razin-4-yl) | XVI.7 XXV.2 | $C_{31}H_{32}FN_5O_4$ | 558 [M + H]$^+$ | 163–167 | 0.6 (P) |
| 1.108 | F | 1,2-(ethylene-dioxy)-phen-4-yl- | —SO$_2$—N(Me)—(CH$_2$)$_2$—NMe$_2$ | XVI.7 XXI.9 | $C_{28}H_{29}FN_4O_5S$ | 553 [M + H]$^+$ | 170–175 | 0.6 (P) |
| 1.109 | F | 1,2-(ethylene-dioxy)-phene-4-yl- | —CO—N(Et)—(CH$_2$)$_2$—NMe$_2$ | XVI.7 XXI.12 | $C_{30}H_{31}FN_4O_4$ | 531 [M + H]$^+$ | 237–242 | 0.6 (P) |
| 1.110 | F | 1,2-(ethylene-dioxy)-phen-4-yl- | —CH$_2$—N(Me)Et | XVI.7 XXV.10 | $C_{27}H_{26}FN_3O_3$ | 460 [M + H]$^+$ | 118–123 | 0.6 (P) |
| 1.111 | F | 1,2-(ethylene-dioxy)-phen-4-yl- | —CH$_2$—N(Me)—(CH$_2$)$_2$—OH | XVI.7 XXV.24 | $C_{27}H_{26}FN_3O_4$ | 474 [M − H]$^-$ | 181–188 | 0.6 (P) |
| 1.112 | F | 1,2-(ethylene-dioxy)-phen-4-yl- | —N(SO$_2$Me)—(CH$_2$)$_2$—NMe$_2$ | XVI.7 XXV.6 | $C_{28}H_{29}FN_4O_5S$ | 553 [M + H]$^+$ | 180–183 | 0.6 (P) |
| 1.113 | F | 1,2-(ethylene-dioxy)-phen-4-yl- | —CH$_2$—N(Me)—(CH$_2$)$_2$—OMe | XVI.7 XXV.31 | $C_{28}H_{28}FN_3O_4$ | 490 [M + H]$^+$ | 103–106 | 0.6 (P) |
| 1.114 | F | 1,2-(ethylene-dioxy)-phen-4-yl- | (R)—CH$_2$-(3-hydroxy-pyrrolidin-1-yl) | XVI.7 XXV.25 | $C_{28}H_{26}FN_3O_4$ | 488 [M + H]$^+$ | 145–148 | 0.6 (P) |
| 1.115 | F | 1,2-(ethylene-dioxy)-phen-4-yl- | (S)—CH$_2$-(3-hydroxy-pyrrolidin-1-yl) | XVI.7 XXV.26 | $C_{28}H_{26}FN_3O_4$ | 488 [M + H]$^+$ | 140–147 | 0.6 (P) |
| 1.116 | F | 1,2-(ethylene-dioxy)-phen-4-yl- | (S)—CH$_2$-(2-[hydroxy-methyl]-pyrrolidin-1-yl) | XVI.7 XXV.32 | $C_{29}H_{28}FN_3O_4$ | 502 [M + H]$^+$ | 149–156 | 0.6 (P) |
| 1.117 | F | 1,2-(ethylene-dioxy)-phen-4-yl- | —N(CH$_3$)—CO—(CH$_2$)$_2$—NMe$_2$ | XVI.7 XXV.23 | $C_{29}H_{29}FN_4O_4$ | 517 [M + H]$^+$ | 131–138 | 0.6 (P) |
| 1.118 | F | 1,2-(ethylene-dioxy)-phen-4-yl- | —N(COEt)—(CH$_2$)$_2$—NMe$_2$ | XVI.7 XXV.29 | $C_{30}H_{31}FN_4O_4$ | 531 [M + H]$^+$ | 143 | 0.6 (P) |

-continued (I.1)

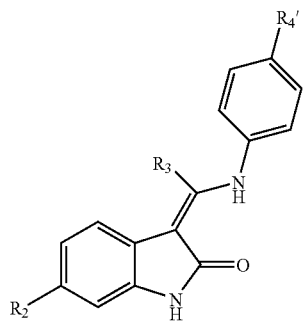

| Example | $R_2$ | $R_3$ | $R_4'$ | Educts | Empirical formula | Mass spectrum | M.p. [° C.] | $R_f$ value * |
|---|---|---|---|---|---|---|---|---|
| 1.119 | F | 1,2-(ethylenedioxy)-phen-4-yl- | —N(COEt)—(CH$_2$)$_3$—NMe$_2$ | XVI.7 XXV.2 | $C_{31}H_{33}FN_4O_4$ | 545 [M + H]$^+$ | 127 | 0.6 (P) |
| 1.120 | F | 1,2-(ethylenedioxy)-phen-4-yl- | —CH$_2$-(1-methylpiperazin-4-yl) | XVI.7 XXV.11 | $C_{29}H_{29}FN_4O_3$ | 501 [M + H]$^+$ | 195–198 | 0.7 (P) |
| 1.121 | F | 1,2-(ethylenedioxy)-phen-4-yl- | —SO$_2$—N(Me)—(CH$_2$)$_3$—NMe$_2$ | XVI.7 XXI.11 | $C_{29}H_{31}FN_4O_5S$ | 567 [M + H]$^+$ | 144–149 | 0.5 (P) |
| 1.122 | F | 1,2-(ethylenedioxy)-phen-4-yl- | —N(SO$_2$Et)—(CH$_2$)$_2$—NMe$_2$ | XVI.7 XXV.27 | $C_{29}H_{31}FN_4O_5S$ | 567 [M + H]$^+$ | 177–178 | 0.7 (P) |
| 1.123 | F | 1,2-(ethylenedioxy)-phen-4-yl- | —CH$_2$-(morpholine-4-yl) | XVI.7 XXV.33 | $C_{28}H_{26}FN_3O_4$ | 486 [M − H]$^−$ | 215–224 | 0.8 (P) |
| 1.124 | F | 1,2-(ethylenedioxy)-phen-4-yl- | —SO$_2$—(CH$_2$)$_2$—NEt$_2$ | XVI.7 XXIV | $C_{29}H_{30}FN_3O_5S$ | 552 [M + H]$^+$ | 186–192 | 0.7 (P) |
| 1.125 | F | 1,2-(ethylenedioxy)-phen-4-yl- | —SO$_2$—NH—(CH$_2$)$_2$—NMe$_2$ | XVI.7 XXIX | $C_{27}H_{27}FN_4O_5S$ | 539 [M + H]$^+$ | 184 | 0.1 (G) |
| 1.126 | F | 1,2-(ethylenedioxy)-phen-4-yl- | —SO$_2$—NH—(CH$_2$)$_3$—NMe$_2$ | XVI.7 XXIX.1 | $C_{28}H_{29}FN_4O_5S$ | 551 [M − H]$^−$ | 223 | 0.1 (G) |
| 1.127 | F | 1,2-(ethylenedioxy)-phen-4-yl- | —CH$_2$—CO-(1-methyl-piperizin-4-yl) | XVI.7 XXI.4 | $C_{30}H_{29}FN_4O_4$ | 527 [M − H]$^−$ | 237 | 0.3 (G) |
| 1.128 | F | 1,2-(ethylenedioxy)-phen-4-yl- | —N(COMe)—(CH$_2$)$_3$—NMe$_2$ | XVI.7 XXV.4 | $C_{30}H_{31}FN_4O_4$ | 529 [M − H]$^−$ | 115 | 0.1 (G) |
| 1.134 | H | 1-methyl-benzimidazol-5-yl | —N(COMe)—(CH$_2$)$_2$—NMe$_2$ | XIX.1 XXV.3 | $C_{29}H_{30}N_6O_2$ | 495 [M + H]$^+$ | 270 (decomposition) | 0.67 (P) |
| 1.135 | H | 1-methyl-benzimidazol-5-yl | —N(CH$_3$)—CO—CH$_2$—NMe$_2$ | XIX.1 XXV.1 | $C_{28}H_{28}N_6O_2$ | 481 [M + H]$^+$ | 243–245 | 0.59 (P) |
| 1.136 | H | 1-methyl-benzimidazol-5-yl | —N(CO-3-pyridyl)-(CH$_2$)$_2$—NMe$_2$ | XIX.1 XXV.9 | $C_{33}H_{31}N_7O_2$ | 558 [M + H]$^+$ | 188 (decomposition) | 0.79 (U) |

-continued (I.1)

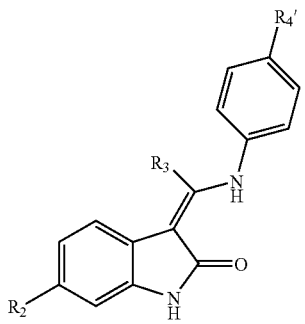

| Example | $R_2$ | $R_3$ | $R_4'$ | Educts | Empirical formula | Mass spectrum | M.p. [° C.] | $R_f$ value * |
|---|---|---|---|---|---|---|---|---|
| 1.137 | COOMe | 1,2-(ethylenedioxy)-phen-4-yl- | —N(COEt)—(CH$_2$)$_2$—NMe$_2$ | XVI.6 XXV.29 | $C_{32}H_{34}N_4O_6$ | 571 [M + H]$^+$ | 212–214 | 0.55 (A) |
| 1.138 | COOMe | 1,2-(ethylenedioxy)-phen-4-yl- | —N(COEt)—(CH$_2$)$_3$—NMe$_2$ | XVI.6 XXV.28 | $C_{33}H_{36}N_4O_6$ | 585 [M + H]$^+$ | 143–145 | 0.47 (A) |
| 1.139 | COOMe | 1,2-(ethylenedioxy)-phen-4-yl- | —N(COMe)—(CH$_2$)$_3$—NMe$_2$ | XVI.6 XXV.4 | $C_{32}H_{34}N_4O_6$ | 571 [M + H]$^+$ | 238–239 | 0.52 (A) |
| 1.140 | F | 1,2-(methylenedioxy)-phen-4-yl- | —N(CH$_3$)—CO—CH$_2$-(1-methylpiperazin-4-yl) | XVI.14 XXV.2 | $C_{30}H_{30}FN_5O_4$ | 544 [M + H]$^+$ | n.d. | 0.30 (A) |
| 1.141 | Br | 1,2-(methylenedioxy)-phen-4-yl- | —N(CH$_3$)—CO—CH$_2$-(1-methylpiperazin-4-yl) | XVI.13 XXV.2 | $C_{30}H_{30}BrN_5O_4$ | 604/606 [M + H]$^+$ | n.d. | 0.30 (A) |

*Eluant mixtures:
(A): silica gel, dichloromethane/methanol/conc. ammonia (90:10:1)
(B): silica gel, dichloromethane/methanol/conc. ammonia (85:15:1.5)
(C): silica gel, ethyl acetate/methanol/conc. ammonia (80:20:1)
(D): silica gel, ethyl acetate/methanol/conc. ammonia (90:10:2)
(E): silica gel, ethyl acetate/methanol/conc. ammonia (90:10:1)
(F): silica gel, dichloromethane/methanol (5:1)
(G): silica gel, dichloromethane/methanol (9:1)
(H): silica gel, dichloromethane/methanol/conc. ammonia (50:10:0.1)
(I): silica gel, dichloromethane/methanol/conc. ammonia (90:10:0.1)
(K): Alox, dichloromethane/ethanol (20:1)
(L): silica gel, dichloromethane/methanol/conc. ammonia (80:20:2)
(M): Alox, ethyl acetate/methanol/conc. ammonia (90:10:1)
(N): silica gel, ethyl acetate/methanol/conc. ammonia (40:10:1)
(O): silica gel, ethyl acetate/methanol (9:1)
(P): silica gel, dichloromethane/methanol/conc. ammonia (80:20:1)
(Q): silica gel, dichloromethane/methanol (50:1)
(R): silica gel, dichloromethane/methanol (30:1)
(S): silica gel, dichloromethane/methanol (4:1)
(T): silica gel, ethyl acetate/methanol/conc. ammonia (70:30:1)
(U): silica gel, dichloromethane/methanol/conc. ammonia (80:10:1)

The following compounds are also prepared analogously to Example 1:

(1.129) 6-fluoro-3-(Z)-[1-(3-{N-(2-dimethylaminoethyl)-N-methyl-aminocarbonyl}-phenylamino)-1-(1-methylbenzimidazol-5-yl)methylene]-2-indolinone from the educts XIX and XXI.13

$R_f$ value:0.6 (silica gel, methylene chloride/methanol/conc. ammonia=80:20:1)

M.p.: 131–138° C. $C_{29}H_{29}FN_6O_2$

Mass spectrum: m/z=513 [M+H]$^+$ (1.130) 6-chloro-3-(Z)-[1-(4-{N-(2-dimethylamino-ethyl)-N-methanesulphonyl-amino}-3-chloro-phenylamino)-1-(1,2-ethylenedioxyphen-4-yl)-methylene]-2-indolinone from educts XVI.1 and XXV.35

$R_f$ value:0.2 (silica gel, methylene chloride/methanol=9:1)

M.p.: 153° C. $C_{28}H_{28}Cl_2N_4O_5S$

Mass spectrum: m/z=601/603/605 [M+H]$^+$ (1.131) 6-chloro-3-(Z)-{1-[4-(N-dimethylaminomethylcarbonyl-N-methyl-amino)-3-methoxy-phenylamino]-1-(1,2-ethylenedioxyphen-4-yl)-methylene}-2-indolinone from educts XVI.1 and XXX $R_f$ value:0.3 (silica gel, methylene chloride/methanol/conc. ammonia=90:10:1)

M.p.: 229° C. $C_{29}H_{29}ClN_4O_5$

Mass spectrum: m/z=549/551 [M+H]$^+$ (1.132) 6-fluoro-3-(Z)-{1-[4-(N-dimethylaminomethylcarbonyl-N-methyl-amino)-3-methoxy-phenylamino]-1-(1,2-ethylenedioxyphen-4-yl)-methylene}-2-indolinone from educts XVI.7 and XXX $R_f$ value:0.3 (silica gel, methylene chloride/methanol=9:1)

M.p.: 142° C. $C_{29}H_{29}FN_4O_5$

Mass spectrum: m/z=533 [M+H]$^+$ (1.133) 6-fluoro-3-(Z)-[1-(4-{N-(2-dimethylamino-ethyl)-N-methanesulphonyl-amino}-3-chloro-phenylamino)-1-(1,2-ethylenedioxyphen-4-yl)-methylene]-2-indolinone from educts XVI.7 and XXV.35

$R_f$ value:0.2 (silica gel, methylene chloride/methanol=9:1)

M.p.: 173° C. $C_{28}H_{28}ClFN_4O_5S$

Mass spectrum: m/z=687/589 [M+H]$^+$

EXAMPLE 2.0

3-(Z)-{1-[4-(N-dimethylaminomethylcarbonyl-N-methyl-amino)-phenylamino]-1-(2-pyrazinyl)-methylene}-2-indolinone 0.281 g of 1-acetyl-3-(1-hydroxy-1-(2-pyrazinyl)-methylene-2-indolinone (educt X) and 0.416 g of phosphorus pentachloride are refluxed in 10 ml dioxane for 3 hours. Volatile constituents are distilled off, the residue is taken up in 15 ml dioxane and after the addition of 0.415 g of N-(dimethylaminomethylcarbonyl)-N-methyl-p-phenylenediamine (educt XXV.1) it is refluxed for a further 5 hours. After cooling and adding 50 ml of water it is extracted five times with dichloromethane. The residue obtained from the combined organic phases, which have been dried over magnesium sulphate, by distilling off the solvent is purified by chromatography through a silica gel column with dichloromethane/methanol/conc. ammonia=190:10:1 as eluant. The crude product thus obtained is stirred with diisopropylether, suction filtered and dried at 80° C.

Yield: 0.07 g (16% of theory)

$R_f$ value:0.2 (silica gel, methylene chloride/methanol/conc. ammonia=90:10:1)

M.p.: 198–199° C. $C_{24}H_{24}N_6O_2$

Mass spectrum: m/z=429 [M+H]$^+$; m/z=427 [M−H]$^-$; m/z=451 [M+Na]$^+$

The following compounds of general formula I.2 are prepared analogously to Example 2.0 from the educts specified in each case:

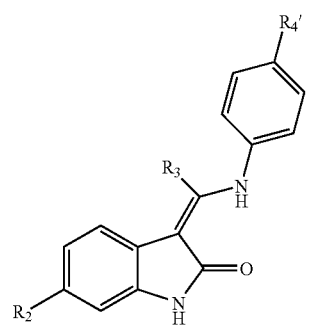

(I.2)

| Example | $R_2$ | $R_3$ | $R_4'$ | Educts | Empirical formula | Mass spectrum | M.p. [° C.] | $R_f$ value * |
|---|---|---|---|---|---|---|---|---|
| 2.1 | H | 1,2-(methylenedioxy)-phen-4-yl- | —N(CH$_3$)—CO—CH$_2$—NMe$_2$ | X.1 XXV.1 | $C_{27}H_{26}N_4O_4$ | 471 [M + H]$^+$ 469 [M − H]$^-$ 493 [M + Na]$^+$ | 221–222 | 0.3 (A) |

-continued (I.2)

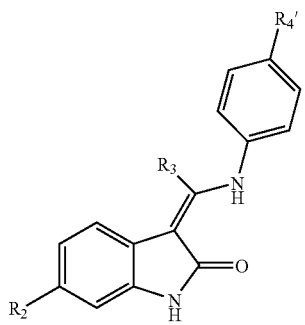

| Example | $R_2$ | $R_3$ | $R_4'$ | Educts | Empirical formula | Mass spectrum | M.p. [° C.] | $R_f$ value * |
|---|---|---|---|---|---|---|---|---|
| 2.2 | H | 1,2-(methylene-dioxy)-phen-4-yl- | —$CH_2$—$NMe_2$<br>—$CH_2$—$NMe_2$ | X.1<br>XXV.8 | $C_{25}H_{23}N_3O_3$ | 414 [M + H]$^+$<br>412 [M − H]$^-$<br>436 [M + Na]$^+$ | 221–222 | 0.4 (A) |

*Eluant mixtures:
see the List following Example 1

EXAMPLE 3.0

6-Chloro-3-(Z)-[1-(4-{N-(dimethylaminomethylcarbonyl)-N-methyl-amino}-phenyl-amino)-1-(4-pyridyl)-methylene]-2-indolinone 0.270 g of 1-acetyl-6-chloro-3-[1-chloro-1-(4-pyridyl)-methylene]-2-indolinone (educt XIII.3), 0.232 g N-(dimethylaminomethylcarbonyl)-N-methyl-p-phenylenediamine and 0.40 ml triethylamine are refluxed in 10 ml of tetrahydrofuran for 15 hours. After cooling 0.50 ml piperidine is added and the mixture is stirred for 2 hours at ambient temperature. The residue obtained by distilling off the volatile constituents is purified by chromatography through a silica gel column with dichloromethane/methanol=9:1 as eluant. The crude product thus obtained is stirred with methanol, suction filtered and dried at 80° C.

Yield: 0.075 g (20% of theory)

$R_f$ value:0.3 (silica gel, dichloromethane/methanol=9:1)

M.p.: 274–276° C. $C_{25}H_{24}ClN_5O_2$

Mass spectrum: m/z=462/464 [M+H]$^+$; m/z=460/462 [M−H]$^-$

The following compounds of general formula I.3 are prepared analogously to Example 3.0 from the educts specified in each case:

(I.3)

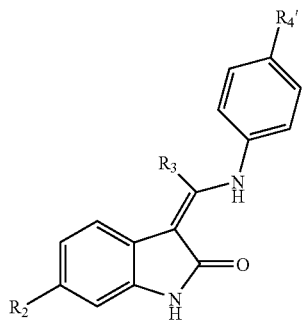

| Example | $R_2$ | $R_3$ | $R_4'$ | Educts | Empirical formula | Mass spectrum | M.p. [° C.] | $R_f$ value * |
|---|---|---|---|---|---|---|---|---|
| 3.1 | Cl | 4-pyridyl- | —$CH_2$—$NMe_2$ | XIII.3<br>XXV.8 | $C_{23}H_{21}ClN_4$ | 405/407 [M + H]$^+$<br>403/405 [M − H]$^-$ | 250–251 | 0.5 (F) |

-continued (I.3)

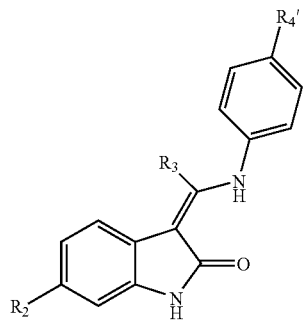

| Example | $R_2$ | $R_3$ | $R_4'$ | Educts | Empirical formula | Mass spectrum | M.p. [° C.] | $R_f$ value * |
|---|---|---|---|---|---|---|---|---|
| 3.2 | Cl | 4-pyridyl- | —N(SO$_2$—(CH$_2$)$_2$—CH$_3$)—(CH$_2$)$_2$—NMe$_2$ | XIII.3 XXV.7 | C$_{27}$H$_{30}$ClN$_5$O$_3$S | 540/542 [M + H]$^+$ 538/540 [M − H]$^-$ | 228–232 | 0.3 (G) |
| 3.3 | H | 5-methyl-isoxazol-3-yl- | —N(CH$_3$)—C(O)CH$_3$ | XV XXII | C$_{22}$H$_{20}$N$_4$O$_3$S | 388 [M$^+$] | 238–239 | 0.7 (A) |
| 3.4 | H | 5-methyl-isoxazol-3-yl- | —N(SO$_2$—CH$_3$)—(CH$_2$)$_2$—NMe$_2$ | XV XXV.6 | C$_{24}$H$_{27}$N$_5$O$_4$S | 481 [M$^+$] | 241–242 | 0.3 (A) |
| 3.5 | H | 3-methyl-pyrazol-5-yl- | —N(CH$_3$)—C(O)CH$_3$ | XV.1 XXII | C$_{22}$H$_{21}$N$_5$O$_2$ | 388 [M + H]$^+$ 386 [M − H]$^-$ 410 [M + Na]$^+$ | 195–196 | 0.4 (A) |
| 3.6 | H | 3-methyl-pyrazol-5-yl- | —N(SO$_2$—CH$_3$)—(CH$_2$)$_2$—NMe$_2$ | XV.1 XXV.6 | C$_{24}$H$_{28}$N$_6$O$_3$S | 480 [M$^+$] | 253–254 | 0.3 (A) |
| 3.7 | Cl | 2-pyrrolyl- | —N(CH$_3$)—C(O)CH$_2$—NMe$_2$ | XIV XXV.1 | C$_{24}$H$_{24}$ClN$_5$O$_2$ | 450/452 [M + H]$^+$ 448/450 [M − H]$^-$ | 270–272 | 0.5 (G) |
| 3.8 | Cl | 2-pyrrolyl- | —CH$_2$—NMe$_2$ | XIV XXV.8 | C$_{22}$H$_{21}$ClN$_4$O | 393/395 [M + H]$^+$ 391/393 [M − H]$^-$ | 201–203 | 0.3 (H) |
| 3.9 | Cl | 2-pyrrolyl- | —N(C(O)—CH$_3$)—(CH$_2$)$_2$—NMe$_2$ | XIV XXV.3 | C$_{25}$H$_{26}$ClN$_5$O$_2$ | 464/462 [M + H]$^+$ 462/464 [M − H]$^-$ | 240–243 | 0.3 (I) |
| 3.10 | Cl | 2-pyrrolyl- | —N(SO$_2$—(CH$_2$)$_2$—CH$_3$)—(CH$_2$)$_2$—NMe$_2$ | XIV XXV.7 | C$_{26}$H$_{30}$ClN$_5$O$_3$S | 528/530 [M + H]$^+$ 526/528 [M − H]$^-$ | 203–205 | 0.3 (G) |
| 3.11 | Cl | 1-benzyl-imidazol-5-yl- | —CH$_2$—NMe$_2$ | XIII.5 XXV.8 | C$_{28}$H$_{26}$ClN$_5$O | 482/484 [M − H]$^-$ 506/508 [M + Na]$^+$ | 270–272 (M.p. of the hydrochloride) | 0.5 (K) |
| 3.12 | Cl | 3-pyridyl- | —CH$_2$—NMe$_2$ | XIII.2 XXV.8 | C$_{23}$H$_{21}$ClN$_4$O | 403/405 [M − H]$^-$ | 205–208 | 0.3 (F) |
| 3.13 | Cl | 3-pyridyl- | —N(SO$_2$—(CH$_2$)$_2$—CH$_3$)—(CH$_2$)$_2$—NMe$_2$ | XIII.2 XXV.7 | C$_{27}$H$_{30}$ClN$_5$O$_3$S | 464/462 [M + H]$^+$ | 204–205 | 0.7 (F) |
| 3.14 | Cl | 3-pyridyl | —N(CH$_3$)—C(O)CH$_2$—NMe$_2$ | XIII.2 XXV.1 | C$_{25}$H$_{24}$ClN$_5$O$_2$ | 462/464 [M + H]$^+$ | 243–245 | 0.6 (F) |

*Eluant mixtures: see the List following Example 1

EXAMPLE 4.0

6-Chloro-3-(Z)-{1-[4-(pyrrolidin-1-ylmethyl)phenylamino]-1-(benzimidazol-5-yl)-methylene}-2-indolinone 0.184 6-chloro-3-(1-(4-(pyrrolidin-1-ylmethyl)phenylamino)-1-(3,4-diaminophenyl)-methylene)-2-indolinone (educt XVIII.1) are refluxed in 5 ml formic acid for 1 hour. The residue obtained by distilling off the solvent is suspended in water, made alkaline by the addition of soda solution and extracted with ethyl acetate. The ethyl acetate phase is counter-extracted three times with water and dried over sodium sulphate. The residue obtained by distilling off the solvent is stirred with diethyl ether, suction filtered, washed with diethyl ether and dried at 80° C.

Yield: 0.150 g (80% of theory)

$R_f$ value:0.5 (silica gel, methylene chloride/methanol/conc. ammonia=85:15:1.5)

M.p.: 277–279° C. $C_{27}H_{24}ClN_5O$

Mass spectrum: m/z=468/470 [M–H]$^-$

The following compounds of general formula I.4 are prepared analogously to Example 4.0 under the reaction conditions specified in each case:

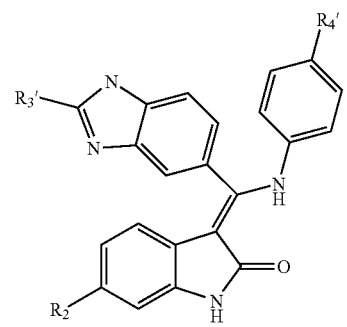

(I.4)

| Example | $R_2$ | $R_3'$ Solvent Reaction time | $R_4'$ | educt | Empirical formula | Mass spectrum | M.p. [° C.] | $R_f$ value * |
|---|---|---|---|---|---|---|---|---|
| 4.1 | Cl | $CH_3$- acetic acid 1 h | —$CH_2$- pyrrolidin-1-yl- | XVIII.1 | $C_{28}H_{26}ClN_5O$ | 484/486 [M + H]$^+$ 482/484 [M – H]$^-$ | 295–297 (decomposition) | 0.5 (B) |
| 4.2 | Cl | H- formic acid 1 h | —$N(CH_3)$— $C(O)CH_2$— $NMe_2$ | XVIII.2 | $C_{27}H_{25}ClN_6O_2$ | 500/502 [M*] 501/503 [M + H]$^+$ 499/501 [M – H]$^-$ | 285–288 (decomposition) | 0.3 (B) |
| 4.3 | Cl | $CH_3$- acetic acid 7.5 h | —$N(CH_3)$— $C(O)CH_2$— $NMe_2$ | XVIII.2 | $C_{28}H_{27}ClN_6O_2$ | 515/517 [M + H]$^+$ 513/515 [M – H]$^-$ | 230–235 (decompositions; sinters from 200) | 0.4 (B) |
| 4.4 | Cl | H- formic acid 7 h | —$C(O)$-(1-methyl-piperazin-4-yl) | XVIII | $C_{28}H_{25}ClN_6O_2$ | 515/515 [M + H]$^+$ 511/513 [M – H]$^-$ | 240–243, sinters 215–220 | 0.4 (B) |
| 4.5 | Cl | H- formic acid 2.5 h | —$N(C(O)$— $CH_3)$— $(CH_2)_2$— $NMe_2$ | XVIII.3 | $C_{28}H_{27}ClN_6O_2$ | 513/515 [M – H]$^-$ | 283–287 (decomposition) | 0.4 (B) |
| 4.6 | Cl | $CH_3$- acetic acid 7 h | —$N(C(O)$— $CH_3)$— $(CH_2)_2$— $NMe_2$ | XVII.3 | $C_{29}H_{29}ClN_6O_2$ | 527/529 [M – H]$^-$ | 266–268 | 0.4 (B) |
| 4.7 | Cl | H- formic acid 4 h | —$N(C(O)$— $CH_3)$— $(CH_2)_3$— $NMe_2$ | XVIII.4 | $C_{29}H_{29}ClN_6O_2$ | 529/531 [M + H]$^+$ 527/529 [M – H]$^-$ | 232–234 (sinters at 180) | 0.3 (L) |
| 4.8 | Cl | $CH_3$- acetic acid 9 h | —$N(C(O)$— $CH_3)$— $(CH_2)_3$— $NMe_2$ | XVIII.4 | $C_{29}H_{29}ClN_6O_2$ | 543/545 [M + H]$^+$ 541/543 [M – H]$^-$ | 298–299 (decomposition) | 0.4 (M) |

-continued (I.4)

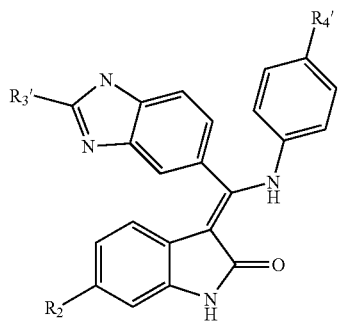

| Example | $R_2$ | $R_3'$ Solvent Reaction time | $R_4'$ | educt | Empirical formula | Mass spectrum | M.p. [° C.] | $R_f$ value * |
|---|---|---|---|---|---|---|---|---|
| 4.9 | Cl | $CH_3$- acetic acid 4.5 h | —C(O)-(1-methyl-piperazin-4-yl) | XVIII | $C_{29}H_{27}ClN_6O_2$ | 527/529 $[M+H]^+$ | 265–268 | 0.5 (B) |

*Eluant mixtures: see the List following Example 1

EXAMPLE 5.0

3-(Z)-{1-[4-(dimethylaminomethyl)phenylamino]-1-(benzimidazol-5-yl)methylene}-2-indolinone 0.429 g of 3-(1-(4-(dimethylaminomethyl)phenylamino)-1-(4-amino-3-nitrophenyl)-methylene)-2-indolinone (educt XVII.6), are hydrogenated in 30 ml formic acid with the addition of 0.50 g Raney nickel at ambient temperature for 3.5 hours under 50 psi of hydrogen pressure. The catalyst is eliminated by suction filtering, the solution is evaporated down and the residue is dissolved in dichloromethane/methanol/ammonia=50:50:1. The solution is filtered through silica gel, the residue obtained by distilling off the solvent is taken up in soda solution and stirred overnight. The precipitate formed is filtered off, washed with water, dried, stirred with diethyl ether, filtered off again and dried at 100° C.

Yield: 0.320 g (78% of theory)

$R_f$ value:0.4 (silica gel, methylene chloride/methanol/conc. ammonia=80:20:2)

M.p.: 273–277° C. (decomposition) $C_{25}H_{23}N_5O$

Mass spectrum: m/z=408 $[M-H]^-$

The following compound is prepared analogously to Example 5.0:

(5.1) 6-chloro-3-(Z)-[1-(4-{N-methanesulphonyl-N-(2-dimethylamino-ethyl)-amino}-phenylamino)-1-(benzimidazol-5-yl)methylene]-2-indolinone from 6-chloro-3-[1-(4-{N-methanesulphonyl-N-(2-dimethylamino-ethyl)-amino}-phenyl-amino)-1-(4-amino-3-nitrophenyl)-methylene]-2-indolinone.

$R_f$ value:0.5 (silica gel, methylene chloride/methanol/conc. ammonia=85:15:1.5)

M.p: 160° C. (sintering) $C_{27}H_{27}ClN_6O_3S$

Mass spectrum: m/z=551/553 $[M+H]^+$; m/z=549/551 $[M-H]^{31}$

EXAMPLE 6.0

3-(Z)-[1-(1-methylpiperidin-4-ylamino)-1-(3-furyl)-methylene]-2-indolinone 4.30 g of 1-acetyl-3-[1-hydroxy-1-(3-furyl)-methylene]-2-indolinone (educt X.14) and 3.6 g of 4-amino-1-methylpiperidine are heated to 140° C. for 1.5 hours. After cooling 2 N hydrochloric acid and ethyl acetate are added and the mixture is stirred until completely dissolved. The aqueous phase is separated off and made alkaline with conc. ammonia solution. The precipitate formed is suction filtered, washed with ice water, dried, stirred with acetone, suction filtered again and then dried.

Yield: 0.287 g (5.6% of theory)

$R_f$ value:0.5 (silica gel, dichloromethane/methanol/conc. ammonia=50:10:0.1)

M.p.: 255–260° C. $C_{19}H_{21}N_3O_2$

Mass spectrum: m/z=323 $[M^-]^+$

The following compounds are prepared analogously to Example 6.0:

(6.1) 3-(Z)-[1-(1-methylpiperidin-4-ylamino)-1-(3-thienyl)methylene]-2-indolinone from 1-acetyl-3-(1-hydroxy-1-(3-thienyl)-methylene-2-indolinone (educt X.2).

The product precipitates out during working up in the form of the hydrochloride, which is washed and dried.

$R_f$ value:0.55 (silica gel, dichloromethane/methanol/conc. ammonia=50:10:0.1)

M.p.: 360° C. $C_{19}H_{21}N_3OS$

Mass spectrum: m/z=339 $[M^-]^+$ (6.2) 3-(Z)-[1-(1-methylpiperidin-4-ylamino)-1-(4-imidazolyl)-methylene]-2-indolinone from 1-acetyl-3-[1-hydroxy-1-(4-imidazolyl)-methylene]-2-indolinone (educt XI.3).

$R_f$ value: 0.18 (silica gel, ethyl acetate/methanol/conc. ammonia 5:5:1)

M.p.: 274–279° C. $C_{18}H_{18}ClN_3O$

Mass spectrum: m/z=324 $[M+H]^+$; m/z=322 $[M-H]^-$ (6.3) 3-(Z)-[1-(1-methylpiperidin-4-ylamino)-1-(2-furyl)-methylene]-2-indolinone from 1-acetyl-3-[1-hydroxy-1-(2-furyl)-methylene]-2-indolinone $R_f$ value: 0.45 (silica gel, dichloromethane/methanol/conc. ammonia=50:10:1)

M.p.: 255–260° C. $C_{19}H_{21}N_3O_2$

Mass spectrum: m/z=323 $[M^-]^+$

EXAMPLE 7.0

6-chloro-3-(Z)-{1-[4-(dimethylaminomethyl)-phenylamino]-1-(1-methylbenzimidazol-5-yl)-methylene}-2-indolinone 0.344 g of 6-chloro-3-[1-chloro-1-(1-methylbenzimidazol-5-yl)-methylene]-2-indolinone (educt XIII.4), 0.195 g of 4-(dimethylaminomethyl)-aniline and 0.513 ml of ethyldiisopropylamine are stirred in 5 ml of DMF for 6 hours at 100° C. After the addition of a further 0.090 g of 4-(dimethylaminomethyl)-aniline and 0.34 ml ethyldiisopropylamine the mixture is stirred for a further 6 hours at 100° C. After cooling and adding water, the precipitate formed is suction filtered and washed with water. The crude product thus obtained is purified by chromatography through an alox column with ethyl acetate/methanol=95:5 as eluant. The product is stirred with ice-cold diethyl ether, suction filtered and dried at 80° C.

Yield: 0.060 g (13% of theory)
$R_f$ value:0.52 (Alox, ethyl acetate/methanol=95:5)
M.p.: 288° C. (decomposition) $C_{26}H_{24}ClN_5O$
Mass spectrum: m/z=458/460 $[M+H]^+$ The following compounds of general formula I.7 are prepared analogously to Example 7.0:

EXAMPLE 8.0

6-chloro-3-(Z)-{1-[4-(ethylaminomethyl)-phenylamino]-1-(3,4-methylenedioxyphenyl)-methylene}-2-indolinone 0.8 g of 1-acetyl-6-chloro-3-(Z)-{1-[4-(N-tert-butoxycarbonyl-N-ethyl-aminomethyl)-phenylamino]-1-(3,4-methylenedioxyphenyl)-methylene}-2-indolinone (Example 1.17) are stirred in 7 ml of trifluoroacetic acid and 14 ml of dichloromethane for 1.5 hours at ambient temperature. The residue obtained after the volatile constituents have been evaporated off is triturated with diethyl ether, the precipitate obtained is suction filtered and dried at 100° C.

Yield: 0.78 g (95% of theory)

$R_f$ value:0.42 (silica gel, dichloromethane/methanol/conc. ammonia=90:10:1)

M.p.: 248–250° C. $C_{25}H_{22}ClN_3O_3.C_2HF_3O_2$

Mass spectrum: m/z=470/472 $[M+Na]^+$

The following compounds of general formula 1.8 are prepared analogously to Example 8.0:

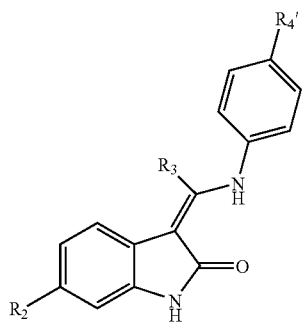

(I.7)

| Example | $R_2$ | $R_3$ | $R_4'$ | Educts | Empirical formula | Mass spectrum | M.p. [° C.] | $R_f$ value * |
|---|---|---|---|---|---|---|---|---|
| 7.1 | Cl | 1-methylbenzimidazol-5-yl- | —CO-(1-methyl-piperazin-4-yl) | XIII.4 XXI | $C_{29}H_{27}ClN_6O_2$ | 527/529 $[M + H]^+$ | 292 | 0.4 (O) |
| 7.2 | Cl | 1-methyl-benzimidazol-5-yl- | —N(CH$_3$)—C(O)CH$_2$—NMe$_2$ | XIII.4 XXV.1 | $C_{28}H_{27}ClN_6O_2$ | 515/517 $[M + H]^+$ | 270 | 0.41 (O) |
| 7.3 | Cl | pyridazin-4-yl- | —N(CO—Me)—(CH$_2$)$_2$—NMe$_2$ | XIV.1 XXV.3 | $C_{25}H_{25}ClN_6O_2$ | 477/479 $[M + H]^+$ 475/477 $[M - H]^-$ 476/478 $[M]^+$ | n.d. | 0.3 (A) |

*Eluant mixtures: see the List following Example 1

(I.8)

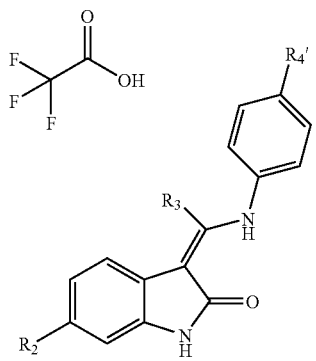

| Example | $R_2$ | $R_3$ | $R_4'$ | Educt | Empirical formula | Mass spectrum | M.p. [°C.] | $R_f$ value * |
|---|---|---|---|---|---|---|---|---|
| 8.1 | Cl | 1,2-(methylene-dioxy)-phen-4-yl- | —CH$_2$—NHMe | 1.18 | $C_{24}H_{20}ClN_3O_3 \cdot C_2HF_3O_2$ | 465/458 $[M + H]^+$ | 252–254 | 0.13 (A) |
| 8.2 | Cl | 1,2-(methylene-dioxy)-phen-4-yl- | —CH$_2$-1-piperazinyl | 1.19 | $C_{27}H_{25}ClN_4O_3 \cdot C_2HF_3O_2$ | 489/491 $[M + H]^+$ | 201 | 0.32 (A) |
| 8.3 | Cl | 1,2-(difluoro-methylene-dioxy)-phen-4-yl- | —CH$_2$—NHMe | 1.27 | $C_{24}H_{18}ClF_2N_3O_3 \cdot C_2HF_3O_2$ | 470/472 $[M + H]^+$ | 267–271 | 0.1 (C) |
| 8.4 | F | 1,2-(difluoro-methylene-dioxy)-phen-4-yl- | —CH$_2$—NHEt | 1.37 | $C_{26}H_{24}FN_3O_3 \cdot C_2HF_3O_2$ | 468 $[M + Na]^+$ | 153–154 | 0.66 (A) |
| 8.5 | COOMe | 1,2-(ethylene-dioxy)-phen-4-yl- | —CH$_2$—NHEt | 1.51 | $C_{28}H_{27}FN_3O_5 \cdot C_2HF_3O_2$ | 486 $[M + H]^+$ 484 $[M - H]^-$ | 266 | 0.12 (S) |
| 8.6 | COOMe | 1,2-(methylene-dioxy)-phen-4-yl- | —CH$_2$—NHEt | 1.62 | $C_{27}H_{25}FN_3O_5 \cdot C_2HF_3O_2$ | 472 $[M + H]^+$ | 258 | 0.55 (S) |

*Eluant mixtures:
see the List following Example 1

EXAMPLE 9.0

6-carboxy-3-(Z)-{1-[4-(1-methylpiperazin-4-yl-methyl)-phenylamino]-1-(3,4-ethylenedioxyphenyl)-methylene}-2-indolinone 0.36 g of 6-methoxycarbonyl-3-(Z)-{1-[4-(1-methylpiperazin-4-yl-methyl)-phenylamino]-1-(3,4-ethylenedioxyphenyl)-methylene}-2-indolinone (Example 1.57) in 5 ml of ethanol are combined at 80° C. with 1.6 ml of 1 molar sodium hydroxide solution and stirred for 2 hours at 80° C. After the addition of 1.6 ml of 1 molar hydrochloric acid and 2 ml of water the mixture is stirred overnight without any heating. The precipitate formed is suction filtered, washed successively with water, a little ethanol and finally diethyl ether and then dried at 80° C.

Yield: 0.32 g (91% of theory)

$R_f$ value: 0.15 (silica gel, dichloromethane/methanol=4:1) $C_{30}H_{30}N_4O_5$ Mass spectrum: m/z=527 $[M+H]^+$; m/z=525 $[M-H]^-$

EXAMPLE 10.0

6-methylaminocarbonyl-3-(Z)-{1-[4-(1-methylpiperazin-4-yl-methyl)-phenylamino]-1-(3,4-ethylenedioxyphenyl)-methylene}-2-indolinone 0.100 g of 6-carboxy-3-(Z)-{1-[4-(1-methylpiperazin-4-yl-methyl)-phenylamino]-1-(3,4-ethylenedioxyphenyl)-methylene}-2-indolinone, 0.103 g of dimethylamine hydrochloride, 73 mg of TBTU, 35 mg of HOBT and 0.416 ml of triethylamine are stirred in 3 ml of DMF for 6 hours at ambient temperature. The reaction mixture is poured onto water and extracted three times with dichloromethane/methanol 19:1. The combined organic phases are washed with water and dried over sodium sulphate. Undissolved constituents are filtered off and the filtrate is evaporated to dryness in vacuo. The residue is triturated with diethyl ether, suction filtered and dried at 80° C.

Yield: 0.075 g (73% of theory)

$R_f$ value: 0.38 (silica gel, dichloromethane/methanol=9:1)

M.p.: 172° C. $C_{31}H_{33}N_5O_4$
Mass spectrum: m/z=540 [M+H]⁺; m/z=538 [M−H]⁻

The following compound is prepared analogously to Example 10.0:

(10.1) 6-dimethylaminocarbonyl-3-(Z)-{1-[4-(1-methylpiperazin-4-yl-methyl)-phenylamino]-1-(3,4-ethylenedioxyphenyl)-methylene}-2-indolinone using dimethylamine hydrochloride.

$R_f$-value: 0.51 (silica gel, dichloromethane/methanol=9:1)
M.p.: 257° C. $C_{32}H_{35}N_5O_4$
Mass spectrum: m/z=554 [M+H]⁺; m/z=552 [M−H]⁻

EXAMPLE 11

6-fluoro-3-(Z)-{1-[4-(ethylaminomethyl)-phenylamino]-1-(1-methylbenzimidazol-5-yl)-methylene}-2-indolinone A solution of 0.30 g of 1-acetyl-6-fluoro-3-[1-methoxy-1-(1-methylbenzimidazol-5-yl)methylene]-2-indolinone (Example XIX) and 0.206 g 4-(N-ethyl-N-tert-butoxycarbonyl-aminomethyl)-aniline (Example XXV.12) in 5 ml DMF is stirred for 15 hours at 115° C. The residue obtained by distilling off the solvent is taken up in 5 ml of methanol and after the addition of 1 ml of 1 M sodium hydroxide solution it is stirred for 1 hour. The solution is neutralised by the addition of ammonium chloride solution and then evaporated to dryness. The residue is purified by chromatography over a silica gel column with dichloromethane/methanol/ammonia=90:10:1. The intermediate product thus obtained is dissolved in 5 ml dichloromethane, combined with 1 ml trifluoroacetic acid and stirred for 30 minutes. After the volatile constituents have been distilled off the residue is crystallised from diethyl ether and then dried at 80° C.

Yield: 0.143 g (31% of theory)

$R_f$-value: 0.2 (silica gel, dichloromethane/methanol/conc. ammonia solution=80:20:1)

M.p.: 226–228° C. $C_{26}H_{24}FN_5O \cdot C_2HF_3O_2$

The following compounds of general formula I.11 are prepared analogously to Example 11.0:

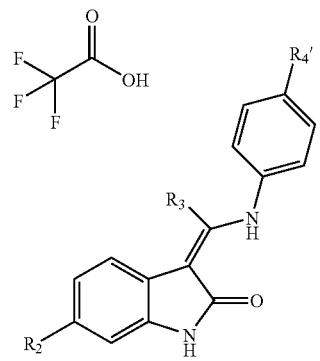

(I.11)

| Example | $R_2$ | $R_3$ | $R_4'$ | Educts | Empirical formula | Mass spectrum | M.p. [° C.] | $R_f$ value * |
|---|---|---|---|---|---|---|---|---|
| 11.1 | Cl | 1,2-(ethylenedioxy)-phen-4-yl- | —CH₂—NHMe | XVI.1 XXV.13 | $C_{25}H_{22}ClN_3O_3 \cdot C_2HF_3O_2$ | 446/448 [M − H]⁻ | 260 (decomposition) | 0.07 (E) |
| 11.2 | Cl | 1,2-(ethylenedioxy)-phen-4-yl- | —CH₂—NHEt | XVI.1 XXV.12 | $C_{26}H_{24}ClN_3O_3 \cdot C_2HF_3O_2$ | 460/462 [M − H]⁻ | 247 (decomposition) | 0.11 (E) |
| 11.3 | Cl | 1,2-(ethylenedioxy)-phene-4-yl- | —CH₂—NHiBu | XVI.1 XXV.34 | $C_{28}H_{28}ClN_3O_3 \cdot C_2HF_3O_2$ | 490/492 [M + H]⁺ | 248 (decomposition) | 0.38 (E) |
| 11.4 | F | 1,2-(ethylenedioxy)-phen-4-yl- | —CH₂—NHMe | XVI.7 XXV.13 | $C_{25}H_{22}FN_3O_3 \cdot C_2HF_3O_2$ | 430 [M − H]⁻ | 125–133 | 0.6 (P) |
| 11.5 | F | 1,2-(ethylenedioxy)-phen-4-yl- | —CH₂—NHiBu | XVI.7 XXV.34 | $C_{28}H_{28}FN_4O_3 \cdot C_2HF_3O_2$ | 474 [M + H]⁺ | 239–242 | 0.6 (P) |
| 11.6 | F | 1,2-(ethylenedioxy)-phen-4-yl- | —CO-(perhydrodiazepin-1-yl) | XVI.7 XXI.15 | $C_{29}H_{27}FN_4O_4 \cdot C_2HF_3O_2$ | 515 [M + H]⁺ | 247–253 | 0.6 (P) |
| 11.7 | Cl | 1,2-(ethylenedioxy)-phene-4-yl- | —CO—NMe—(CH₂)₂—NHMe | XVI.1 XXI.16 | $C_{28}H_{27}ClN_4O_4 \cdot C_2HF_3O_2$ | 519/521 [M + H]⁺ | 185 (decomposition) | 0.05 (E) |

-continued (I.11)

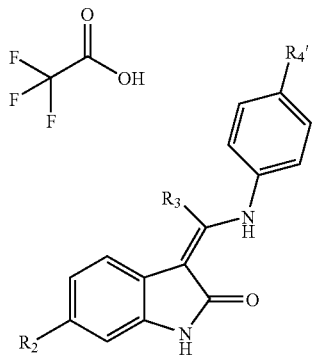

| Example | R$_2$ | R$_3$ | R$_4$' | Educts | Empirical formula | Mass spectrum | M.p. [° C.] | R$_f$ value * |
|---|---|---|---|---|---|---|---|---|
| 11.8 | F | 1,2-(ethylene-dioxy)-phen-4-yl- | —CO-(pipe-razin-1-yl) | XVI.7 XXV.14 | C$_{28}$H$_{25}$FN$_4$O$_4$· C$_2$HF$_3$O$_2$ | 501 [M + H]$^+$ | 256–263 | 0.6 (P) |
| 11.9 | F | 1,2-(ethylene-dioxy)-phene-4-yl- | —CO—NMe—(CH$_2$)$_2$—NHMe | XVI.7 XXI.16 | C$_{28}$H$_{27}$FN$_4$O$_4$· C$_2$HF$_3$O$_2$ | 503 [M + H]$^+$ | 166 | 0.1 (G) |

*Eluant mixtures: see the List following Example 1

EXAMPLE 13

Dry Ampoule Containing 75 mg of Active Substance Per 10 ml

Composition:

| | |
|---|---|
| Active substance | 75.0 mg |
| Mannitol | 50.0 mg |
| water for injections | ad 10.0 ml |

Preparation:

Active substance and mannitol are dissolved in water. After packaging, the solution is freeze-dried. To produce the solution ready for use, the product is dissolved in water for injections.

EXAMPLE 14

Dry Ampoule Containing 35 mg of Active Substance Per 2 ml

Composition:

| | |
|---|---|
| Active substance | 35.0 mg |
| Mannitol | 100.0 mg |
| water for injections | ad 2.0 ml |

Preparation:

Active substance and mannitol are dissolved in water. After packaging, the solution is freeze-dried.

To produce the solution ready for use, the product is dissolved in water for injections.

EXAMPLE 15

Tablet Containing 50 mg of Active Substance

Composition:

| | |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

EXAMPLE 16

Tablet Containing 350 mg of Active Substance

Composition:

| | |
|---|---|
| (1) Active substance | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

89

Preparation (1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

EXAMPLE 17

Capsules Containing 50 mg of Active Substance
Composition:

| | | |
|---|---|---|
| (1) Active substance | 50.0 mg |
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing.

This powder mixture is packed into size 3 hard gelatine capsules in a capsule filling machine.

EXAMPLE 18

Capsules Containing 350 mg of Active Substance
Composition:

| | | |
|---|---|---|
| (1) Active substance | 350.0 mg |
| (2) Dried maize starch | 46.0 mg |
| (3) Powdered lactose | 30.0 mg |
| (4) Magnesium stearate | 4.0 mg |
| | 430.0 mg |

Preparation:

(1) is triturated with (3). This trituration is added to the mixture of (2) and (4) with vigorous mixing.

This powder mixture is packed into size 0 hard gelatine capsules in a capsule filling machine.

EXAMPLE 19

Suppositories Containing 100 mg of Active Substance
1 suppository contains:

| | | |
|---|---|---|
| Active substance | 100.0 mg |
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

Preparation:

The polyethyleneglycol is melted together with polyethylene sorbitan monostearate. At 40° C. the ground active substance is homogeneously dispersed in the melt. It is cooled to 38° C. and poured into slightly chilled suppository moulds.

90

The following compounds may be prepared analogously to the foregoing Examples:

(1) 3-(Z)-{1-[4-(dimethylaminomethyl)-phenylamino]-1-(3,4-methylenedioxyphenyl)-methylene}-6-cyano-2-indolinone (2) 3-(Z)-{1-[4-(diethylaminomethyl)-phenylamino]-1-(3,4-methylenedioxyphenyl)-methylene}-6-cyano-2-indolinone (3) 3-(Z)-{1-[4-(1-methylpiperazin-4-yl-methyl)-phenylamino]-1-(3,4-methylenedioxyphenyl)-methylene}-6-cyano-2-indolinone (4) 3-(Z)-{1-[4-(ethylaminomethyl)-phenylamino]-1-(3,4-methylenedioxyphenyl)-methylene}-6-cyano-2-indolinone (5) 3-(Z)-{1-[4-(N-methyl-N-{dimethylaminomethyl-carbonyl}-amino)-phenylamino]-1-(3,4-methylenedioxyphenyl)-methylene}-6-cyano-2-indolinone (6) 3-(Z)-{1-[4-(N-methyl-N-{1-methylpiperazin-4-yl-methylcarbonyl}-amino)-phenylamino]-1-(3,4-methylenedioxyphenyl)-methylene}-6-cyano-2-indolinone (7) 3-(Z)-{1-[4-(N-acetyl-N-{2-dimethylamino-ethyl}-amino)-phenylamino]-1-(3,4-methylenedioxyphenyl)-methylene}-6-cyano-2-indolinone (8) 3-(Z)-{1-[4-(N-acetyl-N-{3-dimethylamino-propyl}-amino)-phenylamino]-1-(3,4-methylenedioxyphenyl)-methylene}-6-cyano-2-indolinone (9) 3-(Z)-{1-[4-(N-methyl-N-{2-dimethylamino-ethyl}-aminocarbonyl)-phenylamino]-1-(3,4-methylenedioxyphenyl)-methylene}-6-cyano-2-indolinone

(10) 3-(Z)-{1-[4-(N-methanesulphonyl-N-{2-dimethylamino-ethyl}-amino)-phenyl-amino]-1-(3,4-methylenedioxyphenyl)-methylene}-6-cyano-2-indolinone

(11) 3-(Z)-{1-[4-(1-methylpiperazin-4-yl-carbonylmethyl)-phenylamino]-1-(3,4-methylenedioxyphenyl)-methylene}-6-cyano-2-indolinone

(12) 3-(Z)-{1-[4-(N-methyl-N-{2-dimethylamino-ethyl-carbonyl}-amino)-phenyl-amino]-1-(3,4-methylenedioxyphenyl)-methylene}-6-cyano-2-indolinone

(13) 3-(Z)-{1-[4-(1-methyl-imidazol-2-yl)-phenylamino]-1-(3,4-methylenedioxy-phenyl)-methylene}-6-cyano-2-indolinone

(14) 3-(Z)-{1-[4-(dimethylaminomethyl)-phenylamino]-1-(3,4-ethylenedioxyphenyl)-methylene}-6-cyano-2-indolinone

(15) 3-(Z)-{1-[4-(diethylaminomethyl)-phenylamino]-1-(3,4-ethylenedioxyphenyl)-methylene}-6-cyano-2-indolinone

(16) 3-(Z)-{1-[4-(1-methylpiperazin-4-yl-methyl)-phenylamino]-1-(3,4-ethylenedioxyphenyl)-methylene}-6-cyano-2-indolinone

(17) 3-(Z)-{1-[4-(ethylaminomethyl)-phenylamino]-1-(3,4-ethylenedioxyphenyl)-methylene}-6-cyano-2-indolinone

(18) 3-(Z)-{1-[4-(N-methyl-N-{dimethylaminomethyl-carbonyl}-amino)-phenylamino]-1-(3,4-ethylenedioxyphenyl)-methylene}-6-cyano-2-indolinone

(19) 3-(Z)-{1-[4-(N-methyl-N-{1-methylpiperazin-4-yl-methylcarbonyl}-amino)-phenylamino]-1-(3,4-ethylenedioxyphenyl)-methylene}-6-cyano-2-indolinone

(20) 3-(Z)-{1-[4-(N-acetyl-N-{2-dimethylamino-ethyl}-amino)-phenylamino]-1-(3,4-ethylenedioxyphenyl)-methylene}-6-cyano-2-indolinone

(21) 3-(Z)-{1-[4-(N-acetyl-N-{3-dimethylamino-propyl}-amino)-phenylamino]-1-(3,4-ethylenedioxyphenyl)-methylene}-6-cyano-2-indolinone

(22) 3-(Z)-{1-[4-(N-methyl-N-{2-dimethylamino-ethyl}-aminocarbonyl)-phenylamino]-1-(3,4-ethylenedioxyphenyl)-methylene}-6-cyano-2-indolinone

(23) 3-(Z)-{1-[4-(N-methanesulphonyl-N-{2-dimethylamino-ethyl}-amino)-phenyl-amino]-1-(3,4-ethylenedioxyphenyl)-methylene}-6-cyano-2-indolinone

(24) 3-(Z)-{1-[4-(1-methylpiperazin-4-yl-carbonylmethyl)-phenylamino]-1-(3,4-ethylenedioxyphenyl)-methylene}-6-cyano-2-indolinone

(25) 3-(Z)-{1-[4-(N-methyl-N-{2-dimethylamino-ethyl-carbonyl}-amino)-phenyl-amino]-1-(3,4-ethylenedioxyphenyl)-methylene}-6-cyano-2-indolinone

(26) 3-(Z)-{1-[4-(1-methyl-imidazol-2-yl)-phenylamino]-1-(3,4-ethylenedioxyphenyl)-methylene}-6-cyano-2-indolinone

(27) 3-(Z)-{1-[4-(dimethylaminomethyl)-phenylamino]-1-(3,4-methylenedioxyphenyl)-methylene}-6-nitro-2-indolinone

(28) 3-(Z)-{1-[4-(diethylaminomethyl)-phenylamino]-1-(3,4-methylenedioxyphenyl)-methylene}-6-nitro-2-indolinone

(29) 3-(Z)-{1-[4-(1-methylpiperazin-4-yl-methyl)-phenylamino]-1-(3,4-methylenedioxy-phenyl)-methylene}-6-nitro-2-indolinone

(30) 3-(Z)-{1-[4-(ethylaminomethyl)-phenylamino]-1-(3,4-methylenedioxyphenyl)-methylene}-6-nitro-2-indolinone

(31) 3-(Z)-{1-[4-(N-methyl-N-{dimethylaminomethyl-carbonyl}-amino)-phenylamino]-1-(3,4-methylenedioxyphenyl)-methylene}-6-nitro-2-indolinone

(32) 3-(Z)-{1-[4-(N-methyl-N-{1-methylpiperazin-4-yl-methylcarbonyl}-amino)-phenylamino]-1-(3,4-methylenedioxyphenyl)-methylene}-6-nitro-2-indolinone

(33) 3-(Z)-{1-[4-(N-acetyl-N-{2-dimethylamino-ethyl}-amino)-phenylamino]-1-(3,4-methylenedioxyphenyl)-methylene}-6-nitro-2-indolinone

(34) 3-(Z)-{1-[4-(N-acetyl-N-{3-dimethylamino-propyl}-amino)-phenylamino]-1-(3,4-methylenedioxyphenyl)-methylene}-6-nitro-2-indolinone

(35) 3-(Z)-{1-[4-(N-methyl-N-{2-dimethylamino-ethyl}-aminocarbonyl)-phenylamino]-1-(3,4-methylenedioxyphenyl)-methylene}-6-nitro-2-indolinone

(36) 3-(Z)-{1-[4-(N-methanesulphonyl-N-{2-dimethylamino-ethyl}-amino)-phenyl-amino]-1-(3,4-methylenedioxyphenyl)-methylene}-6-nitro-2-indolinone

(37) 3-(Z)-{1-[4-(1-methylpiperazin-4-yl-carbonylmethyl)-phenylamino]-1-(3,4-methylenedioxyphenyl)-methylene}-6-nitro-2-indolinone

(38) 3-(Z)-{1-[4-(N-methyl-N-{2-dimethylamino-ethyl-carbonyl}-amino)-phenyl-amino]-1-(3,4-methylenedioxyphenyl)-methylene}-6-nitro-2-indolinone

(39) 3-(Z)-{1-[4-(1-methyl-imidazol-2-yl)-phenylamino]-1-(3,4-methylenedioxy-phenyl)-methylene}-6-nitro-2-indolinone

(40) 3-(Z)-{-[4-(dimethylaminomethyl)-phenylamino]-1-(3,4-ethylenedioxyphenyl)-methylene}-6-nitro-2-indolinone

(41) 3-(Z)-{1-[4-(diethylaminomethyl)-phenylamino]-1-(3,4-ethylenedioxyphenyl)-methylene}-6-nitro-2-indolinone

(42) 3-(Z)-{1-[4-(1-methylpiperazin-4-yl-methyl)-phenylamino]-1-(3,4-ethylenedioxy-phenyl)-methylene}-6-nitro-2-indolinone

(43) 3-(Z)-{1-[4-(ethylaminomethyl)-phenylamino]-1-(3,4-ethylenedioxyphenyl)-methylene}-6-nitro-2-indolinone

(44) 3-(Z)-{1-[4-(N-methyl-N-{dimethylaminomethyl-carbonyl}-amino)-phenylamino]-1-(3,4-ethylenedioxyphenyl)-methylene}-6-nitro-2-indolinone

(45) 3-(Z)-{1-[4-(N-methyl-N-{1-methylpiperazin-4-yl-methylcarbonyl}-amino)-phenylamino]-1-(3,4-ethylenedioxyphenyl)-methylene}-6-nitro-2-indolinone

(46) 3-(Z)-{1-[4-(N-acetyl-N-{2-dimethylamino-ethyl}-amino)-phenylamino]-1-(3,4-ethylenedioxyphenyl)-methylene}-6-nitro-2-indolinone

(47) 3-(Z)-{1-[4-(N-acetyl-N-{3-dimethylamino-propyl}-amino)-phenylamino]-1-(3,4-ethylenedioxyphenyl)-methylene}-6-nitro-2-indolinone

(48) 3-(Z)-{1-[4-(N-methyl-N-{2-dimethylamino-ethyl}-aminocarbonyl)-phenylamino]-1-(3,4-ethylenedioxyphenyl)-methylene}-6-nitro-2-indolinone

(49) 3-(Z)-{1-[4-(N-methanesulphonyl-N-{2-dimethylamino-ethyl}-amino)-phenyl-amino]-1-(3,4-ethylenedioxyphenyl)-methylene}-6-nitro-2-indolinone

(50) 3-(Z)-{1-[4-(1-methylpiperazin-4-yl-carbonylmethyl)-phenylamino]-1-(3,4-ethylenedioxyphenyl)-methylene}-6-nitro-2-indolinone

(51) 3-(Z)-{1-[4-(N-methyl-N-{2-dimethylamino-ethyl-carbonyl}-amino)-phenyl-amino]-1-(3,4-ethylenedioxyphenyl)-methylene}-6-nitro-2-indolinone

(52) 3-(Z)-{1-[4-(1-methyl-imidazol-2-yl)-phenylamino]-1-(3,4-ethylenedioxyphenyl)-methylene}-6-nitro-2-indolinone

(53) 3-(Z)-{1-[4-(dimethylaminomethyl)-phenylamino]-1-(2-thienyl)-methylene}-6-methoxycarbonyl-2-indolinone

(54) 3-(Z)-{1-[4-(diethylaminomethyl)-phenylamino]-1-(2-thienyl)-methylene}-6-methoxycarbonyl-2-indolinone

(55) 3-(Z)-{1-[4-(1methylpiperazin-4-yl-methyl)-phenylamino]-1-(2-thienyl)-methylene}-6-methoxycarbonyl-2-indolinone

(56) 3-(Z)-{1-[4-(ethylaminomethyl)-phenylamino]-1-(2-thienyl)-methylene}-6-methoxycarbonyl-2-indolinone

(57) 3-(Z)-{1-[4-(N-methyl-N-{dimethylaminomethyl-carbonyl}-amino)-phenylamino]-1-(2-thienyl)-methylene}-6-methoxycarbonyl-2-indolinone

(58) 3-(Z)-{1-[4-(N-methyl-N-{1-methylpiperazin-4-yl-methylcarbonyl}-amino)-phenylamino]-1-(2-thienyl)-methylene}-6-methoxycarbonyl-2-indolinone

(59) 3-(Z)-{1-[4-(N-acetyl-N-{2-dimethylamino-ethyl}-amino)-phenylamino]-1-(2-thienyl)-methylene}-6-methoxycarbonyl-2-indolinone

(60) 3-(Z)-{1-[4-(N-acetyl-N-{3-dimethylamino-propyl}-amino)-phenylamino]-1-(2-thienyl)-methylene}-6-methoxycarbonyl-2-indolinone

(61) 3-(Z)-{1-[4-(N-methyl-N-{2-dimethylamino-ethyl}-aminocarbonyl)-phenylamino]-1-(2-thienyl)-methylene}-6-methoxycarbonyl-2-indolinone

(62) 3-(Z)-{1-[4-(N-methanesulphonyl-N-{2-dimethylamino-ethyl}-amino)-phenyl-amino]-1-(2-thienyl)-methylene}-6-methoxycarbonyl-2-indolinone

(63) 3-(Z)-{1-[4-(1-methylpiperazin-4-yl-carbonylmethyl)-phenylamino]-1-(2-thienyl)-methylene}-6-methoxycarbonyl-2-indolinone

(64) 3-(Z)-{1-[4-(N-methyl-N-{2-dimethylamino-ethyl-carbonyl}-amino)-phenyl-amino]-1-(2-thienyl)-methylene}-6-methoxycarbonyl-2-indolinone

(65) 3-(Z)-{1-[4-(1-methyl-imidazol-2-yl)-phenylamino]-1-(2-thienyl)-methylene}-6-methoxycarbonyl-2-indolinone

(66) 3-(Z)-{1-[4-(dimethylaminomethyl)-phenylamino]-1-(3-thienyl)-methylene}-6-methoxycarbonyl-2-indolinone

(67) 3-(Z)-{1-[4-(diethylaminomethyl)-phenylamino]-1-(3-thienyl)-methylene}-6-methoxycarbonyl-2-indolinone

(68) 3-(Z)-{1-[4-(1-methylpiperazin-4-yl-methyl)-phenylamino]-1-(3-thienyl)-methylene}-6-methoxycarbonyl-2-indolinone

(69) 3-(Z)-{1-[4-(ethylaminomethyl)-phenylamino]-1-(3-thienyl)-methylene}-6-methoxycarbonyl-2-indolinone

(70) 3-(Z)-{1-[4-(N-methyl-N-{dimethylaminomethyl-carbonyl}-amino)-phenylamino]-1-(3-thienyl)-methylene}-6-methoxycarbonyl-2-indolinone
(71) 3-(Z)-{1-[4-(N-methyl-N-{1-methylpiperazin-4-yl-methylcarbonyl}-amino)-phenylamino]-1-(3-thienyl)-methylene}-6-methoxycarbonyl-2-indolinone
(72) 3-(Z)-{1-[4-(N-acetyl-N-{2-dimethylamino-ethyl}-amino)-phenylamino]-1-(3-thienyl)-methylene}-6-methoxycarbonyl-2-indolinone
(73) 3-(Z)-{1-[4-(N-acetyl-N-{3-dimethylamino-propyl}-amino)-phenylamino]-1-(3-thienyl)-methylene}-6-methoxycarbonyl-2-indolinone
(74) 3-(Z)-{1-[4-(N-methyl-N-{2-dimethylamino-ethyl}-aminocarbonyl)-phenylamino]-1-(3-thienyl)-methylene}-6-methoxycarbonyl-2-indolinone
(75) 3-(Z)-{1-[4-(N-methanesulphonyl-N-{2-dimethylamino-ethyl}-amino)-phenyl-amino]-1-(3-thienyl)-methylene}-6-methoxycarbonyl-2-indolinone
(76) 3-(Z)-{1-[4-(1-methylpiperazin-4-yl-carbonylmethyl)-phenylamino]-1-(3-thienyl)-methylene}-6-methoxycarbonyl-2-indolinone
(77) 3-(Z)-{1-[4-(N-methyl-N-{2-dimethylamino-ethyl-carbonyl}-amino)-phenyl-amino]-1-(3-thienyl)-methylene}-6-methoxycarbonyl-2-indolinone
(78) 3-(Z)-{1-[4-(1-methyl-imidazol-2-yl)-phenylamino]-1-(3-thienyl)-methylene}-6-methoxycarbonyl-2-indolinone
(79) 3-(Z)-{1-[4-(dimethylaminomethyl)-phenylamino]-1-(3,4-methylenedioxyphenyl)-methylene}-6-ethoxycarbonyl-2-indolinone
(80) 3-(Z)-{1-[4-(diethylaminomethyl)-phenylamino]-1-(3,4-methylenedioxyphenyl)-methylene}-6-ethoxycarbonyl-2-indolinone
(81) 3-(Z)-{1-[4-(1-methylpiperazin-4-yl-methyl)-phenylamino]-1-(3,4-methylenedioxyphenyl)-methylene}-6-ethoxycarbonyl-2-indolinone
(82) 3-(Z)-{1-[4-(ethylaminomethyl)-phenylamino]-1-(3,4-methylenedioxyphenyl)-methylene}-6-ethoxycarbonyl-2-indolinone
(83) 3-(Z)-{1-[4-(N-methyl-N-{dimethylaminomethyl-carbonyl}-amino)-phenylamino]-1-(3,4-methylenedioxyphenyl)-methylene}-6-ethoxycarbonyl-2-indolinone
(84) 3-(Z)-{1-[4-(N-methyl-N-{1-methylpiperazin-4-yl-methylcarbonyl}-amino)-phenylamino]-1-(3,4-methylenedioxyphenyl)-methylene}-6-ethoxycarbonyl-2-indolinone
(85) 3-(Z)-{1-[4-(N-acetyl-N-{2-dimethylamino-ethyl}-amino)-phenylamino]-1-(3,4-methylenedioxyphenyl)-methylene}-6-ethoxycarbonyl-2-indolinone
(86) 3-(Z)-{1-[4-(N-acetyl-N-{3-dimethylamino-propyl}-amino)-phenylamino]-1-(3,4-methylenedioxyphenyl)-methylene}-6-ethoxycarbonyl-2-indolinone
(87) 3-(Z)-{1-[4-(N-methyl-N-{2-dimethylamino-ethyl}-aminocarbonyl)-phenylamino]-1-(3,4-methylenedioxyphenyl)-methylene}-6-ethoxycarbonyl-2-indolinone
(88) 3-(Z)-{1-[4-(N-methanesulphonyl-N-{2-dimethylamino-ethyl}-amino)-phenyl-amino]-1-(3,4-methylenedioxyphenyl)-methylene}-6-ethoxycarbonyl-2-indolinone
(89) 3-(Z)-{1-[4-(1-methylpiperazin-4-yl-carbonylmethyl)-phenylamino]-1-(3,4-methylenedioxyphenyl)-methylene}-6-ethoxycarbonyl-2-indolinone
(90) 3-(Z)-{1-[4-(N-methyl-N-{2-dimethylamino-ethyl-carbonyl}-amino)-phenyl-amino]-1-(3,4-methylenedioxyphenyl)-methylene}-6-ethoxycarbonyl-2-indolinone
(91) 3-(Z)-{1-[4-(1-methyl-imidazol-2-yl)-phenylamino]-1-(3,4-methylenedioxy-phenyl)-methylene}-6-ethoxycarbonyl-2-indolinone
(92) 3-(Z)-{1-[4-(dimethylaminomethyl)-phenylamino]-1-(3,4-ethylenedioxyphenyl)-methylene}-6-ethoxycarbonyl-2-indolinone
(93) 3-(Z)-{1-[4-(diethylaminomethyl)-phenylamino]-1-(3,4-ethylenedioxyphenyl)-methylene}-6-ethoxycarbonyl-2-indolinone
(94) 3-(Z)-{1-[4-(1-methylpiperazin-4-yl-methyl)-phenylamino]-1-(3,4-ethylenedioxyphenyl)-methylene}-6-ethoxycarbonyl-2-indolinone
(95) 3-(Z)-{1-[4-(ethylaminomethyl)-phenylamino]-1-(3,4-ethylenedioxyphenyl)-methylene}-6-ethoxycarbonyl-2-indolinone
(96) 3-(Z)-{1-[4-(N-methyl-N-{dimethylaminomethyl-carbonyl}-amino)-phenylamino]-1-(3,4-ethylenedioxyphenyl)-methylene}-6-ethoxycarbonyl-2-indolinone
(97) 3-(Z)-{1-[4-(N-methyl-N-{1-methylpiperazin-4-yl-methylcarbonyl}-amino)-phenylamino]-1-(3,4-ethylenedioxyphenyl)-methylene}-6-ethoxycarbonyl-2-indolinone
(98) 3-(Z)-{1-[4-(N-acetyl-N-{2-dimethylamino-ethyl}-amino)-phenylamino]-1-(3,4-ethylenedioxyphenyl)-methylene}-6-ethoxycarbonyl-2-indolinone
(99) 3-(Z)-{1-[4-(N-acetyl-N-{3-dimethylamino-propyl}-amino)-phenylamino]-1-(3,4-ethylenedioxyphenyl)-methylene}-6-ethoxycarbonyl-2-indolinone
(100) 3-(Z)-{1-[4-(N-methyl-N-{2-dimethylamino-ethyl}-aminocarbonyl)-phenylamino]-1-(3,4-ethylenedioxyphenyl)-methylene}-6-ethoxycarbonyl-2-indolinone
(101) 3-(Z)-{1-[4-(N-methanesulphonyl-N-{2-dimethylamino-ethyl}-amino)-phenyl-amino]-1-(3,4-ethylenedioxyphenyl)-methylene}-6-ethoxycarbonyl-2-indolinone
(102) 3-(Z)-{1-[4-(1-methylpiperazin-4-yl-carbonylmethyl)-phenylamino]-1-(3,4-ethylenedioxyphenyl)-methylene}-6-ethoxycarbonyl-2-indolinone
(103) 3-(Z)-{1-[4-(N-methyl-N-{2-dimethylamino-ethyl-carbonyl}-amino)-phenyl-amino]-1-(3,4-ethylenedioxyphenyl)-methylene}-6-ethoxycarbonyl-2-indolinone
(104) 3-(Z)-{1-[4-(1-methyl-imidazol-2-yl)-phenylamino]-1-(3,4-ethylenedioxyphenyl)-methylene}-6-ethoxycarbonyl-2-indolinone
(105) 3-(Z)-{1-[4-(dimethylaminomethyl)-phenylamino]-1-(quinoxalin-6-yl)-methylene}-6-methoxycarbonyl-2-indolinone
(106) 3-(Z)-{1-[4-(diethylaminomethyl)-phenylamino]-1-(quinoxalin-6-yl)-methylene}-6-methoxycarbonyl-2-indolinone
(107) 3-(Z)-{1-[4-(1-methylpiperazin-4-yl-methyl)-phenylamino]-1-(quinoxalin-6-yl)-methylene}-6-methoxycarbonyl-2-indolinone
(108) 3-(Z)-{1-[4-(ethylaminomethyl)-phenylamino]-1-(quinoxalin-6-yl)-methylene}-6-methoxycarbonyl-2-indolinone
(109) 3-(Z)-{1-[4-(N-methyl-N-{dimethylaminomethylcarbonyl}-amino)-phenylamino]-1-(quinoxalin-6-yl)-methylene}-6-methoxycarbonyl-2-indolinone
(110) 3-(Z)-{1-[4-(N-methyl-N-{1-methylpiperazin-4-yl-methylcarbonyl}-amino)-phenylamino]-1-(quinoxalin-6-yl)-methylene}-6-methoxycarbonyl-2-indolinone
(111) 3-(Z)-{1-[4-(N-acetyl-N-{2-dimethylamino-ethyl}-amino)-phenylamino]-1-(quinoxalin-6-yl)-methylene}-6-methoxycarbonyl-2-indolinone
(112) 3-(Z)-{1-[4-(N-acetyl-N-{3-dimethylamino-propyl}-amino)-phenylamino]-1-(quinoxalin-6-yl)-methylene}-6-methoxycarbonyl-2-indolinone (113) 3-(Z)-{1-[4-(N-methyl-N-{2-dimethylamino-ethyl}-aminocarbonyl)-phenylamino]-1-(quinoxalin-6-yl)-methylene}-6-methoxycarbonyl-2-indolinone (114) 3-(Z)-{1-[4-(N-methanesulphonyl-N-{2-dimethylamino-ethyl}-amino)-phenylamino]-1-(quinoxalin-6-yl)-methylene}-6-methoxycarbonyl-2-indolinone (115) 3-(Z)-{1-[4-(1-methylpiperazin-4-yl-carbonylmethyl)-phenylamino]-1-(quinoxalin-6-yl)-methylene}-6-methoxycarbonyl-2-indolinone (116) 3-(Z)-{1-[4-(N-methyl-N-{2-dimethylamino-ethylcarbonyl}-amino)-phenyl-amino]-1-(quinoxalin-6-yl)-methylene}-6-methoxycarbonyl-2-indolinone (117) 3-(Z)-{1-[4-(1-methyl-imidazol-2-yl)-phenylamino]-1-(quinoxalin-6-yl)-methylene}-6-methoxycarbonyl-2-indolinone (118) 3-(Z)-{1-[4-(dimethylaminomethyl)-phenylamino]-1-(quinoxalin-6-yl)-methylene}-6-fluoro-2-indolinone (119) 3-(Z)-{1-[4-(diethylaminomethyl)-phenylamino]-1-(quinoxalin-6-yl)-methylene}-6-fluoro-2-indolinone (120) 3-(Z)-{1-[4-(1-methylpiperazin-4-yl-methyl)-phenylamino]-1-(quinoxalin-6-yl)-methylene}-6-fluoro-2-indolinone (121) 3-(Z)-{1-[4-(ethylaminomethyl)-phenylamino]-1-(quinoxalin-6-yl)-methylene}-6-fluoro-2-indolinone (122) 3-(Z)-{1-[4-(N-methyl-N-{dimethylaminomethylcarbonyl}-amino)-phenylamino]-1-(quinoxalin-6-yl)-methylene}-6-fluoro-2-indolinone (123) 3-(Z)-{1-[4-(N-methyl-N-{1-methylpiperazin-4-yl-methylcarbonyl}-amino)-phenylamino]-1-(quinoxalin-6-yl)-methylene}-6-fluoro-2-indolinone (124) 3-(Z)-{1-[4-(N-acetyl-N-{2-dimethylamino-ethyl}-amino)-phenylamino]-1-(quinoxalin-6-yl)-methylene}-6-fluoro-2-indolinone (125) 3-(Z)-{1-[4-(N-acetyl-N-{3-dimethylamino-propyl}-amino)-phenylamino]-1-(quinoxalin-6-yl)-methylene}-6-fluoro-2-indolinone (126) 3-(Z)-{1-[4-(N-methyl-N-{2-dimethylamino-ethyl}-aminocarbonyl)-phenylamino]-1-(quinoxalin-6-yl)-methylene}-6-fluoro-2-indolinone (127) 3-(Z)-{1-[4-(N-methanesulphonyl-N-{2-dimethylamino-ethyl}-amino)-phenyl-amino]-1-(quinoxalin-6-yl)-methylene}-6-fluoro-2-indolinone (128) 3-(Z)-{1-[4-(1-methylpiperazin-4-yl-carbonylmethyl)-phenylamino]-1-(quinoxalin-6-yl)-methylene}-6-fluoro-2-indolinone (129) 3-(Z)-{1-[4-(N-methyl-N-{2-dimethylamino-ethylcarbonyl}-amino)-phenylamino]1-(quinoxalin-6-yl)-methylene}-6-fluoro-2-indolinone (130) 3-(Z)-{1-[4-(1-methyl-imidazol-2-yl)-phenylamino]-1-(quinoxalin-6-yl)-methylene}-6-fluoro-2-indolinone (131) 3-(Z)-{1-[4-(diethylaminomethyl)-phenylamino]-1-(quinoxalin-6-yl)-methylene}-6-chloro-2-indolinone (132) 3-(Z)-{1-[4-(1-methylpiperazin-4-yl-methyl)-phenylamino]-1-(quinoxalin-6-yl)-methylene}-6-chloro-2-indolinone (133) 3-(Z)-{1-[4-(ethylaminomethyl)-phenylamino]-1-(quinoxalin-6-yl)-methylene}-6-chloro-2-indolinone (134) 3-(Z)-{1-[4-(N-methyl-N-{dimethylaminomethylcarbonyl}-amino)-phenylamino]-1-(quinoxalin-6-yl)-methylene}-6-chloro-2-indolinone (135) 3-(Z)-{1-[4-(N-acetyl-N-{3-dimethylamino-propyl}-amino)-phenylamino]-1-(quinoxalin-6-yl)-methylene}-6-chloro-2-indolinone (136) 3-(Z)-{1-[4-(N-methyl-N-{2-dimethylamino-ethyl}-aminocarbonyl)-phenylamino]-1-(quinoxalin-6-yl)-methylene}-6-chloro-2-indolinone (137) 3-(Z)-{1-[4-(1-methylpiperazin-4-yl-carbonylmethyl)-phenylamino]-1-(quinoxalin-6-yl)-methylene}-6-chloro-2-indolinone (138) 3-(Z)-{1-[4-(N-methyl-N-{2-dimethylamino-ethylcarbonyl}-amino)-phenyl-amino]-1-(quinoxalin-6-yl)-methylene}-6-chloro-2-indolinone (139) 3-(Z)-{1-[4-(dimethylaminomethyl)-phenylamino]-1-(benzo[1,4]dioxin-6-yl)-methylene}-6-methoxycarbonyl-2-indolinone (140) 3-(Z)-{1-[4-(diethylaminomethyl)-phenylamino]-1-(benzo[1,4]dioxin-6-yl)-methylene}-6-methoxycarbonyl-2-indolinone (141) 3-(Z)-{1-[4-(1-methylpiperazin-4-yl-methyl)-phenylamino]-1-(benzo[1,4]dioxin-6-yl)-methylene}-6-methoxycarbonyl-2-indolinone (142) 3-(Z)-{1-[4-(ethylaminomethyl)-phenylamino]-1-(benzo[1,4]dioxin-6-yl)-methylene}-6-methoxycarbonyl-2-indolinone (143) 3-(Z)-{1-[4-(N-methyl-N-{dimethylaminomethylcarbonyl}-amino)-phenylamino]-1-(benzo[1,4]dioxin-6-yl)-methylene}-6-methoxycarbonyl-2-indolinone (144) 3-(Z)-{1-[4-(N-methyl-N-{1-methylpiperazin-4-yl-methylcarbonyl}-amino)-phenylamino]-1-(benzo[1,4]dioxin-6-yl)-methylene}-6-methoxycarbonyl-2-indolinone (145) 3-(Z)-{1-[4-(N-acetyl-N-{2-dimethylamino-ethyl}-amino)-phenylamino]-1-(benzo[1,4]dioxin-6-yl)-methylene}-6-methoxycarbonyl-2-indolinone (146) 3-(Z)-{1-[4-(N-acetyl-N-{3-dimethylamino-propyl}-amino)-phenylamino]-1-(benzo[1,4]dioxin-6-yl)-methylene}-6-methoxycarbonyl-2-indolinone (147) 3-(Z)-{1-[4-(N-methyl-N-{2-dimethylamino-ethyl}-aminocarbonyl)-phenylamino]-1-(benzo[1,4]dioxin-6-yl)-methylene}-6-methoxycarbonyl-2-indolinone (148) 3-(Z)-{1-[4-(N-methanesulphonyl-N-{2-dimethylamino-ethyl}-amino)-phenyl-amino]-1-(benzo[1,4]dioxin-6-yl)-methylene}-6-methoxycarbonyl-2-indolinone (149) 3-(Z)-{1-[4-(1-methylpiperazin-4-yl-carbonylmethyl)-phenylamino]-1-(benzo[1,4]dioxin-6-yl)-methylene}-6-methoxycarbonyl-2-indolinone (150) 3-(Z)-{1-[4-(N-methyl-N-{2-dimethylamino-ethylcarbonyl}-amino)-phenyl-amino]-1-(benzo[1,4]dioxin-6-yl)-methylene}-6-methoxycarbonyl-2-indolinone (151) 3-(Z)-{1-[4-(1-methyl-imidazol-2-yl)-phenylamino]-1-(benzo[1,4]dioxin-6-yl)-methylene}-6-methoxycarbonyl-2-indolinone (152) 3-(Z)-{1-[4-(dimethylaminomethyl)-phenylamino]-1-(benzo[1,4]dioxin-6-yl)-methylene}-6-fluoro-2-indolinone (153) 3-(Z)-{1-[4-(diethylaminomethyl)-phenylamino]-1-(benzo[1,4]dioxin-6-yl)-methylene}-6-fluoro-2-indolinone (154) 3-(Z)-{1-[4-(1-methylpiperazin-4-yl-methyl)-phenylamino]-1-(benzo[1,4]dioxin-6-yl)-methylene}-6-fluoro-2-indolinone (155) 3-(Z)-{1-[4-(ethylaminomethyl)-phenylamino]-1-(benzo[1,4]dioxin-6-yl)-methylene}-6-fluoro-2-indolinone (156) 3-(Z)-{1-[4-(N-methyl-N-{dimethylaminomethylcarbonyl}-amino)-phenylamino]-1-(benzo[1,4]dioxin-6-yl)-methylene}-6-fluoro-2-indolinone (157) 3-(Z)-{1-[4-(N-methyl-N-{1-methylpiperazin-4-yl-methylcarbonyl}-amino)-phenylamino]-1-(benzo[1,4]dioxin-6-yl)-methylene}-6-fluoro-2-indolinone (158) 3-(Z)-{1-[4-(N-acetyl-N-{2-dimethylamino-ethyl}-amino)-phenylamino]-1-(benzo[1,4]dioxin-6-yl)-methylene}-6-fluoro-2-indolinone (159) 3-(Z)-{1-[4-(N-acetyl-N-{3-dimethylamino-propyl}-amino)-phenylamino]-1-(benzo[1,4]dioxin-6-yl)-methylene}-6-fluoro-2-indolinone
(160) 3-(Z)-{1-[4-(N-methyl-N-{2-dimethylamino-ethyl}-aminocarbonyl)-phenylamino]-1-(benzo[1,4]dioxin-6-yl)-methylene}-6-fluoro-2-indolinone
(161) 3-(Z)-{1-[4-(N-methanesulphonyl-N-{2-dimethylamino-ethyl}-amino)-phenylamino]-1-(benzo[1,4]dioxin-6-yl)-methylene}-6-fluoro-2-indolinone
(162) 3-(Z)-{1-[4-(1-methylpiperazin-4-yl-carbonylmethyl)-phenylamino]-1-(benzo[1,4]dioxin-6-yl)-methylene}-6-fluoro-2-indolinone
(163) 3-(Z)-{1-[4-(N-methyl-N-{2-dimethylamino-ethylcarbonyl}-amino)-phenyl-amino]-1-(benzo[1,4]dioxin-6-yl)-methylene}-6-fluoro-2-indolinone
(164) 3-(Z)-{1-[4-(1-methyl-imidazol-2-yl)-phenylamino]-1-(benzo[1,4]dioxin-6-yl)-methylene}-6-fluoro-2-indolinone
(165) 3-(Z)-{1-[4-(dimethylaminomethyl)-phenylamino]-1-(benzo[1,4]dioxin-6-yl)-methylene}-6-chloro-2-indolinone
(166) 3-(Z)-{1-[4-(diethylaminomethyl)-phenylamino]-1-(benzo[1,4]dioxin-6-yl)-methylene}-6-chloro-2-indolinone
(167) 3-(Z)-{1-[4-(1-methylpiperazin-4-yl-methyl)-phenylamino]-1-(benzo[1,4]dioxin-6-yl)-methylene}-6-chloro-2-indolinone
(168) 3-(Z)-{1-[4-(ethylaminomethyl)-phenylamino]-1-(benzo[1,4]dioxin-6-yl)-methylene}-6-chloro-2-indolinone
(169) 3-(Z)-{1-[4-(N-methyl-N-{dimethylaminomethylcarbonyl}-amino)-phenylamino]-1-(benzo[1,4]dioxin-6-yl)-methylene}-6-chloro-2-indolinone
(170) 3-(Z)-{1-[4-(N-methyl-N-{1-methylpiperazin-4-yl-methylcarbonyl}-amino)-phenylamino]-1-(benzo[1,4]dioxin-6-yl)-methylene}-6-chloro-2-indolinone
(171) 3-(Z)-{1-[4-(N-acetyl-N-{2-dimethylamino-ethyl}-amino)-phenylamino]-1-(benzo[1,4]dioxin-6-yl)-methylene}-6-chloro-2-indolinone
(172) 3-(Z)-{1-[4-(N-acetyl-N-{3-dimethylamino-propyl}-amino)-phenylamino]-1-(benzo[1,4]dioxin-6-yl)-methylene}-6-chloro-2-indolinone
(173) 3-(Z)-{1-[4-(N-methyl-N-{2-dimethylamino-ethyl}-aminocarbonyl)-phenylamino]-1-(benzo[1,4]dioxin-6-yl)-methylene}-6-chloro-2-indolinone
(174) 3-(Z)-{1-[4-(N-methanesulphonyl-N-{2-dimethylamino-ethyl}-amino)-phenylamino]-1-(benzo[1,4]dioxin-6-yl)-methylene}-6-chloro-2-indolinone
(175) 3-(Z)-{1-[4-(1-methylpiperazin-4-yl-carbonylmethyl)-phenylamino]-1-(benzo[1,4]dioxin-6-yl)-methylene}-6-chloro-2-indolinone
(176) 3-(Z)-{1-[4-(N-methyl-N-{2-dimethylamino-ethylcarbonyl}-amino)-phenyl-amino]-1-(benzo[1,4]dioxin-6-yl)-methylene}-6-chloro-2-indolinone
(177) 3-(Z)-{1-[4-(1-methyl-imidazol-2-yl)-phenylamino]-1-(benzo[1,4]dioxin-6-yl)-methylene}-6-chloro-2-indolinone
(178) 3-(Z)-{1-[4-(dimethylaminomethyl)-phenylamino]-1-(3-methyl-benzoxazol-2-on-6-yl)-methylene}-6-chloro-2-indolinone
(179) 3-(Z)-{1-[4-(diethylaminomethyl)-phenylamino]-1-(3-methyl-benzoxazol-2-on-6-yl)-methylene}-6-chloro-2-indolinone
(180) 3-(Z)-{1-[4-(1-methylpiperazin-4-yl-methyl)-phenylamino]-1-(3-methyl-benzoxazol-2-on-6-yl)-methylene}-6-chloro-2-indolinone
(181) 3-(Z)-{1-[4-(ethylaminomethyl)-phenylamino]-1-(3-methyl-benzoxazol-2-on-6-yl)-methylene}-6-chloro-2-indolinone
(182) 3-(Z)-{1-[4-(N-methyl-N-{dimethylaminomethylcarbonyl}-amino)-phenylamino]-1-(3-methyl-benzoxazol-2-on-6-yl)-methylene}-6-chloro-2-indolinone
(183) 3-(Z)-{1-[4-(N-methyl-N-{1-methylpiperazin-4-yl-methylcarbonyl}-amino)-phenylamino]-1-(3-methyl-benzoxazol-2-on-6-yl)-methylene}-6-chloro-2-indolinone
(184) 3-(Z)-{1-[4-(N-acetyl-N-{2-dimethylamino-ethyl}-amino)-phenylamino]-1-(3-methyl-benzoxazol-2-on-6-yl)-methylene}-6-chloro-2-indolinone
(184) 3-(Z)-{1-[4-(N-acetyl-N-{3-dimethylamino-propyl}-amino)-phenylamino]-1-(3-methyl-benzoxazol-2-on-6-yl)-methylene}-6-chloro-2-indolinone
(185) 3-(Z)-{1-[4-(N-methyl-N-{2-dimethylamino-ethyl}-aminocarbonyl)-phenylamino]-1-(3-methyl-benzoxazol-2-on-6-yl)-methylene}-6-chloro-2-indolinone
(186) 3-(Z)-{1-[4-(N-methanesulphonyl-N-{2-dimethylamino-ethyl}-amino)-phenyl-amino]-1-(3-methyl-benzoxazol-2-on-6-yl)-methylene}-6-chloro-2-indolinone
(187) 3-(Z)-{1-[4-(1-methylpiperazin-4-yl-carbonylmethyl)-phenylamino]-1-(3-methyl-benzoxazol-2-on-6-yl)-methylene}-6-chloro-2-indolinone
(188) 3-(Z)-{1-[4-(N-methyl-N-{2-dimethylamino-ethylcarbonyl}-amino)-phenyl-amino]-1-(3-methyl-benzoxazol-2-on-6-yl)-methylene}-6-chloro-2-indolinone
(189) 3-(Z)-{1-[4-(1-methyl-imidazol-2-yl)-phenylamino]-1-(3-methyl-benzoxazol-2-on-6-yl)-methylene}-6-chloro-2-indolinone
(190) 3-(Z)-{1-[4-(dimethylaminomethyl)-phenylamino]-1-(benzoxazol-2-on-6-yl)-methylene}-6-chloro-2-indolinone
(191) 3-(Z)-{1-[4-(diethylaminomethyl)-phenylamino]-1-(benzoxazol-2-on-6-yl)-methylene}-6-chloro-2-indolinone
(192) 3-(Z)-{1-[4-(1-methylpiperazin-4-yl-methyl)-phenylamino]-1-(benzoxazol-2-on-6-yl)-methylene}-6-chloro-2-indolinone
(193) 3-(Z)-{1-[4-(ethylaminomethyl)-phenylamino]-1-(benzoxazol-2-on-6-yl)-methylene}-6-chloro-2-indolinone
(194) 3-(Z)-{1-[4-(N-methyl-N-{dimethylaminomethylcarbonyl}-amino)-phenylamino]-1-(benzoxazol-2-on-6-yl)-methylene}-6-chloro-2-indolinone
(195) 3-(Z)-{1-[4-(N-methyl-N-{1-methylpiperazin-4-yl-methylcarbonyl}-amino)-phenylamino]-1-(benzoxazol-2-on-6-yl)-methylene}-6-chloro-2-indolinone
(196) 3-(Z)-{1-[4-(N-acetyl-N-{2-dimethylamino-ethyl}-amino)-phenylamino]-1-(benzoxazol-2-on-6-yl)-methylene}-6-chloro-2-indolinone
(197) 3-(Z)-{1-[4-(N-acetyl-N-{3-dimethylamino-propyl}-amino)-phenylamino]-1-(benzoxazol-2-on-6-yl)-methylene}-6-chloro-2-indolinone
(198) 3-(Z)-{1-[4-(N-methyl-N-{2-dimethylamino-ethyl}-aminocarbonyl)-phenylamino]-1-(benzoxazol-2-on-6-yl)-methylene}-6-chloro-2-indolinone
(199) 3-(Z)-{1-[4-(N-methanesulphonyl-N-{2-dimethylamino-ethyl}-amino)-phenyl-amino]-1-(benzoxazol-2-on-6-yl)-methylene}-6-chloro-2-indolinone
(200) 3-(Z)-{1-[4-(1-methylpiperazin-4-yl-carbonylmethyl)-phenylamino]-1-(benzoxazol-2-on-6-yl)-methylene}-6-chloro-2-indolinone
(201) 3-(Z)-{1-[4-(N-methyl-N-{2-dimethylamino-ethylcarbonyl}-amino)-phenyl-amino]-1-(benzoxazol-2-on-6-yl)-methylene}-6-chloro-2-indolinone (202) 3-(Z)-{1-[4-(1-methyl-imidazol-2-yl)-phenylamino]-1-(benzoxazol-2-on-6-yl)-methylene}-6-chloro-2-indolinone (203) 3-(Z)-{1-[4-(dimethylaminomethyl)-phenylamino]-1-(benzoxazol-2-on-5-yl)-methylene}-6-chloro-2-indolinone (204) 3-(Z)-{1-[4-(diethylaminomethyl)-phenylamino]-1-(benzoxazol-2-on-5-yl)-methylene}-6-chloro-2-indolinone (205) 3-(Z)-{1-[4-(1-methylpiperazin-4-yl-methyl)-phenylamino]-1-(benzoxazol-2-on-5-yl)-methylene}-6-chloro-2-indolinone (206) 3-(Z)-{1-[4-(ethylaminomethyl)-phenylamino]-1-(benzoxazol-2-on-5-yl)-methylene}-6-chloro-2-indolinone (207) 3-(Z)-{1-[4-(N-methyl-N-{dimethylaminomethylcarbonyl}-amino)-phenylamino]-1-(benzoxazol-2-on-5-yl)-methylene}-6-chloro-2-indolinone (208) 3-(Z)-{1-[4-(N-methyl-N-{1-methylpiperazin-4-yl-methylcarbonyl}-amino)-phenylamino]-1-(benzoxazol-2-on-5-yl)-methylene}-6-chloro-2-indolinone (209) 3-(Z)-{1-[4-(N-acetyl-N-{2-dimethylamino-ethyl}-amino)-phenylamino]-1-(benzoxazol-2-on-5-yl)-methylene}-6-chloro-2-indolinone (210) 3-(Z)-{1-[4-(N-acetyl-N-{3-dimethylamino-propyl}-amino)-phenylamino]-1-(benzoxazol-2-on-5-yl)-methylene}-6-chloro-2-indolinone (211) 3-(Z)-{1-[4-(N-methyl-N-{2-dimethylamino-ethyl}-aminocarbonyl)-phenylamino]-1-(benzoxazol-2-on-5-yl)-methylene}-6-chloro-2-indolinone (212) 3-(Z)-{1-[4-(N-methanesulphonyl-N-{2-dimethylamino-ethyl}-amino)-phenyl-amino]-1-(benzoxazol-2-on-5-yl)-methylene}-6-chloro-2-indolinone (213) 3-(Z)-{1-[4-(1-methylpiperazin-4-yl-carbonylmethyl)-phenylamino]-1-(benzoxazol-2-on-5-yl)-methylene}-6-chloro-2-indolinone (214) 3-(Z)-{1-[4-(N-methyl-N-{2-dimethylamino-ethylcarbonyl}-amino)-phenyl-amino]-1-(benzoxazol-2-on-5-yl)-methylene}-6-chloro-2-indolinone (215) 3-(Z)-{1-[4-(1-methyl-imidazol-2-yl)-phenylamino]-1-(benzoxazol-2-on-5-yl)-methylene}-6-chloro-2-indolinone (216) 3-(Z)-{1-[4-(dimethylaminomethyl)-phenylamino]-1-(quinolin-7-yl)-methylene}-6-chloro-2-indolinone (217) 3-(Z)-{1-[4-(diethylaminomethyl)-phenylamino]-1-(quinolin-7-yl)-methylene}-6-chloro-2-indolinone (218) 3-(Z)-{1-[4-(1-methylpiperazin-4-yl-methyl)-phenylamino]-1-(quinolin-7-yl)-methylene}-6-chloro-2-indolinone (219) 3-(Z)-{1-[4-(ethylaminomethyl)-phenylamino]-1-(quinolin-7-yl)-methylene}-6-chloro-2-indolinone (220) 3-(Z)-{1-[4-(N-methyl-N-{dimethylaminomethylcarbonyl}-amino)-phenylamino]-1-(quinolin-7-yl)-methylene}-6-chloro-2-indolinone (221) 3-(Z)-{1-[4-(N-methyl-N-{1-methylpiperazin-4-yl-methylcarbonyl}-amino)-phenylamino]-1-(quinolin-7-yl)-methylene}-6-chloro-2-indolinone (222) 3-(Z)-{1-[4-(N-acetyl-N-{2-dimethylamino-ethyl}-amino)-phenylamino]-1-(quinolin-7-yl)-methylene}-6-chloro-2-indolinone (223) 3-(Z)-{1-[4-(N-acetyl-N-{3-dimethylamino-propyl}-amino)-phenylamino]-1-(quinolin-7-yl)-methylene}-6-chloro-2-indolinone (224) 3-(Z)-{1-[4-(N-methyl-N-{2-dimethylamino-ethyl}-aminocarbonyl)-phenylamino]-1-(quinolin-7-yl)-methylene}-6-chloro-2-indolinone (225) 3-(Z)-{1-[4-(N-methanesulphonyl-N-{2-dimethylamino-ethyl}-amino)-phenyl-amino]-1-(quinolin-7-yl)-methylene}-6-chloro-2-indolinone (226) 3-(Z)-{1-[4-(1-methylpiperazin-4-yl-carbonylmethyl)-phenylamino]-1-(quinolin-7-yl)-methylene}-6-chloro-2-indolinone (227) 3-(Z)-{1-[4-(N-methyl-N-{2-dimethylamino-ethylcarbonyl}-amino)-phenyl-amino]-1-(quinolin-7-yl)-methylene}-6-chloro-2-indolinone (228) 3-(Z)-{1-[4-(1-methyl-imidazol-2-yl)-phenylamino]-1-(quinolin-7-yl)-methylene}-6-chloro-2-indolinone (229) 3-(Z)-{1-[4-(dimethylaminomethyl)-phenylamino]-1-(quinolin-6-yl)-methylene}-6-chloro-2-indolinone (230) 3-(Z)-{1-[4-(diethylaminomethyl)-phenylamino]-1-(quinolin-6-yl)-methylene}-6-chloro-2-indolinone (231) 3-(Z)-{1-[4-(1-methylpiperazin-4-yl-methyl)-phenylamino]-1-(quinolin-6-yl)-methylene}-6-chloro-2-indolinone (232) 3-(Z)-{1-[4-(ethylaminomethyl)-phenylamino]-1-(quinolin-6-yl)-methylene}-6-chloro-2-indolinone (233) 3-(Z)-{1-[4-(N-methyl-N-{dimethylaminomethylcarbonyl}-amino)-phenylamino]-1-(quinolin-6-yl)-methylene}-6-chloro-2-indolinone (234) 3-(Z)-{1-[4-(N-methyl-N-{1-methylpiperazin-4-yl-methylcarbonyl}-amino)-phenylamino]-1-(quinolin-6-yl)-methylene}-6-chloro-2-indolinone (235) 3-(Z)-{1-[4-(N-acetyl-N-{2-dimethylamino-ethyl}-amino)-phenylamino]-1-(quinolin-6-yl)-methylene}-6-chloro-2-indolinone (236) 3-(Z)-{1-[4-(N-acetyl-N-{3-dimethylamino-propyl}-amino)-phenylamino]-1-(quinolin-6-yl)-methylene}-6-chloro-2-indolinone (237) 3-(Z)-{1-[4-(N-methyl-N-{2-dimethylamino-ethyl}-aminocarbonyl)-phenylamino]-1-(quinolin-6-yl)-methylene}-6-chloro-2-indolinone (238) 3-(Z)-{1-[4-(N-methanesulphonyl-N-{2-dimethylamino-ethyl}-amino)-phenyl-amino]-1-(quinolin-6-yl)-methylene}-6-chloro-2-indolinone (239) 3-(Z)-{1-[4-(1-methylpiperazin-4-yl-carbonylmethyl)-phenylamino]-1-(quinolin-6-yl)-methylene}-6-chloro-2-indolinone (240) 3-(Z)-{1-[4-(N-methyl-N-{2-dimethylamino-ethylcarbonyl}-amino)-phenyl-amino]-1-(quinolin-6-yl)-methylene}-6-chloro-2-indolinone (241) 3-(Z)-{1-[4-(1-methyl-imidazol-2-yl)-phenylamino]-1-(quinolin-6-yl)-methylene}-6-chloro-2-indolinone (242) 3-(Z)-{1-[4-(dimethylaminomethyl)-phenylamino]-1-(benzothiazol-5-yl)-methylene}-6-methoxycarbonyl-2-indolinone (243) 3-(Z)-{1-[4-(diethylaminomethyl)-phenylamino]-1-(benzothiazol-5-yl)-methylene}-6-methoxycarbonyl-2-indolinone (244) 3-(Z)-{1-[4-(1-methylpiperazin-4-yl-methyl)-phenylamino]-1-(benzothiazol-5-yl)-methylene}-6-methoxycarbonyl-2-indolinone (245) 3-(Z)-{1-[4-(ethylaminomethyl)-phenylamino]-1-(benzothiazol-5-yl)-methylene}-6-methoxycarbonyl-2-indolinone (246) 3-(Z)-{1-[4-(N-methyl-N-{dimethylaminomethylcarbonyl}-amino)-phenylamino]-1-(benzothiazol-5-yl)-methylene}-6-methoxycarbonyl-2-indolinone (247) 3-(Z)-{1-[4-(N-methyl-N-{1-methylpiperazin-4-yl-methylcarbonyl}-amino)-phenylamino]-1-(benzothiazol-5-yl)-methylene}-6-methoxycarbonyl-2-indolinone (248) 3-(Z)-{1-[4-(N-acetyl-N-{2-dimethylamino-ethyl}-amino)-phenylamino]-1-(benzothiazol-5-yl)-methylene}-6-methoxycarbonyl-2-indolinone (249) 3-(Z)-{1-[4-(N-acetyl-N-{3-dimethylamino-propyl}-amino)-phenylamino]-1-(benzothiazol-5-yl)-methylene}-6-methoxycarbonyl-2-indolinone (250) 3-(Z)-{1-[4-(N-methyl-N-{2-dimethylamino-ethyl}-aminocarbonyl)-phenylamino]-1-(benzothiazol-5-yl)-methylene}-6-methoxycarbonyl-2-indolinone (251) 3-(Z)-{1-[4-(N-methanesulphonyl-N-{2-dimethylamino-ethyl}-amino)-phenyl-amino]-1-(benzothiazol-5-yl)-methylene}-6-methoxycarbonyl-2-indolinone (252) 3-(Z)-{1-[4-(1-methylpiperazin-4-yl-carbonylmethyl)-phenylamino]-1-(benzo-thiazol-5-yl)-methylene}-6-methoxycarbonyl-2-indolinone (253) 3-(Z)-{1-[4-(N-methyl-N-{2-dimethylamino-ethylcarbonyl}-amino)-phenyl-amino]-1-(benzothiazol-5-yl)-methylene}-6-methoxycarbonyl-2-indolinone (254) 3-(Z)-{1-[4-(1-methyl-imidazol-2-yl)-phenylamino]-1-(benzothiazol-5-yl)-methylene}-6-methoxycarbonyl-2-indolinone (255) 3-(Z)-{1-[4-(dimethylaminomethyl)-phenylamino]-1-(benzothiazol-6-yl)-methylene}-6-methoxycarbonyl-2-indolinone (256) 3-(Z)-{1-[4-(diethylaminomethyl)-phenylamino]-1-(benzothiazol-6-yl)-methylene}-6-methoxycarbonyl-2-indolinone (257) 3-(Z)-{1-[4-(1-methylpiperazin-4-yl-methyl)-phenylamino]-1-(benzothiazol-6-yl)-methylene}-6-methoxycarbonyl-2-indolinone (258) 3-(Z)-{1-[4-(ethylaminomethyl)-phenylamino]-1-(benzothiazol-6-yl)-methylene}-6-methoxycarbonyl-2-indolinone (259) 3-(Z)-{1-[4-(N-methyl-N-{dimethylaminomethylcarbonyl}-amino)-phenylamino]-1-(benzothiazol-6-yl)-methylene}-6-methoxycarbonyl-2-indolinone (260) 3-(Z)-{1-[4-(N-methyl-N-{1-methylpiperazin-4-yl-methylcarbonyl}-amino)-phenylamino]-1-(benzothiazol-6-yl)-methylene}-6-methoxycarbonyl-2-indolinone (261) 3-(Z)-{1-[4-(N-acetyl-N-{2-dimethylamino-ethyl}-amino)-phenylamino]-1-(benzothiazol-6-yl)-methylene}-6-methoxycarbonyl-2-indolinone (262) 3-(Z)-{1-[4-(N-acetyl-N-{3-dimethylamino-propyl}-amino)-phenylamino]-1-(benzothiazol-6-yl)-methylene}-6-methoxycarbonyl-2-indolinone (263) 3-(Z)-{1-[4-(N-methyl-N-{2-dimethylamino-ethyl}-aminocarbonyl)-phenylamino]-1-(benzothiazol-6-yl)-methylene}-6-methoxycarbonyl-2-indolinone (264) 3-(Z)-{1-[4-(N-methanesulphonyl-N-{2-dimethylamino-ethyl}-amino)-phenyl-amino]-1-(benzothiazol-6-yl)-methylene}-6-methoxycarbonyl-2-indolinone (265) 3-(Z)-{1-[4-(1-methylpiperazin-4-yl-carbonylmethyl)-phenylamino]-1-(benzo-thiazol-6-yl)-methylene}-6-methoxycarbonyl-2-indolinone (266) 3-(Z)-{1-[4-(N-methyl-N-{2-dimethylamino-ethylcarbonyl}-amino)-phenyl-amino]-1-(benzothiazol-6-yl)-methylene}-6-methoxycarbonyl-2-indolinone (267) 3-(Z)-{1-[4-(1-methyl-imidazol-2-yl)-phenylamino]-1-(benzothiazol-6-yl)-methylene}-6-methoxycarbonyl-2-indolinone (268) 3-(Z)-{1-[4-(dimethylaminomethyl)-phenylamino]-1-(indol-5-yl)-methylene}-6-methoxycarbonyl-2-indolinone (269) 3-(Z)-{1-[4-(diethylaminomethyl)-phenylamino]-1-(indol-5-yl)-methylene}-6-methoxycarbonyl-2-indolinone (270) 3-(Z)-{1-[4-(1-methylpiperazin-4-yl-methyl)-phenylamino]-1-(indol-5-yl)-methylene}-6-methoxycarbonyl-2-indolinone (271) 3-(Z)-{1-[4-(ethylaminomethyl)-phenylamino]-1-(indol-5-yl)-methylene}-6-methoxycarbonyl-2-indolinone (272) 3-(Z)-{1-[4-(N-methyl-N-{dimethylaminomethylcarbonyl}-amino)-phenylamino]-1-(indol-5-yl)-methylene}-6-methoxycarbonyl-2-indolinone (273) 3-(Z)-{1-[4-(N-methyl-N-{1-methylpiperazin-4-yl-methylcarbonyl}-amino)-phenylamino]-1-(indol-5-yl)-methylene}-6-methoxycarbonyl-2-indolinone (274) 3-(Z)-{1-[4-(N-acetyl-N-{2-dimethylamino-ethyl}-amino)-phenylamino]-1-(indol-5-yl)-methylene}-6-methoxycarbonyl-2-indolinone (275) 3-(Z)-{1-[4-(N-acetyl-N-{3-dimethylamino-propyl}-amino)-phenylamino]-1-(indol-5-yl)-methylene}-6-methoxycarbonyl-2-indolinone (276) 3-(Z)-{1-[4-(N-methyl-N-{2-dimethylamino-ethyl}-aminocarbonyl)-phenylamino]-1-(indol-5-yl)-methylene}-6-methoxycarbonyl-2-indolinone (277) 3-(Z)-{1-[4-(N-methanesulphonyl-N-{2-dimethylamino-ethyl}-amino)-phenyl-amino]-1-(indol-5-yl)-methylene}-6-methoxycarbonyl-2-indolinone (278) 3-(Z)-{1-[4-(1-methylpiperazin-4-yl-carbonylmethyl)-phenylamino]-1-(indol-5-yl)-methylene}-6-methoxycarbonyl-2-indolinone (279) 3-(Z)-{1-[4-(N-methyl-N-{2-dimethylamino-ethylcarbonyl}-amino)-phenyl-amino]-1-(indol-5-yl)-methylene}-6-methoxycarbonyl-2-indolinone (280) 3-(Z)-{1-[4-(1-methyl-imidazol-2-yl)-phenylamino]-1-(indol-5-yl)-methylene}-6-methoxycarbonyl-2-indolinone (281) 3-(Z)-{1-[4-(dimethylaminomethyl)-phenylamino]-1-(phthalazin-6-yl)-methylene}-6-methoxycarbonyl-2-indolinone (282) 3-(Z)-{1-[4-(diethylaminomethyl)-phenylamino]-1-(phthalazin-6-yl)-methylene}-6-methoxycarbonyl-2-indolinone (283) 3-(Z)-{1-[4-(1-methylpiperazin-4-yl-methyl)-phenylamino]-1-(phthalazin-6-yl)-methylene}-6-methoxycarbonyl-2-indolinone (284) 3-(Z)-{1-[4-(ethylaminomethyl)-phenylamino]-1-(phthalazin-6-yl)-methylene}-6-methoxycarbonyl-2-indolinone (285) 3-(Z)-{1-[4-(N-methyl-N-{dimethylaminomethylcarbonyl}-amino)-phenylamino]-1-(phthalazin-6-yl)-methylene}-6-methoxycarbonyl-2-indolinone (286) 3-(Z)-{1-[4-(N-methyl-N-{1-methylpiperazin-4-yl-methylcarbonyl}-amino)-phenylamino]-1-(phthalazin-6-yl)-methylene}-6-methoxycarbonyl-2-indolinone (287) 3-(Z)-{1-[4-(N-acetyl-N-{2-dimethylamino-ethyl}-amino)-phenylamino]-1-(phthalazin-6-yl)-methylene}-6-methoxycarbonyl-2-indolinone (288) 3-(Z)-{1-[4-(N-acetyl-N-{3-dimethylamino-propyl}-amino)-phenylamino]-1-(phthalazin-6-yl)-methylene}-6-methoxycarbonyl-2-indolinone (289) 3-(Z)-{1-[4-(N-methyl-N-{2-dimethylamino-ethyl}-aminocarbonyl)-phenylamino]-1-(phthalazin-6-yl)-methylene}-6-methoxycarbonyl-2-indolinone (290) 3-(Z)-{1-[4-(N-methanesulphonyl-N-{2-dimethylamino-ethyl}-amino)-phenyl-amino]-1-(phthalazin-6-yl)-methylene}-6-methoxycarbonyl-2-indolinone (291) 3-(Z)-{1-[4-(1-methylpiperazin-4-yl-carbonylmethyl)-phenylamino]-1-(phthalazin-6-yl)-methylene}-6-methoxycarbonyl-2-indolinone (292) 3-(Z)-{1-[4-(N-methyl-N-{2-dimethylamino-ethylcarbonyl}-amino)-phenyl-amino]-1-(phthalazin-6-yl)-methylene}-6-methoxycarbonyl-2-indolinone (293) 3-(Z)-{1-[4-(1-methyl-imidazol-2-yl)-phenylamino]-1-(phthalazin-6-yl)-methylene}-6-methoxycarbonyl-2-indolinone
(294) 3-(Z)-{1-[4-(dimethylaminomethyl)-phenylamino]-1-(4-methyl-3,4-dihydro-2H-benzo[1,4]oxazin-7-yl)-methylene}-6-chloro-2-indolinone
(295) 3-(Z)-{1-[4-(diethylaminomethyl)-phenylamino]-1-(4-methyl-3,4-dihydro-2H-benzo[1,4]oxazin-7-yl)-methylene}-6-chloro-2-indolinone
(296) 3-(Z)-{1-[4-(1-methylpiperazin-4-yl-methyl)-phenylamino]-1-(4-methyl-3,4-dihydro-2H-benzo[1,4]oxazin-7-yl)-methylene}-6-chloro-2-indolinone
(297) 3-(Z)-{1-[4-(ethylaminomethyl)-phenylamino]-1-(4-methyl-3,4-dihydro-2H-benzo[1,4]oxazin-7-yl)-methylene}-6-chloro-2-indolinone
(298) 3-(Z)-{1-[4-(N-methyl-N-{dimethylaminomethylcarbonyl}-amino)-phenylamino]-1-(4-methyl-3,4-dihydro-2H-benzo[1,4]oxazin-7-yl)-methylene}-6-chloro-2-indolinone
(299) 3-(Z)-{1-[4-(N-methyl-N-{1-methylpiperazin-4-yl-methylcarbonyl}-amino)-phenylamino]-1-(4-methyl-3,4-dihydro-2H-benzo[1,4]oxazin-7-yl)-methylene}-6-chloro-2-indolinone
(300) 3-(Z)-{1-[4-(N-acetyl-N-{2-dimethylamino-ethyl}-amino)-phenylamino]-1-(4-methyl-3,4-dihydro-2H-benzo[1,4]oxazin-7-yl)-methylene}-6-chloro-2-indolinone
(301) 3-(Z)-{1-[4-(N-acetyl-N-{3-dimethylamino-propyl}-amino)-phenylamino]-1-(4-methyl-3,4-dihydro-2H-benzo[1,4]oxazin-7-yl)-methylene}-6-chloro-2-indolinone
(302) 3-(Z)-{1-[4-(N-methyl-N-{2-dimethylamino-ethyl}-aminocarbonyl)-phenylamino]-1-(4-methyl-3,4-dihydro-2H-benzo[1,4]oxazin-7-yl)-methylene}-6-chloro-2-indolinone
(303) 3-(Z)-{1-[4-(N-methanesulphonyl-N-{2-dimethylamino-ethyl}-amino)-phenyl-amino]-1-(4-methyl-3,4-dihydro-2H-benzo[1,4]oxazin-7-yl)-methylene}-6-chloro-2-indolinone
(304) 3-(Z)-{1-[4-(1-methylpiperazin-4-yl-carbonylmethyl)-phenylamino]-1-(4-methyl-3,4-dihydro-2H-benzo[1,4]oxazin-7-yl)-methylene}-6-chloro-2-indolinone
(305) 3-(Z)-{1-[4-(N-methyl-N-{2-dimethylamino-ethylcarbonyl}-amino)-phenyl-amino]-1-(4-methyl-3,4-dihydro-2H-benzo [1,4]oxazin-7-yl)-methylene}-6-chloro-2-indolinone
(306) 3-(Z)-{1-[4-(1-methyl-imidazol-2-yl)-phenylamino]-1-(4-methyl-3,4-dihydro-2H-benzo[1,4]oxazin-7-yl)-methylene}-6-chloro-2-indolinone
(307) 3-(Z)-{1-[4-(dimethylaminomethyl)-phenylamino]-1-(4-pyridyl)-methylene}-6-methoxycarbonyl-2-indolinone
(308) 3-(Z)-{1-[4-(diethylaminomethyl)-phenylamino]-1-(4-pyridyl)-methylene}-6-methoxycarbonyl-2-indolinone
(309) 3-(Z)-{1-[4-(1-methylpiperazin-4-yl-methyl)-phenylamino]-1-(4-pyridyl)-methylene}-6-methoxycarbonyl-2-indolinone
(310) 3-(Z)-{1-[4-(ethylaminomethyl)-phenylamino]-1-(4-pyridyl)-methylene}-6-methoxycarbonyl-2-indolinone
(311) 3-(Z)-{1-[4-(N-methyl-N-{dimethylaminomethyl-carbonyl}-amino)-phenylamino]-1-(4-pyridyl)-methylene}-6-methoxycarbonyl-2-indolinone
(312) 3-(Z)-{1-[4-(N-methyl-N-{1-methylpiperazin-4-yl-methylcarbonyl}-amino)-phenylamino]-1-(4-pyridyl)-methylene}-6-methoxycarbonyl-2-indolinone
(313) 3-(Z)-{1-[4-(N-acetyl-N-{2-dimethylamino-ethyl}-amino)-phenylamino]-1-(4-pyridyl)-methylene}-6-methoxycarbonyl-2-indolinone
(314) 3-(Z)-{1-[4-(N-acetyl-N-{3-dimethylamino-propyl}-amino)-phenylamino]-1-(4-pyridyl)-methylene}-6-methoxycarbonyl-2-indolinone
(315) 3-(Z)-{1-[4-(N-methyl-N-{2-dimethylamino-ethyl}-aminocarbonyl)-phenylamino]-1-(4-pyridyl)-methylene}-6-methoxycarbonyl-2-indolinone
(316) 3-(Z)-{1-[4-(N-methanesulphonyl-N-{2-dimethylamino-ethyl}-amino)-phenyl-amino]-1-(4-pyridyl)-methylene}-6-methoxycarbonyl-2-indolinone
(317) 3-(Z)-{1-[4-(1-methylpiperazin-4-yl-carbonylmethyl)-phenylamino]-1-(4-pyridyl)-methylene}-6-methoxycarbonyl-2-indolinone
(318) 3-(Z)-{1-[4-(N-methyl-N-{2-dimethylamino-ethylcarbonyl}-amino)-phenyl-amino]-1-(4-pyridyl)-methylene}-6-methoxycarbonyl-2-indolinone
(319) 3-(Z)-{1-[4-(1-methyl-imidazol-2-yl)-phenylamino]-1-(4-pyridyl)-methylene}-6-methoxycarbonyl-2-indolinone
(320) 3-(Z)-{1-[4-(dimethylaminomethyl)-phenylamino]-1-(3-pyridyl)-methylene}-6-methoxycarbonyl-2-indolinone
(321) 3-(Z)-{1-[4-(diethylaminomethyl)-phenylamino]-1-(3-pyridyl)-methylene}-6-methoxycarbonyl-2-indolinone
(322) 3-(Z)-{1-[4-(1-methylpiperazin-4-yl-methyl)-phenylamino]-1-(3-pyridyl)-methylene}-6-methoxycarbonyl-2-indolinone
(323) 3-(Z)-{1-[4-(ethylaminomethyl)-phenylamino]-1-(3-pyridyl)-methylene}-6-methoxycarbonyl-2-indolinone
(324) 3-(Z)-{1-[4-(N-methyl-N-{dimethylaminomethylcarbonyl}-amino)-phenylamino]-1-(3-pyridyl)-methylene}-6-methoxycarbonyl-2-indolinone
(325) 3-(Z)-{1-[4-(N-methyl-N-{1-methylpiperazin-4-yl-methylcarbonyl}-amino)-phenylamino]-1-(3-pyridyl)-methylene}-6-methoxycarbonyl-2-indolinone
(326) 3-(Z)-{1-[4-(N-acetyl-N-{2-dimethylamino-ethyl}-amino)-phenylamino]-1-(3-pyridyl)-methylene}-6-methoxycarbonyl-2-indolinone
(327) 3-(Z)-{1-[4-(N-acetyl-N-{3-dimethylamino-propyl}-amino)-phenylamino]-1-(3-pyridyl)-methylene}-6-methoxycarbonyl-2-indolinone
(328) 3-(Z)-{1-[4-(N-methyl-N-{2-dimethylamino-ethyl}-aminocarbonyl)-phenylamino]-1-(3-pyridyl)-methylene}-6-methoxycarbonyl-2-indolinone
(329) 3-(Z)-{1-[4-(N-methanesulphonyl-N-{2-dimethylamino-ethyl}-amino)-phenyl-amino]-1-(3-pyridyl)-methylene}-6-methoxycarbonyl-2-indolinone
(330) 3-(Z)-{1-[4-(1-methylpiperazin-4-yl-carbonylmethyl)-phenylamino]-1-(3-pyridyl)-methylene}-6-methoxycarbonyl-2-indolinone
(331) 3-(Z)-{1-[4-(N-methyl-N-{2-dimethylamino-ethylcarbonyl}-amino)-phenyl-amino]-1-(3-pyridyl)-methylene}-6-methoxycarbonyl-2-indolinone
(332) 3-(Z)-{1-[4-(1-methyl-imidazol-2-yl)-phenylamino]-1-(3-pyridyl)-methylene}-6-methoxycarbonyl-2-indolinone
(333) 3-(Z)-{1-[3-fluoro-4-(N-methyl-N-{dimethylaminomethyl-carbonyl}-amino)-phenylamino]-1-(3,4-methylenedioxyphenyl)-methylene}-6-chloro-2-indolinone
(334) 3-(Z)-{1-[3-fluoro-4-(N-methyl-N-{dimethylaminomethyl-carbonyl}-amino)-phenylamino]-1-(3,4-methylenedioxyphenyl)-methylene}-6-methoxycarbonyl-2-indolinone
(335) 3-(Z)-{1-[3-fluoro-4-(N-methyl-N-{dimethylaminomethyl-carbonyl}-amino)-phenylamino]-1-(3,4-ethylenedioxyphenyl)-methylene}-6-chloro-2-indolinone (336) 3-(Z)-{1-[3-fluoro-4-(N-methyl-N-{dimethylaminomethyl-carbonyl}-amino)-phenylamino]-1-(3,4-ethylenedioxyphenyl)-methylene}-6-methoxycarbonyl-2-indolinone
(337) 3-(Z)-{1-[3-fluoro-4-(N-methyl-N-{dimethylaminomethyl-carbonyl}-amino)-phenylamino]-1-(2-thienyl)-methylene}-6-chloro-2-indolinone
(338) 3-(Z)-{1-[3-fluoro-4-(N-methyl-N-{dimethylaminomethyl-carbonyl}-amino)-phenylamino]-1-(2-thienyl)-methylene}-6-methoxycarbonyl-2-indolinone
(339) 3-(Z)-{1-[3-fluoro-4-(N-methyl-N-{dimethylaminomethyl-carbonyl}-amino)-phenylamino]-1-(3-thienyl)-methylene}-6-chloro-2-indolinone
(340) 3-(Z)-{1-[3-fluoro-4-(N-methyl-N-{dimethylaminomethyl-carbonyl}-amino)-phenylamino]-1-(3-thienyl)-methylene}-6-methoxycarbonyl-2-indolinone
(341) 3-(Z)-{1-[3-fluoro-4-(N-methyl-N-{dimethylaminomethyl-carbonyl}-amino)-phenylamino]-1-(quinoxalin-6-yl)-methylene}-6-chloro-2-indolinone
(342) 3-(Z)-{1-[3-fluoro-4-(N-methyl-N-{dimethylaminomethyl-carbonyl}-amino)-phenylamino]-1-(quinoxalin-6-yl)-methylene}-6-methoxycarbonyl-2-indolinone
(343) 3-(Z)-{1-[3-fluoro-4-(N-methanesulphonyl-N-{2-dimethylamino-ethyl}-amino)-phenylamino]-1-(3,4-methylenedioxyphenyl)-methylene}-6-chloro-2-indolinone
(344) 3-(Z)-{1-[3-fluoro-4-(N-methanesulphonyl-N-{2-dimethylamino-ethyl}-amino)-phenylamino]-1-(3,4-methylenedioxyphenyl)-methylene}-6-methoxycarbonyl-2-indolinone
(345) 3-(Z)-{1-[3-fluoro-4-(N-methanesulphonyl-N-{2-dimethylamino-ethyl}-amino)-phenylamino]-1-(3,4-ethylenedioxyphenyl)-methylene}-6-chloro-2-indolinone
(346) 3-(Z)-{1-[3-fluoro-4-(N-methanesulphonyl-N-{2-dimethylamino-ethyl}-amino)-phenylamino]-1-(3,4-ethylenedioxyphenyl)-methylene}-6-methoxycarbonyl-2-indolinone
(347) 3-(Z)-{1-[3-fluoro-4-(N-methanesulphonyl-N-{2-dimethylamino-ethyl}-amino)-phenylamino]-1-(2-thienyl)-methylene}-6-chloro-2-indolinone
(348) 3-(Z)-{1-[3-fluoro-4-(N-methanesulphonyl-N-{2-dimethylamino-ethyl}-amino)-phenylamino]-1-(2-thienyl)-methylene}-6-methoxycarbonyl-2-indolinone
(349) 3-(Z)-{1-[3-fluoro-4-(N-methanesulphonyl-N-{2-dimethylamino-ethyl}-amino)-phenylamino]-1-(3-thienyl)-methylene}-6-chloro-2-indolinone
(350) 3-(Z)-{1-[3-fluoro-4-(N-methanesulphonyl-N-{2-dimethylamino-ethyl}-amino)-phenylamino]-1-(3-thienyl)-methylene}-6-methoxycarbonyl-2-indolinone
(351) 3-(Z)-{1-[3-fluoro-4-(N-methanesulphonyl-N-{2-dimethylamino-ethyl}-amino)-phenylamino]-1-(quinoxalin-6-yl)-methylene}-6-chloro-2-indolinone
(352) 3-(Z)-{1-[3-fluoro-4-(N-methanesulphonyl-N-{2-dimethylamino-ethyl}-amino)-phenylamino]-1-(quinoxalin-6-yl)-methylene}-6-methoxycarbonyl-2-indolinone
(353) 3-(Z)-{1-[1-methyl-2-(N-{2-dimethylamino-ethyl}-N-methyl-aminocarbonyl)-pyrrol-4-yl-amino]-1-(3,4-methylenedioxyphenyl)-methylene}-6-chloro-2-indolinone
(354) 3-(Z)-{1-[1-methyl-2-(N-{2-dimethylamino-ethyl}-N-methyl-aminocarbonyl)-pyrrol-4-yl-amino]-1-(3,4-methylenedioxyphenyl)-methylene}-6-methoxycarbonyl-2-indolinone
(355) 3-(Z)-{1-[1-methyl-2-(N-{2-dimethylamino-ethyl}-N-methyl-aminocarbonyl)-pyrrol-4-yl-amino]-1-(3,4-ethylenedioxyphenyl)-methylene}-6-chloro-2-indolinone
(356) 3-(Z)-{1-[1-methyl-2-(N-{2-dimethylamino-ethyl}-N-methyl-aminocarbonyl)-pyrrol-4-yl-amino]-1-(3,4-ethylenedioxyphenyl)-methylene}-6-methoxycarbonyl-2-indolinone
(357) 3-(Z)-{1-[1-methyl-2-(N-{2-dimethylamino-ethyl}-N-methyl-aminocarbonyl)-pyrrol-4-yl-amino]-1-(2-thienyl)-methylene}-6-chloro-2-indolinone
(358) 3-(Z)-{1-[1-methyl-2-(N-{2-dimethylamino-ethyl}-N-methyl-aminocarbonyl)-pyrrol-4-yl-amino]-1-(2-thienyl)-methylene}-6-methoxycarbonyl-2-indolinone
(359) 3-(Z)-{1-[1-methyl-2-(N-{2-dimethylamino-ethyl}-N-methyl-aminocarbonyl)-pyrrol-4-yl-amino]-1-(3-thienyl)-methylene}-6-chloro-2-indolinone
(360) 3-(Z)-{1-[1-methyl-2-(N-{2-dimethylamino-ethyl}-N-methyl-aminocarbonyl)-pyrrol-4-yl-amino]-1-(3-thienyl)-methylene}-6-methoxycarbonyl-2-indolinone
(361) 3-(Z)-{1-[1-methyl-2-(N-{2-dimethylamino-ethyl}-N-methyl-aminocarbonyl)-pyrrol-4-yl-amino]-1-(quinoxalin-6-yl)-methylene}-6-chloro-2-indolinone
(362) 3-(Z)-{1-[1-methyl-2-(N-{2-dimethylamino-ethyl}-N-methyl-aminocarbonyl)-pyrrol-4-yl-amino]-1-(quinoxalin-6-yl)-methylene}-6-methoxycarbonyl-2-indolinone
(363) 3-(Z)-{1-[4-(dimethylaminomethyl)-phenylamino]-1-(3,4-methylenedioxyphenyl)-methylene}-6-fluoro-2-indolinone
(364) 3-(Z)-{1-[4-(diethylaminomethyl)-phenylamino]-1-(3,4-methylenedioxyphenyl)-methylene}-6-fluoro-2-indolinone
(365) 3-(Z)-{1-[4-(1-methylpiperazin-4-yl-methyl)-phenylamino]-1-(3,4-methylenedioxyphenyl)-methylene}-6-fluoro-2-indolinone
(366) 3-(Z)-{1-[4-(ethylaminomethyl)-phenylamino]-1-(3,4-methylenedioxyphenyl)-methylene}-6-fluoro-2-indolinone
(367) 3-(Z)-{1-[4-(N-methyl-N-{dimethylaminomethylcarbonyl}-amino)-phenylamino]-1-(3,4-methylenedioxyphenyl)-methylene}-6-fluoro-2-indolinone
(368) 3-(Z)-{1-[4-(N-methyl-N-{1-ethylpiperazin-4-yl-methylcarbonyl}-amino)-phenylamino]-1-(3,4-methylenedioxyphenyl)-methylene}-6-chloro-2-indolinone
(369) 3-(Z)-{1-[4-(N-acetyl-N-{2-dimethylamino-ethyl}-amino)-phenylamino]-1-(3,4-methylenedioxyphenyl)-methylene}-6-fluoro-2-indolinone
(370) 3-(Z)-{1-[4-(N-acetyl-N-{3-dimethylamino-propyl}-amino)-phenylamino]-1-(3,4-methylenedioxyphenyl)-methylene}-6-fluoro-2-indolinone
(371) 3-(Z)-{1-[4-(N-methyl-N-{2-dimethylamino-ethyl}-aminocarbonyl)-phenylamino]-1-(3,4-methylenedioxyphenyl)-methylene}-6-fluoro-2-indolinone
(372) 3-(Z)-{1-[4-(N-methanesulphonyl-N-{2-dimethylamino-ethyl}-amino)-phenylamino]-1-(3,4-methylenedioxyphenyl)-methylene}-6-fluoro-2-indolinone
(373) 3-(Z)-{1-[4-(1-methylpiperazin-4-yl-carbonylmethyl)-phenylamino]-1-(3,4-methylenedioxyphenyl)-methylene}-6-fluoro-2-indolinone
(374) 3-(Z)-{1-[4-(N-methyl-N-{2-dimethylamino-ethylcarbonyl}-amino)-phenylamino]-1-(3,4-methylenedioxyphenyl)-methylene}-6-fluoro-2-indolinone
(375) 3-(Z)-{1-[4-(1-methyl-imidazol-2-yl)-phenylamino]-1-(3,4-methylenedioxyphenyl)-methylene}-6-fluoro-2-indolinone
(376) 3-(Z)-{1-[4-(dimethylaminomethyl)-phenylamino]-1-(3,4-methylenedioxyphenyl)-methylene}-6-bromo-2-indolinone (377) 3-(Z)-{1-[4-(diethylaminomethyl)-phenylamino]-1-(3,4-methylenedioxyphenyl)-methylene}-6-bromo-2-indolinone
(378) 3-(Z)-{1-[4-(1-methylpiperazin-4-yl-methyl)-phenylamino]-1-(3,4-methylenedioxyphenyl)-methylene}-6-bromo-2-indolinone
(379) 3-(Z)-{1-[4-(ethylaminomethyl)-phenylamino]-1-(3,4-methylenedioxyphenyl)-methylene}-6-bromo-2-indolinone
(380) 3-(Z)-{1-[4-(N-methyl-N-{dimethylaminomethylcarbonyl}-amino)-phenylamino]-1-(3,4-methylenedioxyphenyl)-methylene}-6-bromo-2-indolinone
(381) 3-(Z)-{1-[4-(N-ethyl-N-{1-methylpiperazin-4-yl-methylcarbonyl}-amino)-phenylamino]-1-(3,4-methylenedioxyphenyl)-methylene}-6-chloro-2-indolinone
(382) 3-(Z)-{1-[4-(N-acetyl-N-{2-dimethylamino-ethyl}-amino)-phenylamino]-1-(3,4-methylenedioxyphenyl)-methylene}-6-bromo-2-indolinone
(383) 3-(Z)-{1-[4-(N-acetyl-N-{3-dimethylamino-propyl}-amino)-phenylamino]-1-(3,4-methylenedioxyphenyl)-methylene}-6-bromo-2-indolinone
(384) 3-(Z)-{1-[4-(N-methyl-N-{2-dimethylamino-ethyl}-aminocarbonyl)-phenylamino]-1-(3,4-methylenedioxyphenyl)-methylene}-6-bromo-2-indolinone
(385) 3-(Z)-{1-[4-(N-methanesulphonyl-N-{2-dimethylamino-ethyl}-amino)-phenylamino]-1-(3,4-methylenedioxyphenyl)-methylene}-6-bromo-2-indolinone
(386) 3-(Z)-{1-[4-(1-methylpiperazin-4-yl-carbonylmethyl)-phenylamino]-1-(3,4-methylenedioxyphenyl)-methylene}-6-bromo-2-indolinone
(387) 3-(Z)-{1-[4-(N-methyl-N-{2-dimethylamino-ethylcarbonyl}-amino)-phenylamino]-1-(3,4-methylenedioxyphenyl)-methylene}-6-bromo-2-indolinone
(388) 3-(Z)-{1-[4-(1-methyl-imidazol-2-yl)-phenylamino]-1-(3,4-methylenedioxyphenyl)-methylene}-6-bromo-2-indolinone
(389) 3-(Z)-{1-[4-(dimethylaminomethyl)-phenylamino]-1-(2-[2-carboxyethyl]-thien-5-yl)-methylene}-6-fluoro-2-indolinone
(390) 3-(Z)-{1-[4-(dimethylaminomethyl)-phenylamino]-1-(3-[2-carboxyethyl]-thien-5-yl)-methylene}-6-fluoro-2-indolinone
(391) 3-(Z)-{1-[4-(dimethylaminomethyl)-phenylamino]-1-(2-[2-carboxyethyl]-thien-4-yl)-methylene}-6-fluoro-2-indolinone
(392) 3-(Z)-{1-[4-(dimethylaminomethyl)-phenylamino]-1-(2-[2-carboxyethyl]-pyridine-4-yl)-methylene}-6-fluoro-2-indolinone
(393) 3-(Z)-{1-[4-(dimethylaminomethyl)-phenylamino]-1-(3-[2-carboxyethyl]-pyridine-5-yl)-methylene}-6-fluoro-2-indolinone
(394) 3-(Z)-{1-[4-(dimethylaminomethyl)-phenylamino]-1-(2-[2-carboxyethyl]-pyridine-5-yl)-methylene}-6-fluoro-2-indolinone
(395) 3-(Z)-{1-[4-(dimethylaminomethyl)-phenylamino]-1-(2-[2-carboxyethyl]-thien-5-yl)-methylene}-6-chloro-2-indolinone
(396) 3-(Z)-{1-[4-(dimethylaminomethyl)-phenylamino]-1-(3-[2-carboxyethyl]-thien-5-yl)-methylene}-6-chloro-2-indolinone
(397) 3-(Z)-{1-[4-(dimethylaminomethyl)-phenylamino]-1-(2-[2-carboxyethyl]-thien-4-yl)-methylene}-6-chloro-2-indolinone
(398) 3-(Z)-{1-[4-(dimethylaminomethyl)-phenylamino]-1-(2-[2-carboxyethyl]-pyridine-4-yl)-methylene}-6-chloro-2-indolinone
(399) 3-(Z)-{1-[4-(dimethylaminomethyl)-phenylamino]-1-(3-[2-carboxyethyl]-pyridine-5-yl)-methylene}-6-chloro-2-indolinone
(400) 3-(Z)-{1-[4-(dimethylaminomethyl)-phenylamino]-1-(2-[2-carboxyethyl]-pyridine-5-yl)-methylene}-6-chloro-2-indolinone
(401) 3-(Z)-{1-[4-(dimethylaminomethyl)-phenylamino]-1-(2-[2-carboxyethyl]-thien-5-yl)-methylene}-6-cyano-2-indolinone
(402) 3-(Z)-{1-[4-(dimethylaminomethyl)-phenylamino]-1-(3-[2-carboxyethyl]-thien-5-yl)-methylene}-6-cyano-2-indolinone
(403) 3-(Z)-{1-[4-(dimethylaminomethyl)-phenylamino]-1-(2-[2-carboxyethyl]-thien-4-yl)-methylene}-6-cyano-2-indolinone
(404) 3-(Z)-{1-[4-(dimethylaminomethyl)-phenylamino]-1-(2-[2-carboxyethyl]-pyridine-4-yl)-methylene}-6-cyano-2-indolinone
(405) 3-(Z)-{1-[4-(dimethylaminomethyl)-phenylamino]-1-(3-[2-carboxyethyl]-pyridine-5-yl)-methylene}-6-cyano-2-indolinone
(406) 3-(Z)-{1-[4-(dimethylaminomethyl)-phenylamino]-1-(2-[2-carboxyethyl]-pyridine-5-yl)-methylene}-6-cyano-2-indolinone
(407) 3-(Z)-{1-[4-(dimethylaminomethyl)-phenylamino]-1-(2-[2-carboxyethyl]-thien-5-yl)-methylene}-6-methoxycarbonyl-2-indolinone
(408) 3-(Z)-{1-[4-(dimethylaminomethyl)-phenylamino]-1-(3-[2-carboxyethyl]-thien-5-yl)-methylene}-6-methoxycarbonyl-2-indolinone
(409) 3-(Z)-{1-[4-(dimethylaminomethyl)-phenylamino]-1-(2-[2-carboxyethyl]-thien-4-yl)-methylene}-6-methoxycarbonyl-2-indolinone
(410) 3-(Z)-{1-[4-(dimethylaminomethyl)-phenylamino]-1-(2-[2-carboxyethyl]-pyridine-4-yl)-methylene}-6-methoxycarbonyl-2-indolinone
(411) 3-(Z)-{1-[4-(dimethylaminomethyl)-phenylamino]-1-(3-[2-carboxyethyl]-pyridine-5-yl)-methylene}-6-methoxycarbonyl-2-indolinone
(412) 3-(Z)-{1-[4-(dimethylaminomethyl)-phenylamino]-1-(2-[2-carboxyethyl]-pyridine-5-yl)-methylene}-6-methoxycarbonyl-2-indolinone
(413) 3-(Z)-{1-[4-(dimethylaminomethyl)-phenylamino]-1-(2,3-dihydrobenzofuran-6-yl)-methylene}-6-fluoro-2-indolinone
(414) 3-(Z)-{1-[4-(N-methyl-N-{1-methylpiperazin-4-yl-methylcarbonyl}-amino)-phenylamino]-1-(2,3-dihydrobenzofuran-6-yl)-methylene}-6-fluoro-2-indolinone
(415) 3-(Z)-{1-[4-(N-methanesulphonyl-N-{2-dimethylamino-ethyl}-amino)-phenylamino]-1-(2,3-dihydrobenzofuran-6-yl)-methylene}-6-fluoro-2-indolinone
(416) 3-(Z)-{1-[4-(dimethylaminomethyl)-phenylamino]-1-(2,3-dihydrobenzofuran-5-yl)-methylene}-6-fluoro-2-indolinone
(417) 3-(Z)-{1-[4-(N-methyl-N-{1-methylpiperazin-4-yl-methylcarbonyl}-amino)-phenylamino]-1-(2,3-dihydrobenzofuran-5-yl)-methylene}-6-fluoro-2-indolinone
(418) 3-(Z)-{1-[4-(N-methanesulphonyl-N-{2-dimethylamino-ethyl}-amino)-phenylamino]-1-(2,3-dihydrobenzofuran-5-yl)-methylene}-6-fluoro-2-indolinone
(419) 3-(Z)-{1-[4-(dimethylaminomethyl)-phenylamino]-1-(imidazo[1,2-a]pyridin-7-yl)-methylene}-6-fluoro-2-indolinone
(420) 3-(Z)-{1-[4-(N-methyl-N-{1-methylpiperazin-4-yl-methylcarbonyl}-amino)-phenylamino]-1-(imidazo[1,2-a]pyridin-7-yl)-methylene}-6-fluoro-2-indolinone (421) 3-(Z)-{1-[4-(N-methanesulphonyl-N-{2-dimethylamino-ethyl}-amino)-phenylamino]-1-(imidazo[1,2-a]pyridin-7-yl)-methylene}-6-fluoro-2-indolinone (422) 3-(Z)-{1-[4-(dimethylaminomethyl)-phenylamino]-1-(imidazo[1,2-a]pyridin-6-yl)-methylene}-6-fluoro-2-indolinone (423) 3-(Z)-{1-[4-(N-methyl-N-{1-methylpiperazin-4-yl-methylcarbonyl}-amino)-phenylamino]-1-(imidazo[1,2-a]pyridin-6-yl)-methylene}-6-fluoro-2-indolinone (424) 3-(Z)-{1-[4-(N-methanesulphonyl-N-{2-dimethylamino-ethyl}-amino)-phenylamino]-1-(imidazo[1,2-a]pyridin-6-yl)-methylene}-6-fluoro-2-indolinone (425) 3-(Z)-{1-[4-(dimethylaminomethyl)-phenylamino]-1-(2,3-dihydrobenzofuran-6-yl)-methylene}-6-chloro-2-indolinone (426) 3-(Z)-{1-[4-(N-methyl-N-{1-methylpiperazin-4-yl-methylcarbonyl}-amino)-phenylamino]-1-(2,3-dihydrobenzofuran-6-yl)-methylene}-6-chloro-2-indolinone (427) 3-(Z)-{1-[4-(N-methanesulphonyl-N-{2-dimethylamino-ethyl}-amino)-phenylamino]-1-(2,3-dihydrobenzofuran-6-yl)-methylene}-6-chloro-2-indolinone (428) 3-(Z)-{1-[4-(dimethylaminomethyl)-phenylamino]-1-(2,3-dihydrobenzofuran-5-yl)-methylene}-6-chloro-2-indolinone (429) 3-(Z)-{1-[4-(N-methyl-N-{1-methylpiperazin-4-yl-methylcarbonyl}-amino)-phenylamino]-1-(2,3-dihydrobenzofuran-5-yl)-methylene}-6-chloro-2-indolinone (430) 3-(Z)-{1-[4-(N-methanesulphonyl-N-{2-dimethylamino-ethyl}-amino)-phenylamino]-1-(2,3-dihydrobenzofuran-5-yl)-methylene}-6-chloro-2-indolinone (431) 3-(Z)-{1-[4-(dimethylaminomethyl)-phenylamino]-1-(imidazo[1,2-a]pyridin-7-yl)-methylene}-6-chloro-2-indolinone (432) 3-(Z)-{1-[4-(N-methyl-N-{1-methylpiperazin-4-yl-methylcarbonyl}-amino)-phenylamino]-1-(imidazo[1,2-a]pyridin-7-yl)-methylene}-6-chloro-2-indolinone (433) 3-(Z)-{1-[4-(N-methanesulphonyl-N-{2-dimethylamino-ethyl}-amino)-phenylamino]-1-(imidazo[1,2-a]pyridin-7-yl)-methylene}-6-chloro-2-indolinone (434) 3-(Z)-{1-[4-(dimethylaminomethyl)-phenylamino]-1-(imidazo[1,2-a]pyridin-6-yl)-methylene}-6-chloro-2-indolinone (435) 3-(Z)-{1-[4-(N-methyl-N-{1-methylpiperazin-4-yl-methylcarbonyl}-amino)-phenylamino]-1-(imidazo[1,2-a]pyridin-6-yl)-methylene}-6-chloro-2-indolinone (436) 3-(Z)-{1-[4-(N-methanesulphonyl-N-{2-dimethylamino-ethyl}-amino)-phenylamino]-1-(imidazo[1,2-a]pyridin-6-yl)-methylene}-6-chloro-2-indolinone (437) 3-(Z)-{1-[4-(dimethylaminomethyl)-phenylamino]-1-(2,3-dihydrobenzofuran-6-yl)-methylene}-6-cyano-2-indolinone (438) 3-(Z)-{1-[4-(N-methyl-N-{1-methylpiperazin-4-yl-methylcarbonyl}-amino)-phenylamino]-1-(2,3-dihydrobenzofuran-6-yl)-methylene}-6-cyano-2-indolinone (439) 3-(Z)-{1-[4-(N-methanesulphonyl-N-{2-dimethylamino-ethyl}-amino)-phenylamino]-1-(2,3-dihydrobenzofuran-6-yl)-methylene}-6-cyano-2-indolinone (440) 3-(Z)-{1-[4-(dimethylaminomethyl)-phenylamino]-1-(2,3-dihydrobenzofuran-5-yl)-methylene}-6-cyano-2-indolinone (441) 3-(Z)-{1-[4-(N-methyl-N-{1-methylpiperazin-4-yl-methylcarbonyl}-amino)-phenylamino]-1-(2,3-dihydrobenzofuran-5-yl)-methylene}-6-cyano-2-indolinone (442) 3-(Z)-{1-[4-(N-methanesulphonyl-N-{2-dimethylamino-ethyl}-amino)-phenylamino]-1-(2,3-dihydrobenzofuran-5-yl)-methylene}-6-cyano-2-indolinone (443) 3-(Z)-{1-[4-(dimethylaminomethyl)-phenylamino]-1-(imidazo[1,2-a]pyridin-7-yl)-methylene}-6-cyano-2-indolinone (444) 3-(Z)-{1-[4-(N-methyl-N-{1-methylpiperazin-4-yl-methylcarbonyl}-amino)-phenylamino]-1-(imidazo[1,2-a]pyridin-7-yl)-methylene}-6-cyano-2-indolinone (445) 3-(Z)-{1-[4-(N-methanesulphonyl-N-{2-dimethylamino-ethyl}-amino)-phenylamino]-1-(imidazo[1,2-a]pyridin-7-yl)-methylene}-6-cyano-2-indolinone (446) 3-(Z)-{1-[4-(dimethylaminomethyl)-phenylamino]-1-(imidazo[1,2-a]pyridin-6-yl)-methylene}-6-cyano-2-indolinone (447) 3-(Z)-{1-[4-(N-methyl-N-{1-methylpiperazin-4-yl-methylcarbonyl}-amino)-phenylamino]-1-(imidazo[1,2-a]pyridin-6-yl)-methylene}-6-cyano-2-indolinone (448) 3-(Z)-{1-[4-(N-methanesulphonyl-N-{2-dimethylamino-ethyl}-amino)-phenylamino]-1-(imidazo[1,2-a]pyridin-6-yl)-methylene}-6-cyano-2-indolinone (449) 3-(Z)-{1-[4-(dimethylaminomethyl)-phenylamino]-1-(2,3-dihydrobenzofuran-6-yl)-methylene}-6-methoxycarbonyl-2-indolinone (450) 3-(Z)-{1-[4-(N-methyl-N-{1-methylpiperazin-4-yl-methylcarbonyl}-amino)-phenylamino]-1-(2,3-dihydrobenzofuran-6-yl)-methylene}-6-methoxycarbonyl-2-indolinone (451) 3-(Z)-{1-[4-(N-methanesulphonyl-N-{2-dimethylamino-ethyl}-amino)-phenylamino]-1-(2,3-dihydrobenzofuran-6-yl)-methylene}-6-methoxycarbonyl-2-indolinone (452) 3-(Z)-{1-[4-(dimethylaminomethyl)-phenylamino]-1-(2,3-dihydrobenzofuran-5-yl)-methylene}-6-methoxycarbonyl-2-indolinone (453) 3-(Z)-{1-[4-(N-methyl-N-{1-methylpiperazin-4-yl-methylcarbonyl}-amino)-phenylamino]-1-(2,3-dihydrobenzofuran-5-yl)-methylene}-6-methoxycarbonyl-2-indolinone (454) 3-(Z)-{1-[4-(N-methanesulphonyl-N-{2-dimethylamino-ethyl}-amino)-phenylamino]-1-(2,3-dihydrobenzofuran-5-yl)-methylene}-6-methoxycarbonyl-2-indolinone (455) 3-(Z)-{1-[4-(dimethylaminomethyl)-phenylamino]-1-(imidazo[1,2-a]pyridin-7-yl)-methylene}-6-methoxycarbonyl-2-indolinone (456) 3-(Z)-{1-[4-(N-methyl-N-{1-methylpiperazin-4-yl-methylcarbonyl}-amino)-phenylamino]-1-(imidazo[1,2-a]pyridin-7-yl)-methylene}-6-methoxycarbonyl-2-indolinone (457) 3-(Z)-{1-[4-(N-methanesulphonyl-N-{2-dimethylamino-ethyl}-amino)-phenylamino]-1-(imidazo[1,2-a]pyridin-7-yl)-methylene}-6-methoxycarbonyl-2-indolinone (458) 3-(Z)-{1-[4-(dimethylaminomethyl)-phenylamino]-1-(imidazo[1,2-a]pyridin-6-yl)-methylene}-6-methoxycarbonyl-2-indolinone (459) 3-(Z)-{1-[4-(N-methyl-N-{1-methylpiperazin-4-yl-methylcarbonyl}-amino)-phenylamino]-1-(imidazo[1,2-a]pyridin-6-yl)-methylene}-6-methoxycarbonyl-2-indolinone (460) 3-(Z)-{1-[4-(N-methanesulphonyl-N-{2-dimethylamino-ethyl}-amino)-phenylamino]-1-(imidazo[1,2-a]pyridin-6-yl)-methylene}-6-methoxycarbonyl-2-indolinone

The invention claimed is:
1. A compound of formula

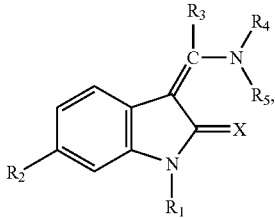

(I)

wherein

X denotes an oxygen or sulphur atom, $R_1$ denotes a hydrogen atom or a prodrug group such as a $C_{1-4}$-alkoxy-carbonyl or $C_{2-4}$-alkanoyl group, $R_2$ denotes a hydrogen, fluorine, chlorine or bromine atom, a cyano or nitro group, a carboxy group, a straight-chain or branched $C_{1-6}$-alkoxy-carbonyl group, a $C_{3-6}$-cycloalkoxy-carbonyl or an aryloxycarbonyl group, an allyloxy-carbonyl group optionally substituted by one or two methyl groups, a straight-chain or branched $C_{1-4}$-alkoxy-carbonyl group which is terminally substituted in the alkyl moiety by a phenyl, heteroaryl, carboxy, $C_{1-3}$-alkoxy-carbonyl, aminocarbonyl, $C_{1-3}$-alkylamino-carbonyl or di-($C_{1-3}$-alkyl)-aminocarbonyl group, a straight-chain or branched $C_{2-6}$-alkoxy-carbonyl group which is terminally substituted in the alkyl moiety by a chlorine atom or a hydroxy, $C_{1-3}$-alkoxy, amino, $C_{1-3}$-alkylamino or di-($C_{1-3}$-alkyl)-amino group, or an aminocarbonyl, $C_{1-4}$-alkyl-aminocarbonyl or a di-($C_{1-4}$-alkyl)-aminocarbonyl group, while the alkyl groups, if they have more than one carbon atom, may be terminally substituted by a hydroxy, $C_{1-3}$-alkoxy or di-($C_{1-3}$-alkyl)-amino group, $R_3$ denotes a five or six-membered heteroaryl group, where the 6-membered heteroaryl group contains one, two or three nitrogen atoms and the 5-membered heteroaryl group contains an imino group optionally substituted by a $C_{1-3}$-alkyl, carboxy-$C_{1-3}$-alkyl or phenyl-$C_{1-3}$-alkyl group, an oxygen or sulphur atom or an imino group optionally substituted by a $C_{1-3}$-alkyl, carboxy-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group, an oxygen atom or a sulphur atom and two nitrogen atoms, and furthermore a phenyl ring may be fused to the abovementioned monocyclic heterocyclic groups via two adjacent carbon atoms, the hydrogen atom of a methyne group may be replaced by a $C_{1-3}$-alkyl, carboxy-$C_{1-3}$-alkyl, amino, $C_{1-3}$-alkyl-amino, di-($C_{1-3}$-alkyl)-amino, phenyl-$C_{1-3}$-alkyl-amino or di-(phenyl-$C_{1-3}$-alkyl)-amino group and the bond is made via a carbon atom of the heterocyclic moiety, a 5- to 6-membered cyclic oxime ether which is linked to the methylidene group via the carbon atom adjacent to the nitrogen atom, an imidazo[1,2-a]pyridin-6-yl or imidazo[1,2-a]pyridin-7-yl group or a bicyclic group consisting of a phenyl ring which is linked to the methylidene group, and an —O—CH$_2$—CH$_2$, O—CH$_2$—O, —O—CF$_2$—O, —O—CH$_2$—CH$_2$—O, —O—CH═CH—O, —S—CH═N, —NH—CH═N, —N═C($C_{1-3}$-alkyl)-NH, —N═C(carboxy-$C_{1-3}$-alkyl)-NH, —N($C_{1-3}$-alkyl)-CH═N, —N(carboxy-$C_{1-3}$-alkyl)-CH═N, —N($C_{1-3}$-alkyl)-C($C_{1-3}$-alkyl)═N, —N═CH—CH═N, —N═CH—N═CH, —N═CH—N═C($C_{1-3}$-alkyl), —N═CH—N═C(carboxy-$C_{1-3}$-alkyl), —N═CH—CH═CH, —N═CH—CH═C($C_{1-3}$-alkyl), —N═CH—CH═C(carboxy-$C_{1-3}$-alkyl), —N═N—NH, —N═N—N($C_{1-3}$-alkyl), —N═N—N(carboxy-$C_{1-3}$-alkyl), —CH═CH—NH, —CH═CH—N($C_{1-3}$-alkyl), —CH═CH—N(carboxy-$C_{1-3}$-alkyl), —N═CH—C(O)—N($C_{1-3}$-alkyl), —O—CH$_2$—C(O)—N($C_{1-3}$-alkyl), —CH═N—N═CH, —O—C(O)—CH$_2$—N($C_{1-3}$-alkyl), —O—CH$_2$—C(O)—NH, —O—CH$_2$—CH$_2$—N($C_{1-3}$-alkyl), —O—C(O)—N($C_{1-3}$-alkyl), —O—C(O)—NH, —CO—NH—CO or —CO—N($C_{1-3}$-alkyl)-CO bridge, which is linked in each case to two adjacent carbon atoms of the phenyl ring, while the hydrogen atom of any carboxy group contained in $R_3$ may be replaced by a prodrug group, $R_4$ denotes a $C_{3-7}$-cycloalkyl group, while the methylene group in the 4 position of a 6- or 7-membered cycloalkyl group may be substituted by an amino, $C_{1-3}$-alkylamino or di-($C_{1-3}$-alkyl)-amino group or may be replaced by an —NH or —N($C_{1-3}$-alkyl) group, or a phenyl group substituted by the group $R_6$ in the 3- or 4-position which may additionally be mono- or disubstituted by fluorine, chlorine, bromine or iodine atoms, by $C_{1-5}$-alkyl, trifluoromethyl, hydroxy, $C_{1-3}$-alkoxy, carboxy, $C_{1-3}$-alkoxycarbonyl, amino, acetylamino, $C_{1-3}$-alkyl-sulphonylamino, aminocarbonyl, $C_{1-3}$-alkyl-aminocarbonyl, di-($C_{1-3}$-alkyl)-aminocarbonyl, aminosulphonyl, $C_{1-3}$-alkyl-aminosulphonyl, di-($C_{1-3}$-alkyl)-aminosulphonyl, nitro or cyano groups, while the substituents may be identical or different and $R_6$ denotes a hydrogen, fluorine, chlorine, bromine or iodine atom, a cyano, nitro, amino, $C_{1-5}$-alkyl, $C_{3-7}$-cycloalkyl, trifluoromethyl, phenyl or heteroaryl group, a tetrazolyl group optionally substituted by a $C_{1-3}$-alkyl group, a 2-pyrrolidon-1-yl group wherein the methylene group adjacent to the carbonyl group may be replaced by an oxygen atom or an —NH or —N($C_{1-3}$-alkyl) group, the group of formula

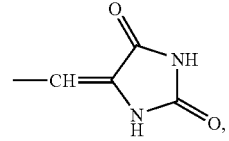

wherein the hydrogen atoms bound to a nitrogen atom may each be replaced independently of one another by a $C_{1-3}$-alkyl group, a group of formula

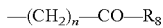

wherein $R_8$ denotes a hydroxy or $C_{1-4}$-alkoxy group, a 5- to 7-membered cycloalkyleneimino group, while the methylene group in position 3 or 4 of a 5-, 6- or 7-membered cycloalkyleneimino group may be substituted by an amino, $C_{1-3}$-alkyl-amino or di-($C_{1-3}$-alkyl)-amino group or the methylene group in the 4 position of a 6- or 7-membered cycloalkyleneimino group may be replaced by an oxygen atom, a sulphur atom, a sulphinyl or sulphonyl group, an —NH, —N(allyl) or —N($C_{1-3}$-alkyl) group and in the abovementioned cyclic groups one or two hydrogen atoms may be replaced by a $C_{1-3}$-alkyl group, a 2,5-dihydropyrrol-1-yl group or a $C_{3-7}$-cycloalkyl group, while the methylene group in position 3 or 4 of the 5-, 6- or 7-membered cycloalkyl moiety may be substituted by an amino, $C_{1-3}$-alkylamino or di-($C_{1-3}$-alkyl)-amino group or the methylene group in the 4 position of the 6- or 7-membered cycloalkyl moiety may be replaced by an —NH, —N(allyl) or —N($C_{1-3}$-alkyl) group, and n denotes one of the numbers 0, 1 or 2, a group of formula

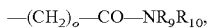

wherein $R_9$ denotes a hydrogen atom, an allyl group, a $C_{1-4}$-alkyl group optionally substituted by a cyano, carboxy, phenyl or pyridyl group or a $C_{2-4}$-alkyl group terminally substituted by a hydroxy or $C_{1-3}$-alkoxy group, $R_{10}$ denotes a hydrogen atom, a $C_{1-3}$-alkyl group, a $C_{2-3}$-alkyl group terminally substituted by a hydroxy, $C_{1-3}$-alkoxy, $C_{1-3}$-alkylamino or di-($C_{1-3}$-alkyl)-amino group or a 3- to 7-membered cycloalkyl group, wherein a methylene group may be replaced by an oxygen atom or an —NH or —N($C_{1-3}$-alkyl) group and independently thereof a methylene group may be replaced by a carbonyl group, and o denotes one of the numbers 0, 1 or 2, a $C_{1-3}$-alkyl group substituted by the group $R_7$, where $R_7$ denotes a $C_{3-7}$-cycloalkyl group, while one of the methylene groups may be substituted by an amino, $C_{1-3}$-alkylamino or di-($C_{1-3}$-alkyl)-amino group or the methylene group in position 3 or 4 of a 5-, 6- or 7-membered cycloalkyl group may be replaced by an —NH, —N(allyl) or —N($C_{1-3}$-alkyl) group or in a 5- to 7-membered cycloalkyl group a —(CH$_2$)$_2$ group may be replaced by a —CO—NH group, a —(CH$_2$)$_3$ group may be replaced by an —NH—CO—NH or —CO—NH—CO group or a —(CH$_2$)$_4$ group may be replaced by an —NH—CO—NH—CO group, while in each case a hydrogen atom bound to a nitrogen atom may be replaced by a $C_{1-3}$-alkyl group, an aryl or heteroaryl group, a triazolyl group, a hydroxy or $C_{1-3}$-alkoxy group, an amino, $C_{1-7}$-alkylamino, di-($C_{1-7}$-alkyl)-amino, N—($C_{1-7}$-alkyl)-allylamino, phenylamino, N-phenyl-$C_{1-3}$-alkyl-amino, phenyl-$C_{1-3}$-alkylamino, N—($C_{1-3}$-alkyl)-phenyl-$C_{1-3}$-alkylamino or di-(phenyl-$C_{1-3}$-alkyl)-amino group, an allylamino group wherein one or two vinylic hydrogen atoms may each be replaced by a methyl group, a ω-hydroxy-$C_{2-3}$-alkyl-amino, N—($C_{1-3}$-alkyl)-ω-hydroxy-$C_{2-3}$-alkyl-amino, di-(ω-hydroxy-$C_{2-3}$-alkyl)-amino, ω-($C_{1-3}$-alkoxy)-$C_{2-3}$-alkyl-amino-N—($C_{1-3}$-alkyl)-[ω-($C_{1-3}$-alkoxy)-$C_{2-3}$-alkyl]-amino, di-[ω-($C_{1-3}$-alkoxy)-$C_{2-3}$-alkyl]-amino or N-(dioxolan-2-yl)-$C_{1-3}$-alkyl-amino group, a $C_{1-3}$-alkylcarbonylamino-$C_{2-3}$-alkyl-amino or $C_{1-3}$-alkylcarbonylamino-$C_{2-3}$-alkyl-N—($C_{1-3}$-alkyl)-amino group, a pyridylamino group, a $C_{1-3}$-alkylsulphonylamino, N—($C_{1-3}$-alkyl)-$C_{1-3}$-alkylsulphonylamino, $C_{1-3}$-alkyl-sulphonylamino-$C_{2-3}$-alkyl-amino or $C_{1-3}$-alkylsulphonylamino-$C_{2-3}$-alkyl-N—($C_{1-3}$-alkyl)-amino group, a hydroxycarbonyl-$C_{1-3}$-alkylamino or N—($C_{1-3}$-alkyl)-hydroxycarbonyl-$C_{1-3}$-alkyl-amino group, a guanidino group wherein one or two hydrogen atoms may each be replaced by a. $C_{1-3}$-alkyl group, a 2-pyrrolidon-1-yl group wherein the methylene group adjacent to the carbonyl group may be replaced by an oxygen atom or by an —NH or —N($C_{1-3}$-alkyl) group, a group of formula

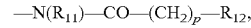

wherein $R_{11}$ denotes a hydrogen atom or an allyl, $C_{1-3}$-alkyl, $C_{1-3}$-alkyl-amino-$C_{2-3}$-alkyl or di-($C_{1-3}$-alkyl)-amino-$C_{2-3}$-alkyl group, p denotes one of the numbers 0, 1, 2 or 3 and $R_{12}$ denotes an amino, $C_{1-4}$-alkylamino, allylamino, di-allyl-amino, di-($C_{1-4}$-alkyl)-amino, phenylamino, N—($C_{1-4}$-alkyl)-phenylamino, benzylamino, N—($C_{1-4}$-alkyl)-benzylamino, $C_{1-4}$-alkoxy or 2,5-dihydropyrrol-1-yl group or a 4- to 7-membered cycloalkyleneimino group, while in each case the methylene group in the 4 position of a 6- or 7-membered cycloalkyleneimino group may be replaced by an oxygen or sulphur atom, by a sulphinyl, sulphonyl, —NH, —N($C_{1-3}$-alkyl), —N(allyl), —N(phenyl), —N($C_{1-3}$-alkyl-carbonyl) or —N(benzoyl) group, or, if n denotes one of the numbers 1, 2 or 3, it may also represent a hydrogen atom, a group of formula

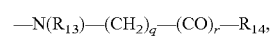

wherein $R_{13}$ denotes a hydrogen atom or a $C_{1-3}$-alkyl, allyl, $C_{1-3}$-alkyl-carbonyl, arylcarbonyl, pyridylcarbonyl, phenyl-$C_{1-3}$-alkyl-carbonyl, $C_{1-3}$-alkylsulphonyl, arylsulphonyl or phenyl-$C_{1-3}$-alkylsulphonyl group, q denotes one of the numbers 1, 2, 3 or 4, r denotes the number 1 or, if q denotes one of the numbers 2, 3 or 4, r may also denote the number 0 and $R_{14}$ denotes a hydroxy, amino, $C_{1-4}$-alkylamino, di-($C_{1-4}$-alkyl)-amino, phenylamino, N—($C_{1-4}$-alkyl)-phenylamino, benzylamino, N—($C_{1-4}$-alkyl)-benzylamino, $C_{1-4}$-alkoxy or $C_{1-3}$-alkoxy-$C_{1-3}$-alkoxy group, a di-($C_{1-4}$-alkyl)-amino-$C_{1-3}$-alkylamino group optionally substituted in the 1 position by a $C_{1-3}$-alkyl group or a 4- to 7-membered cycloalkyleneimino group,
while the cycloalkylene moiety may be fused to a phenyl ring or
in each case the methylene group in the 4 position of a 6- or 7-membered cycloalkyleneimino group may be replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl) group, a $C_{4-7}$-cycloalkylamino, $C_{4-7}$-cycloalkyl-$C_{1-3}$-alkylamino or $C_{4-7}$-cycloalkenylamino group wherein position 1 of the ring is not involved in the double bond and the abovementioned groups may each additionally be substituted at the amino-nitrogen atom by a $C_{5-7}$-cycloalkyl, $C_{2-4}$-alkenyl or $C_{1-4}$-alkyl group, a 2,5-dihydro-pyrrol-1-yl group or a 4- to 7-membered cycloalkyleneimino group wherein the cycloalkylene moiety may be fused to a phenyl group or to an oxazolo, imidazolo, thiazolo, pyridino, pyrazino or pyrimidino group optionally substituted by a fluorine, chlorine, bromine or iodine atom, by a nitro, $C_{1-3}$-alkyl, $C_{1-3}$-alkoxy or amino group and/or one or two hydrogen atoms may each be replaced by a $C_{1-3}$-alkyl, $C_{3-7}$-cyclo-alkyl, hydroxy, $C_{1-3}$-alkoxy, hydroxy-$C_{1-3}$-alkyl, $C_{1-3}$-alkoxy-$C_{1-3}$-alkyl or phenyl group and/or the methylene group in position 3 of a–5-membered cycloalkyleneimino group may be substituted by a hydroxy, hydroxy-$C_{1-3}$-alkyl, $C_{1-3}$-alkoxy or $C_{1-3}$-alkoxy-$C_{1-3}$-alkyl group, in each case the methylene group in position 3 or 4 of a 6- or 7-membered cycloalkyleneimino group may be substituted by a hydroxy, hydroxy-$C_{1-3}$-alkyl, $C_{1-3}$-alkoxy, $C_{1-3}$-alkoxy-$C_{1-3}$-alkyl, carboxy, $C_{1-4}$-alkoxycarbonyl, aminocarbonyl, $C_{1-3}$-alkylaminocarbonyl, di-($C_{1-3}$-alkyl)-aminocarbonyl, di-($C_{1-3}$-alkyl)-amino, phenyl-$C_{1-3}$-alkylamino or N—($C_{1-3}$-alkyl)-phenyl-$C_{1-3}$-alkylamino group or the methylene group in the 4 position of a 6- or 7-membered cycloalkyleneimino group may be replaced by an oxygen or sulphur atom, by a sulphinyl, sulphonyl, —NH, —N($C_{1-3}$-alkyl), —N(allyl), —N(phenyl), —N(phenyl-$C_{1-3}$-alkyl), —N($C_{1-3}$-alkyl-carbonyl), —N($C_4$-hydroxy-carbonyl), —N($C_{1-4}$-alkoxy-carbonyl), —N(benzoyl) or —N(phenyl-$C_{1-3}$-alkyl-carbonyl) group, while a methylene group linked to an imino-nitrogen atom of the cycloalkyleneimino group may be replaced by a carbonyl or sulphonyl group or in a 5- to 7-membered monocyclic cycloalkyleneimino group or a cycloalkyleneimino group fused to a phenyl group the two methylene groups linked to the imino-nitrogen atom may each be replaced by a carbonyl group, or $R_6$ denotes a group of formula

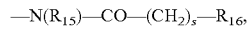
—N($R_{15}$)—CO—(CH$_2$)$_s$—$R_{16}$, wherein $R_{15}$ denotes a hydrogen atom, an allyl, $C_{1-6}$-alkyl, $C_{3-7}$-cycloalkyl or pyridinyl group, a $C_{1-3}$-alkyl group terminally substituted by a phenyl, heteroaryl, trifluoromethyl, aminocarbonyl, $C_{1-4}$-alkylamino-carbonyl, di-($C_{1-4}$-alkyl)-amino-carbonyl, $C_{1-3}$-alkyl-carbonyl, $C_{1-3}$-alkyl-aminosulphonyl or di-($C_{1-3}$-alkyl)-aminosulphonyl group or a $C_{2-3}$-alkyl group terminally substituted by a hydroxy, $C_{1-3}$-alkoxy, amino, $C_{1-3}$-alkylamino, allylamino, di-($C_{1-3}$-alkyl)-amino, $C_{1-3}$-alkyl-sulphonylamino or N—($C_{1-3}$-alkyl)-$C_{1-3}$-alkyl-sulphonylamino group and s denotes one of the numbers 0, 1, 2 or 3 and $R_{16}$ takes on the meanings of the abovementioned group $R_7$ or denotes a carboxy group or, if s denotes one of the numbers 1, 2 or 3, $R_{16}$ also denotes a hydrogen atom, a group of formula

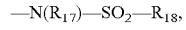
—N($R_{17}$)—SO$_2$—$R_{18}$, wherein $R_{17}$ denotes a hydrogen atom, an allyl, $C_{1-4}$-alkyl or cyanomethyl group or a $C_{2-4}$-alkyl group terminally substituted by a cyano, amino, $C_{1-3}$-alkylamino, di-($C_{1-3}$-alkyl)-amino, trifluoromethyl-carbonyl-amino or N—($C_{1-3}$-alkyl)-trifluoromethyl-carbonyl-amino group and $R_{18}$ denotes a $C_{1-4}$-alkyl, phenyl or pyridyl group, an amino group substituted by a di-($C_{1-3}$-alkyl)-amino-$C_{1-3}$-alkyl-carbonyl or di-($C_{1-3}$-alkyl)-amino-$C_{1-3}$-alkyl-sulphonyl group and a di-($C_{1-3}$-alkyl)-aminocarbonyl-$C_{1-3}$-alkyl group, or a group of formula

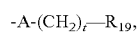
-A-(CH$_2$)$_t$—$R_{19}$, wherein

A denotes an oxygen or sulphur atom or a sulphinyl or sulphonyl group, $R_{19}$ denotes a hydrogen atom, a hydroxy, $C_{1-3}$-alkoxy, aryl, heteroaryl, amino, $C_{1-4}$-alkylamino or di-($C_{1-3}$-alkyl)-amino group or a 4- to 7-membered cycloalkyleneimino group,
while the methylene group in position 3 of a 5-membered cycloalkyleneimino group may be substituted by a hydroxy, hydroxy-$C_{1-3}$-alkyl, $C_{1-3}$-alkoxy-$C_{1-3}$-alkyl group, in each case the methylene group in position 3 or 4 of a 6- or 7-membered cycloalkyleneimino group may be substituted by a hydroxy, hydroxy-$C_{1-3}$-alkyl, $C_{1-3}$-alkoxy, $C_{1-3}$-alkoxy-$C_{1-3}$-alkyl, carboxy, $C_{1-4}$-alkoxycarbonyl, aminocarbonyl, $C_{1-3}$-alkylaminocarbonyl or di-($C_{1-3}$-alkyl)-aminocarbonyl group or may be replaced by an oxygen or sulphur atom, by a sulphinyl, sulphonyl, —NH or —N($C_{1-3}$-alkyl-) group, and t denotes one of the numbers 2 or 3 or, if $R_{19}$ denotes a hydrogen atom, an aryl or heteroaryl group, it may also denote the number 1 or, if A denotes a sulphonyl group, it may also denote the number 0,
or a group of formula

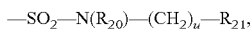
—SO$_2$—N(R$_{20}$)—(CH$_2$)$_u$—R$_{21}$, wherein
R$_{20}$ denotes a hydrogen atom, an allyl or C$_{1-3}$-alkyl group,
R$_{2}$, denotes a hydrogen atom, a hydroxy, C$_{1-3}$-alkoxy, amino, C$_{1-3}$-alkylamino or a di-(C$_{1-3}$-alkyl)-amino group and
u denotes one of the numbers 2, 3 or 4 or,
if R$_{21}$ denotes a hydrogen atom, it may also denote the number 1, while all the single-bonded or fused-on phenyl groups contained in the groups mentioned under R$_6$ may be mono- or disubstituted by fluorine, chlorine, bromine or iodine atoms, by C$_{1-5}$-alkyl, trifluoromethyl, hydroxy, C$_{1-3}$-alkoxy, carboxy, C$_{1-3}$-alkoxy-carbonyl, aminocarbonyl, C$_{1-4}$-alkylamino-carbonyl, di-(C$_{1-4}$-alkyl)-amino-carbonyl, aminosulphonyl, C$_{1-3}$-alkyl-aminosulphonyl, di-(C$_{1-3}$-alkyl)-aminosulphonyl, C$_{1-3}$-alkyl-sulphonylamino, nitro or cyano groups, while the substituents may be identical or different, or two adjacent hydrogen atoms of the phenyl groups may be replaced by a methylenedioxy group,
or R$_4$ denotes a group of formula

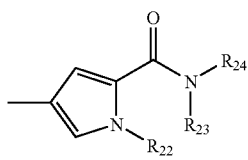

wherein
R$_{22}$ denotes a C$_{1-3}$-alkyl group,
R$_{23}$ denotes a hydrogen atom,
an allyl group,
a C$_{1-4}$-alkyl group optionally substituted by a cyano, carboxy, phenyl or pyridyl group or
a C$_{2-4}$-alkyl group terminally substituted by a hydroxy or C$_{1-3}$-alkoxy group and
R$_{24}$ denotes a hydrogen atom,
a C$_{1-3}$-alkyl group,
a C$_{2-3}$-alkyl group terminally substituted by a hydroxy, C$_{1-3}$-alkoxy, C$_{1-3}$-alkylamino or di-(C$_{1-3}$-alkyl)-amino group,
or a 3–7-membered cycloalkyl group,
while a methylene group may be replaced by an oxygen atom or by a —NH or —N(C$_{1-3}$-alkyl) group and independently thereof a methylene group may be replaced by a carbonyl group,
or R$_{23}$ and R$_{24}$ together with the nitrogen atom to which they are linked form
a 2,5-dihydro-pyrrol-1-yl group or
a 5- to 7-membered cycloalkyleneimino group,
while the methylene group in the 4 position of a 6- or 7-membered cycloalkyleneimino group may be substituted by an amino, C$_{1-3}$-alkylamino or di-(C$_{1-3}$-alkyl)-amino group or may be replaced by an oxygen atom, a sulphur atom, a sulphinyl or sulphonyl group or an —NH or —N(C$_{1-3}$-alkyl) group and one or two hydrogen atoms in the 5- to 7-membered cycloalkyleneimino group may be replaced by a C$_{1-3}$-alkyl group, and
R$_5$ denotes a hydrogen atom or a C$_{1-3}$-alkyl group,
while by the term aryl group is meant a phenyl or naphthyl group optionally mono- or disubstituted by a fluorine, chlorine, bromine or iodine atom, by a cyano, trifluoromethyl, nitro, carboxy, aminocarbonyl, C$_{1-3}$-alkyl or C$_{1-3}$-alkoxy group and
by the term heteroaryl group is meant, unless otherwise stated, a monocyclic 5- or 6-membered heteroaryl group optionally substituted in the carbon skeleton by one or two C$_{1-3}$-alkyl groups, wherein
the 6-membered heteroaryl group contains one, two or three nitrogen atoms and
the 5-membered heteroaryl group contains an imino group optionally substituted by a C$_{1-3}$-alkyl or phenyl-C$_{1-3}$-alkyl group, an oxygen or sulphur atom or
an imino group optionally substituted by a C$_{1-3}$-alkyl or phenyl-C$_{1-3}$-alkyl group or an oxygen or sulphur atom and additionally a nitrogen atom or
an imino group optionally substituted by a C$_{1-3}$-alkyl or phenyl-C$_{1-3}$-alkyl group and two nitrogen atoms,
and moreover a phenyl ring may be fused to the abovementioned monocyclic heterocyclic groups via two adjacent carbon atoms, the hydrogen atom of one or two methyne groups may be replaced by a C$_{1-3}$-alkyl, amino, C$_{1-3}$-alkyl-amino or di-(C$_{1-3}$-alkyl)-amino group and the bond is via a nitrogen atom or via a carbon atom of the heterocyclic moiety or of a fused phenyl ring,
the hydrogen atoms in the abovementioned alkyl and alkoxy groups or in the alkyl moieties contained in the above-defined groups of formula I may be wholly or partly replaced by fluorine atoms,
the saturated alkyl and alkoxy moieties containing more than 2 carbon atoms present in the groups defined above, also include the branched isomers thereof such as for example the isopropyl, tert.butyl, isobutyl group, unless otherwise stated, and
wherein additionally the hydrogen atom of any carboxy group present or a hydrogen atom bound to a nitrogen atom, for example an amino, alkylamino or imino group or a saturated N-heterocycle such as the piperidinyl group, may each be replaced by a group which can be cleaved in vivo,
the tautomers, the diastereomers, the enantiomers, the mixtures thereof, the prodrugs thereof and the salts thereof.

2. The compound according to claim 1, wherein
X denotes an oxygen atom,
R$_1$ denotes a hydrogen atom or a prodrug group such as a C$_{1-4}$-alkoxy-carbonyl or C$_{2-4}$-alkanoyl group,
R$_2$ denotes a hydrogen, fluorine, chlorine or bromine atom,
a cyano or nitro group,
a carboxy group, a straight-chain or branched C$_{1-4}$-alkoxy-carbonyl group or a C$_{3-4}$-cycloalkoxy-carbonyl group,
an allyloxycarbonyl group optionally substituted by one or two methyl groups,
a straight-chain or branched C$_{2-3}$-alkoxy-carbonyl group which is terminally substituted in the alkyl moiety by a hydroxy or C$_{1-3}$-alkoxy group, or an aminocarbonyl, $C_{1-4}$-alkyl-aminocarbonyl or a di-($C_{1-3}$-alkyl)-aminocarbonyl group, while the alkyl groups, if they have more than one carbon atom, may be terminally substituted by a $C_{1-3}$-alkoxy group, $R_3$ denotes a 2-pyrrolyl, 3-pyrrolyl, 1-($C_{1-3}$-alkyl)-3-pyrrolyl-,1-(carboxy-$C_{1-3}$-alkyl)-3-pyrrolyl, 2-furyl, 3-furyl, 2-thienyl, 3-thienyl, 2-(carboxy-$C_{1-3}$-alkyl)-thien-5-yl, 2-(carboxy-$C_{1-3}$-alkyl)-thien-4-yl, 3-(carboxy-$C_{1-3}$-alkyl)-thien-5-yl, 4-imidazolyl, 1-($C_{1-3}$-alkyl)-5-imidazolyl, 1-($C_{1-3}$-alkyl)-4-imidazolyl, 1-benzyl-5-imidazolyl, 5-($C_{1-3}$-alkyl)-isoxazol-3-yl, 3-pyridyl, 4-pyridyl, 2-(carboxy-$C_{1-3}$-alkyl)-pyridine-5-yl, 3-(carboxy-$C_{1-3}$-alkyl)-pyridine-5-yl, 2-(carboxy-$C_{1-3}$-alkyl)-pyridine-4-yl, 2-pyrazinyl, 4-pyridazinyl group or a pyrazol-3-yl group,
in which independently of one another the 1- and/or 5-position may be substituted in each case by a $C_{1-3}$-alkyl or carboxy-$C_{1-3}$-alkyl group, a 5- to 6-membered cyclic oxime ether which is linked to the methylidene group via the carbon atom adjacent to the nitrogen atom, an imidazo[1,2-a]pyridin-6-yl or imidazo[1,2-a]pyridin-7-yl group or a bicyclic group consisting of
a phenyl ring which is linked to the methylidene group, and
an —O—CH$_2$—CH$_2$, —O—CH$_2$—O, —O—CF$_2$—O, —O—CH$_2$—CH$_2$—O, —O—CH=CH—O, —S—CH=N, —NH—CH=N, —N=C($C_{1-3}$-alkyl)-NH, —N=C(carboxy-$C_{1-3}$-alkyl)-NH, —N($C_{1-3}$-alkyl)-CH=N, —N(carboxy-$C_{1-3}$-alkyl)-CH=N, —N($C_{1-3}$-alkyl)-C($C_{1-3}$-alkyl)=N—, —N=CH—CH=N, —N=CH—N=CH, —N=CH—N=C($C_{1-3}$-alkyl), —N=CH—CH=CH—, —N=CH—CH=C($C_{1-3}$-alkyl), —CH=N—N=CH, —CH=CH—NH, —CH=CH—N($C_{1-3}$-alkyl), —N=N—NH, —N=N—N($C_{1-3}$-alkyl), —O—CH$_2$—C(O)—N($C_{1-3}$-alkyl), —O—C(O)—CH$_2$—N($C_{1-3}$-alkyl), —O—C(O)—N($C_{1-3}$-alkyl), —O—C(O)—NH, —O—CH$_2$—CH$_2$—N($C_{1-3}$-alkyl), or —CO—N($C_{1-3}$-alkyl)-CO bridge, which is linked in each case to two adjacent carbon atoms of the phenyl ring, while the hydrogen atom of a carboxy group optionally contained in $R_3$ may be replaced by a prodrug group, $R_4$ denotes a phenyl group substituted in the 3- or 4-position by the group $R_6$ which may additionally be substituted in a remaining 3, 4 or 5 position by a fluorine, chlorine, bromine or iodine atom or by a $C_{1-3}$-alkyl, trifluoromethyl, hydroxy, $C_{1-3}$-alkoxy, amino, nitro or cyano group, while $R_6$ denotes a hydrogen, fluorine, chlorine, bromine or iodine atom, a tetrazolyl group optionally substituted by a $C_{1-3}$-alkyl group, an imidazolyl group substituted at the imino-nitrogen and/or at a carbon atom by a $C_{1-3}$-alkyl group, a pyrazolyl group substituted at the imino-nitrogen and/or at one or two carbon atoms in each case independently of one another by a $C_{1-3}$-alkyl group, a 2-pyrrolidon-1-yl group wherein the methylene group adjacent to the carbonyl group may be replaced by an oxygen atom or an —NH or —N($C_{1-3}$-alkyl) group, a group of formula —(CH$_2$)$_n$—CO—R$_8$, wherein
$R_8$ denotes a hydroxy group,
a 2,5-dihydropyrrol-1-yl group or
a 5- to 7-membered cycloalkyleneimino group,
while the methylene group in the 3 or 4 position of a 5-, 6- or 7-membered cycloalkyleneimino group may be substituted by an amino, $C_{1-3}$-alkyl-amino or di-($C_{1-3}$-alkyl)-amino group
or the methylene group in the 4 position of a 6- or 7-membered cycloalkyleneimino group may be replaced by an oxygen atom, a sulphur atom, a sulphinyl or sulphonyl group, an —NH or —N($C_{1-3}$-alkyl) group
and in the abovementioned cyclic groups one or two hydrogen atoms may be replaced by a $C_{1-3}$-alkyl group,
and n denotes one of the numbers 0 or 1, a group of formula —(CH$_2$)$_o$—CO—NR$_9$R$_{10}$, wherein
$R_9$ denotes a hydrogen atom,
an allyl group,
a $C_{1-4}$-alkyl group optionally substituted by a cyano or carboxy group or
a $C_{2-4}$-alkyl group terminally substituted by a hydroxy or $C_{1-3}$-alkoxy group,
$R_{10}$ denotes a hydrogen atom,
a $C_{1-3}$-alkyl group,
a $C_{2-3}$-alkyl group terminally substituted by a hydroxy, $C_{0-3}$-alkoxy, $C_{1-3}$-alkylamino or di-($C_{1-3}$-alkyl)-amino group or
a 3- to 7-membered cycloalkyl group,
wherein a methylene group may be replaced by an oxygen atom or an —NH or —N($C_{1-3}$-alkyl) group,
and o denotes one of the numbers 0 or 1, a $C_{1-2}$-alkyl group substituted by the group $R_7$, where
$R_7$ denotes a $C_{3-7}$-cycloalkyl group,
while the methylene group in the 4 position of a 6- or 7-membered cycloalkyl group may be replaced by an —NH or —N($C_{1-3}$-alkyl) group or
a pyridyl or imidazolyl group optionally substituted by a $C_{1-3}$-alkyl group,
a triazolyl group,
a hydroxy or $C_{1-3}$-alkoxy group,
an amino, $C_{1-4}$-alkylamino, di-($C_{1-3}$-alkyl)-amino, N—($C_{1-3}$-alkyl)-allylamino, phenyl-$C_{1-2}$-alkylamino or N—($C_{1-3}$alkyl)-phenyl-$C_{1-2}$-alkylamino group,
an allylamino group wherein one or two vinylic hydrogen atoms may each be replaced by a methyl group,
a ω-hydroxy-$C_{2-3}$-alkyl-amino, N—($C_{1-3}$-alkyl)-ω-hydroxy-$C_{2-3}$-alkyl-amino, di-(ω-hydroxy-$C_{2-3}$-alkyl)-amino, ω-($C_{1-3}$-alkoxy)-$C_{2-3}$-alkyl-amino-N—($C_{1-3}$-alkyl)-[ω-($C_{1-3}$-alkoxy)-$C_{2-3}$-alkyl]-amino or di-[ω-($C_{1-3}$-alkoxy)-$C_{2-3}$-alkyl]-amino group,
a pyridylamino group,
an N—($C_{1-3}$-alkyl)-$C_{1-3}$-alkylsulphonylamino group,
a hydroxycarbonyl-$C_{1-3}$-alkylamino or N—($C_{1-3}$-alkyl)-hydroxycarbonyl-$C_{1-3}$-alkyl-amino group,
a 2-pyrrolidon-1-yl group wherein the methylene group adjacent to the carbonyl group may be replaced by an oxygen atom or an —NH or —N($C_{1-3}$-alkyl) group, a group of formula

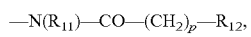

wherein
- $R_{11}$ denotes a hydrogen atom or an allyl, $C_{1-3}$-alkyl group, $C_{1-3}$-alkyl-amino-$C_{2-3}$-alkyl or di-($C_{1-3}$-alkyl)-amino-$C_{2-3}$-alkyl group,
- p denotes one of the numbers 0, 1 or 2 and
- $R_{12}$ denotes an amino, $C_{1-3}$-alkylamino, allylamino, di-($C_{1-2}$-alkyl)-amino, $C_{1-3}$-alkoxy or 2,5-dihydro-pyrrol-1-yl group or
- a 4- to 7-membered cycloalkyleneimino group,
  - while in each case the methylene group in the 4 position of a 6- or 7-membered cycloalkyleneimino group may be replaced by an oxygen or sulphur atom or by an —NH, —N(allyl) or —N($C_{1-3}$-alkyl) group, or, if n denotes one of the numbers 1 or 2, it may also represent a hydrogen atom, a group of formula —N($R_{13}$)—($CH_2$)$_q$—(CO)$_r$—$R_{14}$, wherein
- $R_{13}$ denotes a hydrogen atom or a $C_{1-3}$-alkyl or pyridylcarbonyl group,
- q denotes one of the numbers 1 or 2,
- r denotes the number 1 or, if q is the number 2, it may also denote the number 0 and
- $R_{14}$ denotes a hydroxy, amino, $C_{1-3}$-alkylamino, di-($C_{1-3}$-alkyl)-amino, $C_{1-3}$-alkoxy group or
- a 4- to 7-membered cycloalkyleneimino group,
  - while in each case the methylene group in the 4 position of a 6- or 7-membered cycloalkyleneimino group may be replaced by an oxygen or sulphur atom, by an —NH or —N($C_{1-3}$-alkyl) group,
- a $C_{4-7}$-cycloalkylamino, $C_{3-5}$-cycloalkyl-$C_{1-2}$-alkylamino or $C_{4-7}$-cycloalkenylamino group wherein position 1 of the ring is not involved in the double bond and the abovementioned groups may each additionally be substituted at the amino-nitrogen atom by a $C_{2-4}$-alkenyl or $C_{1-3}$-alkyl group,
- a 2,5-dihydro-pyrrol-1-yl group or
- a 4- to 7-membered cycloalkyleneimino group wherein
  - one or two hydrogen atoms may each be replaced by a $C_{1-3}$-alkyl, hydroxy, $C_{1-3}$-alkoxy, hydroxy-$C_{1-3}$-alkyl or $C_{1-3}$-alkoxy-$C_{1-3}$-alkyl group and/or
  - in each case the methylene group in the 3 or 4 position of a 6- or 7-membered cycloalkyleneimino group may be substituted by a carboxy, aminocarbonyl, $C_{1-3}$-alkylaminocarbonyl or di-($C_{1-3}$-alkyl)-aminocarbonyl group or
  - the methylene group in the 4 position of a 6- or 7-membered cycloalkyleneimino group may be replaced by an oxygen or sulphur atom, by a sulphinyl, sulphonyl, —NH, —N($C_{1-3}$-alkyl-), —N(allyl) or —N($C_{1-3}$-alkyl-carbonyl) group,
  - while a methylene group linked to an imino-nitrogen atom of the cycloalkyleneimino group may be replaced by a carbonyl or sulphonyl group, or $R_6$ denotes a group of formula

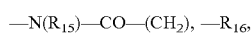

wherein
- $R_{15}$ denotes a hydrogen atom, an allyl, $C_{1-4}$-alkyl, $C_{3-5}$-cycloalkyl or pyridinyl group,
- a $C_{1-3}$-alkyl group terminally substituted by a pyridyl, trifluoromethyl or di-($C_{1-2}$-alkyl)-amino-carbonyl group or
- a $C_{2-3}$-alkyl group terminally substituted by a hydroxy, $C_{1-3}$-alkoxy, amino, $C_{1-3}$-alkylamino or di-($C_{1-3}$-alkyl)-amino group and
- s denotes one of the numbers 0, 1, 2 or 3 and
- $R_{16}$ denotes a hydroxy, $C_{1-3}$-alkoxy, carboxy, amino, $C_{1-3}$-alkylamino, di-($C_{1-3}$-alkyl)-amino, 2,5-dihydropyrrol-1-yl or pyridinyl group or a 5- to 7-membered cycloalkyleneimino group,
  - while the methylene group in position 3 of a 5-membered cycloalkyleneimino group may be substituted by a hydroxy, hydroxy-$C_{1-3}$-alkyl or $C_{1-3}$-alkoxy-$C_{1-3}$-alkyl group,
  - in each case the methylene group in the 3 or 4 position of a 6- or 7-membered cycloalkyleneimino group may be substituted by a di-($C_{1-3}$-alkyl)-amino, hydroxy, hydroxy-$C_{1-3}$-alkyl, $C_{1-3}$-alkoxy or $C_{1-3}$-alkoxy-$C_{1-3}$-alkyl group or
  - the methylene group in the 4 position of a 6- or 7-membered cycloalkyleneimino group may be replaced by an oxygen or sulphur atom or by an —NH or —N($C_{1-3}$-alkyl-) group, or, if s denotes one of the numbers 1, 2 or 3, it may also denote a hydrogen atom, a group of formula

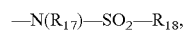

wherein
- $R_{17}$ denotes a hydrogen atom,
- a $C_{1-3}$-alkyl or cyanomethyl group or
- a $C_{2-3}$-alkyl group terminally substituted by a cyano, amino, $C_{1-3}$-alkylamino or di-($C_{1-3}$-alkyl)-amino group and
- $R_{18}$ denotes a $C_{1-4}$-alkyl or pyridyl group, or a group of formula

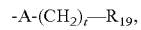

wherein
- A denotes an oxygen or sulphur atom or a sulphinyl or sulphonyl group,
- $R_{19}$ denotes a hydrogen atom or a hydroxy, $C_{1-3}$-alkoxy, amino, $C_{1-4}$-alkylamino or di-($C_{1-3}$-alkyl)-amino group
- or a 4- to 7-membered cycloalkyleneimino group,
  - while in each case the methylene group in the 3 or 4 position of a 6- or 7-membered may be replaced by an oxygen or sulphur atom, by an —NH or —N($C_{1-3}$-alkyl-) group,
- and t denotes one of the numbers 2 or 3
- or, if $R_{19}$ is a hydrogen atom, it may also denote the number 1, or a group of formula

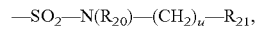

wherein
- $R_{20}$ denotes a hydrogen atom or an allyl or $C_{1-3}$-alkyl group,
- $R_{21}$ denotes a hydrogen atom, a hydroxy, $C_{1-3}$-alkoxy, amino, $C_{1-3}$-alkylamino or a di-($C_{1-3}$-alkyl)-amino group and
- u denotes one of the numbers 2, 3 or 4
- or, if $R_2$, is a hydrogen atom, it may also denote the number 1, or $R_4$ denotes a group of formula

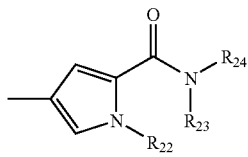

wherein
  $R_{22}$ denotes a methyl group,
  $R_{23}$ denotes a hydrogen atom or an allyl or $C_{1-3}$-alkyl group and
  $R_{24}$ denotes a hydrogen atom, a $C_{1-3}$-alkyl group or a $C_{2-3}$-alkyl group terminally substituted by a hydroxy, $C_{1-3}$-alkoxy, $C_{1-3}$-alkylamino group or by a di-$(C_{1-3}$-alkyl)-amino group,
  or $R_{23}$ and $R_{24}$ together with the nitrogen atom to which they are linked form
    a 2,5-dihydro-pyrrol-1-yl group or
    a 5- to 7-membered cycloalkyleneimino group,
      while the methylene group in the 4 position of a 6- or 7-membered cycloalkyleneimino group may be substituted by an amino, $C_{1-3}$-alkylamino or di-$(C_{1-3}$-alkyl)-amino group or may be replaced by an oxygen atom, an —NH or —N($C_{1-3}$-alkyl) group,
and
$R_5$ denotes a hydrogen atom,
while the hydrogen atoms in the abovementioned alkyl and alkoxy groups or in the alkyl moieties contained in the above-defined groups of formula I may be wholly or partially replaced by fluorine atoms,
the saturated alkyl and alkoxy moieties containing more than 2 carbon atoms present in the groups defined above, also include the branched isomers thereof, such as for example the isopropyl, tert.butyl, isobutyl group, unless otherwise stated,
the tautomers, the diastereomers, the enantiomers, the mixtures thereof, the prodrugs thereof and the salts thereof.

3. The compound according to claim 2, wherein
X denotes an oxygen atom,
$R_1$ and $R_5$ in each case denote a hydrogen atom,
$R_2$ denotes a hydrogen, fluorine, chlorine or bromine atom,
a cyano group or
a carboxy-$C_{1-2}$-alkoxycarbonyl, allyloxycarbonyl, $C_{1-3}$-alkylaminocarbonyl or di-$(C_{1-2}$-alkyl)-aminocarbonyl group
$R_3$ denotes a 2-pyrrolyl, 2-furyl, 3-furyl, 2-thienyl, 3-thienyl, 2-(carboxy-$C_{1-3}$-alkyl)-thien-5-yl, 2-(carboxy-$C_{1-3}$-alkyl)-thien-4-yl, 3-(carboxy-$C_{1-3}$-alkyl)-thien-5-yl, 4-imidazolyl, 5-($C_{1-3}$-alkyl)-pyrazol-3-yl, 5-($C_{1-3}$-alkyl)-isoxazol-3-yl, 3-pyridyl, 4-pyridyl, 2-pyrazinyl, 4-pyridazinyl, benzimidazol-5-yl, 1-($C_{1-3}$-alkyl)-benzimidazol-5-yl, 2-($C_{1-3}$-alkyl)-benzimidazol-5-yl, 2,3-dihydro-benzofuran-5-yl, 2,3-dihydro-benzofuran-6-yl, 3,4-methylenedioxy-1-phenyl, 3,4-ethylenedioxy-1-phenyl, 3,4-(difluoromethylenedioxy)-1-phenyl, 2-($C_{1-3}$-alkyl)-isoindol-1,3-dion-5-yl, quinoxalin-6-yl or 1-($C_{1-3}$-alkyl)-benzo-triazol-5-yl group,
$R_4$ denotes a phenyl group substituted in the 3 or 4 position by the group $R_6$ which may additionally be substituted in the remaining 3 or 4 position by a fluorine or chlorine atom or by a ($C_{1-3}$)-alkoxy or cyano group, while
$R_6$ denotes a 1-($C_{1-3}$-alkyl)-imidazol-2-yl group,
a 5-($C_{1-3}$-alkyl)-pyrazol-1-yl group which may additionally be substituted in the 3 position by a $C_{1-3}$-alkyl group,
a pyrrolid-2-on-1-yl group,
a $C_{1-2}$-alkyl group terminally substituted by the group $R_7$, where
  $R_7$ denotes an amino, allylamino, $C_{1-4}$-alkylamino or di-$(C_{1-3}$-alkyl)-amino group,
  a ω-hydroxy-$C_{2-3}$-alkyl-amino, N—($C_{1-3}$-alkyl)-ω-hydroxy-$C_{2-3}$-alkyl-amino, ω-($C_{1-3}$-alkoxy)-$C_{2-3}$-alkyl-amino or N—($C_{1-3}$-alkyl)-[ω-($C_{1-3}$-alkoxy)-$C_{2-3}$-alkyl]-amino group,
  a pyridylamino group,
  a 5- to 7-membered cycloalkyleneimino group wherein
    a carbon atom may be substituted with a hydroxy or hydroxymethyl group, with the exception of substitution by a hydroxyl group at a carbon atom adjacent to the nitrogen atom,
  a 6- to 7-membered cycloalkyleneimino group wherein the methylene group in the 4 position may be replaced by an oxygen atom or an —NH, —N-(allyl) or —N($C_{1-3}$-alkyl) group, or
  a triazolyl group bonded via the nitrogen atom in position 1 or 2,
or $R_6$ denotes a group of formula —(CH$_2$)$_n$—CO—R$_8$ wherein
  $R_8$ denotes a pyrrolidino, 2,5-dihydro-pyrrol-1-yl, piperidino, morpholino, thiomorpholino or a piperazino or perhydro-1,4-diazepino group optionally substituted in the 4 position by a $C_{1-3}$-alkyl group
  and n denotes one of the numbers 0 or 1,
a group of formula

—CO—NR$_9$R$_{10}$ wherein
  $R_9$ denotes a hydrogen atom, an allyl group or a $C_{1-3}$-alkyl group optionally terminally substituted by a cyano group and
  $R_{10}$ denotes a hydrogen atom,
  a $C_{1-3}$-alkyl group,
  a $C_{2-3}$-alkyl group terminally substituted by a $C_{1-3}$-alkylamino or di-$(C_{1-3}$-alkyl)-amino group or
  a 3- to 7-membered cycloalkyl group wherein a methylene group may be replaced by an —NH or —N($C_{1-3}$-alkyl) group,
a group of formula —N(R$_{15}$)—CO—(CH$_2$)$_s$—R$_{16}$, wherein
  $R_{15}$ denotes a hydrogen atom, an allyl, $C_{1-3}$-alkyl, pyridinyl, ω-[($C_{1-3}$-alkyl)-amino]—$C_{2-3}$-alkyl or ω-[di-($C_{1-3}$-alkyl)-amino]—$C_{2-3}$-alkyl group,
  s denotes one of the numbers 0, 1 or 2 and
  $R_{16}$ denotes a $C_{1-3}$-alkoxy, amino, $C_{1-3}$-alkylamino, di-$(C_{1-3}$-alkyl)-amino or pyridinyl group,
  a pyrrolidino, 2,5-dihydropyrrol-1-yl, piperidino, morpholino or thiomorpholino group or
  a piperazino or perhydro-1,4-diazepino group optionally substituted in the 4 position by a $C_{1-3}$-alkyl group or, if s denotes the number 1 or 2, it may also represent a hydrogen atom,
a group of formula

—N(R$_{17}$)—SO$_2$—R$_{18}$, wherein
R$_{17}$ denotes a hydrogen atom,
a C$_{1-3}$-alkyl group or
a C$_{2-3}$-alkyl group terminally substituted by an amino, C$_{1-3}$-alkyl-amino or di-(C$_{1-3}$-alkyl)-amino group and
R$_{18}$ denotes a C$_{1-3}$-alkyl group,
a group of formula —SO$_2$—(CH$_2$)$_t$—R$_{19}$, wherein
t denotes one of the numbers 1, 2 or 3 and
R$_{19}$ denotes a hydrogen atom or, if n denotes one of the numbers 2 or 3, it may also represent a di-(C$_{1-3}$-alkyl)-amino group,
or a group of formula —O—(CH$_2$)$_t$—R$_{19}$, wherein
t denotes one of the numbers 1, 2 or 3 and
R$_{19}$ denotes a hydrogen atom or, if n denotes one of the numbers 2 or 3, it may also represent a di-(C$_{1-3}$-alkyl)-amino group,
or a group of formula

—SO$_2$—NR$_{20}$R$_{25}$, wherein
R$_{20}$ denotes a hydrogen atom or an allyl or C$_{1-3}$-alkyl group and
R$_{25}$ denotes a C$_{1-3}$-alkyl group or
a C$_{2-3}$-alkyl group substituted by an amino, C$_{1-3}$-alkylamino or di-(C$_{1-3}$-alkyl)-amino group,
while the dialkylamino groups contained in the abovementioned groups may contain two identical or different alkyl groups and
the saturated alkyl and alkoxy moieties which contain more than 2 carbon atoms present in the abovementioned groups may be straight-chain or branched, unless otherwise stated,
the tautomers, diastereomers, enantiomers, the mixtures thereof and the salts thereof.

4. The compound according to claim 3, wherein
X denotes an oxygen atom,
R$_1$ and R$_5$ in each case denote a hydrogen atom,
R$_2$ denotes a hydrogen, fluorine or chlorine atom or a methoxycarbonyl, ethoxycarbonyl, dimethylaminocarbonyl, N-ethyl-N-methyl-aminocarbonyl or diethylaminocarbonyl group,
R$_3$ denotes a 3,4-methylenedioxy-1-phenyl, 3,4-ethylenedioxy-1-phenyl, quinoxalin-6-yl, benzimidazol-5-yl, 2-methylbenzimidazol-5-yl or 1-methyl-benzimidazol-5-yl group and
R$_4$ denotes a phenyl group substituted in the 4 position by the group R$_6$ which may additionally be substituted in the 3 position by a fluorine or chlorine atom or a methoxy group, while
R$_6$ denotes a 1-(C$_{1-2}$-alkyl)-imidazol-2-yl group,
a 3,5-dimethyl-pyrazol-1-yl group,
a pyrrolid-2-on-1-yl group,
a methyl group substituted by the group R$_7$, where
R$_7$ denotes a methylamino, ethylamino, isobutylamino, di-(C$_{1-2}$-alkyl)-amino, N-(2-hydroxyethyl)-methylamino or N-(2-methoxyethyl)-methylamino group,
a pyrrolidino, 3-hydroxypyrrolidino, 2-hydroxymethyl-pyrrolidino, 4-hydroxypiperidino, morpholino, piperazin-1-yl or 1-methyl-piperazin-4-yl group or
a 1,2,4-triazol-1-yl, 1,2,3-triazol-1-yl or 1,2,3-triazol-2-yl group,
or R$_6$ denotes an N-acetyl-methylamino or N-methoxyacetyl-methylamino group,
a group of formula

—CO—R$_8$, wherein
R$_8$ denotes a piperazino or perhydro-1,4-diazepino group optionally substituted by a methyl group in the 4 position,
a 4-methyl-piperazin-1-yl-carbonyl-methyl group,
a group of formula

—CO—NR$_9$R$_{10}$ wherein
R$_9$ denotes a methyl, cyanomethyl or ethyl group and
R$_{10}$ denotes a methyl, 1-methylpiperidin-4-yl, 2-methylamino-ethyl, 2-dimethyl-amino-ethyl or 3-dimethylamino-propyl group,
a group of formula —N(R$_{15}$)—CO—(CH$_2$)$_s$—NMe$_2$, wherein
s denotes one of the numbers 1 or 2 and
R$_{15}$ denotes a methyl or ethyl group or, if n denotes the number 2, it may also represent a 3-pyridyl group,
a group of formula —N(R$_{15}$')—CO—(CH$_2$)$_s$—H, wherein
s denotes one of the numbers 1 or 2 and
R$_{15}$' denotes a 2-(dimethylamino)-ethyl or 3-(dimethylamino)-propyl group,
or a group of formula —N(Me)—CO—(CH$_2$)$_s$—R$_{16}$', wherein
s denotes one of the numbers 1 or 2 and
R$_{16}$' denotes a dimethylamino group, or, if s denotes the number 1, it may also represent a 4-(C$_{1-2}$-alkyl)-piperazin-1-yl group,
a group of formula

—N(R$_{17}$)—SO$_2$—R$_{18}$, wherein a) R$_{17}$ denotes a dimethylaminoethyl group and R$_{18}$ denotes a methyl, ethyl or propyl group or
wherein b) R$_{17}$ and R$_{18}$ in each case represent a methyl group,
a group of formula —SO$_2$—N(R$_{20}$)—(CH$_2$)$_u$—NMe$_2$, wherein
R$_{20}$ denotes a hydrogen atom or a methyl group and
u denotes one of the numbers 2 or 3,
a group of formula

—SO$_2$—R$_{26}$, wherein
R$_{26}$ denotes a methyl group or a 2-di-(C$_{1-2}$-alkyl)-amino-ethyl group,
or a 2-di-(C$_{1-2}$-alkyl)-amino-ethoxy group,
while the dialkylamino groups contained in the abovementioned groups may contain two identical or two different alkyl groups, the tautomers, diastereomers, enantiomers, the mixtures thereof and the salts thereof.

5. The compound according to claim 1 selected from:
(a) 3-(Z)-{1-[4-(dimethylaminomethyl)-phenylamino]-1-(3,4-methylenedioxyphenyl)-methylene}-6-chloro-2-indolinone
(b) 3-(Z)-{1-(4-[N-methyl-N-(4-methylpiperazin-1-yl-methylcarbonyl)-amino]-phenylamino)-1-(quinoxalin-6-yl)-methylene}-6-chloro-2-indolinone
(c) 3-(Z)-{1-[4-(N-ethyl-N-methyl-aminomethyl)-phenylamino]-1-(3,4-methylenedioxyphenyl)-methylene}-6-chloro-2-indolinone
(d) 3-(Z)-{1-[4-(N-methyl-N-{2-(dimethylamino)-ethylcarbonyl}-amino)-phenylamino]-1-(3,4-ethylenedioxyphenyl)-methylene}-6-fluoro-2-indolinone
(e) 3-(Z)-{1-[4-(1,2,4-triazol-1-yl-methyl)-phenylamino]-1-(1-methyl-benzimidazol-5-yl)-methylene}-6-fluoro-2-indolinone
(f) 3-(Z)-{1-[4-(dimethylaminomethyl)-phenylamino]-1-(1-methyl-benzimidazol-5-yl)-methylene}-6-chloro-2-indolinone
(g) 3-(Z)-{1-[4-(dimethylaminomethyl)-phenylamino]-1-(3,4-ethylenedioxyphenyl)-methylene}-6-chloro-2-indolinone
(h) 3-(Z)-{1-(4-[N-methanesulphonyl-N-(2-dimethylaminoethyl)-amino]-phenylamino)-1-(3,4-ethylenedioxyphenyl)-methylene}-6-chloro-2-indolinone
(i) 3-(Z)-{1-[4-(dimethylaminomethyl)-phenylamino]-1-(3,4-ethylenedioxyphenyl)-methylene}-6-methoxycarbonyl-2-indolinone
(j) 3-(Z)-{1-(4-[N-methyl-N-(4-methylpiperazin-1-yl-methylcarbonyl)-amino]-phenyl-amino)-1-(3,4-ethylenedioxyphenyl)-methylene}-6-methoxycarbonyl-2-indolinone
(k) 3-(Z)-{1-(4-[N-acetyl-N-(2-dimethylaminoethyl)-amino]-phenylamino)-1-(3,4-ethylenedioxyphenyl)-methylene}-6-fluoro-2-indolinone
(l) 3-(Z)-{1-[4-(ethylaminomethyl)-phenylamino]-1-(3,4-ethylenedioxyphenyl)-methylene}-6-fluoro-2-indolinone
(m) 3-(Z)-{1-(4-[N-acetyl-N-(3-dimethylaminopropyl)-amino]-phenylamino)-1-(3,4-ethylenedioxyphenyl)-methylene}-6-chloro-2-indolinone
(n) 3-(Z)-{1-(4-[N-propionyl-N-(3-dimethylaminopropyl)-amino]-phenylamino)-1-(3,4-ethylenedioxyphenyl)-methylene}-6-chloro-2-indolinone
(o) 3-(Z)-{1-(4-[N-propionyl-N-(2-dimethylaminoethyl)-amino]-phenylamino)-1-(3,4-ethylenedioxyphenyl)-methylene}-6-chloro-2-indolinone
(p) 3-(Z)-{1-(4-[N-acetyl-N-(2-dimethylaminoethyl)-amino]-phenylamino)-1-(3,4-ethylenedioxyphenyl)-methylene}-6-chloro-2-indolinone
(q) 3-(Z)-{1-(4-[4-methylpiperazin-1-yl-methyl]-phenylamino)-1-(3,4-methylenedioxyphenyl)-methylene}-6-chloro-2-indolinone
(r) 3-(Z)-{1-(4-[N-methanesulphonyl-N-(2-dimethylaminoethyl)-amino]-phenylamino)-1-(3,4-ethylenedioxyphenyl)-methylene}-6-methoxycarbonyl-2-indolinone
(s) 3-(Z)-{1-(4-[pyrrolidin-1-yl-methyl]-phenylamino)-1-(3,4-ethylenedioxyphenyl)-methylene}-6-methoxycarbonyl-2-indolinone
(t) 3-(Z)-{1-(4-[N-methyl-N-(dimethylaminomethylcarbonyl)-amino]-phenylamino)-1-(3,4-ethylenedioxyphenyl)-methylene}-6-methoxycarbonyl-2-indolinone
(u) 3-(Z)-{1-(4-[ethylamino-methyl]-phenylamino)-1-(3,4-ethylenedioxyphenyl)-methylene}-6-methoxycarbonyl-2-indolinone
(v) 3-(Z)-{1-(4-[4-methylpiperazin-1-yl-methyl]-phenylamino)-1-(3,4-ethylenedioxy-phenyl)-methylene}-6-methoxycarbonyl-2-indolinone
(w) 3-(Z)-{1-(4-[dimethylamino-methyl]-phenylamino)-1-(3,4-methylenedioxyphenyl)-methylene}-6-methoxycarbonyl-2-indolinone
(x) 3-(Z)-{1-(4-[diethylamino-methyl]-phenylamino)-1-(3,4-methylenedioxyphenyl)-methylene}-6-methoxycarbonyl-2-indolinone
(y) 3-(Z)-{1-[4-(dimethylaminocarbonyl)-phenylamino]-1-(1-methyl-benzimidazol-5-yl)-methylene}-6-fluoro-2-indolinone
(z) 3-(Z)-{1-(4-[N-propionyl-N-(3-dimethylaminopropyl)-amino]-phenylamino)-1-(3,4-ethylenedioxyphenyl)-methylene}-6-fluoro-2-indolinone
(aa) 3-(Z)-{1-(4-[N-propionyl-N-(2-dimethylaminoethyl)-amino]-phenylamino)-1-(3,4-ethylenedioxyphenyl)-methylene}-6-fluoro-2-indolinone
(ab) 3-(Z)-{1-(4-[N-methanesulphonyl-N-(2-dimethylaminoethyl)-amino]-phenylamino)-1-(3,4-ethylenedioxyphenyl)-methylene}-6-fluoro-2-indolinone
(ac) 3-(Z)-{1-(4-[N-acetyl-N-(2-dimethylaminoethyl)-amino]-phenylamino)-1-(3,4-ethylenedioxyphenyl)-methylene}-6-methoxycarbonyl-2-indolinone
(ad) 3-(Z)-{1-(4-[N-methyl-N-(2-dimethylaminoethyl)aminocarbonyl]-phenylamino)-1-(3,4-ethylenedioxyphenyl)-methylene}-6-methoxycarbonyl-2-indolinone
(ae) 3-(Z)-{1-(4-[N-methyl-N-(3-dimethylaminopropyl)aminocarbonyl]-phenylamino)-1-(3,4-ethylenedioxyphenyl)-methylene}-6-methoxycarbonyl-2-indolinone
(af) 3-(Z)-{1-(4-[N-methyl-N-(2-dimethylaminoethyl)aminocarbonyl]-phenylamino)-1-(3,4-methylenedioxyphenyl)-methylene}-6-methoxycarbonyl-2-indolinone
(az) 3-(Z)-{1-(4-[N-methyl-N-(4-methylpiperazin-1-yl-methylcarbonyl)-amino]-phenyl-amino)-1-(3,4-methylenedioxyphenyl)-methylene}-6-chloro-2-indolinone
(be) 3-(Z)-{1-(4-[N-methyl-N-(4-methylpiperazin-1-yl-methylcarbonyl)-amino]-phenyl-amino)-1-(3,4-methylenedioxyphenyl)-methylene}-6-fluoro-2-indolinone and
(bf) 3-(Z)-{1-(4-[N-methyl-N-(4-methylpiperazin-1-yl-methylcarbonyl)-amino]-phenyl-amino)-1-(3,4-methylenedioxyphenyl)-methylene}-6-bromo-2-indolinone, the tautomers and the salts thereof.

6. The physiologically acceptable salt of the compound according to claim 1.

7. A pharmaceutical composition comprising a compound according to of claim 1 together with one or more inert carriers and/or diluents.

* * * * *